(12) United States Patent
Yip et al.

(10) Patent No.: US 11,348,661 B2
(45) Date of Patent: *May 31, 2022

(54) PREDICTING TOTAL NUCLEIC ACID YIELD AND DISSECTION BOUNDARIES FOR HISTOLOGY SLIDES

(71) Applicant: TEMPUS LABS, INC., Chicago, IL (US)

(72) Inventors: Stephen Yip, Chicago, IL (US); Irvin Ho, Wilmette, IL (US); Lingdao Sha, Chicago, IL (US); Boleslaw Osinski, Chicago, IL (US); Aly Azeem Khan, Chicago, IL (US); Andrew J. Kruger, Chicago, IL (US); Michael Carlson, Chicago, IL (US); Abel Greenwald, Chicago, IL (US); Caleb Willis, Chicago, IL (US); Andrew Westley, Chicago, IL (US); Ryan Jones, Naperville, IL (US); Brett Mahon, Chicago, IL (US)

(73) Assignee: TEMPUS LABS, INC., Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/139,765

(22) Filed: Dec. 31, 2020

(65) Prior Publication Data

US 2021/0166785 A1 Jun. 3, 2021

Related U.S. Application Data

(63) Continuation-in-part of application No. 16/830,186, filed on Mar. 25, 2020, now Pat. No. 10,957,041, (Continued)

(51) Int. Cl.
*G16B 30/00* (2019.01)
*G16B 50/30* (2019.01)
*C12Q 1/6869* (2018.01)

(52) U.S. Cl.
CPC ........... *G16B 30/00* (2019.02); *C12Q 1/6869* (2013.01); *G16B 50/30* (2019.02); *C12Q 2535/101* (2013.01)

(58) Field of Classification Search
CPC ............ C12Q 1/6886; C12Q 2600/158; C12Q 2600/112; C12Q 2600/118;
(Continued)

(56) References Cited

U.S. PATENT DOCUMENTS 6,463,438 B1   10/2002   Veltri et al.
9,996,664 B2   6/2018    Lloyd et al.
(Continued)

FOREIGN PATENT DOCUMENTS

CN   107369151 A     11/2017
WO   2004/081564 A1  9/2004
(Continued)

OTHER PUBLICATIONS

Bellevicine C, Malapelle U, Vigliar E, et al., "How to prepare cytological samples for molecular testing," Journal of Clinical Pathology 2017;70:819-826. (Year: 2017).*
(Continued)

*Primary Examiner* — Ross Varndell
(74) *Attorney, Agent, or Firm* — Marshall, Gerstein & Borun LLP

(57) ABSTRACT

A method for qualifying a specimen prepared on one or more hematoxylin and eosin (H&E) slides by assessing an expected yield of nucleic acids for tumor cells and providing associated unstained slides for subsequent nucleic acid analysis is provided.

29 Claims, 44 Drawing Sheets
(29 of 44 Drawing Sheet(s) Filed in Color)

Related U.S. Application Data which is a continuation-in-part of application No. 16/732,242, filed on Dec. 31, 2019, and a continuation-in-part of application No. 16/412,362, filed on May 14, 2019.

(60) Provisional application No. 62/983,524, filed on Feb. 28, 2020, provisional application No. 62/889,521, filed on Aug. 20, 2019, provisional application No. 62/824,039, filed on Mar. 26, 2019, provisional application No. 62/787,047, filed on Dec. 31, 2018, provisional application No. 62/671,300, filed on May 14, 2018.

(58) Field of Classification Search
CPC .......... C12Q 2600/106; C12Q 2600/16; G01N 2800/52; G01N 33/57434; G06T 2207/30024; G06T 7/0012; G06T 2207/10056
See application file for complete search history.

(56) References Cited

U.S. PATENT DOCUMENTS

| | | |
|---|---|---|
| 10,049,450 B2 | 8/2018 | Madabhushi et al. |
| 10,078,895 B2 | 9/2018 | Madabhushi et al. |
| 10,102,418 B2 | 10/2018 | Bredno et al. |
| 10,426,442 B1 | 10/2019 | Schnorr |
| 10,699,163 B1 | 6/2020 | Shah et al. |
| 2003/0215936 A1 | 11/2003 | Kallioniemi et al. |
| 2006/0064248 A1 | 3/2006 | Saidi et al. |
| 2010/0111396 A1 | 5/2010 | Boucheron |
| 2011/0188728 A1* | 8/2011 | Sammak .................. G06K 9/00 382/133 |
| 2014/0337052 A1 | 11/2014 | Pellini et al. |
| 2015/0100246 A1 | 4/2015 | Remzi et al. |
| 2016/0063724 A1* | 3/2016 | Tunstall ............... G06K 9/4642 382/128 |
| 2016/0103973 A1 | 4/2016 | Singal et al. |
| 2016/0110584 A1 | 4/2016 | Remiszewski et al. |
| 2016/0217253 A1 | 7/2016 | Newman et al. |
| 2016/0253466 A1 | 9/2016 | Agaian et al. |
| 2016/0333420 A1 | 11/2016 | Stern et al. |
| 2017/0076046 A1 | 3/2017 | Barnes et al. |
| 2017/0076442 A1 | 3/2017 | Schoenmeyer et al. |
| 2017/0337682 A1 | 11/2017 | Liao et al. |
| 2018/0005136 A1 | 1/2018 | Gai et al. |
| 2018/0075597 A1 | 3/2018 | Liu et al. |
| 2018/0089373 A1* | 3/2018 | Matsuguchi ........... G16B 20/10 |
| 2018/0121759 A1 | 5/2018 | Gabrani et al. |
| 2018/0129911 A1 | 5/2018 | Madabhushi et al. |
| 2018/0203974 A1 | 7/2018 | Venn |
| 2018/0239949 A1 | 8/2018 | Chander et al. |
| 2018/0276339 A1 | 9/2018 | Planey et al. |
| 2018/0340870 A1 | 11/2018 | Gustafson et al. |
| 2019/0034591 A1 | 1/2019 | Mossin et al. |
| 2019/0043242 A1 | 2/2019 | Risser |
| 2019/0087532 A1 | 3/2019 | Madabhushi et al. |
| 2019/0169685 A1 | 6/2019 | Georgiadis et al. |
| 2019/0392580 A1 | 12/2019 | Kapil et al. |
| 2020/0381104 A1 | 12/2020 | Ceballos et al. |

FOREIGN PATENT DOCUMENTS

| | | |
|---|---|---|
| WO | 2016/118860 A1 | 7/2016 |
| WO | 2017/198790 A1 | 11/2017 |
| WO | 2018/065434 A1 | 4/2018 |
| WO | 2018/067937 A1 | 4/2018 |
| WO | 2018/136664 A1 | 7/2018 |
| WO | 2018/158412 A1 | 9/2018 |
| WO | 2018/165103 A1 | 9/2018 |
| WO | 2018/191553 A1 | 10/2018 |
| WO | 2018/231771 A1 | 12/2018 |

OTHER PUBLICATIONS

Shah et al., "Deep Learning Assessment of Tumor Proliferation in Breast Cancer Histological Images," Oct. 11, 2016. (Year: 2016).*
Lemery et al., First FDA approval agnostic of cancer site-when a biomarker defines the indication, N. Engl. J. Med., 377:1409-1412 (2017).
Letter from U.S. Department of Health & Human Services to Agfa Healthcare N.V., regarding Enterprise Imaging XERO Viewer 8.1, dated (Jul. 3, 2017).
Letter from U.S. Department of Health & Human Services to Arterys, Inc. regarding Arterys Software v2.0, dated (Oct. 28, 2016).
Letter from U.S. Department of Health & Human Services to Arterys, Inc. regarding Arterys Viewer, dated (Jul. 18, 2017).
Letter from U.S. Department of Health & Human Services to Brainlab AG regarding DICOM Viewer, dated (Apr. 13, 2016).
Letter from U.S. Department of Health & Human Services to Healthmyne Inc. regarding Healthmyne PACS, dated (Aug. 20, 2015).
Letter from U.S. Department of Health & Human Services to Healthmyne Inc. regarding Healthmyne, dated (Jan. 15, 2016).
Letter from U.S. Department of Health and Human Services to Philips Medical Systems Nederland B.V. regarding Philips Intellisite Pathology Solution (PIPS), dated (Oct. 13, 2017).
Letter from U.S. Food & Drug Administration to Arterys, Inc. regarding Arterys Oncology DL, dated (Jan. 25, 2018).
Letter from U.S. Food & Drug Administration to Dako North America, Inc. regarding PD-L1 IHC 22C3 pharmDx, dated (Aug. 16, 2018).
Letter from U.S. Food & Drug Administration to Dako North America, Inc. regarding PD-L1 IHC 22C3 pharmDx, dated (Jun. 12, 2018).
Levenson et al., Pigeons (*Columba livia*) as trainable observers of pathology and radiology breast cancer images, PLoS One, 10:e0141357 (2015).
Levine et al., Rise of the machines: Advances in deep learning for cancer diagnosis, Trends in Cancer, 5(3):157-169 (2019).
Li et al., Deep learning based radiomics (DLR) and its usage in noninvasive IDH1 prediction for low grade glioma, Sci. Rep., 7(1):5467 (2017).
Li et al., Landscape of tumor-infiltrating T cell repertoire of human cancers, Nat. Genet., 48(7):725-732 (2016).
Litjens et al., A survey on deep learning in medical image analysis, Med. Image Anal. Elsevier, 42:60-88 (2017).
Litjens et al., Deep learning as a tool for increased accuracy and efficiency of histopathological diagnosis, Sci. Rep. Nature.com, 6:26286 (2016).
Liu et al., Artificial intelligence-based breast cancer nodal metastasis detection, Arch. Pathol. Lab. Med. arpa., 2018-0147-OA (2018). doi:10.5858/arpa.2018-0147-OA.
Liu et al., Detecting cancer metastases on gigapixel pathology images, 13 (2017).
Long et al., Fully convolutional networks for semantic segmentation, IEEE Transactions on Pattern Analysis and Machine Intelligence, 39:640-651 (2017), https://ieeexplore.ieee.org/document/7298965.
Lowe, Distinctive image features from scale-invariant keypoints, Int. J. Computer Vision, 28 (2004).
Luo et al., Comprehensive computational pathological image analysis predicts lung cancer prognosis, J. Thorac. Oncol., 12:501-509 (2017).
Madabhushi et al., Image analysis and machine learning in digital pathology: Challenges and opportunities, Med. Image Anal., 33:170-175 (2016).
McLaughlin et al., Quantitative assessment of the heterogeneity of PD-L1 expression in non-small-cell lung cancer, JAMA Oncol. American Medical Association, 2:46-54 (2016).
Meng et al., Predictive biomarkers in PD-1/PD-L1 checkpoint blockade immunotherapy, Cancer Treat. Rev., 41:868-76 (2015).
Mobadersany et al., Predicting cancer outcomes from histology and genomics using convolutional networks, Proc. Natl. Acad. Sci. U. S. A., 115:E2970-9 (2018).

(56) References Cited

OTHER PUBLICATIONS

Murphy et al., Comparison of the microsatellite instability analysis system and the bethesda panel for the determination of microsatellite instability in colorectal cancers, Journal of Molecular Diagnostics, 8(3):305-311 (2006).
Myronenko, 3D MRI brain tumor segmentation using autoencoder regularization, downloaded from the Internet at: <https://arxiv.org/pdf/1810.11654.pdf> (published Nov. 19, 2018).
Nalisnik et al., Interactive phenotyping of large-scale histology imaging data with HistomicsML, Sci. Rep., 1-12 (2017).
Nawaz et al., Beyond immune density: critical role of spatial heterogeneity in oestrogen receptor-negative breast cancer, doi:10.1038/modpathol., 37 (2015).
Newburn, Understanding the role of Human Leukocyte Antigen in Cancer Immunotherapy, Personalis, (2019).
Newman et al., Determining cell type abundance and expression from bulk tissues with digital cytometry, Nat. Biotec., 37:773-782 (2019).
Newman et al., Robust enumeration of cell subsets from tissue expression profiles, Nat. Methods, 12(5):453-457 (2015).
Non-Final Office Action received for U.S. Appl. No. 17/169,162, dated Jun. 28, 2021, 17 pages.
O'Rourke et al., Is concurrent chemoradiation the standard of care for locally advanced non-small cell lung cancer?, A review of guidelines and evidence, Clin. Oncol., 22:347-55 (2010).
OpenSeadragon API: Getting Started, available online at <https://openseadragon.github.io/docs/>, 3 (2020).
Orange et al., Identification of three rheumatoid arthritis disease subtypes by machine learning integration of synovial histologic features and RNA sequencing data, Arthritis Rheumatol., 70:690-701 (2018).
Pardoll, The blockade of immune checkpoints in cancer immunotherapy, Nat. Rev. Cancer, 12:252-264 (2012).
Patel et al., Development of immunohistochemistry services for cancer care in western Kenya: Implications for Tow-and middle-income countries, S. Afr. J. Lab. Clin. Med., 5:187 (2016).
Patel et al., PD-L1 expression as a predictive biomarker in cancer immunotherapy, Mol. Cancer Ther., 14:847-56 (2015).
PD-L1 IHC 28-8 pharmDx Guide, 13 pp. Dako North America Inc. (Oct. 2015 edition).
Pellegrino et al., "Controversies in oncology: are genomic tests quantifying homologous recombination repair deficiency (HRD) useful for treatment decision making?," ESMO Open 4(2) (2018).
PMA P170019: FDA Summary of Safety and Effectiveness of Data, FoundationOne CDx (Trademark), 58 pp. (Nov. 30, 2017).
Popovici et al., Image-based surrogate biomarkers for molecular subtypes of colorectal cancer, Bioinformatics, 33(13):2002-2009 (2017).
Press Release—Guardant Health Presents Data on Immunotherapy-related Biomarkers MSI and TMB in blood of advanced cancer patients at European Society of Medical Oncology Annual Meeting, 4 pages, (2018).
Quon et al., Computational purification of individual tumor gene expression profiles leads to significant improvements in prognostic prediction, Genome Med., 5(3):29 (2013).
Quon et al., ISOLATE: a computational strategy for identifying the primary origin of cancers using high-throughput sequencing, Bioinformatics, 25(21):2882-2889 (2009).
Rajpurkar et al., Deep learning for chest radiograph diagnosis: A retrospective comparison of the CheXNeXt algorithm to practicing radiologists, PLOS Medicine, (2018).
Ratcliffe et al., Agreement between programmed cell death ligand-1 diagnostic assays across multiple protein expression cutoffs in non-small cell lung cancer. Clin. Cancer Res., 23:3585-91 (2017).
Redox awarded patent for its electronic medical record integration technology, Aug. 29, 2018.
Rimm et al., A prospective, Multi-institutional, Pathologist-based assessment of 4 immunohistochemistry assays for PD-L1 expression in non-small cell lung cancer, JAMA. Oncol., 3:1051-8 (2017).
Rivenson et al., Deep learning-based virtual histology staining using auto-fluorescence of label-free tissue, Nat. Biomed. Eng., (2019).
Roach et al., Development of a companion diagnostic PD-L1 immunohistochemistry assay for pembrolizumab therapy in non-small-cell lung cancer, Appl. Immunohistochem. Mol. Morphol., 24:392-7 (2016).
Roche Molecular Systems, Inc., NAVIFY Tumor Board, available online at <https://www.navify.com/tumorboard/>, retrieved on (Sep. 2020).
Ronneberger et al., U-Net: Convolutional networks for biomedical image segmentation, arXiv: 1505.04597 [cs] (2015), https://arxiv.org/abs/1505.04597.
Russakovsky et al., ImageNet large scale visual recognition challenge [Internet], arXiv [cs.CV], (2014), Available from: http://arxiv.org/abs/1409.0575.
Saltz et al., Spatial organization and molecular correlation of tumor-infiltrating lymphocytes using deep learning on pathology images, Cell Reports, 23:181-193 (2018).
Schaumberg et al., H&E—stained whole slide image deep learning predicts spop mutation state in prostate cancer, bioRxiv, 1-14 (2016).
Schmidhuber, Deep learning in neural networks: an overview, Neural Netw. Elsevier, 61:85-117 (2015).
Shah et al., Deep learning assessment of tumor proliferation in breast cancer histological images, Int. Conf. Bioinform. Biomed., (2017).
Shah et al., Deep learning assessment of tumor proliferation in breast cancer histological images, Int. Cont. Bioinform. Biomed., (2017).
Shen-Orr et al., Cell type-specific gene expression differences in complex tissues, Nat. Methods, 7(4):287, pp. 5 (2010).
Simonyan et al., Very deep convolutional networks for large-scale image recognition, 10 (2014).
Springenberg et al., Striving for simplicity: The All Convolutional Net., ICLR (2014).
Stanford ML Group, CheXNeXt: Deep learning for chest radiograph diagnosis, downloaded from the Internet at: <https://stanfordmlgroup.github.io/projects/chexnext/> (Nov. 2018).
Sul et al., FDA approval summary: Pembrolizumab for the treatment of patients with metastatic non-small cell lung cancer whose tumors express programmed death-ligand 1, Oncologist., 21:643-50 (2016).
Sundar et al., Nivolumab in NSCLC: latest evidence and clinical potential, Ther. Adv. Med. Oncol., 7:85-96 (2015).
Szegedy et al., Going deeper with convolutions, IEEE, 9 (2015).
Teng et al., Classifying cancers based on T-cell infiltration and PD-L1, Cancer Res., 75:2139-45 (2015).
Thorsson et al., The immune landscape of cancer, Immunity, 48:812-830 (2018).
Thrane et al., Spatially resolved transcriptomics enables dissection of genetic heterogeneity in stage III cutaneous malignant melanoma, Cancer Res., 78(20):5970-5979, (2018).
Tizhoosh et al., Artificial intelligence and digital pathology: Challenges and opportunities, J. Pathol. Inform, 9:38 (2018).
Tsujikawa et al., Quantitative multiplex immunohistochemistry reveals myeloid-inflamed tumor-immune complexity associated with poor prognosis. Cell Reports, 19:203-217 (2017).
Tzeng et al,. Adversarial discriminative domain adaptation, Proceedings of the IEEE Conference on Computer Vision and Pattern Recognition, 7167-7176 (2017).
U.S. Food & Drug Administration (FDA), KEYTRUDA label [Internet], [cited Last accessed Feb. 12, 2019], Available from: https://www.accessdata.fda.gov/drugsatfda_docs/label/2017/125514s024lbl.pdf#page=46.
U.S. Food & Drug Administration (FDA), PD-L1 IHC 22C3 pharmDx. Summary of Safety and Effectiveness Data [Internet], [cited Last accessed Feb. 12, 2019], Available from: https://www.accessdata.fda.gov/cdrh_docs/pdf15/P150013S006b.pdf.
U.S. Food & Drug Administration, Letter of Review of FoundationOne CDx (Trademark), 5 pp. (Nov. 30, 2017).
Ulyanov et al., Instance normalization: the missing ingredient for fast stylization, arXiv:1607.08022, 1-6 (2017).

(56) References Cited

OTHER PUBLICATIONS

Umar et al., Revised bethesda guidelines for hereditary nonpolyposis colorectal cancer (lynch syndrome) and microsatellite instability, Journal of the National Cancer Institute, 96:261-268 (2004).
University Hospital of Liège and Osimis S.A., REST API of Orthanc, available online at <https://book.orthanc-server.com/users/rest.html#>, 17 (2015).
Uzzan et al., Microvessel density as a prognostic factor in women with breast cancer, Cancer Res., 64(9):2941-55 (2004).
Vasconcelos et al., Increasing deep learning melanoma classification by classical and expert knowledge based image transforms, CoRR, (2017).
Vassilakopoulou et al., Evaluation of PD-L1 expression and associated tumor-infiltrating lymphocytes in laryngeal squamous cell carcinoma, Clin. Cancer Res., 22:704-13 (2016).
Velcheti et al., Programmed death ligand-1 expression in non-small cell lung cancer, Lab. Invest., 94:107-16 (2014).
Vilar et al., Microsatellite instability in colorectal cancer-the stable evidence, Nat. Rev. Clin. Oncol., 7:153-162 (2010).
Wang et al., Comprehensive analysis of lung cancer pathology images to discover tumor shape and boundary features that predict survival outcome, Scientific Reports, 8:10393 (2018).
Wang et al., Deep learning assessment of tumor proliferation in breast cancer histological images, IEEE Int. Conf. Bioinfo. Biomed. (BIBM), 600-603 (2017).
Wang et al., Transcriptome deconvolution of heterogeneous tumor samples with immune infiltration, iScience, 9:451-460 (2018).
Way et al., Discovering pathway and cell-type signatures in transcriptomic compendia with machine learning, Peer J .Preprints., Sep. 20, 2018, 157-160.
Weinstein et al., The cancer genome atlas pan-cancer analysis project, Nat. Gene., 45:1113-1120 (2013).
Wimberly et al., PD-L1 expression correlates with tumor-infiltrating lymphocytes and response to neoadjuvant chemotherapy in breast cancer, Cancer Immunol. Res., 3(4):326-332 (2015).
Xu et al., A deep convolutional neural network for segmenting and classifying epithelial and stromal regions in histopathological images, Neurocomputing, 191:214-223 (2016).
Yala et al., A deep learning mammography-based model for improved breast cancer risk prediction, Radiology, 292(1):60-66 (2019).
Yang et al., A deep learning approach for tumor tissue image classification, BioMed., (2016).
Yi et al., Microvessel prediction in H&E stained pathology images using fully convolutional neural networks, BMC Bioinformatics, 19:64 (2018).
Yoshihara et al., Inferring tumour purity and stromal and immune cell admixture from expression data, Nat. Comm., 4:2612, pp. 11 (2013).
Young et al., Gene ontology analysis for RNA-seq: accounting for selection bias, Genome. Biol., 11:R14 (2010).
Yu et al., Predicting non-small cell lung cancer prognosis by fully automated microscopic pathology image features, Nat. Comm., 7:12474 (2016).
Yuan et al. Quantitative image analysis of cellular heterogeneity in breast tumors complements genomic profiling, Science Translational Medicine, 4(157):157ra143 (2012).
Yuan et al., Supplementary materials for quantitative image analysis of cellular heterogeneity in breast tumors complements genomic profiling, (2012), doi:10.1126/scitranslmed.3004330.
Zaslavsky et al., Infino: a bayesian hierarchical model improves estimates of immune infiltration into tumor microenvironment, 25 pp., posted Nov. 21, 2017 (downloaded from the Internet at: https://www.biorxiv.org/content/10.1101/221671v1).
Zhang et al., Adversarial deep learning for microsatellite instability prediction from histopathology, slides, First Conference on Medical Imaging with Deep Learning (MIDL, 2018), Amsterdam, The Netherlands.
Zhang et al., Aspect-augmented adversarial network for domain adaptation, Transactions of the Association for Computational Linguistics, 5:515-528 (2017).
Zhu et al., Deciphering genomic underpinnings of quantitative MRI-based radiomic phenotypes of invasive breast carcinoma, Sci. Rep., 5, Article No. 17787 (2015).
Erkkila et al., Probabilistic analysis of gene expression measurements from heterogeneous tissues, Bioinformatics, 26(10):2571-2577 (2010).
Ertosun et al., Automated grading of gliomas using deep learning in digital pathology images: A modular approach with ensemble of convolutional neural networks, AMIA. Annu. Symp. Proceedings AMIA. Symp., 1899-908 (2015).
Esteva et al., Dermatologist-level classification of skin cancer with deep neural networks, Nature, 542:115-118 (2017).
Evaluation of Automatic Class III Designation for MSK-Impact (Integrated Mutation Profiling of Actionable Cancer Targets), Decision Summary, 57 pp. (publicly available before May 14, 2018).
Fabrizio et al., Beyond microsatellite testing: assessment of tumor mutational burden identifies subsets of colorectal cancer who may respond to immune checkpoint inhibition, Journal of Gastrointestinal Oncology, 9(4):610-617 (2018).
FDA Summary of safety and effectiveness data (SSED), PD-L1 IHC 22C3 pharmDx, Dako North America, Inc., (Oct. 2, 2015).
FDA Summary of safety and effectiveness data (SSED), PD-L1 IHC 22C3 pharmDx, Dako North America, Inc., (Sep. 22, 2017).
Feldman et al., Tissue processing and hematoxylin and eosin staining, Methods Mol. Biol., 1180:31-43 (2014).
FoundationOne CDx (Trademark) Technical Information, Foundation Medicine, Inc., Cambridge, Massachusetts, 43 pp. (Nov. 2017).
FoundationOne Liquid, Genomic Testing 6 pages (2019).
Gan et al., Applicability of Next generation sequencing technology in microsatellite instabilty testing, Genes, 6:46-59 (2015).
Ganin et al., Domain-adversarial training of neural networks, The journal of machine learning research, 17:2096-2030 (2016).
Garg et al., Patterns of locoregional failure in stage III non-small cell lung cancer treated with definitive chemoradiation therapy, Pract. Radiat. Oncol., 4:342-8 (2014).
Gertych et al., Convolutional neural networks can accurately distinguish four histologic growth patterns of lung adenocarcinoma in digital slides, Sci. Rep., nature.com, 9:1483 (2019).
Github, "HistomicsTK", available online at <https://github.com/DigitalSlideArchive/HistomicsTK>, retrieved on Apr. 17, 2020, 3 pages.
Gong et al., DeconRNASeq: a statistical framework for deconvolution of heterogeneous tissue samples based on mRNA-Seq data, Bioinformatics, 29(8):1083-1085 (2013).
Grossman et al., Toward a shared vision for cancer genomic data, The New England Journal of Medicine, 375:1109-1112 (2016).
Grossmann et al., Defining the biological basis of radiomic phenotypes in lung cancer, Elife, 6:e23421 (2017).
Gutman et al., The digital slide archive: a software platform for management, integration, and analysis of histology for cancer research, Cancer Research, 77:e75-e78 (2017).
Hause et al., Classification and characterization of microsatellite instability across 18 cancer types, Nature Medicine, 22:1342-1350 (2016).
He et al., Deep residual learning for image recognition, Proceedings of the IEEE conference on computer vision and pattern recognition, 770-778 (2016).
Heindl et al., Microenvironmental niche divergence shapes BRCA1—dysregulated ovarian cancer morphological plasticity, Nat. Commun., (2018), doi:10.1038/s41467-018-06130-3.
Herbst et al., Pembrolizumab versus docetaxel for previously treated, PD-L1-positive, advanced non-small-cell lung cancer (KEYNOTE-010): a randomised controlled trial Lancet, 387:1540-50 (2016).
Herbst et al., Predictive correlates of response to the anti-PD-L1 antibody MPDL3280A in cancer patients, Nature, 515:563-7 (2014).
Ilse et al., Attention-based deep multiple instance learning, Proceedings of the 35th International Conference on Machine Learning, PMLR 80:2127-2136 (2018).
Ing et al., A novel machine learning approach reveals latent vascular phenotypes predictive of renal cancer outcome, Sci. Rep., 7:13190 (2017).
International Application No. PCT/US19/69161, International Search Report and Written Opinion, dated Apr. 14, 2020.

(56) References Cited

OTHER PUBLICATIONS

International Application No. PCT/US2019/032313, International Search Report and Written Opinion, dated Jul. 26, 2019.
International Application No. PCT/US2019/069164, International Search Report and Written Opinion, dated Apr. 9, 2020.
International Application No. PCT/US2020/024748, International Search Report and Written Opinion, dated Aug. 3, 2020.
International Application No. PCT/US2020/024748, Invitation to Pay Additional Fees, dated Jun. 10, 2020.
Ioffe et al., Batch normalization: Accelerating deep network training by reducing internal covariate shift [Internet], arXiv [cs.LG], (2015), Available from: http://arxiv.org/abs/1502.03167.
Janowczyk et al., Deep learning for digital pathology imageanalysis: A comprehensive tutorial with selected use cases, J. Pathol. Inform., 7:29 (2016).
Janzic et al., PD-L1 Expression in Squamous-cell Carcinoma and Adenocarcinoma of the lung, Radiol. Oncol., 51:357-62 (2017).
Kapil et al., Deep semi supervised generative learning for automated PD-L1 tumor cell scoring on NSCLC tissue needle biopsies, 1-10 (2018).
Kather et al., Deep learning can predict microsatellite instability directly from histology in gastrointestinal cancer, Nat. Med., 25:1054-1054 (2019).
Kather et al., Predicting survival from colorectal cancer histology slides using deep learning: A retrospective multicenter study, PLoS medicine 16:e1002730 (2019).
Kazandjian et al., FDA approval summary: Nivolumab for the treatment of metastatic non-small cell lung cancer with progression on or after platinum-based chemotherapy, Oncologist., 21:634-42 (2016).
Kerr et al., Programmed death ligand-1 immunohistochemistry: Friend or foe?, Arch. Pathol. Lab. Med., 140:326-31 (2016).
KEYTRUDA medication guide, p. 46, from prescribing information guide, Merck & Co. Inc., revised (Sep. 2017) (Reference ID: 4156447).
Kim et al., The landscape of microsatellite instability in colorectal and endometrial cancer genomes, Cell, 155(4):21 (2013).
Kitano et al., Tumour-infiltrating lymphocytes are correlated with higher expression levels of PD-1 and PD-L1 in early breast cancer, ESMO Open, 2:e000150 (2017).
Komura et al., Machine learning methods for histopathological image analysis, Comput. Struct. Biotechnol. J., 16:34-42 (2018).
Korfiatis et al., Residual deep convolutional neural network predicts MGMT methylation status, J. Digit. Imaging, 30(5):622-628 (2017).
Kristensen et al., Principles and methods of integrative genomic analyses in cancer, Nat. Rev., 14:299-313 (2014).
Krupinski et al., A new software platform to improve multidisciplinary tumor board workflows and user satisfaction: A pilot study, J. Pathol. Inform., 9:26 (2018).
Kurakin et al., Adversarial Examples in the Physical World, Technical report, (2016).
Lan et al., Quantitative histology analysis of the ovarian tumour microenvironment, Sci. Rep., 5:16317 (2015).
Lecun et al., Deep learning, Nature, 521:436-444 (2015).
Leek et al., Association of macrophage infiltration with angiogenesis and prognosis in invasive breast carcinoma, Cancer Res., 56:4625-9 (1996).
"John Hopkins University Study Finds Laboratory-Developed Liquid Biopsy Tets Can Give Different Results; Call for 'Improved Certification' of Medical Laboratories That Develop These LDTs", Dark Daily, 6 pages (2018).
"Technical Specifications," FoundationOne (Registered) Liquid, Foundation Medicine, Inc. (2018).
Abdel-Rahman, Correlation between PD-L1 expression and outcome of NSCLC patients treated with anti-PD-1/PD-L1 agents: A meta-analysis, Crit. Rev. Oncol. Hematol., 101:75-85 (2016).
Abels et al., Current state of the regulatory trajectory for whole slide imaging devices in the USA, Journal of Pathology Informatics, 1:23 (2017).

Aderi, Pathology services in developing countries—the West African experience, Arch. Pathol. Lab. Med., 135:183-6 (2011).
Aerts et al., Decoding tumour phenotype by noninvasive imaging using a quantitative radiomics approach, Nat. Commun., 5:4006 (2014).
Ahn et al., DeMix: deconvolution for mixed cancer transcriptomes using raw measured data, Bioinformatics, 29(15): 1865-1871 (2013).
Anders et al., Differential expression analysis for sequence count data, Genome Biology, 11:R106 (2010).
Ash et al., Joint analysis of gene expression levels and histological images identifies genes associated with tissue morphology, 1-28 (2018).
Ayers et al., IFN-g-related mRNA profile predicts clinical response to PD-1 blockade, The Journal of Clinical Investigation, 127(8):2930-2940 (2017).
Baas et al., Relationship between level of PD-L1 expression and outcomes in the KEYNOTE-010 study of pembrolizumab vs docetaxel for previously treated, PD-L1-Positive NSCLC., J. Clin. Orthod. American Society of Clinical Oncology, 34:9015-9015 (2016).
Bandi et al., From detection of individual metastases to classification of lymph node status at the patient level: the CAMELYON17 challenge, IEEE Transactions on Medical Imaging, 38:550-560 (2019).
Bankhead et al., QuPath: Open source software for digital pathology image analysis, Sci. Rep., 7:16878 (2017).
Beaubier et al., Clinical validation of the tempus xT next-generation targeted oncology sequencing assay, Oncotarget, 10:2384-2396 (2019).
Bejnordi et al., Diagnostic assessment of deep learning algorithms for detection of lymph node metastases in women with breast cancer, Jama, 318:2199-2210 (2017).
Bellevicine et al., How to prepare cytological samples for molecular testing, In: schmitt F. (eds) molecular applications in cytology, Springer, Cham., https://doi.org/10.1007/978-3-319-74942-6_2 (2018).
Bensch et al., 89Zr-atezolizumab imaging as a non-invasive approach to assess clinical response to PD-L1 blockade in cancer, Nat. Med., 24:1852-1858 (2018).
Bergado et al., Recurrent multiresolution convolutional networks for vhr image classification, (2018), <Downloaded from the Internet https://arxiv.org/pdf/1806.05793.pdf > <Downloaded on: Mar. 15, 2020> < DOI: 10.1109/TGRS.2018.2837357 > entire document, especially.
Borghaei et al., Nivolumab versus docetaxel in advanced nonsquamous non-small-cell lung cancer, N. Engl. J. Med., 373:1627-39 (2015).
Brahmer et al., Safety and activity of anti-PD-L1 antibody in patients with advanced cancer, N. Engl. J. Med., 366:2455-65 (2012).
Bray et al., Global cancer statistics 2018: GLOBOCAN estimates of incidence and mortality worldwide for 36 cancers in 185 countries, CA Cancer J. Clin., 68:394-424 (2018).
Brugnara et al., Management training for pathology residents: i. results of a national survey, American journal of clinical pathology, 101:559-563 (1994).
Bunescu et al., Multiple instance learning for sparse positive bags, Proceedings of the 24th Annual Intl. Conf, on Machine Learning (ICML-2007).
Buttner et al., Programmed death-ligand 1 immunohistochemistry testing: A review of analytical assays and clinical implementation in non-small-cell lung cancer, J. Clin. Oncol., 35:3867-76 (2017).
Bychkov et al., Deep learning for tissue microarray image-based outcome prediction in patients with colorectal cancer, Proc. of SPIE, 9791:979115 (2016).
Campanella et al., Clinical-grade computational pathology using weakly supervised deep learning on whole slide images, Nature Medicine, 25:1301-1309 (2019).
Caravagna et al., Algorithimic methods to infer the evolutionary trajectories in cancer progression, PNAS., 113(28):E4025-E4034 (2016).
Cardiff et al., Manual hematoxylin and eosin staining of mouse tissue sections, Cold Spring Harb Protoc., 655-8 (2014).
Carter et al,. Absolute quantification of somatic DNA alterations in human cancer, Nat. Biotechnol., 30:413-421 (2012).

(56) References Cited

OTHER PUBLICATIONS

Chang et al., Deep-learning convolutional neural networks accurately classify genetic mutations in gliomas, Am. J. Neuroradiology, (2018).
Chang et al., Residual convolution neural network for determination of IDH status in low- and high-grade gliomas from MR imaging, Clin. Cancer Res., 24(5):1073-1081 (2018).
Chang, Chemotherapy, chemoresistance and the changing treatment landscape for NSCLC, Lung Cancer, 71:3-10 (2011).
Chen et al., Microscope 2.0: An augmented reality microscope with real-time artificial integration, Nat. Med., 25:1453-1457 (2019).
Chen et al., Pathomic fusion: An integrated framework for fusing histopathology and genomic features for cancer diagnosis and prognosis, downloaded from the Internet at: <https://arxiv.org/pdf/1912.08937v1.pdf> (Dec. 18, 2019).
Clark et al., Analytical validation of a hybrid capture—based next-generation sequencing clinical assay for genomic profiling of cell-free circulating tumorDNA, The Journal of Molecular Diagnostics, 20(5):686-702 (2018).
Clarke et al., Statistical expression deconvolution from mixed tissue samples, Bioinformatics, 26(8):1043-1049 (2010).
Clunie, HIMA_2017_DICOMWSI_Clunie [PowerPoint slides]. Retrieved from https://www.dclunie.com/papers/HIMA_2017_DICOMWSI_Clunie.pdf, (2017).
Cobos et al., Computational deconvolution of transcriptomics data from mixed cell populations, Bioinformatics, 1-11 (2018).
Cooper et al., PanCancer insights from the cancer genome atlas: the pathologist's perspective, J. Pathol., 244:512-524 (2018).
Cortes-Ciriano et al., A molecular portrait of microsatellite instability across multiple cancers, Nat. Commun., 8:12 (2017).
Coudray et al., Classification and mutation prediction from non-small cell lung cancer histopathology images using deep learning, bioRxiv, 23 (2017).
Couture et al., Image analysis with deep learning to predict breast cancer grade, ER status, histologic subtype, and intrinsic subtype, NPJ. Breast Cancer, 4:30 (2018).
Cruz-Roa et al., Accurate and reproducible invasive breast cancer detection in whole-slide images: A Deep Learning approach for quantifying tumor extent, Scientific Reports, 7:46450, 14 (2017).
Cruz-Roa et al., High-throughput adaptive sampling for whole-slide histopathology image analysis (HASHI) via convolutional neural networks: Application to invasive breast cancer detection, PLoS One, 13(5):e0196828 (2018).
D'Incecco et al., PD-1 and PD-L1 expression in molecularly selected non-small-cell lung cancer patients, Br. J. Cancer, 112:95-102 (2015).
Daume et al., Domain adaptation for statistical classifiers, Journal of Artificial Intelligence Research, 26:101-126 (2006).
Denkert et al., Standardized evaluation of tumor-infiltrating lymphocytes in breast cancer: results of the ring studies of the international immuno—oncology biomarker working group, Mod. Pathol., 29:1155-64 (2016).
Department of health and human services. Part I. overview information, Integration of imaging and fluid-based tumor monitoring in cancer therapy (R01 Clinical Trial Optional), (Feb. 5, 2018).
Dey et al., Visualizing the structure of RNA-seq expression data using grade of membership models, PLoS Genetics, 13(5) (2017).
Dienstmann et al., Consensus molecular subtypes and the evolution of precision medicine in colorectal cancer, Nat. Rev. Cancer, 17:14 (2017).
Korbar et al., Looking under the hood: Deep neural network visualization to interpret whole-slide image analysis outcomes for colorectal polyps, 2017 IEEE Conference on Computer Vision and Pattern Recognition Workshops, 821-7 (Jul. 21, 2017).

* cited by examiner

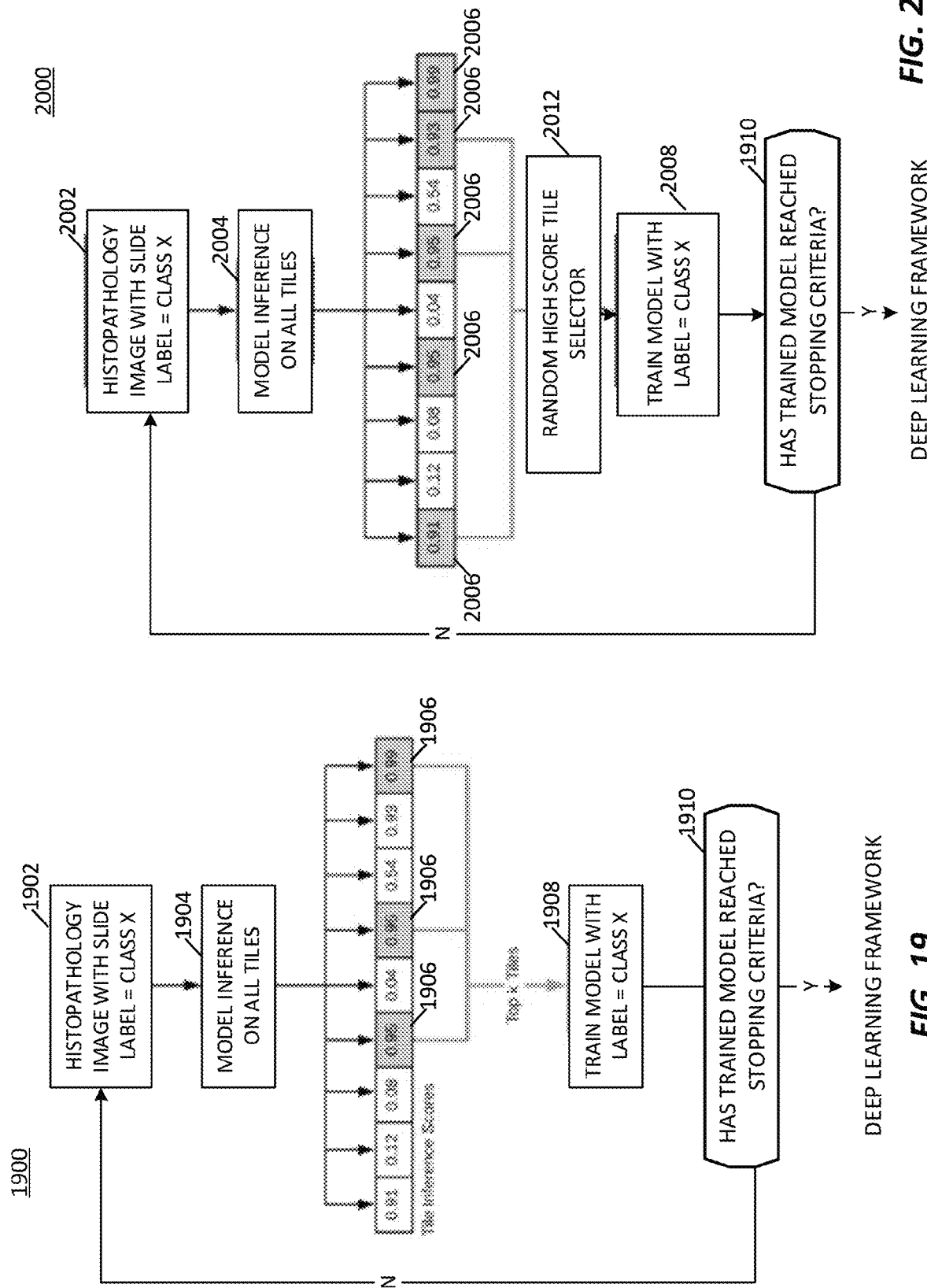

PREDICTING TOTAL NUCLEIC ACID YIELD AND DISSECTION BOUNDARIES FOR HISTOLOGY SLIDES

CROSS-REFERENCE TO RELATED APPLICATIONS

This application is a Continuation-in-Part of U.S. application Ser. No. 16/830,186, filed on Mar. 25, 2020, which is a Continuation-in-Part of U.S. application Ser. No. 16/732,242, filed on Dec. 31, 2019, which claims priority to U.S. Provisional Application Ser. No. 62/787,047, filed Dec. 31, 2018, and is a Continuation-in-Part of U.S. application Ser. No. 16/412,362, filed on May 14, 2019, which claims priority to U.S. Provisional Application No. 62/671,300 filed May 14, 2018, and claims priority to U.S. Provisional Application Ser. No. 62/824,039, filed on Mar. 26, 2019, U.S. Provisional Application Ser. No. 62/889,521, filed Aug. 20, 2019 and to U.S. Provisional Application Ser. No. 62/983,524, filed on Feb. 28, 2020, the entire disclosures of each of which are hereby expressly incorporated by reference herein.

FIELD OF THE INVENTION

The present disclosure relates to qualifying a specimen prepared on one or more hematoxylin and eosin (H&E) slides and, more particularly, qualifying a specimen by assessing an expected yield of nucleic acids for tumor cells and providing associated unstained slides for subsequent nucleic acid analysis is provided.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

To guide a medical professional in diagnosis, prognosis and treatment assessment of a patient's cancer, it is common to extract and inspect tumor samples from the patient. Visual inspection can reveal growth patterns of the cancer cells in the tumor in relation to the healthy cells near them and the presence of immune cells within the tumor. Conventionally, pathologists, members of a pathology team, other trained medical professionals, or other human analysts visually analyze thin slices of tumor tissue mounted on glass microscope slides and identify each region of the tissue as corresponding to one of many tissue types that are present in a tumor sample. This information aids the pathologist in determining characteristics of the cancer tumor in the patient, which can inform treatment decisions. A pathologist will often assign one or more numerical scores to a slide, based on this visual approximation.

To perform these visual approximations, medical professionals attempt to identify a number of characteristics of a tumor, including, for example, tumor grade, tumor purity, degree of invasiveness of the tumor, degree of immune infiltration into the tumor, cancer stage, and anatomic origin site of the tumor, which can be important for diagnosing and treating a metastatic tumor. These details about a cancer can help a physician monitor the progression of cancer within a patient and can help hypothesize which anti-cancer treatments are likely to be successful in eliminating cancer cells from the patient's body.

Another tumor characteristic is the presence of specific biomarkers or other cell types in or near the tumor, including immune cells. For example, tumor-infiltrating lymphocytes (TILs) present in elevated levels have been recognized as a biomarker of anti-tumor immune response across a wide range of tumors. TILS are mononuclear immune cells that infiltrate tumor tissue or stroma and have been described in several tumor types, including breast cancer. A population of TILs is composed of different types of cells (i.e., T cells, B cells, Natural Killer (NK) cells, etc.) in variable proportions. The population of TILs naturally occurring in a cancer patient is largely ineffective in destroying a tumor, but the presence of TILs has been associated with improved prognosis in many cancer types, including, e.g., epithelial ovarian carcinoma, colon cancer, esophageal cancer, melanoma, endometrial cancer, and breast cancer (see, e.g., Melichar et al., Anticancer Res. 2014; 34(3):1115-25; Naito et al., Cancer Res. 1998; 58(16):3491-4).

Yet another tumor characteristic is the presence of specific molecules as a biomarker, including the molecule known as programmed death ligand 1 (PD-L1). PD-L1 has been linked with diagnosing and assessing non-small cell lung cancer (NSCLC), which is the most common type of lung cancer, affecting over 1.5 million people worldwide. NSCLC often responds poorly to standard of care chemoradiotherapy and has a high incidence of recurrence, resulting in low 5-year survival rates. Advances in immunology show that NSCLC frequently elevates the expression of PD-L1 to bind to programmed death-1 (PD-1) expressed on the surface of T-cells. PD-1 and PD-L1 binding deactivates T-cell antitumor responses, enabling NSCLC to evade targeting by the immune system. The discovery of the interplay between tumor progression and immune response has led to the development and regulatory approval of PD-1/PD-L1 checkpoint blockade immunotherapies like nivolumab and pembrolizumab. Anti-PD-1 and anti-PD-L1 antibodies restore antitumor immune response by disrupting the interaction between PD-1 and PD-L1. Notably, PD-L1-positive NSCLC patients treated with these checkpoint inhibitors achieve durable tumor regression and improved survival.

As the role of immunotherapy in oncology expands, accurate assessment of tumor PD-L1 status may be useful in identifying patients who may benefit from PD-1/PD-L1 checkpoint blockade immunotherapy. Currently, immunohistochemistry (IHC) staining of tumor tissues acquired from biopsy or surgical specimens is employed to assess PD-L1 status. However, such IHC staining is often limited by insufficient tissue samples and, in some settings, a lack of resources.

Hematoxylin and eosin (H&E) staining is a longstanding method used by pathologists to analyze tissue morphological features for malignancy diagnosis. H&E slides, for example, can illustrate visual characteristics of tissue structures such as cell nuclei and cytoplasm, to inform identification of cancer tumors.

Similar considerations for sufficiency in tissue samples exist for H&E slides, as well as IHC slides. In some instances, complications from insufficient tissue samples are exacerbated during subsequent sequencing of the available tissue samples when the total nucleic yield of the tumor tissue within a sample is insufficient to generate reliable sequencing results. While reliable analysis requires a sufficient quantity of nucleic yield from the tissue sample, all tissue samples provided to analysis, such as staining or sequencing, which are of insufficient quantity are lost due to the destructive natures of extracting nucleic acid from the tissue samples and therefore an entire new batch is required for processing to generate reliable results. These additional batches of tissue samples, lost due to reprocessing additional samples for staining or sequencing, further reduces the available tissue samples, and a patient may have to undergo another painful and costly biopsy or surgical procedure to acquire sufficient tissue samples. There is a need for identifying the sufficiency of the nucleic acid yield within tumor tissue to prevent processing and waste of attempting analysis of tissue with insufficient total nucleic yield.

Technological advances have enabled the digitization of histopathology H&E and IHC slides into high resolution whole slide images (WSIs), providing opportunities to develop computer vision tools for a wide range of clinical applications. High-resolution, digital images of microscope slides make it possible to use computer based analysis of slides in the hopes of classifying tissue by type or pathology. Generally speaking, for example, deep learning applications have shown promise as a tool in medical diagnostic applications and in predicting treatment outcomes. Deep learning is a subset of machine learning wherein models may be built with a number of discrete neural node layers. A Convolutional Neural Network ("CNN") is a neural network that employs convolution techniques. For example, a CNN may provide for a deep learning process that analyzes digital images by assigning one class label to each input image. WSIs, however, include more than one type of tissue, including the borders between neighboring tissue classes. There is a need to classify different regions as different tissue classes, in part to analyze the borders between neighboring tissue classes and the presence of immune cells among tumor cells. For a traditional CNN to assign multiple tissue classes to one slide image, the CNN would need to separately process each section of the image that needs a tissue class label assignment. However, neighboring sections of the image overlap, such that processing each section separately would create a high number of redundant calculations and would be time consuming.

A Fully Convolutional Network (FCN) is another type of deep learning process. A FCN can analyze an image and assign classification labels to each pixel within the image. As a result, compared to a CNN, a FCN can be more useful for analyzing images that depict objects with more than one classification. Some FCNs generate an overlay map to show the location of each classified object in the original image. However, to be effective, FCN deep learning algorithms would require training data sets of images with each pixel labeled as a tissue class, and that requires too much annotation time and processing time to be practical. In a digital WSI image, each edge of the image may contain more than 10,000-100,000 pixels. The full image may have at least $10,000^2$ to $100,000^2$ pixels, which would force incredibly long algorithm run times to attempt tissue classification. Simply put, the high number of pixels makes it infeasible to use traditional FCNs to segment digital images of slides.

There is a need for new easily accessible techniques of diagnostic testing for biomarkers, such as TILs, PD-L1, and others using H&E images, for identifying and characterizing such biomarkers in an efficient manner, across population groups, for producing better optimized drug treatment recommendations and protocols, and improved forecasting of disease progression.

SUMMARY OF THE INVENTION

The present application presents an image-based nucleic acid yield prediction system formed of a deep learning framework configured and trained to directly learn from histopathology slide images and predict the yield of nucleic acid from the present tumor cells in medical images. In examples, deep learning frameworks are configured and trained to analyze histopathology images and identify tumor cells and predict an expected yield of nucleic acid for the tumor cells. In various examples, these deep learning frameworks are configured to include different trained tissue and/or cell classifiers each configured to receive unlabeled histopathology images and provide yield of nucleic acid from the present tumor cells predictions for those images. These yield of nucleic acid predictions may then be used to reduce a large set of available immunotherapies to a reduced, small subset of targeted immunotherapies that medical professionals may use to treat patients. In various examples, deep learning frameworks are provided that identify biomarkers indicating the presence of a tumor, a tumor state/condition, or information about a tumor of the tissue sample, from which a set of target immunotherapies can be determined.

Cells contain nucleic acids (nucleotides) and analysis processes such as sequencing often destroy cells during extraction of nucleic acids from the cells. As such, the yield of nucleic acids is a quantitative measurement of the nucleic acids which may be extracted from the cells. When this quantity falls below the operating capacity of a sequencing machine to effectively analyze and generate reliable sequencing results for the deoxyribonucleic acid (DNA) or ribonucleic acid (RNA) of the tissue, the extracted nucleic acids are lost and cannot be reused in subsequent attempts. Furthermore, the specific sequencing machine and/or the type of sequencing results to be generated may change the total yield of nucleic acids that are needed to generate reliable results. Therefore, the total nucleic acid yield may be identified based on a combination of the sequencing machine and/or the type of sequencing to be performed and may be selected from, for example, 50-2000 ng. As sequencing machines become more efficient, the lower boundary of the range may be correspondingly decreased to the specification requirements of the sequencing machine and as the type of sequencing analysis to be performed changes, the upper bound may be correspondingly increased to the requirements necessary for generating reliable results of the newer analysis. In some instances, there may be additional tissue on the slide which is not tumor tissue which may affect the quality of the analysis. In these instances, a dissection boundary may be drawn around the tumor tissue of the slide to provide a guide for extracting only the cells which should be sequenced to ensure the highest quality of analysis. This boundary reduces the total nucleic yield because there are fewer cells provided for nucleic acid extraction. Estimates for the number of slides to be scraped may be generated to prevent waste and ensure that the first attempt at analysis is successful. The dissection boundary may be a microdissection boundary, a macrodissection boundary, or a whole slide boundary. The expected yield of nucleic acid for the tumor cells within the dissection boundary may be predicted in various ways, including providing digital images of an H&E slide to a model trained on a H&E slides having labeled dissection boundaries and labeled total nucleic yield, counting the number of tumor cells identified within the dissection boundary and multiplying the count by a tumor cell average nucleic acid yield, calculating the surface area of the dissection boundary and multiplying the surface area by a dissection boundary average nucleic acid yield.

In examples, systems include deep learning frameworks trained to analyze for and predict tumor status for histopathology images received from network-accessible image sources, such as medical labs or medical imaging machines. As used herein, tumor status includes at least the nucleic acid yield from the tissue to be scrapped and analyzed. In examples, the techniques and systems herein may further generate reports of predicted tumor status, e.g., yield of nucleic acid for tumor cells, which can then be stored, displayed, used for further operations, etc. These predicted yield of nucleic acid from the present tumor cells reports may be provided to network-accessible systems, such as pathology labs and primary care physician systems, for storage and display, and in use in determining a cancer treatment protocol (i.e., immunotherapy treatment or chemotherapy treatment) for the patient. In some examples, the predicted yield of nucleic acid from the present tumor cells determined at a pathology lab or primary care physician system or other entity. In some examples, the predicted yield of nucleic acid from the present tumor cells reports may be input to network-accessible next generation sequencing systems for driving subsequent genomic sequencing, or input to computerized cancer therapy decision systems for filtering therapy listings down to tumor-determined matched therapies.

The techniques herein are capable of identifying tumor cells associated with any of a variety of cancers. Exemplary cancers include but are not limited to, adrenocortical carcinoma, lymphoma, anal cancer, anorectal cancer, basal cell carcinoma, skin cancer (non-melanoma), biliary cancer, extrahepatic bile duct cancer, intrahepatic bile duct cancer, bladder cancer, urinary bladder cancer, osteosarcoma, brain tumor, brain stem glioma, breast cancer (including triple negative breast cancer), cervical cancer, colon cancer, colorectal cancer, lymphoma, endometrial cancer, esophageal cancer, gastric (stomach) cancer, head and neck cancer, hepatocellular (liver) cancer, kidney cancer, renal cancer, lung cancer, melanoma, cancer of the tongue, oral cancer, ovarian cancer, pancreatic cancer, prostate cancer, uterine cancer, testicular cancer, and vaginal cancer.

In some examples, the image-based nucleic acid yield prediction systems are formed of deep learning frameworks having a multiscale configuration designed to perform classification on (labeled or unlabeled) histopathology images using classifiers trained to classify tiles of received histopathology images. In some examples, the multiscale configurations contain tile-level tissue classifiers, i.e., classifiers trained using tile-based deep learning training. In some examples, the multiscale configurations contain pixel-level cell classifiers and cell segmentation models. In some examples, the classifications form the tile-level tissue classifiers and from the pixel-level cell classifiers are analyzed to predict biomarker status in the histopathology image. In yet some examples, the multiscale configurations contain tile-level biomarker classifiers.

In some examples, the image-based nucleic acid yield prediction systems are formed of deep learning frameworks having a single-scale configuration designed to perform classifications on (labeled or unlabeled) histopathology images using classifiers trained using multiple instance learning (MIL) techniques. In some examples, the single-scale configurations contain slide-level classifiers trained using gene sequencing data, such as RNA sequencing data. That is, slide-level classifiers are trained using RNA sequence data to develop image-based classifiers capable of predicting biomarker status in histopathology images.

In accordance with an example, a computer-implemented method for qualifying a specimen prepared on one or more hematoxylin and eosin (H&E) slides and for providing associated unstained slides for nucleic acid analysis, the method includes: generating a digital image of each of the one or more H&E slides prepared from the specimen at an image-based nucleic acid yield prediction system having one or more processors; and for each digital image: identifying, using the one or more processors, tumor cells of the H&E slide from the digital image; generating a tumor area mask based at least in part on the identified tumor cells, wherein the tumor area mask defines a dissection boundary of the H&E slide associated with the digital image; predicting an expected yield of nucleic acid for the tumor cells within the dissection boundary; and providing one or more of the associated unstained slides for nucleic acid analysis when the summation of expected yield of nucleic acid predicted for each digital image exceeds a predetermined threshold.

In an example, only associated unstained slides with the H&E slides having predicted expected yield of nucleic acid exceeding a slide yield threshold are included in the summation.

In an example, providing the associated unstained slides for nucleic acid analysis includes sending the associated unstained slides to a third party for sequencing.

In an example, providing the associated unstained slides for nucleic acid analysis includes sequencing the nucleic acids extracted from within the dissection boundary identified from the H&E slides.

In an example, the predetermined threshold is based at least in part on one or more specification requirements.

In an example, specification requirements are based on a minimum surface area within the dissection boundary. In an example, specification requirements are based on a minimum cell count within the dissection boundary. In an example, specification requirements are based on a minimum cell density within the dissection boundary. In an example, specification requirements are set by an entity.

In an example, the predetermined threshold is within a range between and including 50 ng-2000 ng.

In an example, predicting the expected yield of nucleic acid for the tumor cells within the dissection boundary further includes: providing the digital image of the H&E slide to a model trained on a plurality of H&E slides having labeled dissection boundaries and labeled total nucleic yield.

In an example, predicting the expected yield of nucleic acid for the tumor cells within the dissection boundary further includes: counting the number of tumor cells identified within the dissection boundary and multiplying the count by a tumor cell average nucleic acid yield.

In an example, predicting the expected yield of nucleic acid for the tumor cells within the dissection boundary further includes: calculating the surface area of the dissection boundary and multiplying the surface area by a dissection boundary average nucleic acid yield.

In an example, the dissection boundary is a microdissection boundary.

In an example, the dissection boundary is a macrodissection boundary.

In an example, the dissection boundary is a whole slide boundary.

In an example, identifying the tumor cells of the H&E slide from the digital image includes identifying the tumor cells using a trained cell segmentation model.

In an example, identifying the tumor using the trained cell segmentation model includes: applying, using the one or more processors, a plurality of tile images formed from the digital image to the trained cell segmentation model and, for each tile, assigning a cell classification to one or more pixels within the tile image.

In an example, assigning the cell classification to one or more pixels within the tile image includes: identifying, using the one or more processors, the one or more pixels as a cell interior, a cell border, or a cell exterior and classifying the one or more pixels as the cell interior, the cell border, or the cell exterior.

In an example, the trained cell segmentation model is a pixel-resolution three-dimensional UNet classification model trained to classify a cell interior, a cell border, and a cell exterior.

In an example, identifying the tumor cells using the trained cell segmentation model includes: applying, using the one or more processors, each of a plurality of tile images formed from the digital image to the trained cell segmentation model; and performing, using the one or more processors, a registration on segmented cells in each of the tile images by determining a cell border of each cell, determining a centroid of each cell, and shifting coordinates of centroids to a universal coordinate space for the digital image.

In an example, the trained cell segmentation model is trained using a set of H&E slide training images annotated with identified cell borders, identified cell interiors, and identified cell exteriors.

In an example, the method further includes superimposing, using a viewer, the tumor area mask over the digital image to visually indicate to a user which tumor cells to scrape.

In an example, generating the tumor area mask further includes providing the digital image of the H&E slide to a model trained on a plurality of H&E slides having dissection labels.

In an example, a system includes a pathology slide scanner system configured to perform the methods herein.

In an example, the pathology slide scanner system is communicatively coupled to an image-based tumor cells prediction system through a communication network for providing the one or more of the associated unstained slides for nucleic acid analysis when the summation of expected yield of nucleic acid predicted for each digital image exceeds the predetermined threshold.

In an example, the one or more processors are one or more graphics processing units (GPUs), tensor processing units (TPUs), and/or central processing units (CPUs).

In an example, the expected yield of nucleic acid is confirmed through sequencing the tumor cells within the dissection boundary.

In an example, sequencing is next-generation sequencing.

In an example, sequencing is short-read sequencing.

BRIEF DESCRIPTION OF THE DRAWINGS

This patent or application file contains at least one drawing executed in color. Copies of this patent or patent application publication with color drawing(s) will be provided by the United States Patent and Trademark Office upon request and payment of the necessary fee.

The figures described below depict various aspects of the system and methods disclosed herein. It should be understood that each figure depicts an example of aspects of the present systems and methods.

FIGS. 16A-16C illustrate a representative PD-L1 positive biomarker classification example. FIG. 16A displays an input H&E image; FIG. 16B displays a probability map overlaid on the H&E image: FIG. 16C displays a PD-L1 IHC stain for reference. FIGS. 16D-16F illustrate a representative PD-L1 negative biomarker classification example. FIG. 16D displays an input H&E image; FIG. 16E displays a probability map overlaid on the H&E image; and FIG. 16F displays a PD-L1 IHC stain for reference. The color bar indicates the predicted probability of the tumor PD-L1+ class.

FIGS. 19, 20, 21, and 22 are block diagrams of a framework operation that may be implemented by the multiple instance learning controller in FIG. 18, in accordance with an example.

DETAILED DESCRIPTION

Figure 1:
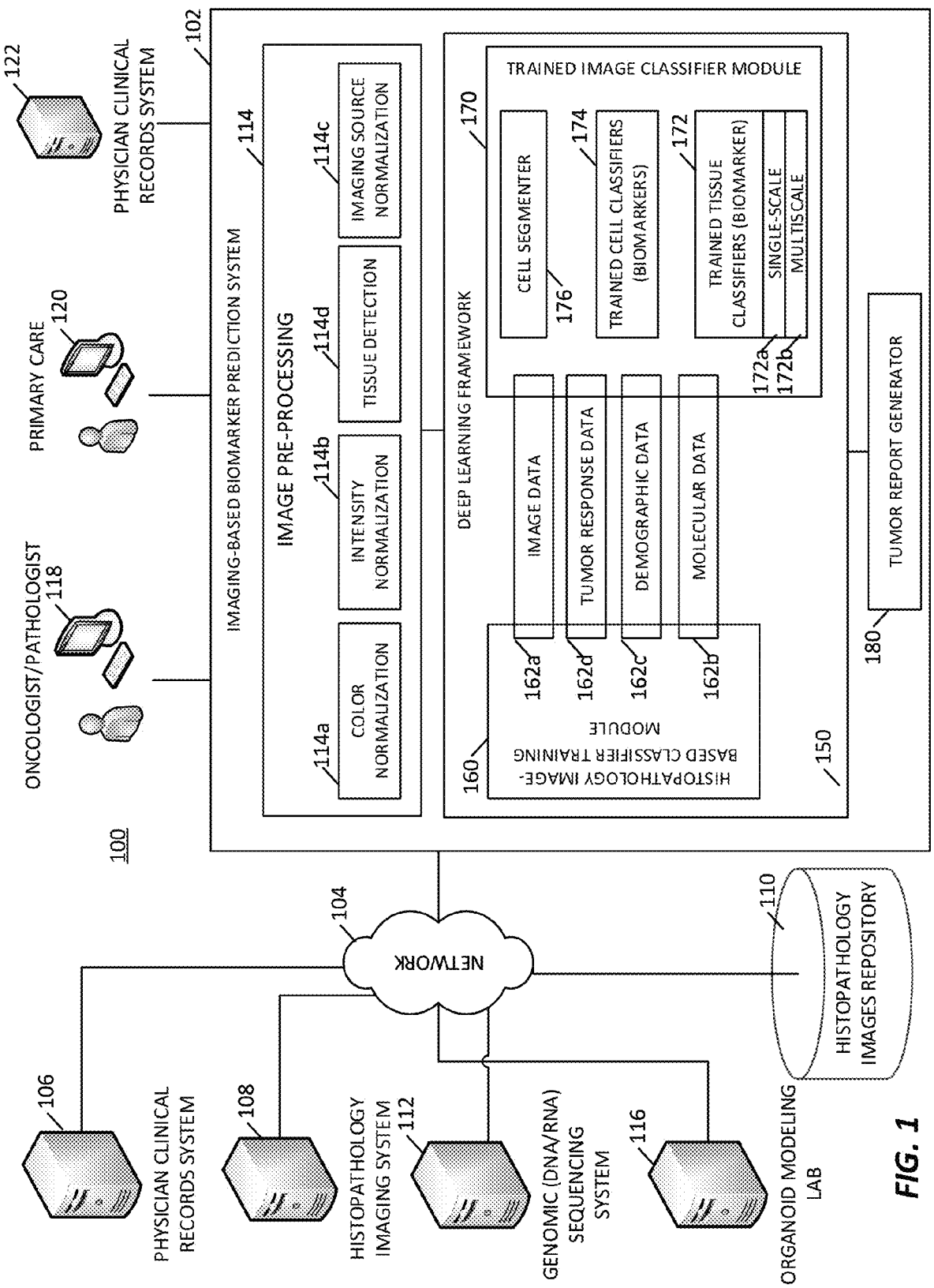
FIG. 1 is a block diagram of a schematic of a prediction system having an imaging-based biomarker prediction system, for example, as may be implemented as an image-based nucleic acid yield prediction system, in accordance with an example.

An imaging-based biomarker prediction system is formed of a deep learning framework configured and trained to directly learn from histopathology slides and predict the presence of biomarkers in medical images. The deep learning frameworks may be configured and trained to analyze medical images and identify biomarkers that indicate the presence of a tumor, a tumor state/condition, or information about a tumor of the tissue sample.

In an implementation, a cloud-based deep learning framework is used for medical image analysis. Deep learning algorithms automatically learn sophisticated imaging features for enhanced diagnosis, prognosis, treatment indication, and treatment response prediction. In examples, the deep learning frameworks are able to directly connect to cloud storage and leverage resources on cloud platforms for efficient deep learning algorithm training, comparison, and deployment.

In some examples, the deep learning frameworks include a multiscale configuration that uses a tiling strategy to accurately capture structural and local histology of various diseases (e.g., cancer tumor prediction). These multiscale configurations perform classification on (labeled or unlabeled) histopathology images using classifiers trained to classify tiles of received histopathology images. In some examples, the multiscale configurations contain tile-level tissue classifiers, i.e., classifiers trained using tile-based deep learning training. In some examples, the multiscale configurations contain pixel-level cell classifiers and cell segmentation models. In some examples, the classifications form the tile-level tissue classifiers and from the pixel-level cell classifiers are analyzed to predict biomarker status in the histopathology image. In yet some examples, the multiscale configurations contain tile-level biomarker classifiers. Once trailed, the multiscale classifiers can receive a new labeled or unlabeled histopathology image and predict the presence of certain biomarkers in the associated histopathological slide.

In some examples, the deep learning frameworks herein include a single-scale configuration trained using a multiple instance learning (MIL) strategy to predict biomarkers presence in histopathology images. A classifier trained using a single-scale configuration may be trained to perform classifications on (labeled or unlabeled) histopathology images using classifiers trained using one or more multiple instance learning (MIL) techniques. In some examples, the single-scale configurations contain slide-level classifiers trained using gene sequencing data, such as RNA sequencing data, and trained to analyze histopathology images having slide-level labels, not tile-level labels. That is, slide-level classifiers are trained using RNA sequence data to develop image-based classifiers capable of predicting biomarker status in histopathology images.

Any of the multiscale and single-scale configurations herein may incorporate various algorithmic optimizations to accelerate computation for such disease analysis.

In an implementation of a multiscale classifier configuration, a deep learning framework may be trained to include classifiers that perform automatic cell segmentation, determine cell/biomarker type, and determine tissue type classification from histopathology images thereby providing image-based biomarker development. Even single-scale classifiers may be trained to include tissue type classification and biomarker classification.

For multiscale classifier configurations, for example, aggregate and spatial imaging features concerning different cell types (e.g. tumor, stroma, lymphocyte) in digital hematoxylin & eosin (H&E) slides may be determined by a deep learning framework and used to predict clinical and therapeutic outcomes. In place of rudimentary manual cell type classification, examples herein employ multiscale configurations in deep learning frameworks to classify each sub-region of an H&E slide histopathology image into a specific cell segmentation, cell type, and tissue type. From there, biomarker detection is performed by another deep learning framework configured to identify various types of imaging metrics. Example imaging metrics include tumor shape, including tumor minimum shape and max shape, tumor area, tumor perimeter, tumor %, cell shape, including cell area, cell perimeter, cell convex area ratio, cell circularity, cell convex perimeter area, cell length, lymphocyte %, cellular characteristics, cell textures, including saturation, intensity, and hue.

Examples of tissue classes include but are not limited to tumor, stroma, normal, lymphocyte, fat, muscle, blood vessel, immune cluster, necrosis, hyperplasia/dysplasia, red blood cells, and tissue classes or cell types that are positive (contain a target molecule of an IHC stain, especially in a quantity larger than a certain threshold) or negative for an IHC stain target molecule (do not contain that molecule or contain a quantity of that molecule lower than a certain threshold).

In some examples, biomarker detection may be enhanced by combining imaging metrics with structured clinical and sequencing data to develop enhanced biomarkers.

Biomarkers may be identified through any of the following models. Any models referenced herein may be implemented as artificial intelligence engines and may include gradient boosting models, random forest models, neural networks (NN), regression models, Naive Bayes models, or machine learning algorithms (MLA). A MLA or a NN may be trained from a training data set. In an exemplary prediction profile, a training data set may include imaging, pathology, clinical, and/or molecular reports and details of a patient, such as those curated from an EHR or genetic sequencing reports. MLAs include supervised algorithms (such as algorithms where the features/classifications in the data set are annotated) using linear regression, logistic regression, decision trees, classification and regression trees, Naive Bayes, nearest neighbor clustering; unsupervised algorithms (such as algorithms where no features/classification in the data set are annotated) using Apriori, means clustering, principal component analysis, random forest, adaptive boosting; and semi-supervised algorithms (such as algorithms where an incomplete number of features/classifications in the data set are annotated) using generative approach (such as a mixture of Gaussian distributions, mixture of multinomial distributions, hidden Markov models), low density separation, graph-based approaches (such as mincut, harmonic function, manifold regularization), heuristic approaches, or support vector machines. NNs include conditional random fields, convolutional neural networks, attention based neural networks, deep learning, long short term memory networks, or other neural models where the training data set includes a plurality of tumor samples, RNA expression data for each sample, and pathology reports covering imaging data for each sample. While MLA and neural networks identify distinct approaches to machine learning, the terms may be used interchangeably herein. Thus, a mention of MLA may include a corresponding NN or a mention of NN may include a corresponding MLA unless explicitly stated otherwise. Training may include providing optimized datasets, labeling these traits as they occur in patient records, and training the MLA to predict or classify based on new inputs. Artificial NNs are efficient computing models which have shown their strengths in solving hard problems in artificial intelligence. They have also been shown to be universal approximators (can represent a wide variety of functions when given appropriate parameters). Some MLA may identify features of importance and identify a coefficient, or weight, to them. The coefficient may be multiplied with the occurrence frequency of the feature to generate a score, and once the scores of one or more features exceed a threshold, certain classifications may be predicted by the MLA. A coefficient schema may be combined with a rule-based schema to generate more complicated predictions, such as predictions based upon multiple features. For example, ten key features may be identified across different classifications. A list of coefficients may exist for the key features, and a rule set may exist for the classification. A rule set may be based upon the number of occurrences of the feature, the scaled weights of the features, or other qualitative and quantitative assessments of features encoded in logic known to those of ordinary skill in the art. In other MLA, features may be organized in a binary tree structure. For example, key features which distinguish between the most classifications may exist as the root of the binary tree and each subsequent branch in the tree until a classification may be awarded based upon reaching a terminal node of the tree. For example, a binary tree may have a root node which tests for a first feature. The occurrence or non-occurrence of this feature must exist (the binary decision), and the logic may traverse the branch which is true for the item being classified. Additional rules may be based upon thresholds, ranges, or other qualitative and quantitative tests. While supervised methods are useful when the training dataset has many known values or annotations, the nature of EMR/EHR documents is that there may not be many annotations provided. When exploring large amounts of unlabeled data, unsupervised methods are useful for binning/bucketing instances in the data set. A single instance of the above models, or two or more such instances in combination, may constitute a model for the purposes of models, artificial intelligence, neural networks, or machine learning algorithms, herein.

In some examples, the present techniques provide for machine learning assisted histopathology image review that includes automatically identifying and contouring a tumor region, and/or characteristics of regions or cell types within a region (for example, lymphocytes, PD-L1 positive cells, tumors having a high degree of tumor budding, etc.), counting cells within that tumor region, and generating a decision score to improve the efficiency and the objectivity of pathology slide review.

As used herein, the term "biomarkers" refers to image-derived information relating to the screening, diagnosis, prognosis, treatment, selection, disease monitoring, progression, and disease reoccurrence of cancer or other diseases, and in particular information in the form of morphological features identifiable in histologically stained samples. The biomarkers herein may be of morphological features determined from labeled based images in some examples. The biomarkers herein may be of morphological features determined from labeled RNA data. References to "biomarkers" herein is intended to include tumor cells and an expected yield of nucleic acid for tumor cells. Image-derived information herein further includes the total nucleic acid yield of tissue, within respective histology samples.

The biomarkers herein may be image-derived information that is correlated with the existence of cancer or of a susceptibility to cancer in the subject; the likelihood that the cancer is one subtype vs. another; the presence or proportion of biological characteristics, such as tissue, cellular, or protein types or classes; the probability that a patient will or will not respond to a particular therapy or class of therapy; the degree of the positive response that would be expected for a therapy or class of therapies (e.g., survival and/or progression-free survival); whether a patient is responding to a therapy; or the likelihood that a cancer will regress, has progressed, or will progress beyond its site of origin (i.e., metastasize).

Example biomarkers predicted from histopathology images using the various techniques herein include the following.

Tumor-infiltrating lymphocytes (TILs), as used herein, refers to mononuclear immune cells that infiltrate tumor tissue or stroma. TILs include, e.g., T cells, B cells, and NK cells, populations of which can be subcategorized based on function, activity, and/or biomarker expression. For example, a population of TILs may include cytotoxic T cells expressing, e.g., CD3 and/or CD8, and regulatory T cells (also known as suppressor T cells), which are often characterized by FOXP3 expression. Information regarding TIL density, location, organization, and composition provide valuable insight as to prognosis and potential treatment options. In various aspects, the disclosure provides a method of predicting TIL density in a sample, a method of distinguishing subpopulations of TILs in a sample (e.g., distinguishing CD3/CD8-expressing cytotoxic T cells from FOXP3 Tregs), a method of distinguishing stromal versus intratumoral TILs, and the like.

Programmed death-ligand 1 (PD-L1) is a 40 kDa type 1 transmembrane protein that plays a role in suppressing the immune system, particularly affecting patients with autoimmune disease, cancer, and other disease states. Of relevance for cancer immunotherapy, PD-L1 can be expressed on the surface of tumor cells, tumor-associated macrophages (TAMs), and T lymphocytes and can subsequently inhibit PD-1-positive T cells.

Ploidy refers to the number of sets of homologous chromosomes in the genome of a cell or an organism. Examples include haploid which means one set of chromosomes and diploid means two sets of chromosomes. Having multiple sets of paired chromosomes in a genome of an organism is described as polyploid. Three sets of chromosomes, 3n, is triploid whereas four sets of chromosomes, 4n, is tetraploid. Extremely large number of sets may be designated by number (for example 15-ploid for fifteen sets).

Nucleus-to-cytyoplasm (NC) ratio is a measurement of the ratio of the size of a nucleus of a cell to the size of the cytoplasm of that cell. The NC ratio may be expressed as a volumetric ratio or cross-sectional area. The NC ratio can indicate the maturity of a cell, with the size of a cell nucleus decreasing with cell maturity. By contrast, high NC ratio in cells can be an indication of cell malignancy.

Signet ring morphology is the morphology of a signet ring cell, i.e., a cell with a large vacuole, the malignant type of which appears predominantly in cases of carcinoma. Signet ring cells are most frequently associated with stomach cancer, but can arise from any number of tissues including the prostate, bladder, gallbladder, breast, colon, ovarian stroma and testis. Signet ring cell carcinoma (SRCC), for example, is a rare form of highly malignant adenocarcinoma. It is an epithelial malignancy characterized by the histologic appearance of signet ring cells.

These biomarkers, TILS, NC ratio, ploidy, signet ring morphology, and PD-L1, are examples of biomarkers of morphological features determined from labeled based images, in accordance with techniques herein.

Consensus molecular subtypes ("CMS") are a set of classification subtypes of colorectal cancer (CRC) developed based on comprehensive gene expression profile analysis. CMS classifications in primary colorectal cancer include: CMS1-immune infiltrated (Often BRAFmut, MSI-High, TMB-High); CMS2—canonical (Often ERBB/MYC/ WNT driven); CMS3—metabolic (Often KRASmut); and CMS4—mesenchymal (Often TGF-B driven). More broadly, CMS herein includes these and other subtypes for colorectal cancer. More broadly still, CMS herein refers subtypes derived from comprehensive gene expression profile analysis of other cancer types listed herein.

Homologous recombination deficiency ("HRD") status is a classification indicating deficiency in the normal homologous recombination DNA damage repair process that results in a loss of duplication of chromosomal regions, termed genomic loss of heterozygosity (LOH).

Biomarkers such as CMS and HRD are examples of biomarkers of morphological features determined from labeled RNA data, in accordance with techniques herein.

By way of example, biomarkers herein include HRD status, DNA ploidy scores, karyotypes, CMS scores, chromosomal instability (CIN) status, signet ring morphology scores, NC ratios, cellular pathway activation status, cell state, tumor characteristics, and splice variants.

As used herein, "histopathology images" refers to digital (including digitized) images of microscopic histopathology developed tissue. Examples include images of histological stained specimen tissue, where histological staining is a process undertaken in the preparation of sample tissues to aid in microscopic study. In some examples, the histopathology images are digital images of hematoxylin and eosin stain (H&E) stained histopathology slides, immunohistochemistry (IHC) stained slides, Romanowsky Stains-Giemsa stained slides, Gram stained slides, Trichrome stained slides, carmine stained slides, and silver nitrate stained slide. Other examples include blood smeared slides and tumor smeared slides. In other examples, the histopathology images are of other stained slides known in the art. As used herein, references to digital images, digitized images, slide images, and medical images refers to "histopathology images."

These histopathology images may be captured in visible wavelength region as well as beyond the visible region, such as infrared digital images obtained using spectroscopic examination of histopathology developed tissue. In some examples, histopathology images include z-stack images that represent horizontal cross-sections of a 3-dimensional specimen or histopathology slide, captured at varying levels of the specimen or varying focal points of the slide. In some examples, two or more images may be from adjacent or near-adjacent sections of tissue from a specimen, and one of the two or more images may have tissue features that correspond with tissue features on another of the two or more images. There may be a vertical and/or horizontal shift between the location of the corresponding tissue features in the first image and the location of the corresponding tissue features in the second image. Thus, histopathology images also refers to images, sets of images, or videos generated from multiple different images. It should be understood that the following exemplary embodiments may be interchanged, or model's trained, with differing styles of staining unless explicitly excluded.

Various examples herein are described with reference to a particular class of histopathology image, H&E slide images. A digital H&E slide image may be generated by capturing a digital photograph of an H&E slide. Alternatively or in addition, such an image may be generated through machine learning systems, such as deep learning, from images derived from unstained tissue. For example, a digital H&E slide image may be generated from wide-field autofluorescence images of unlabeled tissue sections. See, e.g., Rivenson et al, Virtual histological staining of unlabeled tissue-autofluorescence images via deep learning. Nature Biomedical Engineering, 3(6):466, 2019.

Figure 38:
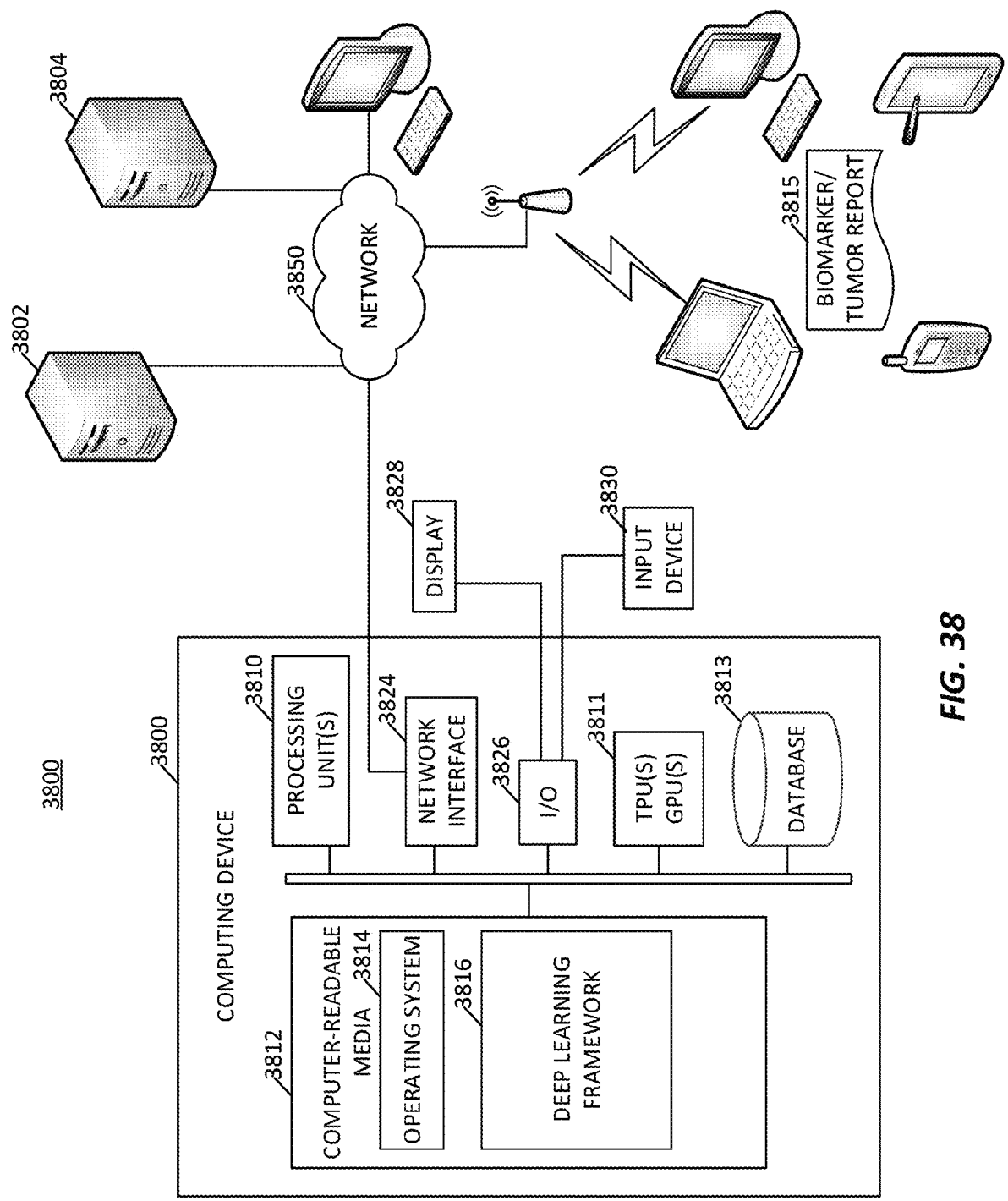
FIG. 38 is a block diagram of an example computing device for use in implementing various systems herein, in accordance with an example.
Figure 39:
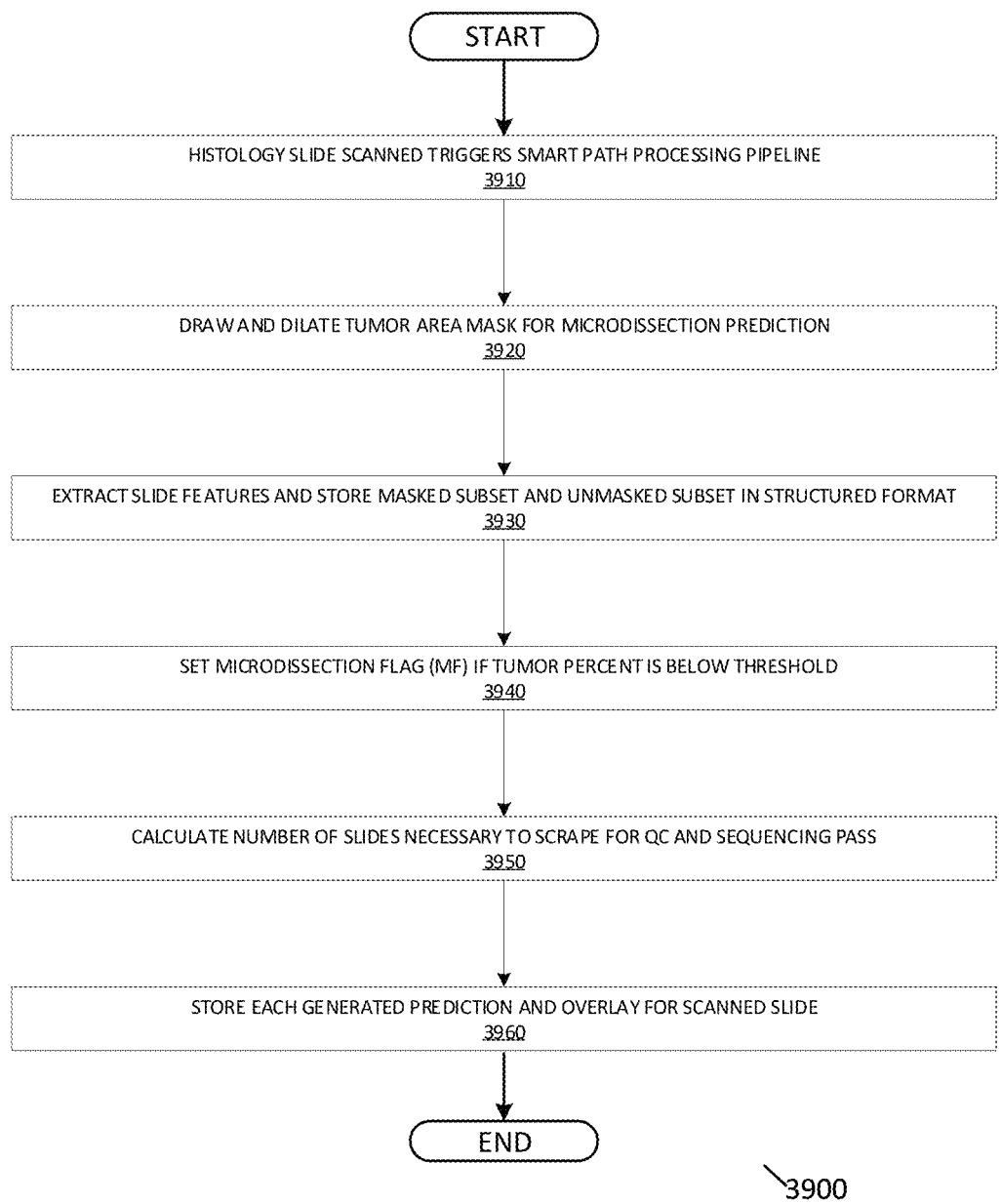
FIG. 39 is a block diagram of data flow for generating a dissection boundary and predicting number of slides, in accordance with an example.
Figure 40:
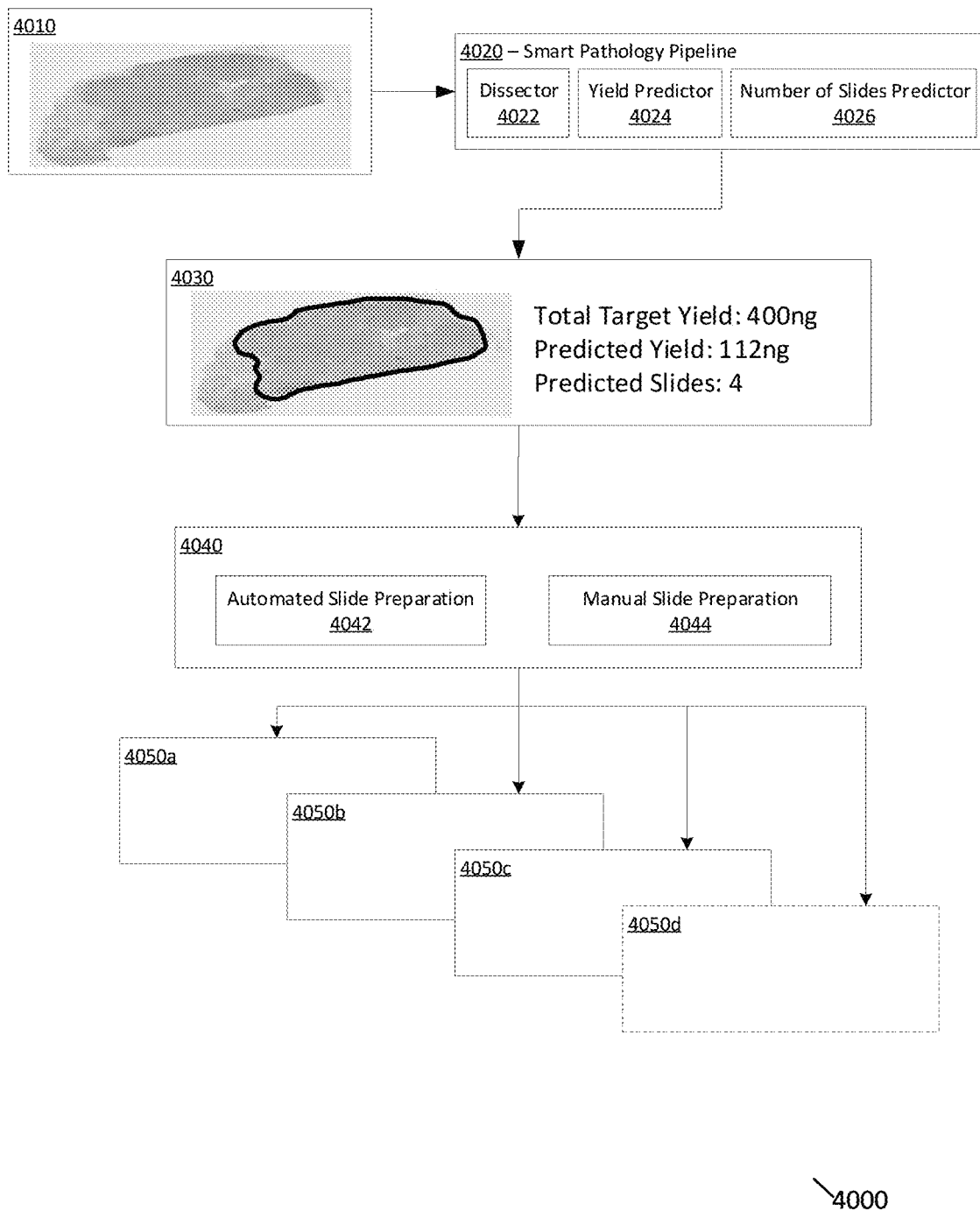
FIG. 40 is an illustration of a Smart Pathology pipeline for generating dissection boundaries, estimating dissection yields, and predicting a number of slides, in accordance with an example.
Figure 41:
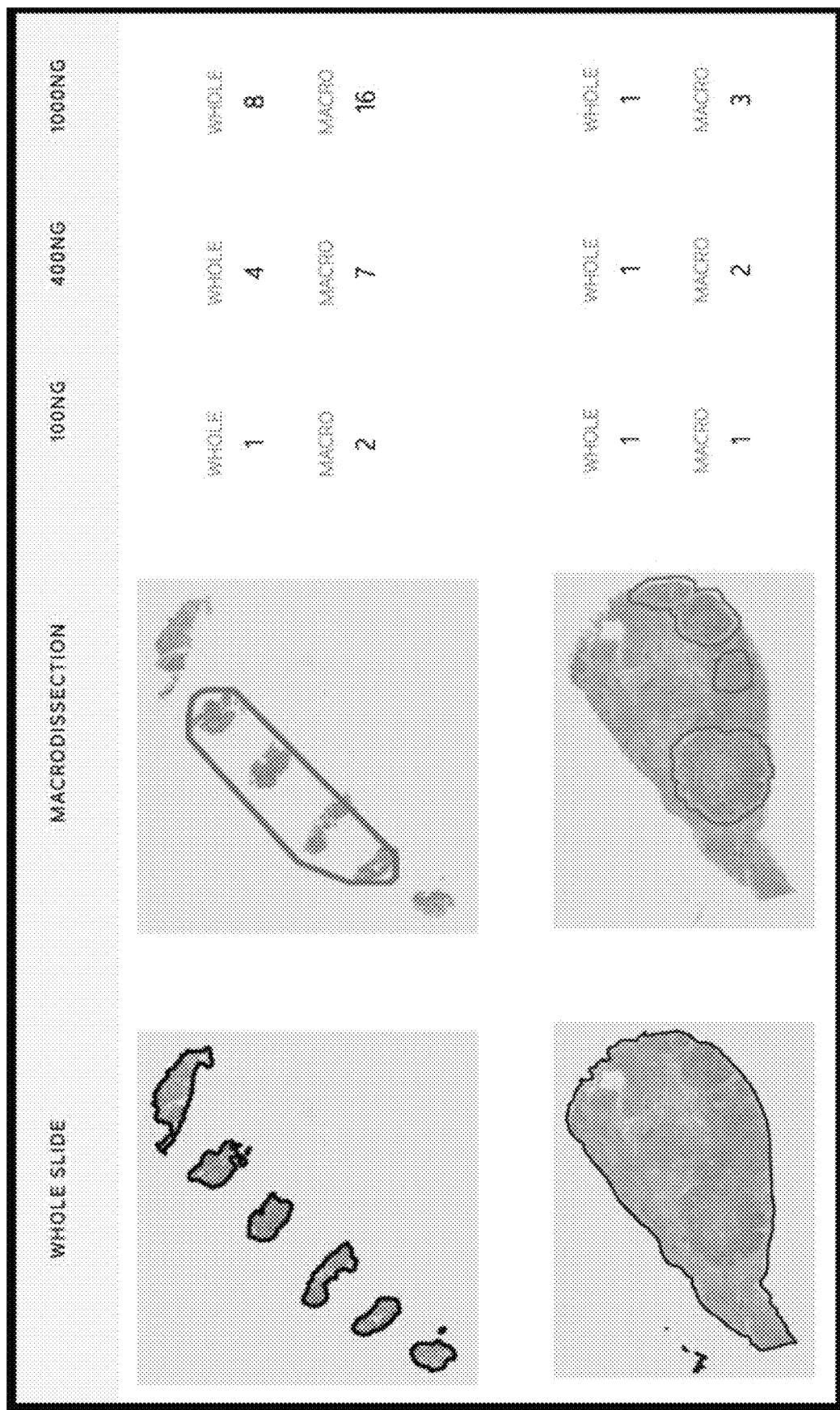
FIG. 41 is an illustration of a Smart Pathology generated graphical user interface display as may be generated by systems such as the systems of FIGS. 1, 3, 30, and 40 in accordance with an example.

In various examples herein, the imaging-based biomarker prediction system may be implemented in whole or in part as Smart Pathology system, as described in reference to processes of FIGS. 39-41. As such, references herein to an imaging-based biomarker prediction system include an implementation as an image-based nucleic acid yield prediction system (or tumor cell prediction system), for example, as described in various features and Aspects herein. For example, any of the systems of FIGS. 1, 3, 30, 38, and 40 may be implemented to perform any of the features or Aspects described herein.

In an example, a Smart Pathology system may be configured to implement, in whole or in part, a computer-implemented method for qualifying a specimen prepared on one or more hematoxylin and eosin (H&E) slides and for providing associated unstained slides for nucleic acid analysis. That method may include generating a digital image of each of the one or more H&E slides prepared from the specimen at an image-based nucleic acid yield prediction system having one or more processors. That method may further include, for each digital image, identifying, using the one or more processors, tumor cells of the H&E slide from the digital image. The method may include generating a tumor area mask based at least in part on the identified tumor cells, wherein the tumor area mask defines a dissection boundary of the H&E slide associated with the digital image. The method may include predicting an expected yield of nucleic acid for the tumor cells within the dissection boundary; and providing one or more of the associated unstained slides for nucleic acid analysis when the summation of expected yield of nucleic acid predicted for each digital image exceeds a predetermined threshold.

In an example, a Smart Pathology system may be configured to implement, in whole or in part, a computer-implemented method including: receiving a first hematoxylin and eosin (H&E) slide prepared from a tumor block at an image-based nucleic acid yield prediction system having one or more processors. The method may further include identifying, using the one or more processors, tumor cells of the H&E slide from a digital image. The method may further include generating a tumor area mask based at least in part on the identified tumor cells, wherein the tumor area mask defines a dissection boundary of the H&E slide associated with the digital image. The method may further include predicting an expected yield of nucleic acid for the tumor cells within the dissection boundary. The method may further include based on the predicted expected yield of nucleic acid, identifying a number of H&E slides to prepare from the tumor block to satisfy a total nucleic yield; and preparing the number of H&E slides from the tumor block when the predicted expected yield of nucleic acid exceeds a predetermined threshold.

In an example, a Smart Pathology system may be configured to implement, in whole or in part, a computer-implemented method for predicting an expected yield of nucleic acid from tumor cells within a dissection boundary on a hematoxylin and eosin (H&E) slide. The method may include receiving a digital image of the H&E slide at an image-based nucleic acid yield prediction system having one or more processors. The method may include identifying, using the one or more processors, tumor cells of the H&E slide from digital image using a trained cell segmentation model. The method may include generating a tumor area mask based at least in part on the identified tumor cells, wherein the tumor area mask defines the dissection boundary of the H&E slide. The method may include predicting the expected yield of nucleic acid for the tumor cells within the dissection boundary.

FIG. 1 illustrates a prediction system 100 capable of analyzing digital images of histopathology slides of a tissue sample and determining the likelihood of biomarker presence in that tissue, where biomarker presence indicates a predictive tumor presence, a predicted tumor state/condition, or other information about a tumor of the tissue sample, such as a possibility of clinical response through the use of a treatment associated with the biomarker.

The system 100 includes an imaging-based biomarker prediction system 102 that implements, among other things, image processing operations, deep learning frameworks, and report generating operations to analyze histopathology images of tissue samples and predict the presence of biomarkers in the tissue samples. In various examples, the system 100 is configured to predict the present of these biomarkers, tissue location(s) associated with these biomarkers, and/or cell location of these biomarkers. In various examples, the imaging-based biomarker prediction system 102 may be implemented in whole or in part as Smart Pathology system, as described in reference to processes of FIGS. 39-41 and the Aspects described herein. As such, the imaging-based biomarker prediction system may be implemented as an image-based nucleic acid yield prediction system (or tumor cell prediction system), for example, as described in various features and Aspects herein.

The imaging-based biomarker prediction system 102 may be implemented on one or more computing device, such as a computer, tablet or other mobile computing device, or server, such as a cloud server. The imaging-based biomarker prediction system 102 may include a number of processors, controllers or other electronic components for processing or facilitating image capture, generation, or storage and image analysis, and deep learning tools for analysis of images, as described herein. An example computing device 3800 for implementing the imaging-based biomarker prediction system 102 is illustrated in FIG. 38.

As illustrated in FIG. 1, the imaging-based biomarker prediction system 102 is connected to one or more medical data sources through a network 104. The network 104 may be a public network such as the Internet, private network such as a research institution's or corporation's private network, or any combination thereof. Networks can include, local area network (LAN), wide area network (WAN), cellular, satellite, or other network infrastructure, whether wireless or wired. The network 104 can be part of a cloud-based platform. The network 104 can utilize communications protocols, including packet-based and/or datagram-based protocols such as internet protocol (IP), transmission control protocol (TCP), user datagram protocol (UDP), or other types of protocols. Moreover, the network 104 can include a number of devices that facilitate network communications and/or form a hardware basis for the networks, such as switches, routers, gateways, access points (such as a wireless access point as shown), firewalls, base stations, repeaters, backbone devices, etc.

Via the network 104, the imaging-based biomarker prediction system 102 is communicatively coupled to receive medical images, for example of histopathology slides such as digital H&E stained slide images, IHC stained slide images, or digital images of any other staining protocols from a variety of different sources. These sources may include a physician clinical records systems 106 and a histopathology imaging system 108. Any number of medical image data sources could be accessible using the system 100. The histopathology images may be images captured by any dedicated digital medical image scanners, e.g., any suitable optical histopathology slide scanner including 20× and 40× resolution magnification scanners. Further still, the biomarker prediction system 102 may receive images from histopathology image repositories 110. In yet other examples, images may be received from a partner genomic sequencing system 112, e.g., the TCGA and NCI Genomic Data Commons. Further still, the biomarker prediction system 102 may receive histopathology images from an organoid modeling lab 116. These image sources may communicate image data, genomic data, patient data, treatment data, historical data, etc., in accordance with the techniques and processes described herein. Each of the image sources may represent multiple image sources. Further, each of these image sources may be considered a different data source, those data sources may be capable of generating and providing imaging data that differs from other providers, hospitals, etc. The imaging data between different sources potentially differs in one or more ways, resulting in different data source-specific bias, such as in different dyes, biospecimen fixations, embeddings, staining protocols, and distinct pathology imaging instruments and settings.

In the example of FIG. 1, the imaging-based biomarker prediction system 102 includes an image pre-processing sub-system 114 that performs initial image processing to enhance image data for faster processing in training a machine learning framework and for performing biomarker prediction using a trained deep learning framework. In the illustrated example, the image pre-processing sub-system 114 performs a normalization process on received image data, including one or more of color normalization 114a, intensity normalization 114b, and imaging source normalization 114c, to compensate for and correct for differences in the received image data. While in some examples the imaging-based biomarker prediction system 102 receives medical images, in other examples the sub-system 114 is able to generate medical images, either from received histopathology slides or from other received images, such as generating composite histopathology images by aligning shifted histopathology images to compensate from vertical/horizontal shift. This image pre-processing allows a deep learning framework to more efficiently analyze images across large data sets (e.g., over 1000s, 10000s, to 100000s, to 1000000s of medical images), thereby resulting in faster training and faster analysis processing.

The image pre-processing sub-system 114 may perform further image processing that removes artifacts and other noise from received images by doing preliminary tissue detection 114d, for example, to identify regions of the images corresponding to histopathology stained tissue for subsequent analysis, classification, and segmentation.

As further described herein, in multiscale configuration where image data is to be analyzed on a tile-basis, in some examples, image pre-processing includes receiving an initial histopathology image, at a first image resolution, downsampling that image to a second image resolution, and then performing a normalization on the downsampled histopathology image, such as color and/or intensity normalization, and removing non-tissue objects from the image.

In single-scale configurations, by contrast, downsampling of the received histopathology image is not used. Single-scale configurations analyze image data on a slide-level basis, not on a tile-basis.

In yet some hybrid versions of each of multiscale and single-scale configurations a tiling process is imposed on received histopathology images to generate tiles for a tile-based analysis thereof.

The imaging-based biomarker prediction system 102 may be a standalone system interfacing with the external (i.e., third party) network-accessible systems 106, 108, 110, 112, and 116. In some examples, the imaging-based biomarker prediction system 102 may be integrated with one or more of these systems, including as part of a distributed cloud-based platform. For example, the system 102 may be integrated with a histopathology imaging system, such as a digital H&E stain imaging system, e.g. to allow for expedited biomarker analysis and reporting at the imaging station. Indeed, any of the functions described in the techniques herein may be distributed across one or more network accessible devices, including cloud-based devices.

In some examples, the imaging-based biomarker prediction system 102 is part of a comprehensive biomarker prediction, patient diagnosis, and patient treatment system. For example, the imaging-based biomarker prediction system 102 may be coupled to communicate predicted biomarker information, tumor prediction, and tumor state information to external systems, including a computer-based pathology lab/oncology system 118 that may receive a generated biomarker report including image overlay mapping and use the same for further diagnosing cancer state of the patient and for identifying matching therapies for use in treating the patient. The imaging-based biomarker prediction system 102 may further send generated reports to a computer system 120 of the patient's primary care provider and to a physician clinical records system 122 for databasing the patients report with previously generated reports on the patient and/or with databases of generated reports on other patients for use in future patient analyses, including deep learning analyses, such as those described herein.

To analyze the received histopathology image data and other data, the imaging-based biomarker prediction system 102 includes a deep learning framework 150 that implements various machine learning techniques to generate trained classifier models for image-based biomarker analysis from received training sets of image data or sets of image data and other patient information. With trained classifier models, the deep learning framework 150 is further used to analyze and diagnose the presence of image-based biomarkers in subsequent images collected from patients. In this manner, images and other data of previously treated and analyzed patients is utilized, through the trained models, to provide analysis and diagnosis capabilities for future patients.

In the example system 100, the deep learning framework 150 includes a histopathology image-based classifier training module 160 that can access received and stored data from the external systems 106, 108, 110, 112, and 116, and any others, where that data may be parsed from received data streams and databased into different data types. The different data types may be divided into image data 162a which may be associated with the other data types molecular data 162b, demographic data 162c, and tumor response data 162d. An association may be formed by labeling the image data 162a with one or more of the different data types. By labeling the image data 162a according to associations with the other data types, the imaging-based biomarker prediction system may train an image classifier module to predict the one or more different data types from image data 162a.

In the illustrated data, the deep learning framework 150 includes image data 162a. For example, to train or use a multiscale PD-L1 biomarker classifier, this image data 162a may include pre-processed image data received from the sub-system 114, images from H&E slides or images from IHC slides (with or without human annotation), including IHC slides targeting PD-L1, PTEN, EGFR, Beta catenin/catenin beta1, NTRK, HRD, PIK3CA, and hormone receptors including HER2, AR, ER, and PR. To train or use other biomarker classifiers, whether multiscale classifiers or single-scale classifiers, the image data 162A may include images from other stained slides. Further, in the example of training a single scale classifier, the image data 162A is image data associated with RNA sequence data for particular biomarker clusters, to allow of multiple instance learning (MIL) techniques herein.

The molecular data 162b may include DNA sequences, RNA sequences, metabolomics data, proteomic/cytokine data, epigenomic data, organoid data, raw karyotype data, transcription data, transcriptomics, metabolomics, microbiomics, and immunomics, identification of SNP, MNP, InDel, MSI, TMB, CNV Fusions, loss of heterozygosity, loss or gain of function. Epigenomic data includes DNA methylation, histone modification, or other factors which deactivate a gene or cause alterations to gene function without altering the sequence of nucleotides in the gene. Microbiomics includes data on viral infections which may affect treatment and diagnosis of certain illnesses as well as the bacteria present in the patient's gastrointestinal tract which may affect the efficacy of medicines ingested by the patient. Proteomic data includes protein composition, structure, and activity; when and where proteins are expressed; rates of protein production, degradation, and steady-state abundance; how proteins are modified, for example, post-translational modifications such as phosphorylation; the movement of proteins between subcellular compartments; the involvement of proteins in metabolic pathways; how proteins interact with one another; or modifications to the protein after translation from the RNA such as phosphorylation, ubiquitination, methylation, acetylation, glycosylation, oxidation, or nitrosylation.

The deep learning framework 150 may further include demographic data 162c and tumor response data 162d (including data about a reduction in the growth of the tumor after exposure to certain therapies, for example immunotherapies, DNA damaging therapies like PARP inhibitors or platinums, or HDAC inhibitors). The demographic data 162c may include age, gender, race, national origin, etc. The tumor response data 162d may include epigenomic data, examples of which include alterations in chromatin morphology and histone modifications.

The tumor response data 162d may include cellular pathways, example of which include IFNgamma, EGFR, MAP KINASE, mTOR, CYP, CIMP, and AKT pathways, as well as pathways downstream of HER2 and other hormone receptors. The tumor response data 162d may include cell state indicators, examples of which include Collagen composition, appearance, or refractivity (for example, extracellular vs fibroblast, nodular fasciitis), density of stroma or other stromal characteristics (for example, thickness of stroma, wet vs. dry) and/or angiogenesis or general appearance of vasculature (including distribution of vasculature in collagen/stroma, also described as epithelial-mesenchymal transition or EMT). The tumor response data 162d may include tumor characteristics, examples of which include the presence of tumor budding or other morphological features/characteristics demonstrating tumor complexity, tumor size (including the bulky or light status of a tumor), aggressiveness of tumor (for example, known as high grade basaloid tumor, especially in colorectal cancer, or high grade dysplasia, especially in barrett's esophagus), and/or the immune state of a tumor (for example, inflamed/"hot" vs. non-inflamed/"cold" vs immune excluded).

The histopathology image-based classifier training module 160 may be configured with an image-analysis adapted machine learning techniques, including, for example, deep learning techniques, including, by way of example, a CNN model and, more particular, a tile-resolution CNN, that in some examples is implemented as a FCN model, and, more particularly still, implemented as a tile-resolution FCN model. Any of the data types 162a-162d may be obtained directly from data communicated to the imaging-based biomarker prediction system 102, such as contained within and communicated along with the histopathology images. The data types 162a-162d may be used by the histopathology image-based classifier training module 160 to develop classifiers for identifying one of more of the biomarkers discussed herein.

In one example, a histopathology image may be segmented and each segment of the image may be labeled according to one or more data types that may be classified to that segment. In another example, the histopathology image may be labeled as a whole according to the one or more data types that may be classified to the image or at least one segment of the image. Data types may indicate one or more biomarkers and labeling a histopathology image or a segment with a data type may identify the biomarker.

In the example system 100, the deep learning framework 150 further includes a trained image classifier module 170 that may also be configured with the deep learning techniques, including those implementing the module 160. In some examples, the trained image classifier module 170 accesses the image data 162 for analysis and biomarker classification. In some examples, the module 170 further accesses the molecular data 162, the demographic data 162c, and/or tumor response data 162d for analysis and tumor prediction, matched therapy predictions, etc.

The trained image classifier module 170 includes trained tissue classifiers 172, trained by the module 160 using one or more training image sets, to identify and classify tissue type in regions/areas of received image data. In some examples, these trained tissue classifiers are trained to identify biomarkers via the tissue classification, where these include single-scale configured classifiers 172a and multi-scale classifiers 172b.

The module 170 may further include other trained classifiers, including, trained cell classifiers 174 that identify biomarkers via cell classification. The module 170 may further include a cell segmenter 176 that identifies cells within a histopathology image, including cell borders, interiors, and exteriors.

In examples herein, the tissue classifiers 172 may include biomarker classifiers specifically trained to identify tumor infiltration (such as by ratio of lymphocytes in tumor tissue to all cells in tumor tissue), PD-L1 (such as positive or negative status), ploidy (such as by a score), CMS (such as to identify subtype), NC Ratio (such as nucleus size identification), signet ring morphology (such as a classification of a signet cell or vacuole size), HRD (such as by a score, or by a positive or negative classification), etc. in accordance with the biomarkers herein.

As detailed herein, the trained image classifier module 170 and associated classifiers may be configured with an image-analysis adapted machine learning techniques, including, for example, deep learning techniques, including, by way of example, a CNN model and, more particular, a tile-resolution CNN, that in some examples is implemented as a FCN model, and, more particularly still, implemented as a tile-resolution FCN model, etc.

The system 102 further includes a tumor report generator 180 configured to receive classification data from the trained tissue (biomarker) classifiers 172, the trained cell (biomarker) classifiers 174 and the cell segmenter 172 and determine tumor metrics for the image data and generate digital image and statistical data reports, where such output data may be provided to the pathology lab 118, primary care physician system 120, genomic sequencing system 112, a tumor board, a tumor board electronic software system, or other external computer system for display or consumption in further processes.

Figure 2:
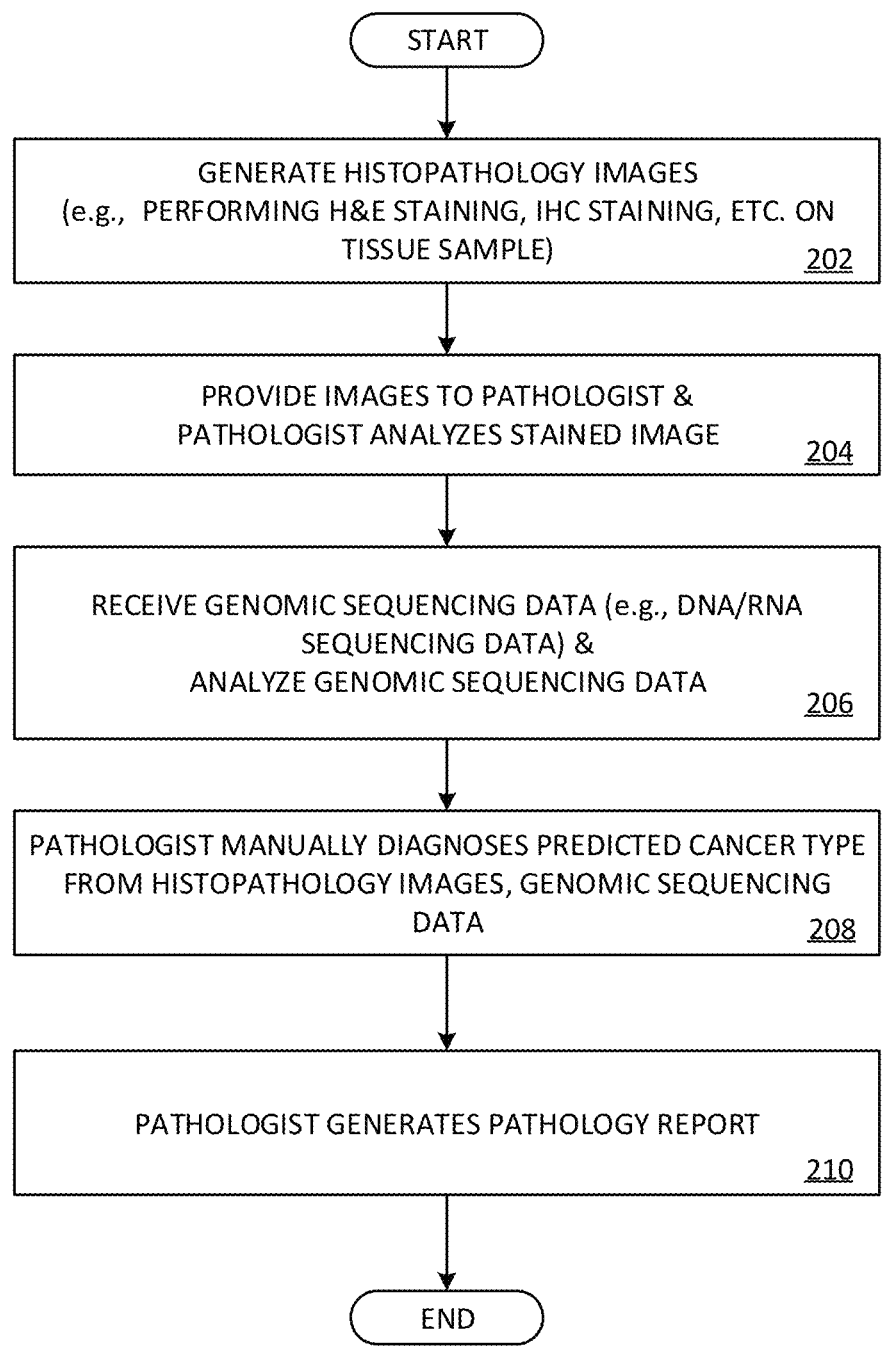
FIG. 2 is a block diagram of process for a conventional pathologist cancer diagnosis workflow.

A conventional cancer diagnosis workflow 200 using histopathology images is shown in FIG. 2. A biopsy is performed to collect tissue samples from a patient. A medical lab generates digital histopathology images (202) for the tissue sample, for example using known staining techniques such as H&E or IHC staining and a digital medical imager (for example, a slide scanner). These histopathology images are provided to a pathologist who visually analyzes them (204) to identify tumors within the received image. The pathologist may optionally receive genomic sequencing data for the patient (e.g., DNA Seq data or RNA Seq data from a genomic sequencing lab) and analyze that data (206). From the visual analysis of a histopathology slide and from the optional genomic sequencing data, the pathologist then diagnoses a cancer type other characteristics of the tumor/cancer cells (208) and generates a pathology report (210).

Figure 3:
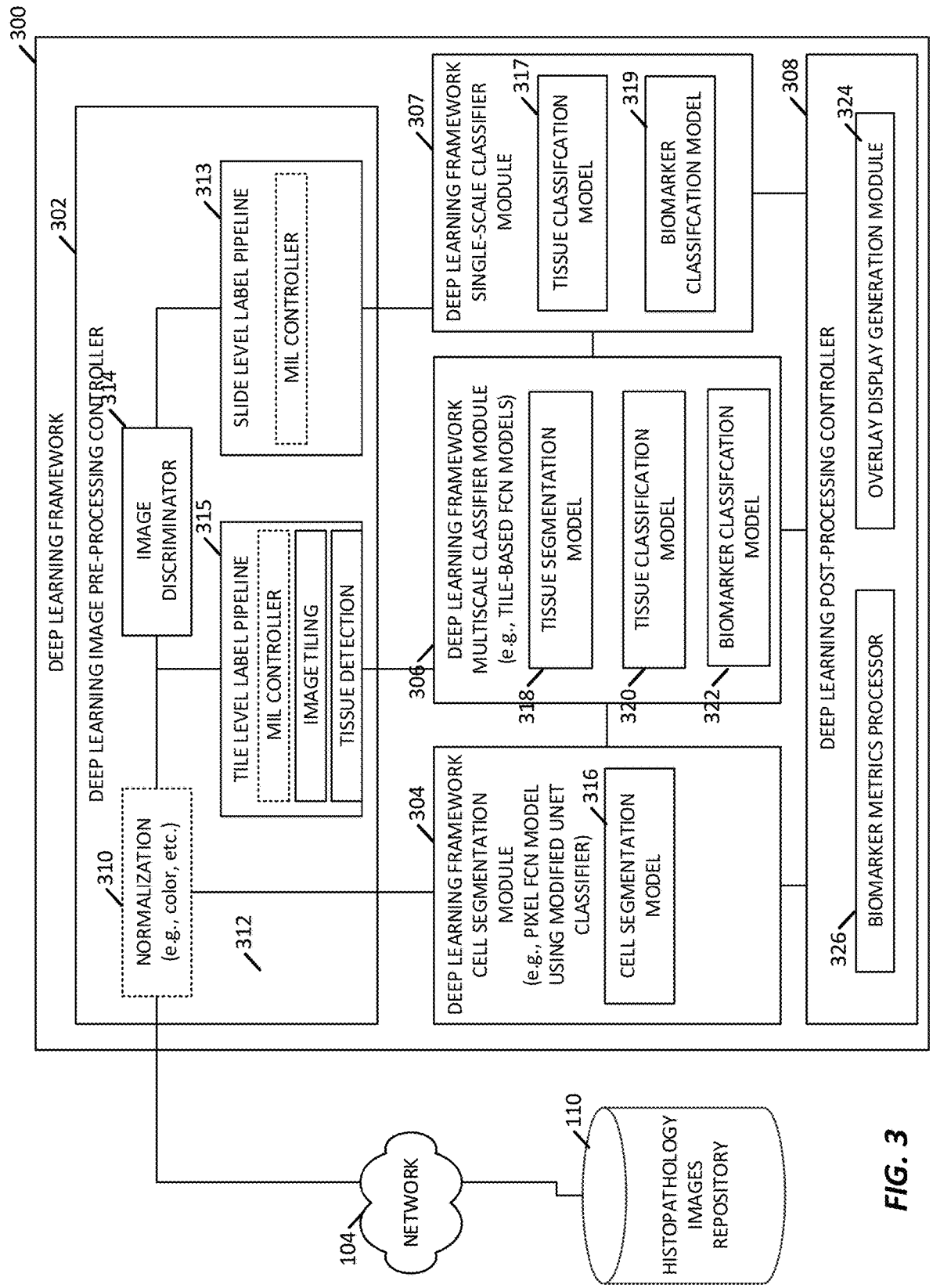
FIG. 3 is a block diagram of a schematic of a deep learning framework that may be implemented in the system of FIG. 1, in accordance with an example.

FIG. 3 illustrates an example implementation of the imaging-based biomarker prediction system 102, and more particularly, of the deep learning framework 150 in the form of deep learning framework 300. The framework 300 may be communicatively coupled to receive histopathology image data and other data (molecular data, tumor response data, demographic data, etc.) from external systems, such as the physician clinical records system 106, the histopathology imaging system 108, the genomic sequencing system 112, the medical images repository 110, and/or the organoid modeling lab 116 of FIG. 1 and through the network 104. The organoid modeling lab 116 may collect various types of data, such as, for example, the sensitivity of an organoid to a drug (for example, determined by measuring cell death or cell viability after exposure to the drug), single-cell analysis data or detection of cellular products (including proteins, lipids, and other molecules) indicating the presence of specific cell populations, including effector data, stimulatory data, regulatory data, inflammatory data, chemoattractive data, as well as organoid image data, any of which may be stored within the molecular data 162b.

The framework 300 includes a pre-processing controller 302, a deep learning framework cell segmentation module 304, a deep learning framework multiscale classifier module 306, a deep learning framework single-scale classifier module 307, and a deep learning post-processing controller 308.

To prepare the medical images for multiscale and single-scale deep learning, in an example, the pre-processing controller 302 includes normalization processes 310, which may include color normalization, intensity normalization, and imaging source normalization. The normalization process 310 is option and may be excluded to expedite deep learning training, image analysis, and/or biomarker prediction.

An image discriminator 314 receives the normalized histopathology images from the normalization processes 310 and examines the images, including image metadata, to determine image type. The image discriminator 314 may analyze image data to determine if the image is a training image, e.g., an image from a training dataset. The image discriminator 314 may analyze image data to determine the labeling type on the image, for example, whether the image has a tile-level labeling, slide-level labeling, or no labeling. The image discriminator 314 may analyze the image data to determine the slide staining used to generate the digital image, H&E, IHC, etc.

In response to examining this image data, the image discriminator 314 determines which images are to be provided to a slide-level label pipeline 313 for feeding into the deep learning framework single-scale classifier module 307 and which images are to be provided to a tile-level label pipeline 315 for feeding into the deep learning framework multiscale classifier 306.

In the illustrated example, images having tile-level labeling the pipeline 315 includes tissue detection processes and image tiling processes. These processes may be performed on all received imaged data, only on training image data, only on received image data for analysis, or some combination thereof. In some examples, the tissue detection process, for example, may be excluded to expedite deep learning training, image analysis, and/or biomarker prediction. Indeed, any of the processes of the controller 302 may be performed in a dedicated biomarker prediction system or distributed for performance by externally-connected systems. For example, a histopathology imaging system may be configured to perform normalization processes before sending image data to the biomarker prediction system. In some examples, the biomarker prediction system may communicate an executable normalization software package to the connected external systems that configures those systems to perform normalization or other pre-processing.

In examples in which the image discriminator 314 sends unlabeled images to the pipeline 315, the pipeline 315 includes a multiple instance learning (MIL) controller, discussed further herein, configured to convert all or portions of these histopathology images to tile-labeled images. The MIL controller may be configured to perform processes herein, such as those described in FIGS. 18-26.

To expedite tissue detection of the trained tissue classifier, the tissue detection process of the pipeline 315 may perform initial tissue identification, to locate and segment the tissue regions of interest for biomarker analysis. Such issue tissue identification may include, for example, identifying tissue boundaries and segmenting an image into tissue and non-tissue regions, so that metadata identifying the tissue regions is stored with the image data to expedite processing and prevent biomarker analysis attempts on non-tissue regions or on regions not corresponding to the tissue to be examined.

To facilitate deep learning classification in various multiscale configurations, the deep learning framework multiscale classifier module 306 is configured to classify tissue using a tiling analysis. For example, in the pipeline 315, the tissue detection process sends histopathology images (e.g., image data enhanced with tissue detection metadata) to the image tiling process that selects and applies a tiling mask to the received images to parse the images into small sub-images for analysis by the framework module 306. The pipeline 315 may store a plurality of different tiling masks and select a tiling mask. In some examples, the image tiling process selects one or more tiling masks optimized for different biomarkers, i.e., in some examples, image tiling is biomarker specific. This allows, for example, to have tiles of different pixel sizes and different pixel shapes that are selected specifically to increase accuracy and/or to decrease processing time associated with a particular biomarker. For example, tile sizes optimized for identifying the presence of TILs in an image may be different from tile sizes optimized for identifying PD-L1 or another biomarker. As such, in some examples, the pre-processor controller 302 is configured to perform imaging processing and tiling specific to a type of biomarker, and after the system 300 analyzes image data for that biomarker, the controller 302 may re-process the original image data for analyzing for the next biomarker, and so on, until all biomarkers have been examined for.

Generally speaking, the tiling masks applied by the image tiling process of the pipeline 315 may be selected to increase efficiency of operation of the deep learning framework module 306. The tiling mask may be selected based on the size of the received image data, based on the configuration of the deep learning framework 306, based on the configuration of the framework module 304, or some combination thereof.

Tiling masks may vary in the size of tiling blocks. Some tiling masks have uniform tiling blocks, i.e., each the same size. Some tiling masks having tiling blocks of different sizes. The tiling mask applied by the image tiling process may be chosen based on the number of classification layers in the deep learning framework 306, for example. In some examples, the tiling mask may be chosen based on the processor configuration of the biomarker prediction system, for example, if the multiple parallel processors are available or if graphical processing units or tensor processing units are used.

In the illustrated example, the deep learning multiscale classifier module 304 is configured to perform cell segmentation through a cell segmentation model 316, where cell segmentation may be a pixel-level process of the histopathology image from normalization process 310. In other examples, this pixel-level process may be performed on image tiles received from the pipeline 315. In some examples, the cell segmentation process of the framework 304 results in classifications that biomarker classifications, because some of the biomarkers identified herein are determined from cell level analysis, in contrast to tissue level analysis. These include signet ring, large nuclei and high NC ratio, for example. The module 304 may be configured using a CNN configuration, in particular an FCN configuration for implementing each separate segmentation.

The deep learning framework multiscale classifier module 306 includes a tissue segmentation model 318, a tissue classification model 320, and a biomarker classification model 320. Like the module 304, the module 306 may be configured using a CNN configuration, in particular an FCN configuration for implementing each separate segmentation.

In an example, the cell segmentation model 316 of the module 304 may be configured as a three-class semantic segmentation FCN model developed by modifying a UNet classifier replacing a loss function with a cross-entropy function, focal loss function, or mean square error function to form a three-class segmentation model. Three-class nature of the FCN model means that the cell segmentation model 316 may be configured as a first pixel-level FCN model, that identifies and assigns each pixel of image data into a cell-subunit class: (i) cell interior, (ii) a cell border, or (iii) a cell exterior. This is provided by way of example. The segmentation size of the module model 316 may be determined based on the type of cell to be segmented. For both TILs biomarkers, for example, the model 316 may be configured to perform lymphocyte identification and segmentation using a three-class FCN model. For example, the cell segmentation model 316 may be configured to classify pixels in an image as corresponding to the (i) interior, (ii) border, or (iii) exterior of lymphocyte cell. The cell segmentation model 316 may be configured to identify and segment any number of cells, examples of which include tumor positive, tumor negative, lymphocyte positive, lymphocyte negative, immune cells, including lymphocytes, cytotoxic T cells, B cells, NK cells, macrophages, etc.

In some examples, the module 304 receives tiled, sub-images from the pipeline 315, and the cell segmentation model 316 determines the list of locations of all lymphocytes, and those locations are compared to the other three class model's list of all cells determined from the model 316 to eliminate any falsely detected lymphocytes that are not cells. The system 300 then takes this new list of locations of confirmed lymphocytes from the module 304 and compares to a tissue segmenter module 318 list of tissue, e.g., tumor and non-tumor tissue locations determined from tissue classification model 320 and determines whether the lymphocyte is in tumor or non-tumor region.

The use of a three-class model facilitates, among other things, the counting of each individual cell, especially when two or more cells overlap each other for more accurate classification. Tumor infiltrating lymphocytes will overlap tumor cells. In traditional two-class cell outlining models that only label whether a pixel contains a cell outer edge or not, each clump of two or more overlapping cells would be counted as one cell, which can produce inaccurate results.

In addition to using a three-class model, the cell segmentation model 316 may be configured to avoid the possibility that a cell that spans two tiles is counted twice, by adding a buffer around all four sides of each tile that is slightly wider than an average cell. The intention is to only count cells that appear in the center, non-buffered region for each tile. In this case, tiles will be placed so that the center, non-buffered region of neighboring tiles are adjacent and non-overlapping. Neighboring tiles will overlap in their respective buffer regions.

In one example, the cell segmentation algorithm of the model 316 may be formed of two UNet models. One UNet model may be trained with images of mixed tissue classes, where a human analyst has highlighted the outer edge of each cell and classified each cell according to tissue class. In one example, training data includes digital slide images where every pixel has been labeled as either the interior of a cell, the outer edge of a cell, or the background which is exterior to every cell. In another example, the training data includes digital slide images where every pixel has been labeled with a yes or no to indicate whether it depicts the outer edge of a cell. This UNet model can recognize the outer edges of many types of cells and may classify each cell according to cell shape or its location within a tissue class region assigned by the tissue classification module 320.

Another UNet model may be trained with images of many cells of a single tissue class, or images of a diverse set of cells where cells of only one tissue class are outlined in a binary mask. In one example, the training set is labeled by associating a first value with all pixels showing a cell type of interest and a second value to all other pixels. Visually, an image labeled in this way might appear as a black and white image wherein all pixels showing a tissue class of interest would be white and all other pixels would be black, or vice versa. For example, the images may have only labeled lymphocytes. This UNet model can recognize the outer edges of that particular cell type and assign a label to cells of that type in the digital image of the slide.

Whereas, the cell segmentation model 316 is a trained cell segmentation model that may be used for cell detection, in some examples the model 316 is configured as a biomarker detection model, configured as a pixel-level classifier that classify pixels as corresponding to a biomarker.

Turning to the deep learning framework multiscale classifier module 306, the tissue segmentation model 318 may be configured in a similar manner to the segmentation model 316, that is, as a three-class semantic segmentation FCN model developed by modifying a UNet classifier replacing a loss function with a cross-entropy function, focal loss function, or mean square error function to form a three-class segmentation model. The model 318 may identify the interior, exterior, and boundary of various tissue types in tiles.

The tissue classification model 320 is a tile-based classifier configured to classify tiles as corresponding to one of a plurality of different tissue classifications. Examples of tissue classes include but are not limited to tumor, stroma, normal, lymphocyte, fat, muscle, blood vessel, immune cluster, necrosis, hyperplasia/dysplasia, red blood cells, and tissue classes or cell types that are positive (contain a target molecule of an IHC stain, especially in a quantity larger than a certain threshold) or negative for an IHC stain target molecule (do not contain that molecule or contain a quantity of that molecule lower than a certain threshold). Examples also include tumor positive, tumor negative, lymphocyte positive, and lymphocyte negative.

With the cell segmentation in a histopathology image generated by the cell segmentation model 316 and the tissue classification from the tissue classification model 302, a biomarker classification model 322 receives data from both and determines a predicted biomarker presence in the histopathology image, and in particularly, with the multiscale configuration, the prediction biomarker presence in each tile image of the histopathology image. The biomarker classification model 322 may be a trained classifier implemented in the deep learning framework model 306 as shown or implemented separate from the model 306, such as in the deep learning post-processing controller 308.

In some examples of the biomarker classification model detecting a TILS biomarker, the tissue classification model 320 is trained to identify a percentage TILs within a tile image, the cell segmenter 316 determines the cell boundary, and the biomarker classification model 322 classifies the tile image based on the percentage of TILs within a cell interior resulting in a classification: (i) Tumor—IHC/Lymphocyte positive or (ii) Non-tumor—IHC/Lymphocyte positive.

In some examples of the biomarker classification model detecting a ploidy, the biomarker classification model 322 may be trained with ploidy model based off of histopathology images and associated ploidy scores using techniques provided, for example, in Coudray N, Ocampo P S, Sakellaropoulos T, Narula N, Snuderl M, Fenyo D, et al., Classification and mutation prediction from non-small cell lung cancer histopathology images using deep learning. Nat Med. 2018; 24:1559-67.)

In an example, the training data may be data such as real karyotypes, determined by cytogeneticists, although in some examples, the biomarker classification model 322 may be configured to infer such data. The ploidy data may be formatted in columns of: chromosome number, start position, stop position, region length. Ploidy scores may be determined from DNA sequencing data and may be specific to a gene, chromosome, or an arm of a chromosome. The ploidy score may be global and might describe the entire genome of the sample (global CNV/copy number variation may cause a change in hematoxylin staining of the tumor nuclei), and may be a score calculated by averaging the ploidy score for each region in the genome, where a local, regional ploidy score might be weighted according to the length of each region that is associated with that score. The trained ploidy model of the biomarker classification model 322 may be specific to a gene, an arm of a chromosome, or an entire chromosome, because each section might affect the cell morphology seen in histopathology images differently. Predicted ploidy biomarker data may affect accept/reject analysis, because if the tumor purity or cell count on a slide is low but the ploidy is higher than usual, there might still be enough material for genetic testing. A biomarker metrics processor 326 may be configured to make such determinations prior to report generation.

In some examples of the biomarker classification model detecting a signet ring morphology, the biomarker classification model 322 may be trained with a signet ring morphology model based off classification techniques such as the poorly cohesive (PC), signet ring cell (SRC), and Lauren sub-classifications and others described in Mariette, C., Carneiro, F., Grabsch, H. I. et al. Consensus on the pathological definition and classification of poorly cohesive gastric carcinoma. Gastric Cancer 22, 1-9 (2019) and other signet ring morphology classifications.

In some examples of the biomarker classification model detecting a NC Ratio, the cell segmentation model 316 may be configured with three-class UNet described herein, but where the model is trained to identify three classes: nucleus, cytoplasm, and cell border/non-cell background. In an example, the training data may be images where each pixel is manually annotated with one of these three classes, and/or images that have been annotated in this way by a trained model, as discussed in the example of FIG. 4, updated training images.

Thus, the cell segmentation model 316 may be trained to analyze an input image and assign one of the three classes to each pixel, define cells as a group of adjacent nucleus pixels and all cytoplasm pixels between the nucleus pixels and the next nearest border pixels, and then for each cell, the biomarker classification model 322 may be configured to calculate the nucleus:cytoplasm ratio as the area (number of pixels) of the cell's nucleus divided by the area (number of pixels) of the entire cell (nucleus and cytoplasm).

To identify tumor tissue and tumor status for tissue, the deep learning framework 306 may be configured using a FCN classifier in an example. Whereas in an example the deep learning framework 304 may be configured as a pixel-resolution FCN classifier, the deep learning framework 306 may configured as a tile-resolution FCN classification model, or tile-resolution CNN model, i.e., performing a classification for an entire received tile of image data.

The classification model 320 of the module 306, for example, may be configured to classify tissue in a tile as corresponding to one of a number of tissue classes, such as biomarker status, tumor status, tissue type, and/or tumor state/condition, or other information. The module 306, in the illustrated example, is configured having a tissue classification 320 and a tissue segmentation model 322. In an example implementation of a TILs biomarker, the tissue classification model 320 may classify tissue using tissue classifications, such as Tumor—IHC positive, Tumor—IHC negative, Necrosis, Stroma, Epithelium, or Blood. The tissue segmentation model 328 identifies boundaries for the different tissue types identified by the tissue classification model 320 and generates metadata for use in visually display boundaries and color coding for different tissue types in an overlay mapping report generator by the post-processing controller 308.

In an example implementation, the deep learning framework 300 performs classifications on a tile-basis by receiving tiles (i.e., sub-images) from the processes of classification models 320 and 322. In some examples, tiling may be performed by the framework 306 using a tiling mask, and in addition to performing tissue classifications the module 306 itself may send the generated sub-images to the module 304 for pixel-level segmentation. The module 306 may examine each tile in a sequential manner, one after another, or the module 306 may examine each tile in parallel by the nature of the matrix generated by the FCN model for faster processing of images.

In some examples, the tissue segmentation model 318 receives pixel-resolution cell segmentation data and/or pixel-resolution biomarker segmentation data from the module 304 and performs statistical analysis on a tile basis and on an image basis. In some examples, that statistical analysis determines (i) the area of image data covered by tissue, e.g., the area of the stained histopathology slide covered by tissue, and (ii) the number of cells in the image data, e.g., the number of cells in the stained histopathology slide. The tissue segmentation model 318, for example, can accumulate cell and tissue classifications for each tile of an image until all tiles forming the image have been classified.

Where the deep learning framework is a multiscale classifier module for classifying biomarkers on tile-basis, the deep learning framework 300 is further configured to classify biomarkers using classifications trained from a slide-level training images, without the need for tile-level labeling. For example, and as further discussed hereinbelow, slide-level training images received by the image discriminator may be provided to the slide level label piper 313 having a MIL controller configured to perform processes herein, such as those described in FIGS. 18-26, to generate a plurality of tile images with inferred classifications, and optionally perform tile selection on those tiles to train a tissue classification model 317 and a biomarker classification model 319. Example single-scale classifiers include a CMS biomarker classification model, where the output is a CMS class, and an HRD biomarker classification model, where the output is HRD+ or HRD−. These classifications may be performed for an entire histopathology image to determine a biomarker prediction or on each tile image of that digital image and analyzed by the biomarker metrics processor 326 to determine a biomarker prediction from the tile images.

In some examples of the biomarker classification model detecting HRD, the biomarker classification model 319 may be configured to predict HRD. Training of a HRD model within the classifier 318 may be based off of histopathology images and matched HRD score. For example, training data may be generated by H&E images and RNA sequence data, including, in some examples, RNA expression profile data that is fed to an HRD model and fed back in for further training, as with the updated training data 403 in FIG. 4. The training data may be derived from tumor organoids: H&E images from an organoid paired with a measure of the organoid's sensitivity to PARP inhibitors indicating HRD or a result of the RNA team's HRD model run on the organoid's RNA expression profile. An example HRD prediction model of the biomarker classification model 319 is described in Peng, Guang et al. Genome-wide transcriptome profiling of homologous recombination DNA repair, Nature communications vol. 5 (2014): 3361 and van Laar, R. K., Ma, X.-J., de Jong, D., Wehkamp, D., Floore, A. N., Warmoes, M. O., Simon, I., Wang, W., Erlander, M., van't Veer, L. J. and Glas, A. M. (2009), Implementation of a novel microarray-based diagnostic test for cancer of unknown primary. Int. J. Cancer, 125: 1390-1397.

In an example, a deep learning framework may identify HRD from an H&E slide using RNA expression to identify a slide level label indicative of the percentage of the slide that contains a biomarker expressing cell. In one example, an activation map approach for the RNA label may be applied to the whole slide, either as a binary label (i.e. Positive or Negative HRD expression somewhere in the tissue), or as a continuous percentage (i.e. 62% of cells in the image were found to express HRD). A binary RNA label may be generated by next generation sequencing of a specimen and a cell percentage label may be generated by applying single cell RNA sequencing. In one example, single cell sequencing may identify cell-types and quantities present in the RNA expression from the NGS.

Training a tile based deep learning network to predict a biomarker classification label for each tile of the whole slide image may be performed using any of the methods described herein. Once trained, the model may be applied to a method of activation mapping to each tile. Activation Mapping may be performed using Grad-CAM (gradient class activation mapping) or guided back-propagation. Both allow identification of which regions of a tile contribute most to the classification. In one example, the parts of the tile that contribute most to the HRD positive class may be cells clustered in the upper right corner of a tile. Cells within the identified active regions may then be labeled HRD positive cells.

Proving that the model performs to clinical certainty may include comparing model results to a source of ground truth. One possible generation of ground truth may include isolating small regions of tissue, each containing <100 cells by segmenting through a tissue microarray and sequencing each region separately to get RNA labels of each region. Generating a ground truth may further include classifying these regions with a biomarker classification model, and identifying with what accuracy the activation maps highlight cells in regions that have high HRD expression and ignore most cells in regions that have low HRD expression.

When training a tile based deep learning network to predict a biomarker classification label for each tile utilizes a strongly supervised approach to generate biomarker labels to identify the HRD status (Positive or Negative) of individual cells. Single cell RNA sequencing may be used alone, or in combination with laser guided micro-dissection to extract one cell at a time, to achieve labels for each cell. In one example a cell segmentation model may be incorporated to first get the outline of the cells, then an artificial intelligence engine may classify the pixel values inside each of the cell contours according to biomarker status. In another example masks of the image may be generated where HRD positive cells are assigned a first value and HRD negative cells are assigned a second value. A single scale deep learning framework may then be trained using slides with masks to identify cells that express HRD.

In some examples of the biomarker classification model detecting CMS, the biomarker classification model 319 may be configured to predict CMS. Such biomarker classification may be configured to classify segmented cells as corresponding to cancer specific classifications. For example, four trained CMS classifications in primary colorectal cancer include: 1-immune infiltrated (Often BRAFmut, MSI-High, TMB-High); 2—canonical (Often ERBB/MYC/WNT driven); 3—metabolic (Often KRASmut); and 4—mesenchymal (Often TGF-B driven). In other examples more trained CMS classifications may be used, but generally two or more CMS subtypes are classified in examples herein. Further still, other cancer types may have their own trained CMS categories, and the classifier 318 may be configured to have a model for subtyping each cancer type. Example techniques for developing CMS classifications of 4, 5, 6, 7 or greater numbers of CMS classifications are using the CMSCcaller described in Eide, P. W., Bruun, J., Lothe, R. A. et al. CMScaller: an R package for consensus molecular subtyping of colorectal cancer pre-clinical models. Sci Rep 7, 16618 (2017) and https://github.com/peterawe/CMScaller.

Training of a CMS model within the classifier 318 may be based off of histopathology images matched CMS category assignment. CMS category assignment may be based on RNA expression profiles and in one example, are generated by an R program that uses Nearest Template Prediction, called CMS Caller (see, Eide, P. W., Bruun, J., Lothe, R. A. et al. CMScaller: an R package for consensus molecular subtyping of colorectal cancer pre-clinical models. Sci Rep 7, 16618 (2017) and https://github.com/peterawe/CMScaller). Alternative classifications using random forest model are described in Guinney, J., Dienstmann, R., Wang, X. et al. The consensus molecular subtypes of colorectal cancer. Nat Med 21, 1350-1356 (2015). For example, a CMS Caller looks at each RNA sequence data sample to determine is each gene over or under the mean and gives a binary classification for each gene. This avoids batch effects, for example between different RNA sequence data sets. Training data could also include DNA data, IHC data, mucin markers, therapy response/survival data from clinical reports. These may or may not be associated with a CMS category assignment. For example, CMS 4 IHC should stain positive for TGFbeta, CMS 1 IHC should be positive for CD3/CD8, CMS 2 and 3 have mucin gene changes, CMS 2 responds to cetuximab, CMS 1 responds better to avastin. CMS 1 has best survival prognosis, CMS 4 has worst. (see slide 12 of CMS slides). CMS categories 1 and 4 can be detected from H&E. With training, the architecture of FIG. 4, for example, can be used to train the model to identify and classify the difference between CMS 2 and 3.

In an example, the biomarker classification model 319 may be configured to identify five CRC intrinsic subtypes (CRIS) endowed with distinctive molecular, functional and phenotypic peculiarities: (i) CRIS-A: mucinous, glycolytic, enriched for microsatellite instability or KRAS mutations; (ii) CRIS-B: TGF-β pathway activity, epithelial-mesenchymal transition, poor prognosis; (iii) CRIS-C: elevated EGFR signalling, sensitivity to EGFR inhibitors; (iv) CRIS-D: WNT activation, IGF2 gene overexpression and amplification; and (v) CRIS-E: Paneth cell-like phenotype, TP53 mutations. CRIS subtypes successfully categorize independent sets of primary and metastatic CRCs, with limited overlap on existing transcriptional classes and unprecedented predictive and prognostic performances. See, e.g., Isella, C., Brundu, F., Bellomo, S. et al. Selective analysis of cancer-cell intrinsic transcriptional traits defines novel clinically relevant subtypes of colorectal cancer. Nat Commun 8, 15107 (2017).

For biomarker detection, the biomarker classification model 319 may be trained with a CMS model that predicts for each tile, a CMS classification, identifying different tissue types (e.g., stroma) for that classification, in place of trying to mere average CMS classification across all tiles. In an example, each tile would be processed, and the CMS model would generate a compressed representation with each tile's associated pixel data and each tile would be assigned into a class (cluster 1, cluster 2, etc.), based on patterns in each tile's pixel data and similarities among the tiles. The list of the percentage of tiles in the image that belong to each cluster could be a cluster profile for the image and provided by a report generator. In an example, each profile would be fed to the model with a corresponding CMS designation or RNA expression profile (which was the original method used to define CMS categories) for training. In another example, each tile from every training slide mage is annotated according to the overall CMS category assigned to the entire slide from which the tile originated, then the tiles are clustered and analyzed to determine which clusters are most closely associated with CMS category.

In some examples, the biomarker classification model 319 (as well sa the biomarker classification model 322) may cluster each tile into a discreet number of clusters, in place of performing the same classification on each tile and weighting that tile classification equally. One way to achieve is to include attention layer in the biomarker classification model. In an example, all tiles from all training slides may be categorized into a duster, then, if the number of tiles in a duster isn't statistically related to biomarker, that duster is not weighted as high as a cluster that is associated with biomarker. In other examples, majority voting techniques may be used to train the biomarker classification model 319 (or model 322).

While shown as separate models, the biomarker classification models 322 and 319 may each be configured to include all or parts of corresponding tissue classification models, cell segmentation models, and tissue segmentations models, as may be the case for classifying various biomarkers herein. Furthermore, while the biomarker classification model 322 is shown contained within the multiscale classifier module 306 and the biomarker classification model 319 is shown contained within the single-scale classifier module 307, in some examples, all or parts of these biomarker classification models may be implemented in the post-processing controller 308, as may be the case for classifying various biomarkers herein. Further, while described as tile-level or slide-level classification models, in some examples, the biomarker classification models 322 and 319 may be configured as pixel-level classifiers, in some examples.

From the determinations made by the modules 304, 306, and 307, the post-processing controller 308 can determine whether the image data contains an amount of tissue that exceeds a threshold and/or satisfies a criterion, for example enough tissue for genetic analysis, enough tissue to use the image data as training images during a learning phase of the deep learning framework, or enough tissue to combine the image data with an already existing trained classifier model.

Thus, in various examples herein, including those described in reference to FIG. 3 and elsewhere herein, a patient report may be generated. The report may be presented to a patient, physician, medical personnel, or researcher in a digital copy (for example, a JSON object, a pdf file, or an image on a website or portal), a hard copy (for example, printed on paper or another tangible medium), as audio (for example, recorded or streaming), or in another format.

The report may include information related to gene expression calls (for example, overexpression or underexpression of a given gene), detected genetic variants, other characteristics of a patient's sample and/or clinical records. The report may further include clinical trials for which the patient is eligible, therapies that may match the patient and/or adverse effects predicted if the patient receives a given therapy, based on the detected genetic variants, other characteristics of the sample and/or clinical records.

The results included in the report and/or additional results (for example, from the bioinformatics pipeline) may be used to analyze a database of clinical data, especially to determine whether there is a trend showing that a therapy slowed cancer progression in other patients having the same or similar results as the specimen. The results may also be used to design tumor organoid experiments. For example, an organoid may be genetically engineered to have the same characteristics as the specimen and may be observed after exposure to a therapy to determine whether the therapy can reduce the growth rate of the organoid, and thus may be likely to reduce the growth rate of the patient associated with the specimen.

In an example, the post-processing controller 308 is further configured to determine a number of different biomarker prediction metrics and a number of tumor prediction metrics, e.g., using a biomarker metrics processing module 326. Example prediction metrics include: tumor purity, number of tiles classified as a particular tissue class, number of cells, number of tumor infiltrating lymphocytes, clustering of cell types or tissue classes, densities of cell types or tissue classes, tumor cell characteristics—roundness, length, nuclei density, stroma thickness around tumor tissue, image pixel data stats, predicted patient survival, PD-L1 status, MSI, TMB, origin of a tumor, and immunotherapy/therapy response.

For example, the biomarker metrics processing module 326 may determine the number of tiles classified in one or more single tissue classes, the percentage of tiles classified in each tissue class, the ratio of the number of tiles classified in a first tissue class versus the number classified in a second tissue class for any two classes, and/or the total area of tiles classified in a single tissue class, for each tissue class. The module 326 may determine tumor purity, based on number of tiles classified as tumor versus other tissue classes, or based on number of cells located in tumor tiles versus number of cells located in other tissue class tiles. The module 326 may determine the number of cells for the entire histopathology image, within an area pre-defined by a user, within tiles classified as any one of the tissue classes, within a single grid tile, or over some area or region of interest, whether predetermined, selected by a user during operation of the system 300, or automatically by the system 300, for example, by determining a most-likely region of interest based on the image analysis. The module 326 may determine the clustering of cell types of tissue classes based on spacing and density of classified cells, spacing and distance of tissue class classified tiles, or any visually detectable features. In some examples, the module 326 determines the probability that two neighboring cells will be either two immune cells, two tumor cells, or one of each, for example. The module 326 determines tumor cell characteristics by determining average roundness, perimeter length, and/or nuclei density of identified tumor cells. The thickness of identified stroma may be used as a predictor of patient response to treatment. The image pixel data stats determined by the module 326 may include the mean, standard deviation, and sum for each tile of either a single image or of an aggregate of images for any pixel data, including the following: red green blue (RGB) value, optical density, hue, saturation, grayscale, and stain deconvolution. Further, the module 326 may calculate the location of lines, patterns of alternating brightness, outlines of shapes, staining patterns for segmented tissue classes and/or for segmented cells in the image. In any of these examples, the module 326 may be configured to make the determination/predicted status, and an overlay display generation module 324 then generates a report for displaying the determined information. For example, the overlay map generation module 324 may generate a network accessible user interface that allows a user to select different types of data to be displayed, and the module 324 generates an overlay map showing the selected different types of data overlaid on a rendition of the original stained image data.

Figure 4:
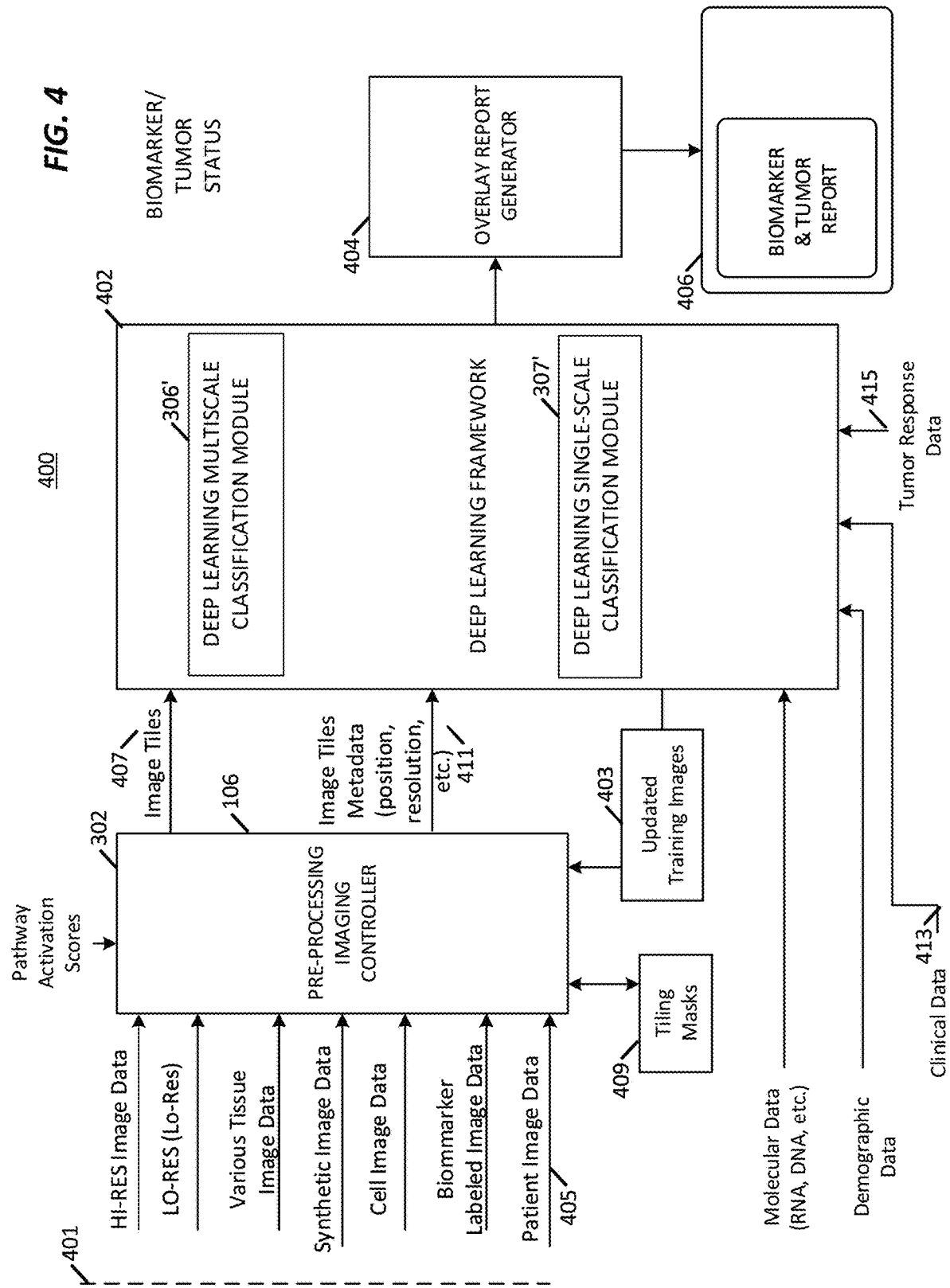
FIG. 4 is a block diagram of a schematic of a machine learning data flow, in accordance with an example.

FIG. 4 illustrates a machine learning data input/flow schematic 400 that may be implemented with the system 300 of FIG. 3 or, more generally, with any of the systems and processes described herein.

In training mode, where the deep learning frameworks in the system 300 are trained, various training data may be obtained. In the illustrated example, training image data 401 in the form of high resolution and low resolution histopathology images are provided to the pre-processing controller 302. As shown, the training images may include annotated tissue image data from various tissue types, e.g., tumor, stroma, normal, immune cluster, necrosis, hyperplasia/dysplasia, and red blood cells. As shown, the training images may include computer generated, synthetic image data, as well as image data of segmented cells (cell image data) and image data of labeled biomarkers (e.g., the biomarkers discussed herein), either slide-level label or tile-level labels (collectively, biomarker labeled image data). These training images may be digitally annotated, but in some examples, the tissue annotations are manually done. In some images, the training image data includes molecular data and/or demographic data, for example, as metadata within the image data. In the illustrated example, such data is separately fed to a deep learning framework 402 (formed of example implementations of a multiscale deep learning framework 306' and a single-scale deep learning framework 307'). Other training data may also be provided to the controller 302, such as pathway activation scores, for additional training of the deep learning framework.

In some examples, the deep learning framework 402 generates updated training images 403 that are annotated and segmented by the deep learning framework 402 and fed back into the framework 402 (or pre-processing controller 302) for use in updated training of the framework 402.

In a diagnostic mode, patient image data 405 is provided to the controller 302, for use in accordance with the examples herein.

Any of the image data herein, including patient image data and training image, may be histopathology image data, such as H&E slide images and/or IHC slide images. For IHC training images, for example, the images may be segmented images that differentiate between cytotoxic and regulatory t cells, or other cell types.

In some examples, the controller 302 generates image tiles 407, accessing one or more tiling masks 409, and tile metadata 411, which the controller 302 feeds as inputs to the deep learning framework 402, for determining predicted biomarker and/or tumor status and metrics, which are then provided to an overlay report generator 404 for generating a biomarker and tumor report 406. Optionally, the report 406 may include an overlay of the histopathology image and further include biomarker scoring data, such as percentage TILs, in an example.

In some examples, clinical data 413 is provided to the deep learning framework 402 for use in analyzing image data. Clinical data 413 may include health records, biopsy tissue type, anatomical location of biopsy. In some examples, tumor response data 415 collected from a patient after therapy is additionally provided to the deep learning framework 402 for determining changes in biomarker status, tumor status, and/or metrics thereof.

Figure 5:
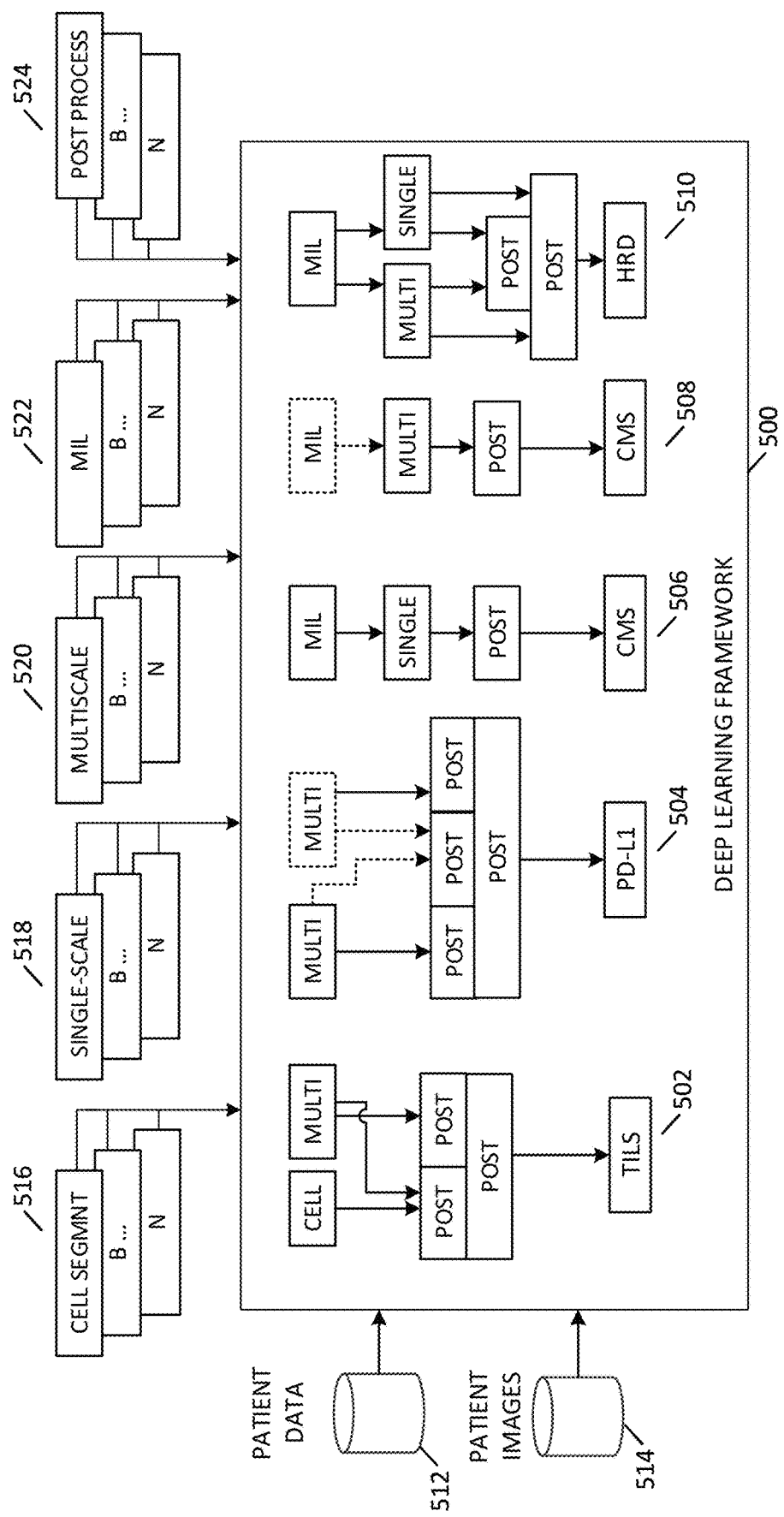
FIG. 5 is a block diagram of a schematic of a deep learning framework formed a plurality of different marker classification models, as may be implemented in the systems of FIG. 1 and FIG. 3, in accordance with an example.

FIG. 5 illustrates an example deep learning framework 500 formed of a plurality of different biomarker classification models. Elements in FIG. 5 are provided as follows. "Cell" refers to a cell segmentation model, e.g., a trained pixel-level segmentation model, in accordance with the examples herein. "Multi" refers to a multiscale (tile-based) tissue classification model, in accordance with the examples herein. "Post" refers to arithmetic calculations that may be performed in the final stages of a biomarker classification model configured to predict biomarker status in an image or in a tile image in response to one or more data from the "Cell" or "Multi" stages, in accordance with the examples herein. In one example, a "Post" may include identifying a majority vote such as summing the number of tiles in an image associated with each biomarker label and assigning the biomarker status in the image to the biomarker label with the largest sum. A two layer "Post" configuration refers to a two stage post-processing configuration where arithmetic calculations may be stacked. In one example, a first layer of post may include summing cells within a tile labeled tissue and summing lymphocyte cells within the same tile. A second layer may divide the lymphocyte cell count by the cell count to generate a ratio, which when compared to a threshold may be used to assign the biomarker status in the image based on whether the ratio exceeds the threshold. The final "Post" configuration may include other post-processing functionality such as report generation processes described herein. "Single" refers to a single-scale classification model, in accordance with the examples herein. "MIL" refers to an MIL controller, in accordance with examples herein. In the illustrated example, the deep learning framework 500 contains a TILS biomarker classification model 502, a PD-L1 classification model 504, a first CMS classification model 506 based on a "Single" classification architecture, a second CMS classification model 508 based on a "Multi" classification architecture, and an HRD classification model 510. Patient data 512, such as molecular data, demographic data, tumor response data, and patient images 514 are stored in datasets accessible by the deep learning framework 500.

Training data is also shown in the form of cell segmentation training data 516, single-scale classification biomarker training data 518, multiscale classification biomarker training data 520, MIL training data 522, and post-processing training data 524.

Figure 6:
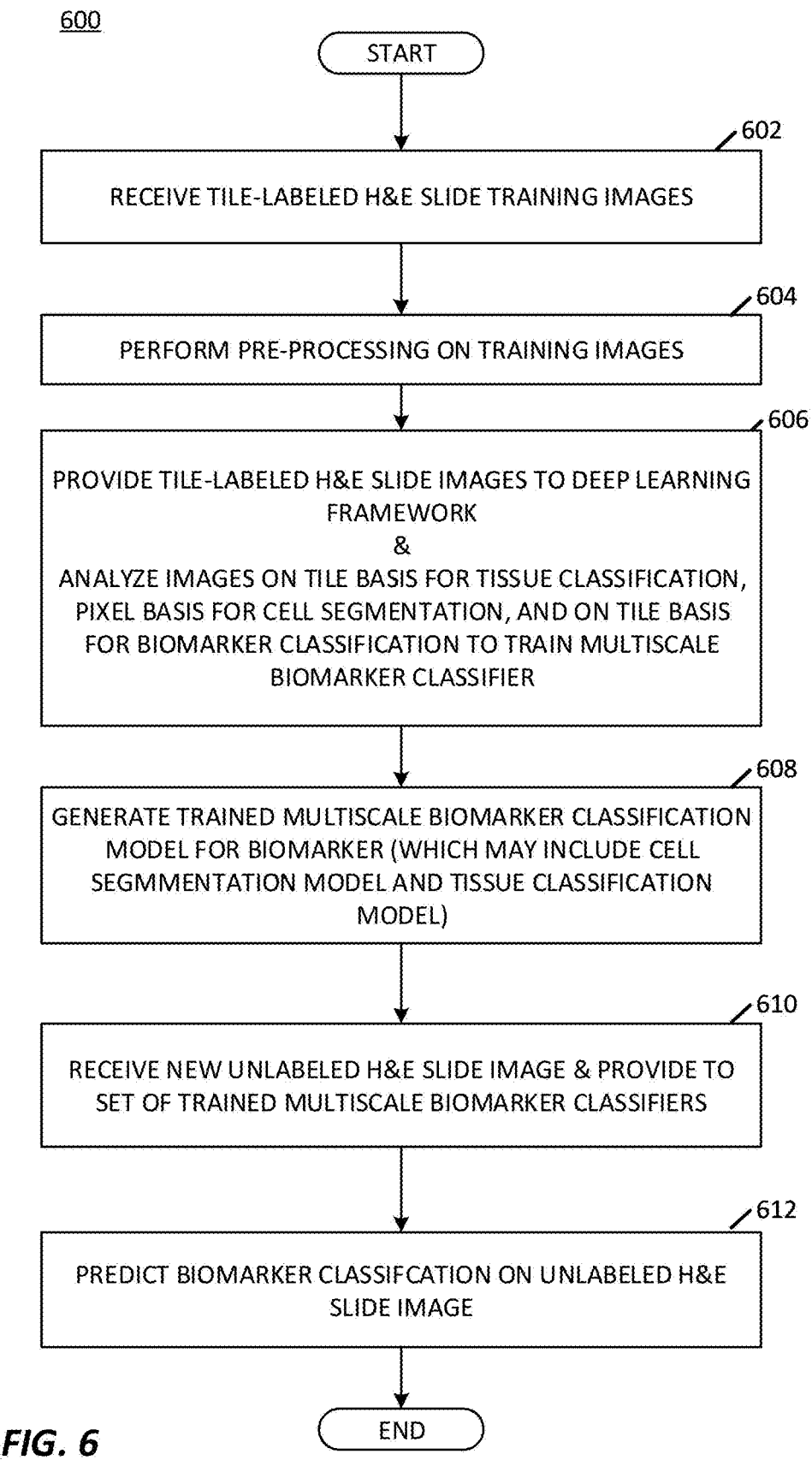
FIG. 6 is a block diagram of a process for imaging-based biomarker prediction, for example, as may be implemented for image-based nucleic acid yield prediction, in accordance with an example multiscale configuration.

FIG. 6 illustrates a process 600 that may be executed by the imaging-based biomarker prediction system 102, the deep learning framework 300, or the deep learning framework 402, in particular in a deep learning framework having a multiscale configuration.

As part of a training process, at a block 602, tile-labeled histopathology images are received at the deep learning framework 300. The histopathology images may be of any type herein, but are illustrated as digital H&E slide images in this example. These images may be training images of a previously-determined and labeled (and thus known) cancer type (e.g., for supervised learning configurations). In some examples, the images may be training images of a plurality of different cancer types. In some examples, the images may be training images that contain some or all images of an unknown or unlabeled cancer type (e.g., for unsupervised learning configurations). In some examples, the training images include digital H&E slide images with tissue classes annotated (for training the tile-resolution FCN tissue classifier) and other, digital H&E slide images with each cell annotated. In the example of training of TILS biomarker classification, each lymphocyte may be annotated in the H&E slide images (e.g., for training the pixel-resolution FCN segmentation classifiers annotated images to train UNet model classifiers). In some examples, the training images may be digital IHC stained images to train the pixel-resolution FCN segmentation classifiers, in particular images where IHC staining targets lymphocyte markers. In some examples, the training images will include molecular data, clinical data, or images paired with other annotations (like pathway activation scores, etc.).

In the illustrated example, at a block 604, a pre-processing is performed on the training images, such as the normalization processes described herein. Other pre-processing processes described herein may also be performed at the block 604.

At block 606, the tile-labeled H&E slide training images are provided to a deep learning framework and analyzed within the machine learning configuration thereof, such as a CNN and, more particular, a tile-resolution CNN, in some examples implemented as a FCN model, and, for analyzing tile images of the training images for tissue classification training, pixels of the training images for cell segmentation training, and in some examples tile images for biomarker classification training. The result, a block 608 generates a trained deep learning framework multiscale biomarker classification model, which may include a cell segmentation model and a tissue classification model. In training multiple biomarker classification models, the block 608 may generate a separate model for each of the biomarkers TILS, PD-L1, ploidy, NC ratio, and signet ring morphology.

As a prediction process, at a block 610 a new unlabeled histopathology image, such as a H&E slide image, is received and provided to the multiscale biomarker classification model, which at a block 612 predicts biomarker status for the received histopathology image as determined by the one or more biomarker classification models.

For example, new (unlabeled or labeled) histopathology images may be received at the block 610 from the physical clinical records system or primary care system and applied to a trained deep learning framework which applies its trained cell segmentation, tissue classification model, and biomarker classification models, and the block 612 determines a biomarker prediction score. That prediction score can be determined for an entire histopathology image or for different regions across the image. For example, for each image, the block 612 may generate an absolute count of how many biomarkers are on the image, a percentage of the number of cells in tumor regions that are associated with each of the biomarkers, and/or a designation of any biomarker classifications or other information. In some examples, the deep learning framework may identify predicted biomarkers for all identified tissue classes within the image. As such, a biomarker prediction probability score may vary across the image. For example, in predicting the presence of TILs, the process 612 may predict the presence of TILs at different locations within a histopathology image. TILs prediction would vary across the image, as a result. This is provided by way of example, block 612 may determine any number of metrics discussed herein.

Figure 9:
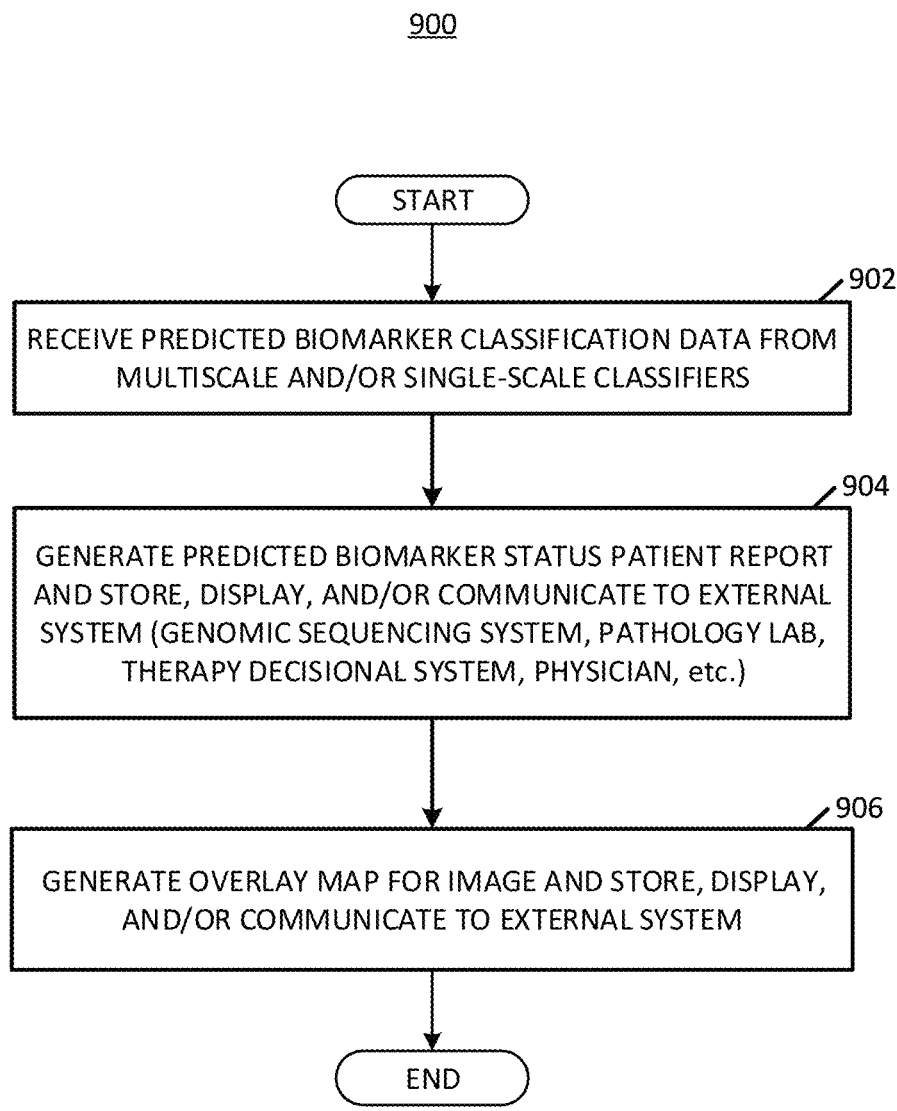
FIG. 9 is a block diagram of a process for generating a biomarker prediction report and overlay map as may be performed by the systems of FIGS. 1 and 3, in accordance with an example.

As shown in process 900 of FIG. 9, after prediction, the predicted biomarker classification may be received at report generator a block 902. A clinical report for the histopathology image, and thus for the patient, may be generated at a block 904 including predicted biomarker status and, at a block 906, an overlay map may be generated showing the predicted biomarker status for display to a clinician or for providing to a pathologist for determining a preferred immunotherapy corresponding to the predicted biomarker.

Figure 7:
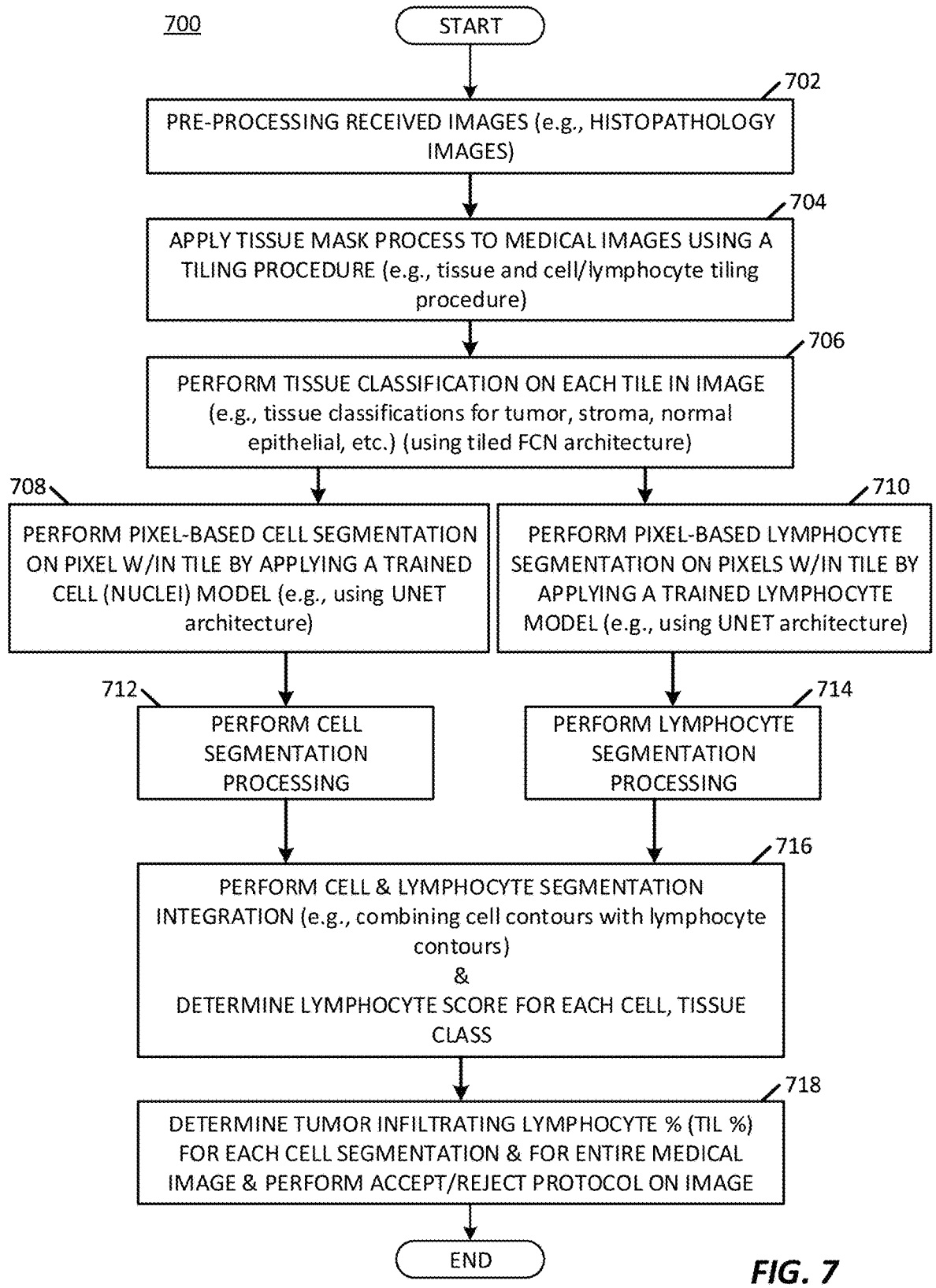
FIG. 7 is a block diagram of an example process for determining a predicted biomarker status, in accordance with an example implementation of the process of FIG. 6, in accordance with an example.

In FIG. 7, an example process 700 for determining predicted biomarker status, in particular predicting TILs status, is provided. Although the process 700 may be used to predict the status of any number of biomarkers and other metrics in accordance with the examples described herein.

A pre-processing controller receives histopathology images (702) and performs initial image processing, as described herein. In an example, the deep learning pre-processing controller receives an entire image file in any pyramidal TIFF format and identifies edges and outlines (e.g., performs a segmentation) of the viable tissue in the image. The output of block 702 may be a binary mask of the input image, e.g., with each pixel having a 0 or 1 value, where 0 denotes background and 1 denotes foreground/tissue. The dimensions of the mask may be the dimensions of the input slide when downsampled 128×. This binary mask may be temporarily buffered and provided to a tiling process 704.

At the process 704, the pre-processing controller applies a tissue mask process using a tiling procedure to divide the image into sub-images (i.e., tiles) that will be examined individually. Since the deep learning framework is configured to perform two different learning models (one for tissue classification and one for cell/lymphocyte segmentation), different tiling procedures for each model may be performed by the procedure 704. The process 704 may generate two outputs, each output containing a list of coordinates, e.g., defined from the upper-left most corner of tiles. The output lists may be temporarily buffered and passed to tissue classification and cell segmentation processes.

In the example of FIG. 7, tissue classification is performed at a process 706, which receives the histopathology image from the process 704 and performs tissue classification on each received tile using a trained tissue classification model. The trained tissue classification model is configured to classify each tile into different tissue classes (e.g., tumor, stroma, normal epithelium, etc.). Multiple layers of tiling may be used by the process 706 to reduce computational redundancy. For each tile, the trained tissue classification model calculates the class probability for each class stored in the model. The process 706 then determines the most likely class and assigns that class to the tile. The process 706 may output, as a result, a list of lists. Each nested interior list serves as nested classification that describes a single tile and contains the position of the tile, the probabilities that the tile is each of the classes contained in the model, and the identity of the most probable class. This information is listed for each tile. The list of lists may be saved into the deep learning framework pipeline output json file.

At processes 708 and 710, cell segmentation and lymphocyte segmentation are performed, respectively. The processes 708 and 710 receive the histopathology image and the tile list from processes 704 and 706. The process 708 applies the trained cell segmentation model; and the process 710 applies the trained lymphocyte segmentation model. That is, in the illustrated example, for each tile in the cell segmentation tile list, two pixel-resolution models are run in parallel. In an example, the two models both use a UNet architecture but have been trained with different training data. The cell segmentation model identifies cells and draws a border around every cell in the received tile. The lymphocyte segmentation model identifies lymphocyte and draws a border around every lymphocyte in the tile. Because Hematoxylin binds to DNA, performing "cell segmentation" using digital H&E slide images may also be referred to as nuclei segmentation. That is, the cell segmentation model process 708 performs nuclei segmentation on all cells, while the lymphocyte segmentation model process 710 performs nuclei segmentation on lymphocytes.

Because, in this example, the same UNet architecture is used for both, the processes 708 and 710 each produce two identically-formatted mask array outputs. Each output is a mask array with the same shape and size as the received tile. Each array element is either 0, 1, or 2, where 0 indicates a pixel/location that is predicted as background (i.e., outside the object); 1 indicates a pixel/location that is a predicted object border; and 2 indicates a pixel/location that is predicted object interior. For the cell segmentation model output, the object refers to a cell. For the lymphocyte segmentation model, the object refers to a lymphocyte. These masks array outputs may be temporarily buffered and provided to processes 712 and 714, respectively.

Processes 712 and 714 receive the output mask array for the cell segmentation (UNet) model and the output mask array for the lymphocyte segmentation (UNet) model, respectively. The processes 712 and 714 are performed for each received tile and are used to express the information in the mask arrays in terms of coordinates that are in the coordinate space of the original whole-slide image.

In an example, the process 712 may access a stored image processing library and use that library to find contours around the cell interior class, i.e., which corresponds to locations that have a 2 value in each mask. In this way, the process 712 may perform a cell registration process. The cell border class (denoted by locations with a 1 value in each mask) ensures separation between neighboring cell interiors. This generates a list of every contour on each mask. Then, by treating each contour as a filled polygon, the process 712 determines the coordinates of the contour's centroid (center of mass), from which the process 712 produces a centroid list. Next, to generate outputs that are in the coordinate space defined by the entire received image instead of the coordinate space that is specific to a single tile in the image, each coordinate in the contour lists and the centroid lists is shifted. Without this shift, each coordinate would be in the coordinate space of the image tile that contains it. The value of each shift is equal to the coordinates of the parent tile's upper-left corner on the received image. In this example, the process 714 performs the same processes as the process 712, but on the lymphocyte classes.

The processes 712 and 714 generate contour list outputs and centroid list outputs, each corresponding to their respective UNet segmentation model. A contour is a set of coordinates that, when connected, outline a detected object. Each contour can be represented as a line of text composed of its constituent coordinates sequentially printed as pairs of numbers. Each contour list from the processes 712 and 714 may be saved as a text file composed of many such lines. The centroid lists are a list of pairs of numbers. Each of these outputs may be buffered temporarily and provided to process 716.

The process 716 receives tissue classification output (list of lists) from process 706, cell centroids and contour lists from process 712, and the lymphocyte centroids and contour lists from process 714, and performs cell segmentation integration.

For example, the process 716 may integrate the paired outputs of the processes 712 and 714 and produce a single concise list that contains the most important information about cells. In an example, there are two main components of the process 716.

In a first component of the process 716, information found in the cell segmentation model and the lymphocyte segmentation model is combined. Before the information is combined, it exists as a list of cell contours and a list of lymphocyte contours, but the lymphocyte contours are not necessarily a subset of the cell contours because they are the outputs of two independent models (712 and 714). Therefore, it is desirable to make the lymphocytes a subset of the cells because (1) biologically, if an object is not a cell, it cannot be a lymphocyte, because lymphocytes are a type of cell (2) it is desirable to report percentages for data sets that have the same denominator. Therefore, the cell segmentation integration process 716 may be performed by comparing the location of each cell with the location of every lymphocyte. (In one example, this may be done only for the objects within a single tile, so the number of comparisons is not too high). In an example, if and only if a cell is "sufficiently close" to a lymphocyte, that cell is considered a lymphocyte. The definition of "sufficiently close" may be established by empirically determining the median radius of objects detected by the lymphocyte segmentation model across a set of training histopathology images. Note this updated training image set (e.g., 403 in FIG. 4) is different than the training set of images used to train the model as this set of training histopathology images are annotated images generated by the model itself, resulting in orders of magnitudes greater numbers of images, e.g., millions of automatically annotated images, that form a new or updated training set. Indeed, the training set for the model may continue to grow with new received medical images that satisfy an accept/reject condition. This may be the case for tissue classification model, as well as the cell segmentation and lymphocyte segmentation models. By generating a new training set from the model, as it assesses subsequent images, the model is able to (1) use the median of millions of cells instead of just the ones outlined on the training tiles and (2) compare the actual size of objects that get detected, not human-drawn annotation sizes). Lymphocyte nuclei are typically spherical, so in an example all of these objects were modeled as circles (since they are two-dimensional slices of spheres). The radius of these circles was calculated, and the median value was used to determine the typical size of lymphocyte detection. The result is that the final cell list is exactly the objects found by the cell segmentation model, while the purpose of the lymphocyte segmentation model is to provide a Boolean True/False label for each cell in that list.

In a second component of the process 716, each cell is binned into one of the tissue classification tiles (from process 706) based on location. It is noted that in the example discussed here, the cell segmentation tiles may be of a different size than the tissue classification tiles because the models have different architectures. Nevertheless, the process 716 has the coordinates for each cell centroid, the coordinates for the top-left corner of each tissue classification tile, and the size of each tissue classification tile, and is configured to determine the parent tile for each cell based on its centroid location.

The process 716 generates an output that is a list of lists. Each nested interior list serves as nested classification that describes a single cell, and contains the cell's centroid's coordinates, the tile number of its parent tile, the tissue class of its parent tile, and whether the cell is classified as a lymphocyte or not. This information is listed for each cell, and the output list is saved into the deep learning framework pipeline output json file.

Process 718, which may be implemented by a post-processing controller such as the biomarker metrics processing module 326, determines any of a number of different biomarker metrics, in particular for this example predicted TILs status and other TILs metrics, as discussed.

For example, the process 718 may be configured to perform tissue area calculations to determine the area covered by tissue, based on the tissue mask used in process 704. Because, in some examples, the tissue mask is a Boolean array that takes on values of 1 where tissue is present and 0 elsewhere, the process 718 may count the number of 1's gives a measure of tissue area. This value is the number of square pixels at $128x$ downsampling. Multiplying this by 16384 (i.e., for a 128*128 tissue mask) gives the number of square pixels at native resolution (referred to as "x"). An image native resolution indicates how many pixels are present per micron, and taking the square of this number gives the number of square pixels per square micron (referred to as "y"). Dividing the number of square pixels at native resolution by this resolution scaling factor (or, using the variables defined above, x/y) yields the number of square microns covered by tissue, and thus a tissue area calculation. That is, the process 718 can generate a floating point number in $[0, \infty)$ that indicates the tissue area in square microns. This value may then be used in an accept/reject model process discussed below.

As an example of other biomarker statistics, the process 718 may be further configured to perform a total nuclei calculation using the cell segmentation integration output from process 716. For example, the total number of nuclei on the slide is determined as the number of entries in the cell segmentation integration output. The process 718 may also perform a tumor nuclei % calculation based on this output from the process 716. The total number of tumor nuclei on an image is the number of entries in the cell segmentation integration output that satisfy requirements: (i) the tissue class of the parent tile is tumor and (ii) the cell is not classified as a lymphocyte.

In addition to determining biomarker statistics, the process 718 may be further configured to perform an accept/reject process based on the determined tissue area, total nuclei count, and tumor nuclei count. In an example, the process 718 may be configured with a logistic regression model, and these three variables are used as inputs, where the model output is a binary recommendation for whether the slide should be accepted for molecular sequencing or rejected. The logistic regression model may be trained on a training set of images using these derived variables. For example, the training images may be formed of accepted histopathology images that were previously sent for sequencing, as well as histopathology images that were rejected during routine pathology review. Alternatively, there may be a set threshold, for example, 20% of nuclei on slide are tumor or a minimum number of tumor cells may be required. In some examples, the model may also consider DNA ploidy of the tumor cells (data from karyotyping or DNA sequencing information) and may calculate an adjusted estimate of available genetic material by multiplying the number of tumor nuclei by the average number of copies of chromosomes detected in each tumor nucleus, divided by the normally expected copy number of 2. In some examples, the logistic regression model may be configured to have three possible outputs (instead of two) by adding an uncertainty zone between accept and reject that recommends manual review. For example, the penultimate output of the logistic regression model is a real number, and the last step of the model would, in some examples, threshold this number at 0 to produce the binary classification. Instead, in some examples, an uncertainty zone is defined as a range of numbers that includes 0; where values higher than this range correspond to rejection, values in the range correspond to manual review, and values below this range correspond to acceptance. The process 718 may be configured to calculate a size of this uncertainty zone by performing a cross-validation experiment. For example, the process 718 may perform a training process repeated many times, but where in each repetition, a different random subset of the images in the training set are used. That will produce many final models that are similar but not identical, and the process 718 may use this variation to determine the uncertainty range in the final logistic regression model. Therefore, the process 718 may generate a binary accept/reject output in some examples and an accept/reject/manual review output in some examples.

Using the recommendation from the process 718, a decision is made. For example, the deep learning output post-processing controller may generate a report for images that are indicated as "accept" and automatically send those images to a genomic sequencing system (112) for molecular sequencing, whereas images that are recommended "reject" are rejected and are not sent for molecular sequencing. If the "manual review" option is configured and recommended, the image may be sent to a pathologist or team of pathologists (118) to review the slide and to decide whether it should be sent for molecular sequencing or rejected.

Figure 8:
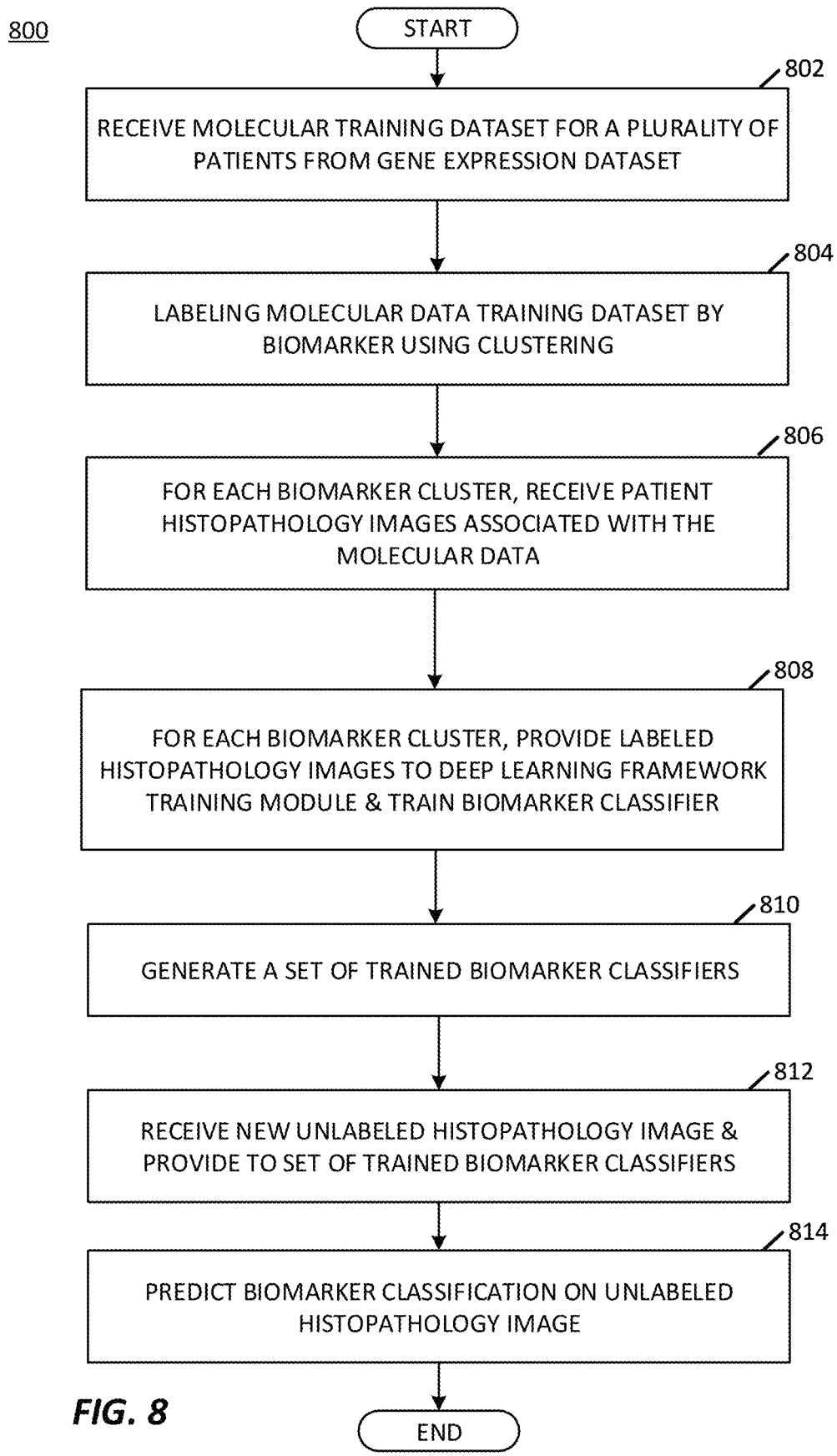
FIG. 8 is a block diagram of a process for imaging-based biomarker prediction, in accordance with an example single-scale configuration.

FIG. 8 illustrates an example process 800 that may be executed by the imaging-based biomarker prediction system 102, the deep learning framework 300, or the deep learning framework 402, in particular in a deep learning framework having a single-scale configuration.

At a process 802, molecular training data is received at the imaging-based biomarker prediction system. This molecular training data is for a plurality of patients and may be obtained from a gene expression dataset, such as from sources described herein. In some examples, the molecular training data includes RNA sequence data. At a block 804, the molecular training data is labeled by biomarker. One form of biomarker clustering includes labeling that may be performed by taking pre-existing labels associated with the specimen, such as tumor sub-type, and associating the label with the molecular training data. Alternately, or in addition, the labeling may be performed by clustering, such as the use of an an automatic clustering algorithm. One exemplary algorithm, in the case of a CMS sub-type biomarker, is an algorithm to identify CMS sub-types in the molecular training data and cluster training data according to CMS sub-type. This automatic clustering may be performed within a deep learning framework single-class classifier module, for example, or within a slide-level label pipeline, such as those in the deep learning framework 300. In some examples, the molecular training data received at block 802 is RNA sequence data generated using an RNA wet lab, for example, and processed using a bioinformatics pipeline.

In various embodiments, for example, each transcriptome data set may be generated by processing a patient or tumor organoid sample through RNA whole exome next generation sequencing (NGS) to generate RNA sequencing data, and the RNA sequencing data may be processed by a bioinformatics pipeline to generate a RNA-seq expression profile for each sample. The patient sample may be a tissue sample or blood sample containing cancer cells.

RNA may be isolated from blood samples or tissue sections using commercially available reagents, for example, proteinase K, TURBO DNase-I, and/or RNA clean XP beads. The isolated RNA may be subjected to a quality control protocol to determine the concentration and/or quantity of the RNA molecules, including the use of a fluorescent dye and a fluorescence microplate reader, standard spectrofluorometer, or filter fluorometer.

cDNA libraries may be prepared from the isolated RNA, purified, and selected for cDNA molecule size selection using commercially available reagents, for example Roche KAPA Hyper Beads. cDNA library preparation may include reverse transcription. In another example, a New England Biolabs (NEB) kit may be used. cDNA library preparation may include the ligation of adapters onto the cDNA molecules. For example, UDI adapters, including Roche SeqCap dual end adapters, or UMI adapters (for example, full length or stubby Y adapters) may be ligated to the cDNA molecules. In this example, adapters are nucleic acid molecules that may serve as barcodes to identify cDNA molecules according to the sample from which they were derived and/or to facilitate the downstream bioinformatics processing and/or the next generation sequencing reaction. The sequence of nucleotides in the adapters may be specific to a sample in order to distinguish between sequencing data obtained for different samples. The adapters may facilitate the binding of the cDNA molecules to anchor oligonucleotide molecules on the sequencer flow cell and may serve as a seed for the sequencing process by providing a starting point for the sequencing reaction.

cDNA libraries may be amplified and purified using reagents, for example, Axygen MAG PCR clean up beads. Amplification may include polymerase chain reaction (PCR) techniques, which are distinct from quantitative or reverse transcription quantitative PCR (qPCR or RT-qPCR). Then the concentration and/or quantity of the cDNA molecules may be quantified using a fluorescent dye and a fluorescence microplate reader, standard spectrofluorometer, or filter fluorometer.

cDNA libraries may be pooled and treated with reagents to reduce off-target capture, for example Human COT-1 and/or IDT xGen Universal Blockers, before being dried in a vacufuge. Pools may then be resuspended in a hybridization mix, for example, IDT xGen Lockdown, and probes may be added to each pool, for example, IDT xGen Exome Research Panel v1.0 probes, IDT xGen Exome Research Panel v2.0 probes, other IDT probe panels, Roche probe panels, or other probes. Pools may be incubated in an incubator, PCR machine, water bath, or other temperature modulating device to allow probes to hybridize. Pools may then be mixed with Streptavidin-coated beads or another means for capturing hybridized cDNA-probe molecules, especially cDNA molecules representing exons of the human genome. In another embodiment, polyA capture may be used. Pools may be amplified and purified once more using commercially available reagents, for example, the KAPA HiFi Library Amplification kit and Axygen MAG PCR clean up beads, respectively.

The cDNA library may be analyzed to determine the concentration or quantity of cDNA molecules, for example by using a fluorescent dye (for example, PicoGreen pool quantification) and a fluorescence microplate reader, standard spectrofluorometer, or filter fluorometer. The cDNA library may also be analyzed to determine the fragment size of cDNA molecules, which may be done through gel electrophoresis techniques and may include the use of a device such as a LabChip GX Touch. Pools may be cluster amplified using a kit (for example, Illumina Paired-end Cluster Kits with PhiX-spike in). In one example, the cDNA library preparation and/or whole exome capture steps may be performed with an automated system, using a liquid handling robot (for example, a SciClone NGSx).

The library amplification may be performed on a device, for example, an Illumina C-Bot2, and the resulting flow cell containing amplified target-captured cDNA libraries may be sequenced on a next generation sequencer, for example, an Illumina HiSeq 4000 or an Illumina NovaSeq 6000 to a unique on-target depth selected by the user, for example, 300×, 400×, 500×, 10,000×, etc. The next generation sequencer may generate a FASTQ, BCL, or other file for each patient sample or each flow cell.

If two or more patient samples are processed simultaneously on the same sequencer flow cell, reads from multiple patient samples may be contained in the same BCL file initially and then divided into a separate FASTQ file for each patient. A difference in the sequence of the adapters used for each patient sample could serve the purpose of a barcode to facilitate associating each read with the correct patient sample and placing it in the correct FASTQ file.

Each FASTQ file contains reads that may be paired-end or single reads, and may be short-reads or long-reads, where each read shows one detected sequence of nucleotides in an mRNA molecule that was isolated from the patient sample, inferred by using the sequencer to detect the sequence of nucleotides contained in a cDNA molecule generated from the isolated mRNA molecules during library preparation. Each read in the FASTQ file is also associated with a quality rating. The quality rating may reflect the likelihood that an error occurred during the sequencing procedure that affected the associated read.

Each FASTQ file may be processed by a bioinformatics pipeline. In various embodiments, the bioinformatics pipeline may filter FASTQ data. Filtering FASTQ data may include correcting sequencer errors and removing (trimming) low quality sequences or bases, adapter sequences, contaminations, chimeric reads, overrepresented sequences, biases caused by library preparation, amplification, or capture, and other errors. Entire reads, individual nucleotides, or multiple nucleotides that are likely to have errors may be discarded based on the quality rating associated with the read in the FASTQ file, the known error rate of the sequencer, and/or a comparison between each nucleotide in the read and one or more nucleotides in other reads that has been aligned to the same location in the reference genome. Filtering may be done in part or in its entirety by various software tools. FASTQ files may be analyzed for rapid assessment of quality control and reads, for example, by a sequencing data QC software such as AfterQC, Kraken, RNA-SeQC, FastQC, (see Illumina, BaseSpace Labs or https://www.illumina.com/products/by-type/informatics-products/basespace-sequence-hub/apps/fastqc.html), or another similar software program. For paired-end reads, reads may be merged.

For each FASTQ file, each read in the file may be aligned to the location in the reference genome having a sequence that best matches the sequence of nucleotides in the read. There are many software programs designed to align reads, for example, Bowtie, Burrows Wheeler Aligner (BWA), programs that use a Smith-Waterman algorithm, etc. Alignment may be directed using a reference genome (for example, GRCh38, hg38, GRCh37, other reference genomes developed by the Genome Reference Consortium, etc.) by comparing the nucleotide sequences in each read with portions of the nucleotide sequence in the reference genome to determine the portion of the reference genome sequence that is most likely to correspond to the sequence in the read. The alignment may take RNA splice sites into account. The alignment may generate a SAM file, which stores the locations of the start and end of each read in the reference genome and the coverage (number of reads) for each nucleotide in the reference genome. The SAM files may be converted to BAM files, BAM files may be sorted, and duplicate reads may be marked for deletion.

In one example, kallisto software may be used for alignment and RNA read quantification (see Nicolas L Bray, Harold Pimentel, Pall Melsted and Lior Pachter, Near-optimal probabilistic RNA-seq quantification, Nature Biotechnology 34, 525-527 (2016), doi:10.1038/nbt.3519). In an alternative embodiment, RNA read quantification may be conducted using another software, for example, Sailfish or Salmon (see Rob Patro, Stephen M. Mount, and Carl Kingsford (2014) Sailfish enables alignment-free isoform quantification from RNA-seq reads using lightweight algorithms. Nature Biotechnology (doi:10.1038/nbt.2862) or Patro, R., Duggal, G., Love, M. I., Irizarry, R. A., & Kingsford, C. (2017). Salmon provides fast and bias-aware quantification of transcript expression. Nature Methods.). These RNA-seq quantification methods may not require alignment. There are many software packages that may be used for normalization, quantitative analysis, and differential expression analysis of RNA-seq data.

For each gene, the raw RNA read count for a given gene may be calculated. The raw read counts may be saved in a tabular file for each sample, where columns represent genes and each entry represents the raw RNA read count for that gene. In one example, kallisto alignment software calculates raw RNA read counts as a sum of the probability, for each read, that the read aligns to the gene. Raw counts are therefore not integers in this example.

Raw RNA read counts may then be normalized to correct for GC content and gene length, for example, using full quantile normalization and adjusted for sequencing depth, for example, using the size factor method. In one example, RNA read count normalization is conducted according to the methods disclosed in U.S. patent application Ser. No. 16/581,706 or PCT19/52801, titled Methods of Normalizing and Correcting RNA Expression Data and filed Sep. 24, 2019, which are incorporated by reference herein in their entirety. The rationale for normalization is the number of copies of each cDNA molecule in the sequencer may not reflect the distribution of mRNA molecules in the patient sample. For example, during library preparation, amplification, and capture steps, certain portions of mRNA molecules may be over or under-represented due to artifacts that arise during various aspects of priming of reverse transcription caused by random hexamers, amplification (PCR enrichment), rRNA depletion, and probe binding and errors produced during sequencing that may be due to the GC content, read length, gene length, and other characteristics of sequences in each nucleic acid molecule. Each raw RNA read count for each gene may be adjusted to eliminate or reduce over- or under-representation caused by any biases or artifacts of NGS sequencing protocols. Normalized RNA read counts may be saved in a tabular file for each sample, where columns represent genes and each entry represents the normalized RNA read count for that gene.

A transcriptome value set may refer to either normalized RNA read counts or raw RNA read counts, as described above.

Returning to FIG. 8, at a block 804, the molecular training data (e.g., such RNA sequence data) is labeled by biomarker and clustered, using an automatic clustering algorithm, such as an algorithm to identify CMS sub-types in the molecular training data and cluster training data according to CMS sub-type. This automatic clustering may be performed within a deep learning framework single-class classifier module, for example, or within a slide-level label pipeline, such as those in the deep learning framework 300.

At a block 806, for each biomarker cluster (each corresponding to a different biomarker, such as a different CMS sub-type or HRD), histopathology images from the associated patients are obtained. These histopathology images may be H&E slide images having a slide-level label, for example. At a block 808, for each biomarker cluster, these labeled histopathology images are provided to the deep learning framework for training biomarker classification models, such as multiple CMS classification models to predict different CMS sub-types. A set of trained biomarker classifiers (classification models) are generated at block 810 as a result. In this way, the blocks 802-810 representing a training process.

A prediction process starts at a block 812, where a new (unlabeled or labeled) histopathology image, such as a H&E slide image, is received and provided to the single-scale biomarker classifiers generated by block 810, and a block 814 predicts biomarker classification on the received histopathology image as determined by the one or more biomarker classification models, such as one or more CMS sub-types or HRD.

As with block 610, new histopathology images may be received at the block 814 from the physical clinical records system or primary care system and applied to a trained deep learning framework which applies its tissue classification model and/or biomarker classification models determines a biomarker prediction. That prediction score can be determined for an entire histopathology image, for example.

Further, as with the process 600, as shown in process 900 of FIG. 9, after prediction, the predicted biomarker classification from block 814 may be received at block 902. A clinical report for the histopathology image, and thus for the patient, may be generated at the block 904 including predicted biomarker status and, at the block 906, an overlay map may be generated showing the predicted biomarker status for display to a clinician or for providing to a pathologist for determining a preferred immunotherapy corresponding to the predicted biomarker.

Figure 10A:
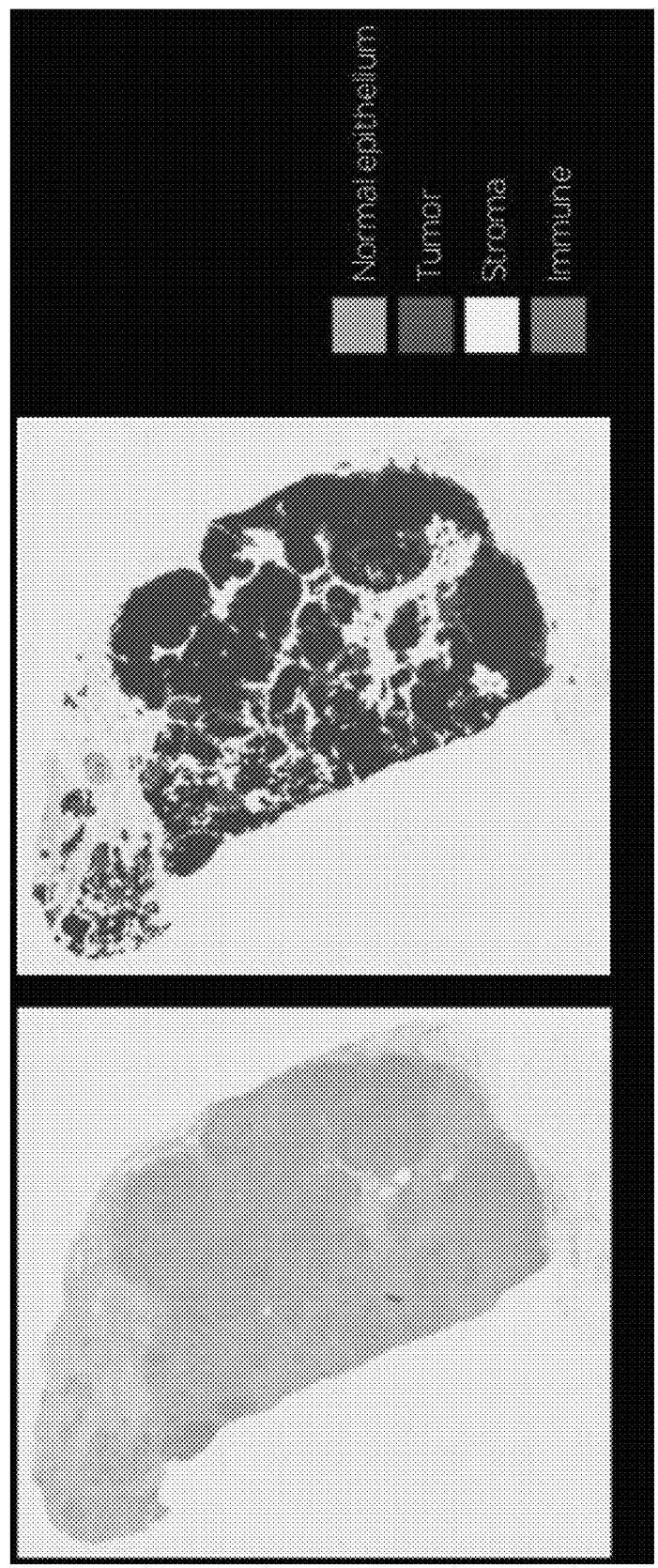
FIGS. 10A and 10B illustrate example overlay maps generated by the process of FIG. 9, showing a tissue overlay map (FIG. 10A) and a cell overlay map (FIG. 10B), in accordance with an example.
Figure 10B:
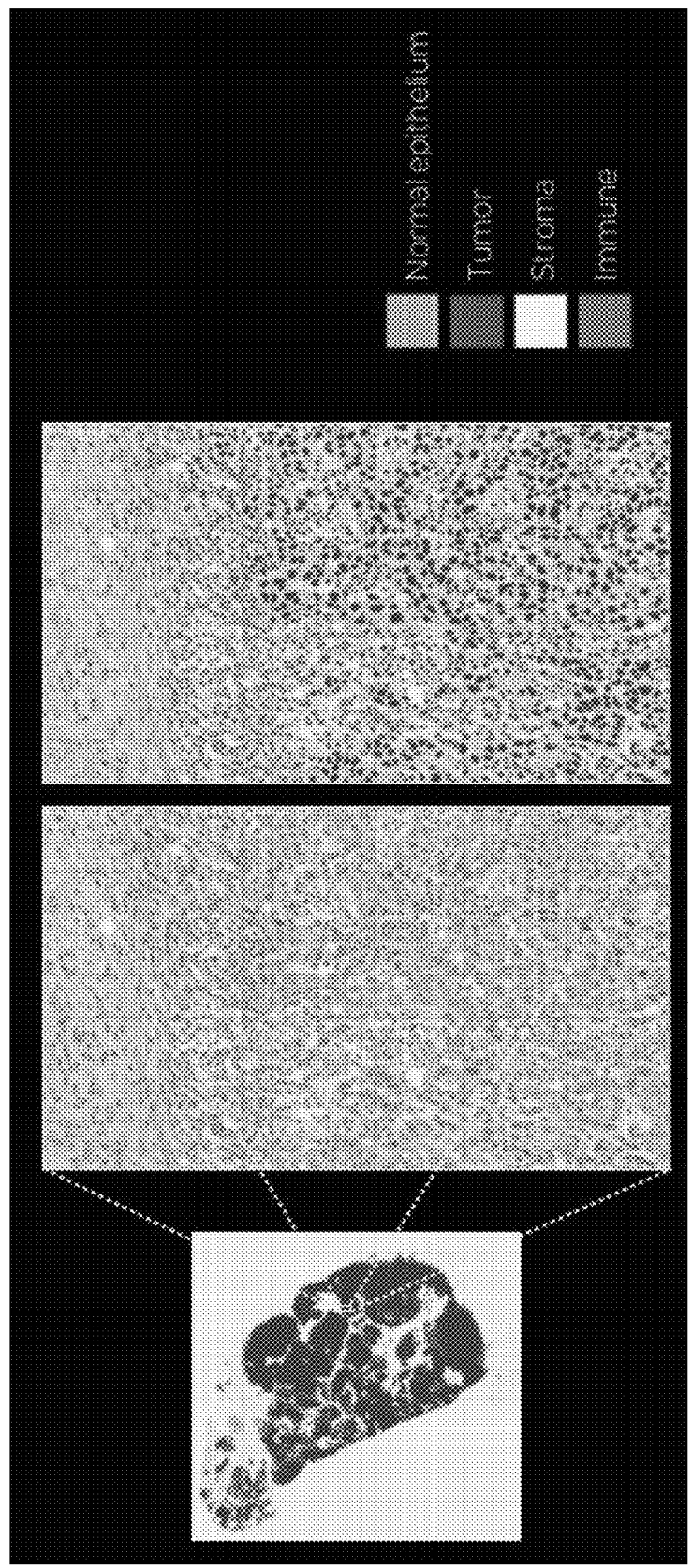

FIGS. 10A and 10B illustrate examples of a digital overlay maps created by the overlay map generator 324 of system 300, for example. These overlay maps may be generated as static digital reports displayed to clinicians or as dynamic reports allowing user interaction through a graphical user interface (GUI). FIG. 10A illustrates a tissue class overlay map generated by the overlay map generator 324. FIG. 10B illustrates a cell outer edge overlay map generated by the overlay map generator 324.

In an example, the overlay map generator 324 may display the digital overlays as transparent or opaque layers that cover the histopathology image, aligned such that the image location shown in the overlay and the histopathology image are in the same location on the display. The overlay map may have varying degrees of transparency. The degree of transparency may be adjustable by the user, in a dynamic reporting mode of the overlay map generator 324. The overlay map generator 326 may report the percentage of the labeled tiles that are associated with each tissue class label, ratios of the number of tiles classified under each tissue class, the total area of all grid tiles classified as a single tissue class, and ratios of the areas of tiles classified under each tissue class. The overlay map may be displayed as a heatmap showing different tissue classifications and having different pixel intensity levels that correspond to different biomarker status levels, e.g., in the TILs example, showing higher intensity pixels for tissue regions having higher predicted TILs status (higher %) and lower intensity pixels for tissue regions having lower predicted TILs status (lower %).

In an example, the deep learning output post-processing controller 308 may also report the total number of cells or the percentage of cells that are located in an area defined by either a user, the entire slide, a single grid tile, by all grid tiles classified under each tissue class, or cells that are classified as immune cells. The controller 308 may also report the number of cells classified as lymphocyte cells that are located within areas classified as tumor or any other tissue class.

In an example, the digital overlays and reports generated by the controller 308 may be used to assist medical professionals in more accurately estimating tumor purity, and in locating regions or diagnoses of interest, including invasive tumors having tumor cells that protrude into the non-tumor tissue region that surrounds the tumor. They can also assist medical professionals in prescribing treatments. For example, the number of lymphocytes in areas classified as tumor may predict whether immunotherapy will be successful in treating a patient's cancer.

In an example, the digital overlays and reports generated by the controller 308 may also be used to determine whether the slide sample has enough high-quality tissue for successful genetic sequence analysis of the tissue, for example implementing an accept/reject/manual determination as discussed in process 700. Genetic sequence analysis of the tissue on a slide is likely to be successful if the slide contains an amount of tissue and/or has a tumor purity value that exceeds a user-defined tissue amount and tumor purity thresholds. The controller 308 may use the process 700 to label a slide as accepted or rejected for sequence analysis, depending on the amount of tissue present on the slide and the tumor purity of the tissue on the slide. The controller 308 may also label a slide as uncertain, according to the process 700, as well, using a user-defined tissue amount threshold and a user-defined uncertainty range obtained from a user interacting with the digital overlays and reports from the generator 324.

In an example, the controller 308, implementing the process 700, e.g., using the biomarker metrics processing module 326, calculates the amount of tissue on a slide by measuring the total area covered by the tissue in the histopathology image or by counting the number of cells on the slide. The number of cells on the slide may be determined by the number of cell nuclei visible on the slide. In an example, the controller 308 calculates the proportion of tissue that is cancer cells by dividing the number of cell nuclei within grid areas that are labeled tumor by the total number of cell nuclei on the slide. The controller 308 may exclude cell nuclei or outer edges of cells that are located in tumor areas but which belong to cells that are characterized as lymphocytes. The proportion of tissue that is cancer cells is known as the tumor purity of the sample. The controller 308 then compares the tumor purity to the user-selected minimum tumor purity threshold and the number of cells in the digital image to a user-selected minimum cell threshold (as input by a user interacting with the overlay map generator 324) and approves the tissue slide depicted in the image for molecular testing, including genetic sequence analysis, if both thresholds are exceeded. In one example, the user-selected minimum tumor purity threshold is 0.20, which is 20%. Although any number of tumor purity thresholds may be selected, including 1%, 5%, 10%, 15%, 20%, 25%, 30%, 35%, 40%, 45%, 50%, or higher.

In another example, the controller 308 gives the image a composite tissue amount score that multiplies the total area covered by tissue detected on the slide by a first multiplier value, multiplies the number of cells counted on the slide by a second multiplier value, and sums the products of these multiplications.

In an example, the controller 308 may calculate whether the grid areas that are labeled tumor are spatially consolidated or dispersed among non-tumor grid areas. If the controller 308 determines that the tumor areas are spatially consolidated, the overlay map generator 324 may produce a digital overlay of a recommended cutting boundary that separates the image regions classified as tumor and the image regions classified as non-tumor or within the areas classified as non-tumor, proximal to the areas classified as tumor. This recommended cutting boundary can be a guide to assist a technician in dissecting a slide to isolate a maximum amount of tumor or non-tumor tissue from the slide, especially for molecular testing, including genetic sequence analysis.

In an example, the controller 308 may include clustering algorithms that calculate and report information about the spacing and density of type classified cells, tissue class classified tiles, or visually detectable features on the slide. The spacing information includes distribution patterns and heat maps for lymphocytes, immune cells, tumor cells, or other cells. These patterns may include clustered, dispersed, dense, and non-existent. This information is useful to determine whether immune cells and tumor cells cluster together and what percentage of the cluster areas overlay, which may facilitate in predicting immune infiltration and patient response to immunotherapy.

The controller 308 may also calculate and report average tumor cell roundness, average tumor cell perimeter length, and average tumor nuclei density.

The spacing information also includes mixture levels of tumor cells and immune cells. The clustering algorithms can calculate the probability that two adjacent cells on a given slide or in a region of a slide will be either two tumor cells, two immune cells, or one tumor cell and one immune cell.

The clustering algorithms may also measure the thickness of any stroma pattern located around an area classified as tumor. The thickness of this stroma surrounding the tumor region may be a predictor of a patient's response to treatment.

In an example, the controller 308 may also calculate and report statistics including mean, standard deviation, sum, etc. for the following information in each grid tile of either a single slide image or aggregated from many slide images: red green blue (RGB) value, optical density, hue, saturation, grayscale, and stain deconvolution. Deconvolution includes the removal of the visual signal created by any individual stain or combination of stains, including hematoxylin, eosin, or IHC staining.

The controller 308 may also incorporate known mathematical formulae from the fields of physics and image analysis to calculate visually detectable basic features for each grid tile. Visually detectable basic features, including lines, patterns of alternating brightness, and outlineable shapes, may be combined to create visually detectable complex features including cell size, cell roundness, cell shape, and staining patterns referred to as texture features.

In other examples, the digital overlays, reports, statistics, and estimates produced by the overlay map generator 324 may be useful for predicting patient survival, patient response to a specific cancer treatment, PD-L1 status of a tumor or immune cluster, microsatellite instability (MSI), tumor mutational burden (TMB), and the origin of a tumor when the origin is unknown or the tumor is metastatic. The biomarker metrics processing module 326 may also calculate quantitative measurements of predicted patient survival, patient response to a specific cancer treatment, PD-L1 status of a tumor or immune cluster, microsatellite instability (MSI), and tumor mutational burden (TMB).

In an example, the controller 308 may calculate relative densities of each type of immune cell on an entire slide, in the areas designated as tumor or another tissue class. Immune tissue classes include lymphocytes, cytotoxic T cells, B cells, NK cells, macrophages, etc.

In an example, the act of scanning or otherwise digitally capturing a histopathology slide automatically triggers the deep learning framework 300 to analyze the digital image of that histopathology slide.

In an example, the overlay map generator 324 allows a user to edit a cell outer edge or a border between two tissue classes on a tissue class overlay map or a cell outer edge overlay map and saves the altered map as a new overlay.

Figure 11:
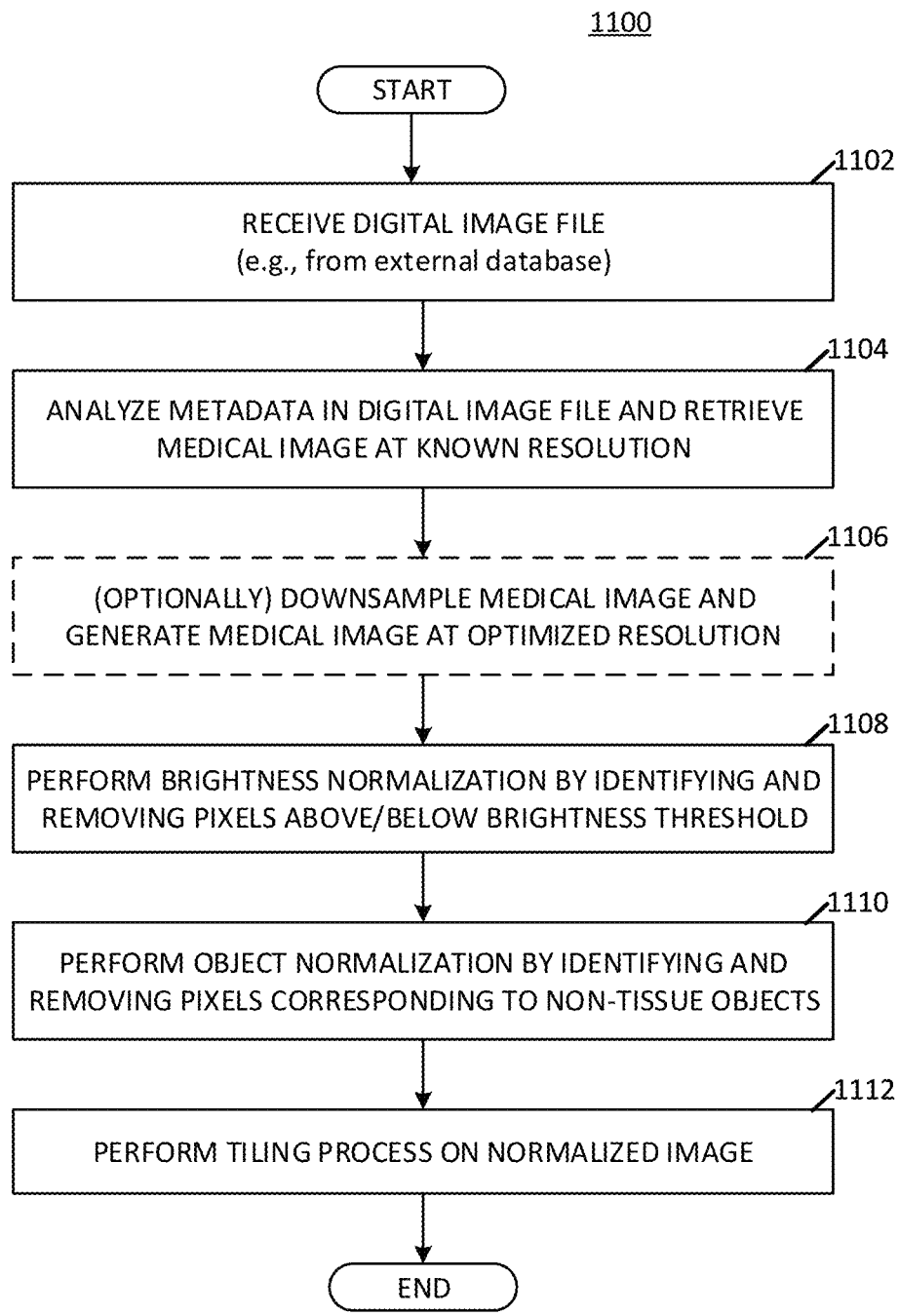
FIG. 11 is a block diagram of a process for preparing digital images of histopathology slides for classification, in accordance with an example.

FIG. 11 illustrates a process 1100 for preparing digital images of histopathology slides for tissue classification, biomarker detection, and mapping analysis, as may be implemented using the system 300. The process 1100 may be performed on each received image for analysis and biomarker prediction. In some examples, the process 1100 may be performed, in whole or in part, on initially received training images. Each of the processes described in FIG. 9 may be performed by the pre-processing controller 302, where any one or more of the processes may be performed by the normalization module 310 and/or the tissue detector 314.

In an example, such as when training a classifier model, each digital image file received by the pre-processing controller 302, at 1102, contains multiple versions of the same image content, and each version has a different resolution. The file stores these copies in stacked layers, arranged by resolution such that the highest resolution image containing the greatest number of bytes is the bottom layer. This is known as a pyramidal structure. In one example, the highest resolution image is the highest resolution achievable by the scanner or camera that created the digital image file.

In an example, each digital image file also contains metadata that indicates the resolution of each layer. The pre-processing controller 302, at process 1104, can detect the resolution of each layer in this metadata and compare it to user-selected resolution criteria to select a layer with optimal resolution for analysis. In one example, the optimal resolution is 1 pixel per micron (downsampled by 4).

In an example, the pre-processing controller 302 receives a Tagged Image File Format (TIFF) file with a bottom layer resolution of four pixels per micron. This resolution of 4 pixels per micron corresponds to the resolution achieved by a microscope objective lens with a magnification power of "40×". In one example, the area that may have tissue on the slide is up to 100,000×100,000 pixels in size.

In an example, the TIFF file has approximately 10 layers, and the resolution of each layer is half as high as the resolution of the layer below it. If the higher resolution layer had a resolution of four pixels per micron, the layer above it will have two pixels per micron. The area represented by one pixel in the upper layer will be the size of the area represented by four pixels in the lower layer, meaning that the length of each side of the area represented by one upper layer pixel will be twice the length of each side of the area represented by one lower layer pixel.

Each layer may be a 2× downsampling of the layer below it, as performed at process 1106. Downsampling is a method by which a new version of an original image can be created with a lower resolution value than the original image. There are many methods known in the art for downsampling, including nearest-neighbor, bilinear, hermite, bell, Mitchell, bicubic, and Lanczos resampling.

In an example, 2× downsampling means that the red green blue (RGB) values from three of four pixels that are located in a square in the higher resolution layer are replaced by the RGB value from the fourth pixel to create a new, larger pixel in the layer above, which occupies the same space as the four averaged pixels.

In an example, the digital image file does not contain a layer or an image with the optimal resolution. In this case, the pre-processing controller 302 can receive an image from the file having a resolution that is higher than the optimal resolution and downsample the image at a ratio that achieves the optimal resolution, at process 1106.

In an example, the optimal resolution is 2 pixels per micron, or "20×" magnification, but the bottom layer of a TIFF file is 4 pixels per micron and each layer is downsampled 4× compared to the layer below it. In this case, the TIFF file has one layer at 40× and the next layer at 10× magnification, but does not have a layer at 20× magnification. In this example, the pre-processing controller 302 reads the metadata and compares the resolution of each layer to the optimal resolution and does not find a layer with the optimal resolution. Instead, the pre-processing controller 302 retrieves the 40× magnification layer, then downsamples the image in that layer at a 2× downsampling ratio to create an image with the optimal resolution of 20× magnification.

Also at process 1106, after the pre-processing controller 302 obtains an image with an optimal resolution, it locates all parts of the image that depict tumor sample tissue and digitally eliminates debris, pen marks, and other non-tissue objects.

In an example, also at process 1106, the pre-processing controller 302 differentiates between tissue and non-tissue regions of the image and uses Gaussian blur removal to edit pixels with non-tissue objects. In an example, any control tissue on a slide that is not part of the tumor sample tissue can be detected and labeled as control tissue by the tissue detector or manually labeled by a human analyst as control tissue that should be excluded from the downstream tile grid projections.

Non-tissue objects include artifacts, markings, and debris in the image. Debris includes keratin, severely compressed or smashed tissue that cannot be visually analyzed, and any objects that were not collected with the sample.

In an example, also at process 1106, a slide image contains marker ink or other writing that the controller 302 detects and digitally deletes. Marker ink or other writing may be transparent over the tissue, meaning that the tissue on the slide may be visible through the ink. Because the ink of each marking is one color, the ink causes a consistent shift in the RGB values of the pixels that contain stained tissue underneath the ink compared to pixels that contain stained tissue without ink.

In an example, also at process 1106, the controller 302 locates portions of the slide image that have ink by detecting portions that have RGB values that are different from the RGB values of the rest of the slide image, where the difference between the RGB values from the two portions is consistent. Then, the tissue detector may subtract the difference between the RGB values of the pixels in the ink portions and the pixels in the non-ink portions from the RGB values of the pixels in the ink portions to digitally delete the ink.

In an example, also at process 1106, the controller 302 eliminates pixels in the image that have low local variability. These pixels represent artifacts, markings, or blurred areas caused by the tissue slice being out of focus, an air bubble being trapped between the two glass layers of the slide, or pen marks on the slide.

In an example, also at process 1106, the controller 302 removes these pixels by converting the image to a grayscale image, passing the grayscale image through a Gaussian blur filter that mathematically adjusts the original grayscale value of each pixel to a blurred grayscale value to create a blurred image. Other filters may be used to blur the image. Then, for each pixel, the controller 302 subtracts the blurred grayscale value from the original grayscale value to create a difference grayscale value. In one example, if a difference grayscale value of a pixel is less than a user-defined threshold, it may indicate that the blur filter did not significantly alter the original grayscale value and the pixel in the original image was located in a blurred region. The difference grayscale values may be compared to a threshold to create a binary mask that indicates where the blurred regions are that may be designated as non-tissue regions. A mask may be a copy of an image, where the colors, RGB values, or other values in the pixels are adjusted to show the presence or absence of an object of a certain type to show the location of all objects of that type. For example, the binary mask may be generated by setting the binary value of each pixel to 0 if the pixel has a difference grayscale value less than a user-defined blur threshold and setting the binary value of each pixel to 1 if the pixel has a difference grayscale value higher than or equal to a user-defined blur threshold. The regions of the binary mask that have pixel binary values of 0 indicate blurred areas in the original image that may be designated as non-tissue.

The controller 302 may also mute or remove extreme brightness or darkness in the image, at process 1108. In one example, the controller 302 converts the input image to a grayscale image, and each pixel receives a numerical value according to how bright the pixel is. In one example, the grayscale values range from 0 to 255, where 0 represents black and 255 represents white. In pixels with a grayscale value above a brightness threshold value, the tissue detector will replace the grayscale value of those pixels with the brightness threshold value. For pixels with a grayscale value below a darkness threshold value, the tissue detector will replace the grayscale value of those pixels equal with the darkness threshold value. In one example, the brightness threshold value is approximately 210. In one example, the darkness threshold value is approximately 45. The tissue detector stores the image with the new grayscale values in a data file.

In an example, the controller 302 analyzes the altered image for any artifacts, debris, or markings that remain after the first analysis, at process 1110. The tissue detector scans the image and categorizes any remaining groups of pixels with a certain color, size, or smoothness as non-tissue.

In an example, the slide has H&E staining and most tissue in the histopathology image will have a pink stain. In this example, the controller 302 categorizes all objects without any pink or red hue, as determined by the RGB value of the pixels that represent the object, as non-tissue. The tissue detector 314 may interpret any color or the lack of any color in a pixel to indicate the presence or absence of tissue in that pixel.

In an example, the controller 302 detects the contours of each object in the image in order to measure the size and smoothness of each object. Pixels that are very dark may be debris, and pixels that are very bright may be background, which are both non-tissue objects. Therefore, the controller 302 may detect the contours of each object by converting the image to grayscale, comparing the grayscale values of each pixel to a range of user-determined range of values that are not too bright or too dark, and determining whether the grayscale value is within the range to produce a binary image where each pixel is assigned one of two numerical values.

For example, to threshold an image, the controller 302 may compare the grayscale values of each pixel to a user-defined range of values and replace each grayscale value outside of the user-defined range with the value 0 and each grayscale value within a user-defined range with the value 1. Then, the controller 302 draws all contours of all objects as the outer edge of each group of adjacent pixels having a value of 1. Closed contours indicate the presence of an object, and the controller 302 measures the area within the contours of each object to measure the size of the object.

In an example, tissue objects on a slide are unlikely to make contact with the outer edges of the slide so the controller 302 categorizes all objects that contact the edge of a slide as non-tissue.

In an example, after measuring the size of each object, the controller 302 ranks the sizes of all objects and designates the largest value to be the size of the largest object. The controller 302 divides the size of each object by the size of the largest object and compares the resulting size quotient to a user-defined size threshold value. If the size quotient for an object is smaller than the user-defined size threshold value, the controller 302 designates that object as non-tissue. In one example, the user-defined size threshold value is 0.1.

Before measuring the size of each object, at process 1106, the controller 302 may first downsample the input image to reduce the likelihood of designating portions of a tissue object as non-tissue. For example, a single tissue object may appear as a first tissue object portion surrounded by one or more additional tissue object portions having a smaller size. After thresholding, the additional tissue object portions may have a size quotient smaller than the user-defined size threshold value and may be erroneously designated as non-tissue. Downsampling before thresholding causes a small group of adjacent pixels having values of 1 surrounded by pixels having values of 0 in the original image to be included in a proximal, larger group of pixels having values of 1. The opposite may also be true, for small groups of adjacent pixels having values of 0 surrounded by pixels having values of 1 in the original image to be included in a proximal, larger group of pixels having values of 0.

In an example, the controller 302 downsamples an image having 40× magnification by a ratio of 16×, so the magnification of the resulting downsampled image is 40/16× and each pixel in the downsampled image represents 16 pixels in the original image.

In an example, at process 1110, the controller 302 detects the boundaries of each object on the slide as a cluster of pixels having binary or RGB values that do not equal zero, surrounded by pixels with RGB values equal to zero, indicating an object border. If the pixels forming the boundaries lie on a relatively straight line, the controller 302 classifies the object as non-tissue. For example, the controller 302 outlines a shape with a closed polygon. If the number of vertices of the polygon is less than a user-defined minimum vertices threshold, the polygon is deemed to be a simple, inorganic shape that is too smooth, and marked as non-tissue. The controller 302 then applies a tiling process to the normalized image, at process 1112.

Figure 12A:
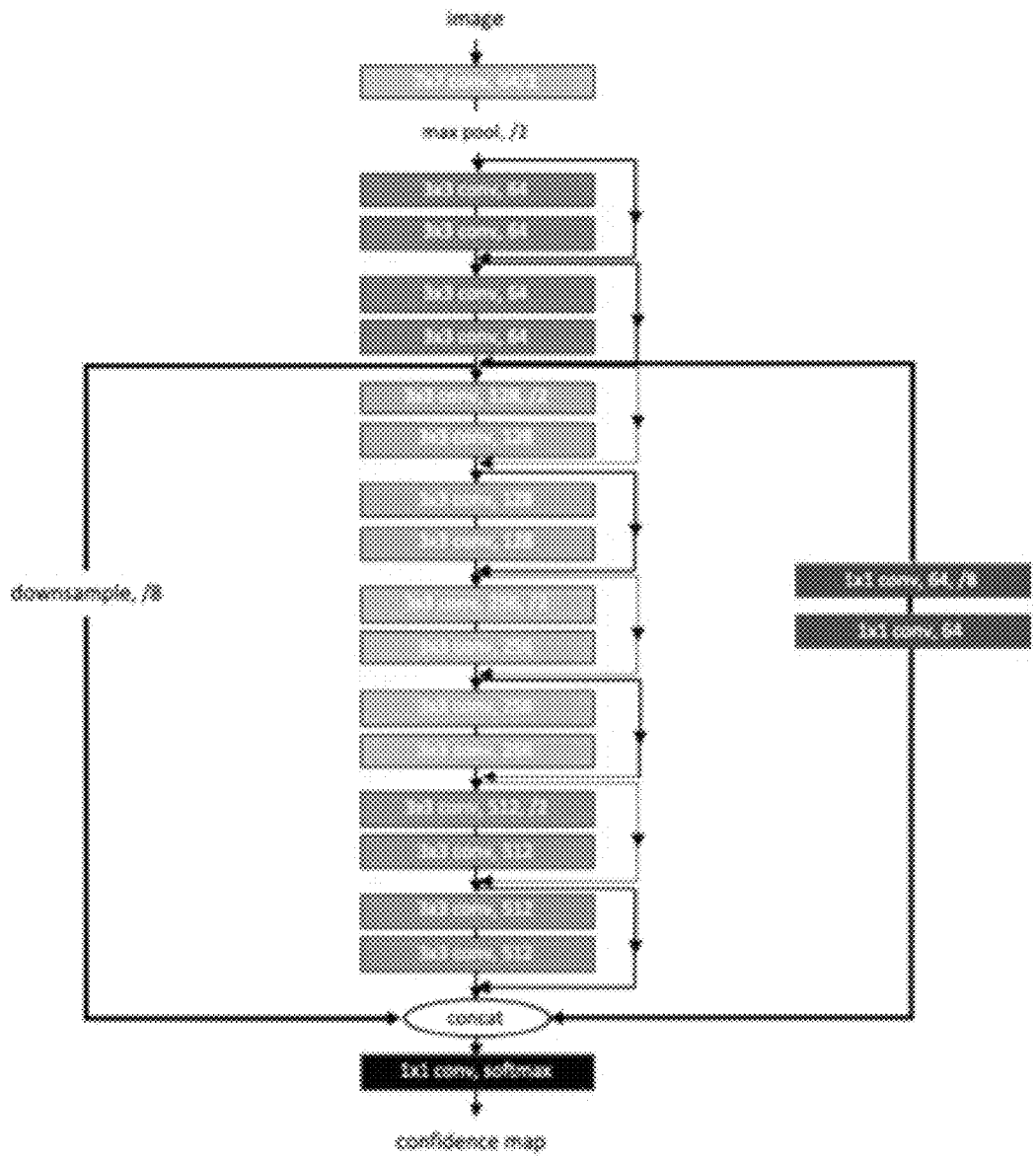
FIGS. 12A-12C illustrate example neural network architectures that may be used for classification models, in accordance with an example.
Figure 12B:
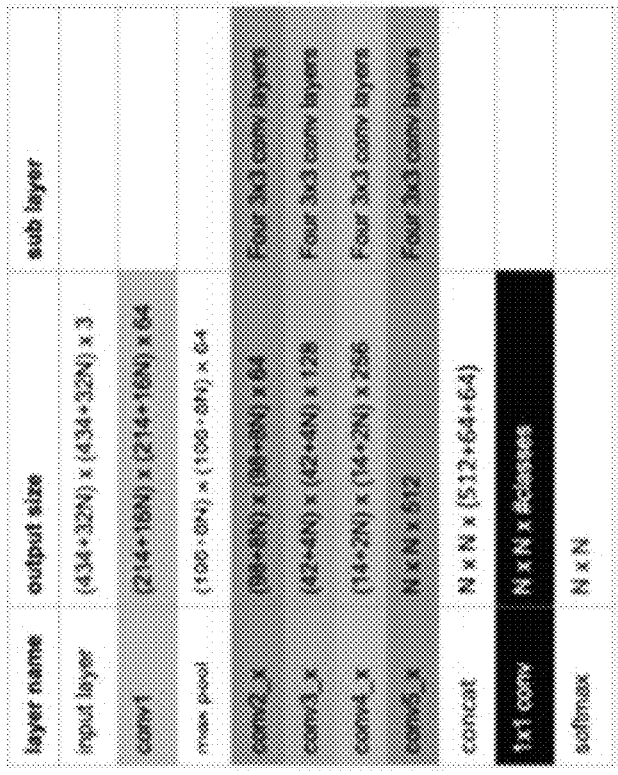
Figure 12C:
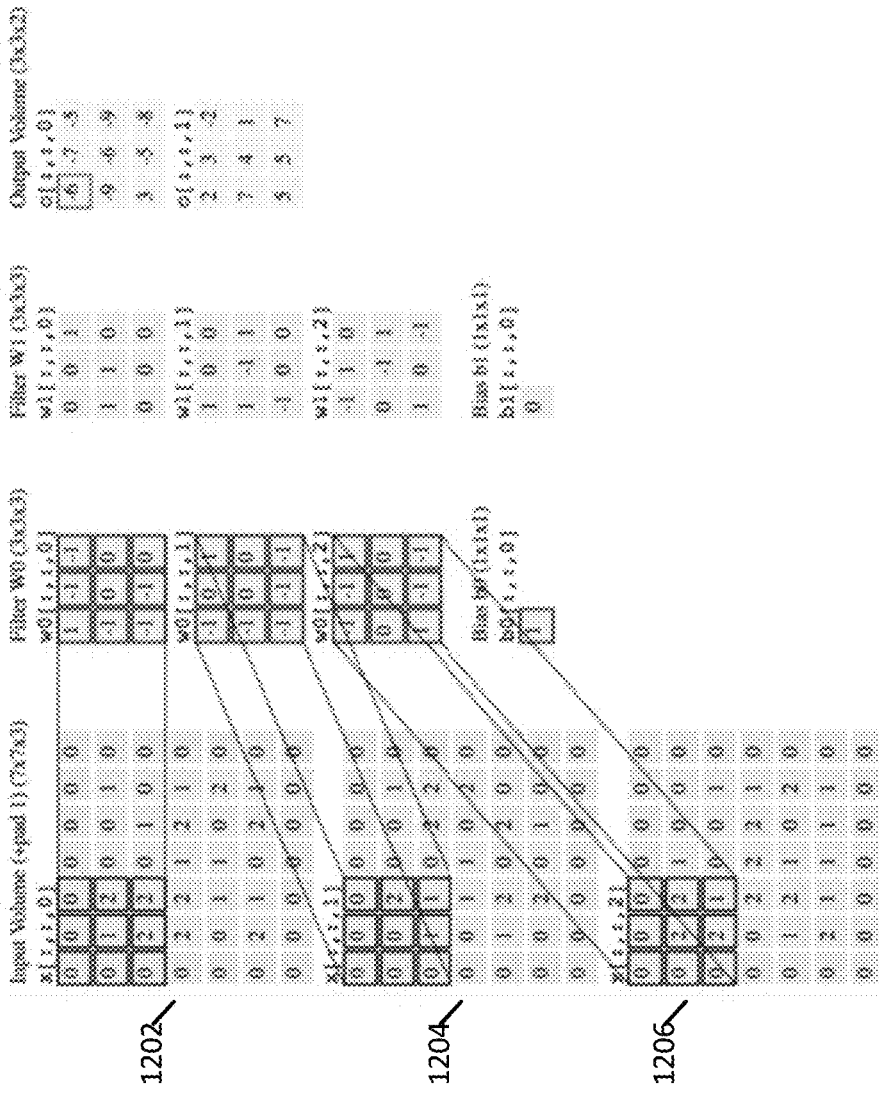
Figure 13:
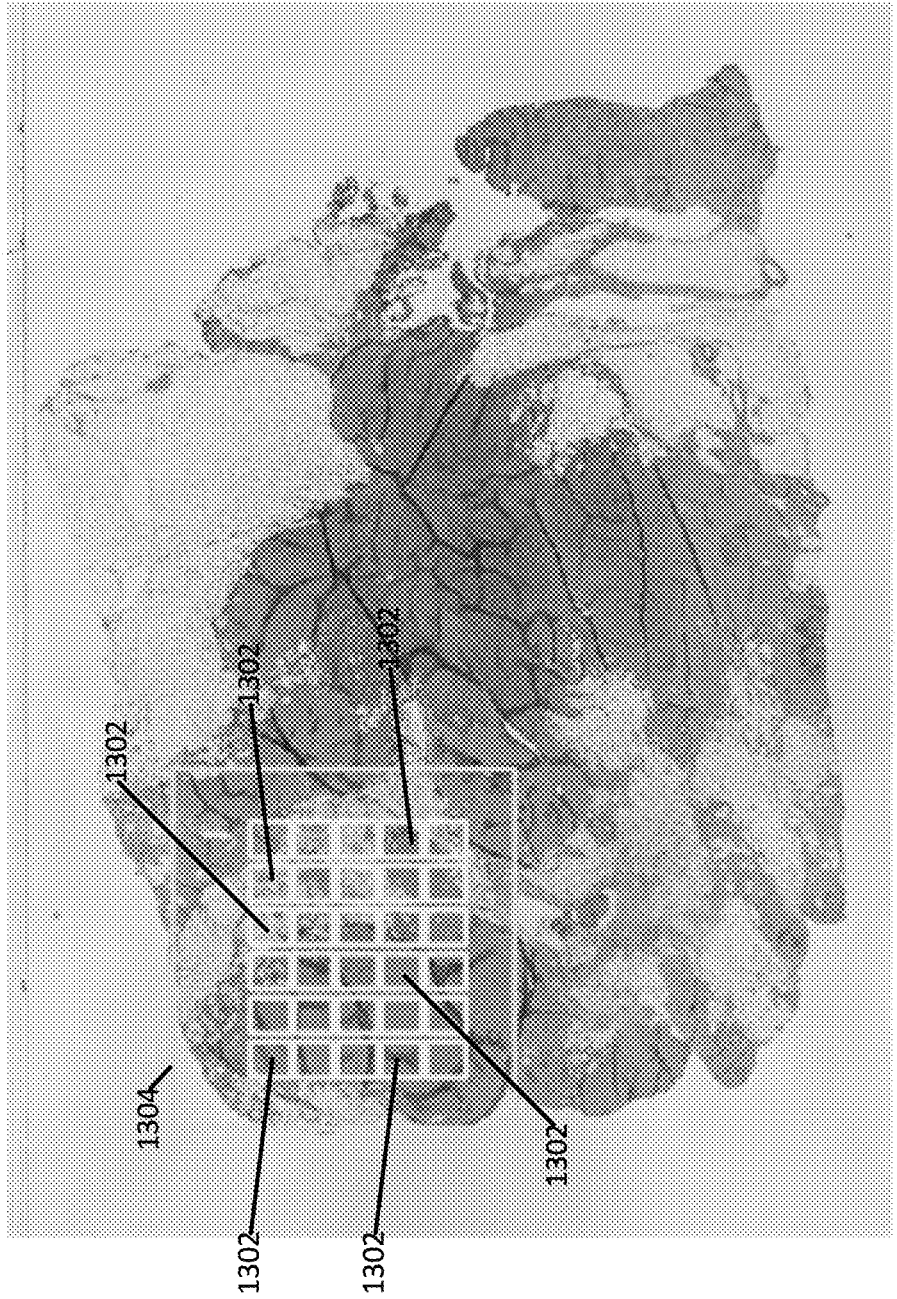
FIG. 13 illustrates a histopathology image showing tile images for classification, in accordance with an example.

FIGS. 12A-12C illustrate an example architecture 1200 that may be used for the classification models of the module 306. For example, The same architecture 1200 may be used for each of the tissue segmentation model 322 and tissue classification model 320, both implemented using an FCN configuration or any neural network herein. The tissue classifier module 306 includes a tissue classification algorithm (see FIGS. 12A-12C) that assigns a tissue class label to the image represented in each received tile (example tiles 1302 are labeled in a first portion 1304 of a histopathology image 1300, shown in FIG. 13). In an example, the overlay map generator 324 may report the assigned tissue class label associated with each small square tile by displaying a grid-based digital overlay map in which each tissue class is represented by a unique color (see FIG. 12A).

A smaller tile size may cause an increase in the amount of time required for the tissue classifier module 306 to analyze the input image. Alternatively, a larger tile size may increase the likelihood that a tile will contain more than one tissue class and make it difficult to assign a single tissue class label to the tile. In this case, the architecture 1200 may calculate an equal probability for two or more tissue class labels being accurately assigned to a single small square tile instead of calculating that one of the tissue class labels has a higher probability of describing the image in the small square tile, compared to the other tissue class labels.

In an example, each side of each small square tile is approximately 32 microns long and approximately 5-10 cells fit in each small square tile. This small tile size allows the tissue classifier module 306 to create more spatially accurate borders when determining the boundary between two neighboring small square tile regions that depict two distinct tissue classes. In one example, each side of the small square tile can be as short as 1 micron.

In an example, the size of each tile may be set by the user to contain a specific number of pixels. In this example, the resolution of the input image will determine the length of each side of the tile, as measured in microns. At different resolutions, the micron length of the tile side will vary and the number of cells in each tile may vary.

The architecture 1200 recognizes various pixel data patterns in the portion of the digital image that is located within or near each small square tile and assigns a tissue class label to each small square tile based on those detected pixel data patterns. In one example, a medium square tile centered around a small square tile contains the area of a slide image that is close enough to the small square tile to contribute to the label assignment for that small square tile.

In an example, each side of a medium square tile is approximately 466 microns long, and each medium square tile contains approximately 225 (15×15) small square tiles. In one example, this medium tile size increases the likelihood that structural tissue features can fit within a single medium tile and provide context to the algorithm when labeling the central small square tile. Structural tissue features may include glands, ducts, vessels, immune clusters, etc.

In an example, this medium tile size is selected such that it can negate the shrinkage that occurs during convolution.

During convolution with the architecture 1200, an input image matrix is multiplied by a filter matrix to create a result matrix, and shrinkage refers to a case where the result matrix is smaller than the input image matrix. The dimensions of a filter matrix in a convolution layer affects the number of rows and columns lost to shrinkage. The total number of matrix entries that are lost to shrinkage by processing an image through a particular CNN can be calculated depending on the number of convolution layers in the CNN and the dimensions of the filter matrices in each convolution layer. (See FIGS. 12A-12C)

In the example shown in FIG. 12B, the convolution layers in combination lose 217 total matrix rows or columns from the top, bottom, and two side edges of the matrix, so the medium square tile is set to equal the small square tile plus 217 pixels on each side of the small square tile.

In an example, two neighboring small square tiles share a side and are each at the center of a medium square tile. The two medium square tiles overlap. Of the 466*466 small pixels located in each medium square tile, the two medium square tiles will share all but 32*466 pixels. In one example, each convolution layer of the algorithm (see FIGS. 12A and 12B) analyzes both medium square areas simultaneously such that the algorithm produces two vectors of values (one for each of the two small square tiles).

The vector of values contains a probability value for each tissue class label, indicating the likelihood that the small square tile depicts that tissue class. The vectors of values are/may be arranged in a matrix, to form a 3-dimensional probability data array. The location of each vector in the 3-dimensional probability data array, relative to the other vectors, will correspond to the location of the associated small square tile, relative to the other small square tiles included in the algorithm analysis.

In the example, 434×434 (188,356) of the 466×466 (217, 156) pixels in each medium square tile are common to both medium square tiles. By analyzing both medium square tiles simultaneously, the algorithm increases efficiency.

In one example, the architecture 1200 can further increase efficiency by analyzing a large tile formed by multiple overlapping medium square tiles, each of which contains many small square tiles surrounding one center small square tile that receives a tissue class label. In this example, the algorithm still generates one data structure in the form of a 3-dimensional probability data array containing one vector of probabilities for each small square tile, wherein the location of the vector within the 3-dimensional array corresponds to the location of the small tile within the large tile.

The architecture 1200, e.g., in the tissue classifier module 306, saves this 3-dimensional probability data array, and the overlay map generator 324 converts the tissue class label probabilities for each small square tile into a tissue class overlay map. In an example, the overlay map generator 324 may compare the probabilities stored in each vector to determine the largest probability value associated with each small square tile. The tissue class label associated with that largest value may be assigned to that small square tile and only the assigned labels will be displayed in the tissue class overlay map.

In an example, matrices generated by each layer of the architecture 1200 for the large square tile are stored in graphics processing unit (GPU) memory. The capacity of the GPU memory and the amount of GPU memory required for each entry in the 3-dimensional probability data array may determine the maximum possible size of the large square tile. In one example, the GPU memory capacity is 250 MB and each entry in the matrices requires 4 bytes of GPU memory. This allows a large tile size of 4,530 pixels by 4,530 pixels, calculated as follows: 4 bytes/entry*4530*4530*3 entries for each large tile=246 (~250) MB of GPU memory required per large square tile. In another example, each entry in the matrices requires 8 bytes of GPU memory. In this example, a 16 GB GPU can process 32 large tiles simultaneously, each large tile having dimensions of 4,530 pixels by 4,530 pixels, calculated as follows: 32 large tiles*8 bytes/entry*4530*4530*3 entries for each large tile=14.7 (~16) GB of GPU memory required.

In an example, each entry in the 3-dimensional probability data array is a single precision floating-point format (float32) data entry.

In an example, there are 16,384 (128$^2$) non-overlapping small square tiles that form a large square tile. Each small square tile is the center of a medium square tile having sides that are each approximately 466 pixels long. The small square tiles form a center region of a large square tile having sides that are each approximately 4,096 pixels long. The medium square tiles all overlap and create a border around all four sides of the center region that is approximately 217 pixels wide. Including the border, each large square tile has sides that are each approximately 4,530 pixels long.

In this example, this large square tile size allows simultaneous calculations that reduce the redundant computation percentage by 99%. This may be calculated as follows: first, select a pixel on the interior of a large square tile (any pixel at least 434 pixels from the edge of the large square tile); construct a region that is the size of a medium square tile (466 pixels per edge) with this model pixel at the center; and then for any small square tile centered within this constructed region, the model pixel is contained within that small square tile's corresponding medium square tile. There are (466/32)$^2$=~217 such small square tiles within the large square tile. For pixels not on the interior of the large square tile, the number of small square tiles that satisfy this condition is smaller. The number decreases linearly as the distance between the selected small square tile and the edge of the large square tile decreases, then again as the distance between the selected small square tile and the corner decreases, where a small number of pixels (~0.005%) only contribute towards the classification of a single small square tile. Performing classification on a single large square tile means the computations for each pixel are only performed once, instead of once per small square tile. Thus, the redundancy is reduced by nearly 217-fold. In one example, redundancy is not completely eliminated because a slide may contain several large square tiles, each of which may overlap slightly with its neighbors.

An upper bound on the redundant calculation percentage can be established (slight deviation from this upper bound depends on the number of large square tiles needed to cover the tissue and the relative arrangement of these tiles). The redundancy percentage is 1−1/r where r is the redundancy ratio, and r can be calculated as (T/N+1)(sqrt(N)*E+434)$^2$/(sqrt(T)*E+434)$^2$; T is the total number of small square tiles on the slide, N is the number of small square tiles per large square tile, and E is the edge size of the small square tiles.

FIG. 12A illustrates the layers of an example of the layer structure of the architecture 1200. FIG. 12B illustrates example output sizes for different layers and resulting sublayers of the architecture 1200, showing the tile-resolution FCN configuration. As shown, the tile-resolution FCN configuration included in the tissue classifier module 306 has additional layers of 1×1 convolution in a skip connection, downsampling by a factor of 8 in a skip connection, and a confidence map layer, and replaces an average pooling layer with a concatenation layer, and a fully connected FCN layer with a 1×1 convolution and Softmax layer. The added layers convert a classification task into a classification-segmentation task. This means that instead of receiving and classifying a whole image as one tissue class label, the added layers allow the tile-resolution FCN to classify each small tile in the user-defined grid as a tissue class.

These added and replacement layers convert a CNN to a tile-resolution FCN without requiring the upsampling performed in the later layers of traditional pixel-resolution FCNs. Upsampling is a method by which a new version of an original image can be created with a higher resolution value than the original image. However, upsampling is a time-consuming, computation-intense process, which can be avoided with the present architecture.

There are many methods known in the art for upsampling, including nearest-neighbor, bilinear, hermite, bell, Mitchell, bicubic, and Lanczos resampling. In one example, 2× upsampling means that a pixel with red green blue (RGB) values will be split into four pixels, and the RGB values for the three new pixels may be selected to match the RGB values of the original pixel. In another example, the RGB values for the three new pixels may be selected as the average of the RGB values from the original pixel and the pixels that are adjacent to the neighboring pixel.

Because the RGB values of the new pixels may not accurately reflect the visible tissue in the original slide that was captured by the digital slide image, upsampling can introduce errors into the final image overlay map produced by the overlay map generator 224.

In an example, instead of labeling individual pixels, the tile-resolution FCN is programmed to analyze a large square tile made of small square tiles, producing a 3D array of values that each represent the probability that one tissue class classification label matches the tissue class depicted in each small tile. A convolution layer performs the multiplication of at least one input image matrix by at least one filter matrix. In the first convolution later, the input image matrix has a value for every pixel in the large square tile input image, representing visual data in that pixel (for example, a value between 0 and 255 for each channel of RGB).

The filter matrix may have dimensions selected by the user, and may contain weight values selected by the user or determined by backpropagation during CNN model training. In one example, in the first convolution layer, the filter matrix dimensions are 7×7 and there are 64 filters. The filter matrix may represent visual patterns that can distinguish one tissue class from another.

In an example where RGB values populate the input image matrix, the input image matrix and the filter matrices will be 3-dimensional (see, FIG. 12C). Each filter matrix is multiplied by each input image matrix to produce a result matrix. All result matrices produced by the filters in one convolution layer may be stacked to create a 3-dimensional result matrix having dimensions such as rows, columns, and depth. The last dimension, depth, in the 3-D result matrix will have a depth equal to the number of filter matrices. The resulting matrix from one convolution layer becomes the input image matrix for the next convolution layer.

Returning to FIG. 12A, a convolution layer title that includes "/n", where n is a number, indicates that there is a downsampling (also known as pooling) of the result matrix produced by that layer. The n indicates the factor by which the downsampling occurs. Downsampling by a factor of 2 means that a downsampled result matrix with half as many rows and half as many columns as the original result matrix will be created by replacing a square of four values in the result matrix by one of those values or a statistic calculated from those values. For example, the minimum, maximum, or average of the values may replace the original values.

The architecture 1200 also adds skip connections (shown in FIG. 12A as black lines with arrows that connect blue convolution layers directly to the concatenation layer). The skip connection on the left includes downsampling by a factor of 8, and the skip connection on the right includes two convolution layers that multiply an input image matrix by filter matrices that each have dimensions of 1×1. Because of the 1×1 dimensions of the filter matrices in these layers, only an individual small square tile contributes to its corresponding probability vector in the result matrices created by the purple convolution layers. These result matrices represent a small focus of view.

In all of the other convolution layers, the larger dimensions of the filter matrices allow the pixels in each medium square tile, including the small square tile at the center of the medium square tile, to contribute to the probability vector in the result matrix that corresponds with that small square tile. These result matrices allow the contextual pixel data patterns surrounding the small square tile to influence the probability that each tissue class label applies to the small square tile. These result matrices represent a large focus of view.

The 1×1 convolution layers in the skip connection allow the algorithm to regard the pixel data patterns in the center small square tile as either more or less important than pixel data patterns in the rest of the surrounding medium square tile. The amount of importance is reflected by the weights that the trained model multiplies by the final result matrix from the skip connection layers (shown on the right side of FIG. 12A) compared to the weights that the trained model multiplies by the final result matrix from the medium tile convolution layers (shown in the center column of FIG. 10A) during the concatenation layer.

The downsampling skip connection shown on the left side of FIG. 12A creates a result matrix with a depth of 64. The 3×3 convolution layer having 512 filter matrices creates a result matrix with a depth of 512. The 1×1 convolution layer having 64 filter matrices creates a result matrix with a depth of 64. All three of these results matrices will have the same number of rows and the same number of columns. The concatenation layer concatenates these three results matrices to form a final result matrix with the same number of rows and the same number of columns as the three concatenated matrices, and a depth of 64+512+64 (640). This final result matrix combines the large and small focus of view matrices.

The final result matrix may be flattened to 2 dimensions by multiplying a factor by every entry, and summing the products along each depth. Each factor may be selected by the user, or may be selected during model training by backpropagation. Flattening will not change the number of rows and columns of the final results matrix, but will change the depth to 1.

The 1×1 convolution layer receives the final result matrix and filters it with one or more filter matrices. The 1×1 convolution layer may include one filter matrix associated with each tissue class label in the trained algorithm. This convolution layer produces a 3-D result matrix that has a depth equal to the number of tissue class labels. Each depth corresponds to one filter matrix and along the depth of the result matrix there may be a probabilities vector for each small square tile. This 3-D result matrix is the 3-dimensional probability data array, and the 1×1 convolution layer stores this 3-D probability data array.

A Softmax layer may create a 2-dimensional probability matrix from the 3-D probability data array by comparing every value in each probabilities vector and selecting the tissue class associated with the maximum value to assign that tissue class to the small square tile associated with that probabilities vector.

The stored 3-dimensional probability data array or the 2-D probability matrix may then be converted to a tissue class overlay map in the final confidence map layer in FIG. 10A, to efficiently assign a tissue class label to each tile.

In one example, to counteract shrinkage, input image matrices have added rows and columns on all four outer edges of the matrices, wherein each value entry in the added rows and columns is a zero. These rows and columns are referred to as padding. In this case, the training data input matrices will have the same number of added rows and columns with value entries equal to zero. A difference in the number of padding rows or columns in the training data input matrices would result in values in the filter matrices that do not cause the tissue class locator 216 to accurately label input images.

In the FCN shown in FIG. 12A, 217 total outer rows or columns on each side of the input image matrix will be lost to shrinkage before the skip connection, due to the gray and blue layers. Only the pixels located in the small square tiles will have a corresponding vector in the result matrices created by the green layers and beyond.

In one example, each medium square tile is not padded by adding rows and columns with value entries of zero around the input image matrix that corresponds to each medium square tile because the zeroes would replace image data values from neighboring medium square tiles that the tissue class locator 216 needs to analyze. In this case, the training data input matrices will not be padded either.

FIG. 12C is a visualization of each depth of an exemplary 3-dimensional input image matrix being convoluted by two exemplary 3-dimensional filter matrices.

In an example where an input image matrix contains RGB channels for each medium square tile, the input image matrix and filter matrices will be 3-dimensional. In one of the three dimensions, the input image matrix and each filter matrix will have three depths, one for red channel, one for green channel, and one for blue channel.

The red channel (first depth) 1202 of the input image matrix is multiplied by the corresponding first depth of the first filter matrix. The green channel (second depth) 1204 is multiplied in a similar fashion, and so on with the blue channel (third depth) 1206. Then, the red, green, and blue product matrices are summed to create a first depth of the 3-dimensional result matrix. This repeats for each filter matrix, to create an additional depth of the 3-dimensional result matrix that corresponds to each filter.

A variety of training sets may be used to train a CNN or FCN model that is included in the tissue classifier module 306.

In one example, the training set may contain JPEG images of medium square tiles, each having a tissue class label assigned to its center small square tile, taken from at least 50 digital images of histopathology slides at a resolution of approximately 1 pixel per micron. In one example, a human analyst has outlined and labeled (annotated various tissue classes) all relevant tissue classes or labeled each small square tile in each histopathology slide as non-tissue or as a specific type of cells. Classes of various tissue may include tumor, stroma, normal, immune cluster, necrosis, hyperplasia/dysplasia, and red blood cells. In one example, each side of each center small square tile is approximately 32 pixels long.

In one example, the training set images are converted to input training image matrices and processed by the tissue classifier module 306 to assign a tissue class label to each tile image of the training image. If the tissue classifier module 306 does not accurately label the validation set of training images to match the corresponding annotations added by a human analyst, the weights of each layer of the deep learning network may be adjusted automatically by stochastic gradient descent through backpropagation until the tissue classifier module 306 accurately labels most of the validation set of training images.

In one example, the training data set has multiple classes where each class represents a tissue class. That training set will generate a unique model with specific hyperparameters (number of epochs, learning rate, etc.) that can recognize and classify the content in a digital slide image into different classes. Tissue classes may include tumor, stroma, immune cluster, normal epithelium, necrosis, hyperplasia/dysplasia, and red blood cells. In one example, the model can classify an unlimited number of tissue classes, provided each tissue class has a sufficient training set.

In one example, the training set images are converted into grayscale masks for annotation where different values (0-255) in the mask image represent different classes.

Each histopathology image can exhibit large degrees of variation in visual features, including tumor appearance, so a training set may include digital slide images that are highly dissimilar to better train the model for the variety of slides that it may analyze. Images in training data may also be subjected to data augmentation (including rotating, scaling, color jitter, etc.), before being used to train the model.

A training set may also be specific to a cancer type. In this case, all of the histopathology slides that generated the digital images in a particular training set contain a tumor sample from the same cancer type. Cancer types may include breast, colorectal, lung, pancreatic, liver, stomach, skin, etc. Each training set may create a unique model specific to the cancer type. Each cancer type may also be split into cancer subtypes, known in the art or defined by the user.

In one example, a training set may be derived from histopathology slide pairs. A histopathology slide pair includes two histopathology slides that each have one slice of tissue, wherein the two slices of tissue were located substantially proximal to each other/approximately adjacent in the tumor sample. Therefore, the two slices of tissue are substantially similar. One of the slides in the pair is stained with H&E staining only, and the other slide in the pair is stained with IHC staining for a specific molecule target. The areas on the H&E stained slide that correspond to areas where IHC staining appears in the paired slide are annotated by a human analyst as containing a specific molecule target and the tissue class locator receives the annotated H&E slides as a training set. Substantially similar slides include other combinations, such as when the paid includes one with H&E staining and the other formed with molecular sequencing data scrapped off one of the adjacent slides, or where one is of IHC staining and the other is formed with molecular sequencing data, or where both are formed of similar molecular sequencing data.

For example, in some embodiments, more than one sample is obtained from a subject—for example, more than one tissue slice can be taken that are adjacent to each other. In some cases, the tissue slices are obtained such that some of the pathology slides prepared from the respective slices are imaged, whereas some of the pathology slides are used for obtaining sequencing information.

A suitable training data set may be used for training an optimization model in accordance with embodiments of the present disclosure. In some embodiments, curation of a training data set may involve collecting a series of pathology reports and associated sequencing information from a plurality of patients. For example, a physician may perform a tumor biopsy of a patient by removing a small amount of tumor tissue/specimen from the patient and sending this specimen to a laboratory. The lab may prepare slides from the specimen using slide preparation techniques such as freezing the specimen and slicing layers, setting the specimen in paraffin and slicing layers, smearing the specimen on a slide, or other methods known to those of ordinary skill. For purposes of the following disclosure, a slide and a slice may be used interchangeably. A slide stores a slice of tissue from the specimen and receives a label identifying the specimen from which the slice was extracted and the sequence number of the slice from the specimen. Traditionally, a pathology slide may be prepared by staining the specimen to reveal cellular characteristics (such as cell nuclei, lymphocytes, stroma, epithelium, or other cells in whole or part). The pathology slide selected for staining is traditionally the terminal slide of the specimen block. Specimen slicing proceeds with a series of initial slides that may be prepared for staining and diagnostic purposes. A series of the next sequential slices may be used for sequencing, and then final, terminal slides may be processed for additional staining. In a case when the terminal, stained slide is too far removed from the sequenced slides, another slide may be stained which is closer to the sequenced slides such that sequencing slides are broken up by staining slides. While there are slight deviations from slice to slice, the deviation is expected to be minimal as the tissue is sliced at thicknesses approaching 4 um for paraffin slides and 35 um for frozen slides. Laboratories generally confirm that the distance, usually less than 40 um (approximately 10 slides/slices), has not produced a substantial deviation in the tissue slices.

In (less frequent) cases where slices of the specimen vary greatly from slice to slice, outliers may be discarded and not further processed. The pathology slides 510 may be varying stained slides taken from tumor samples from patients. Some slides and sequencing data may be taken from the same specimen to ensure data robustness, while other slides and sequencing data may be taken from respective unique specimens. The larger the number of tumor samples in the dataset, the more accuracy can be expected from the predictions of cell-type RNA profiles. In some embodiments, a stained tumor slide may be reviewed by a pathologist for identification of cellular features, such as the quantity of cells and their differences from the normal cells of that or similar type.

In this case, the trained tissue classification model 320 receives digital images of H&E stained tissue to predict tiles that may contain IHC staining or a given molecule target and the overlay map generator 326 produces an overlay map showing which tiles are likely to contain the IHC target or given molecule. In one example, the resolution of the overlay is at the level of an individual cell.

The overlay produced by a model trained by one or more training sets may be reviewed by a human analyst in order to annotate the digital slide image to add it to one of the training sets.

The pixel data patterns that the algorithm detects may represent visually detectable features. Some examples of those visually detectable features may include color, texture, cell size, shape, and spatial organization.

For example, color on a slide provides contextual information. For example, an area on the slide that is purple may have a higher density of cells and may be more likely to be invasive tumor. Tumor also causes the surrounding stroma to become more fibrous in a desmoplastic reaction, which causes normally pink stroma to appear blue-grey. Color intensity also helps to identify individual cells of a certain type (for example, lymphocytes are uniformly very dark blue).

Texture refers to the distribution of stain within cells. Most tumor cells have a rough, heterogeneous appearance, with light pockets and dark nucleoli within their nuclei. A zoomed-out field of view with many tumor cells will have this rough appearance. Many non-tumor tissue classes each have distinguishing features. Furthermore, patterns of tissue classes that are present in a region can indicate the type of tissue or cell structures present in that region.

Additionally, cell size often indicates tissue class. If a cell is several times larger than normal cells elsewhere on the slide, the probability is high that it is a tumor cell.

The shape of individual cells, specifically how circular they are, can indicate what type of cell they are. Fibroblasts (stromal cells) are normally elongated and slim, while lymphocytes are very round. Tumor cells can be more irregularly shaped.

The organization of a group of cells can also indicate tissue class. Frequently, normal cells are organized in a structured and recognizable pattern, but tumor cells grow in denser, disorganized clusters. Each type and subtype of cancer can produce tumors with specific growth patterns, which include cell location relative to tissue features, the spacing of tumor cells relative to each other, formation of geometric elements, etc.

Figure 14:
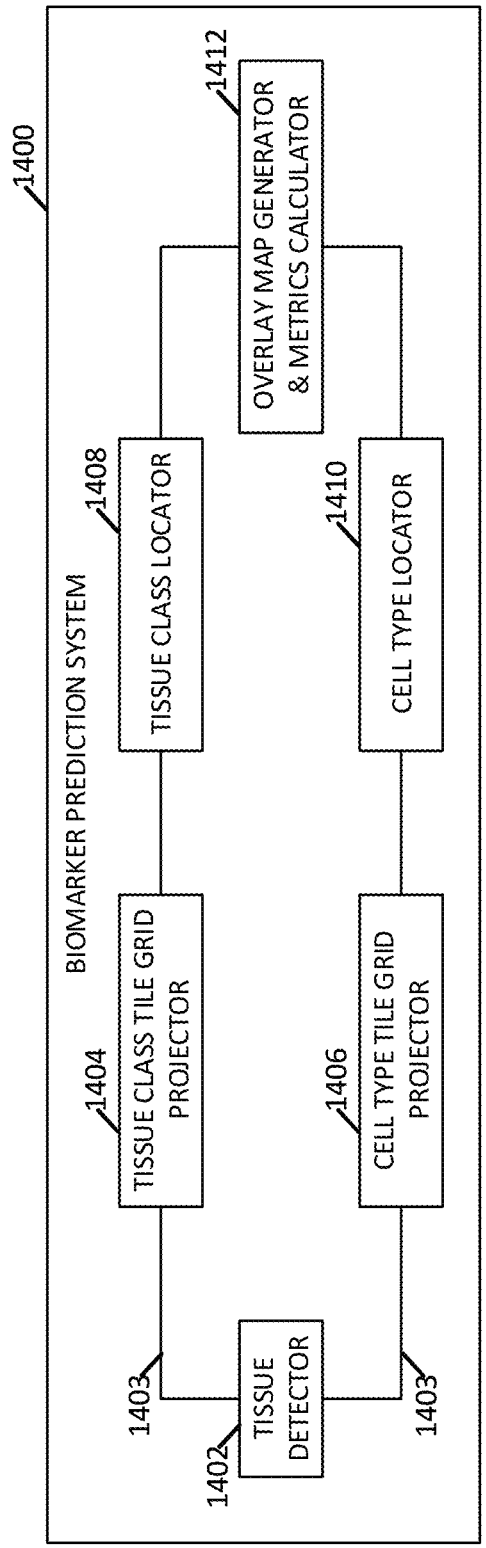
FIG. 14 is a block diagram of a schematic of an imaging-based biomarker prediction system that employs separate pipelines, for example, as may be implemented as an image-based nucleic acid yield prediction system, in accordance with another example.

The techniques herein may be extended to other architectures. FIG. 14, for example, illustrates an imaging-based biomarker prediction system 1400 that similarly employs separate pipelines for tissue classification and cell classification. The system 1400 may be used for various biomarker determinations, including PD-L1 as described in the examples herein. Further, the system 1400, like other architectures herein may be configured to predict biomarker status and tumor status and tumor statistics based on 3D image analysis.

The system 1400 receives one or more digital images of a histopathology slide and creates a high-density, grid-based digital overlay map that identifies the majority class of tissue visible within each grid tile in the digital image. The system 1400 may also generate a digital overlay drawing identifying each cell in a histopathology image, at the resolution level of an individual pixel.

The system 1400 includes a tissue detector 1402 that detects the areas of a digital image that have tissue and stores data that includes the locations of the areas detected to have tissue (e.g., pixel locations using a reference location in an image, such as a 0,0 pixel location). The tissue detector 1402 transfers tissue area location data 1403 to a tissue class tile grid projector 1404 and to a cell tile grid projector 1406. The tissue class tile grid projector 1404 receives the tissue area location data 1403, and, for each of several tissue class labels, performs a tissue classification on a tile. A tissue class locator 1408 receives resulting tile classification and calculates a percentage that represents the likelihood that the tissue class label accurately describes the image within each tile to determine where each tissue class is located in the digital image. For each tile, the total of all of the percentages calculated for all tissue class labels will sum to 1, which reflects 100%. In one example, the tissue class locator 1408 assigns one tissue class label to each tile to determine where each tissue class is located in the digital image. The tissue class locator stores the calculated percentages and assigned tissue class labels associated with each tile.

In an example, the system 1400 includes a multi-tile algorithm that concurrently analyzes many tiles in an image, both individually and in conjunction with the portion of the image that surrounds each tile. The multi-tile algorithm may achieve a multiscale, multiresolution analysis that captures both the contents of the individual tile and the context of the portion of the image that surrounds the tile. Because the portions of the image that surround two neighboring tiles overlap, analyzing many tiles and their surroundings concurrently instead of separately analyzing each tile with its surroundings reduces computational redundancy and results in greater processing efficiency.

In an example, the system 1400 may store the analysis results in a 3-dimensional probability data array, which contains one 1-dimensional data vector for each analyzed tile. In one example, each data vector contains a list of percentages that sum to 100%, each indicating the probability that each grid tile contains one of the tissue classes analyzed. The position of each data vector in the orthogonal 2-dimensional plane of the data array, with respect to the other vectors, corresponds with the position of the tile associated with that data vector in the digital image, with respect to the other tiles.

The cell type tile grid projector 1406 receives the tissue area location data 1403 and identifies and classifies cells in a tile and projects a cell type tile grid onto the areas of an image with tissue. A cell type locator 1410 may detect each biological cell in the digital image within each grid, prepare an outline on the outer edge of each cell, and classify each cell by cell type. The cell type locator 1410 stores data including the location of each cell and each pixel that contains a cell outer edge, and the cell type label assigned to each cell.

The overlay map generator and metric calculator 1412 may retrieve the stored 3-dimensional probability data array from the tissue class locator 1408, and convert it into an overlay map that displays the assigned tissue class label for each tile. The assigned tissue class for each tile may be displayed as a transparent color that is unique for each tissue class. In one example, the tissue class overlay map displays the probabilities for each grid tile for the tissue class selected by the user. The overlay map generator and metric calculator 1412 also retrieves the stored cell location and type data from the cell type locator 1410, and calculates metrics related to the number of cells in the entire image or in the tiles assigned to a specific tissue class.

Figure 15A:
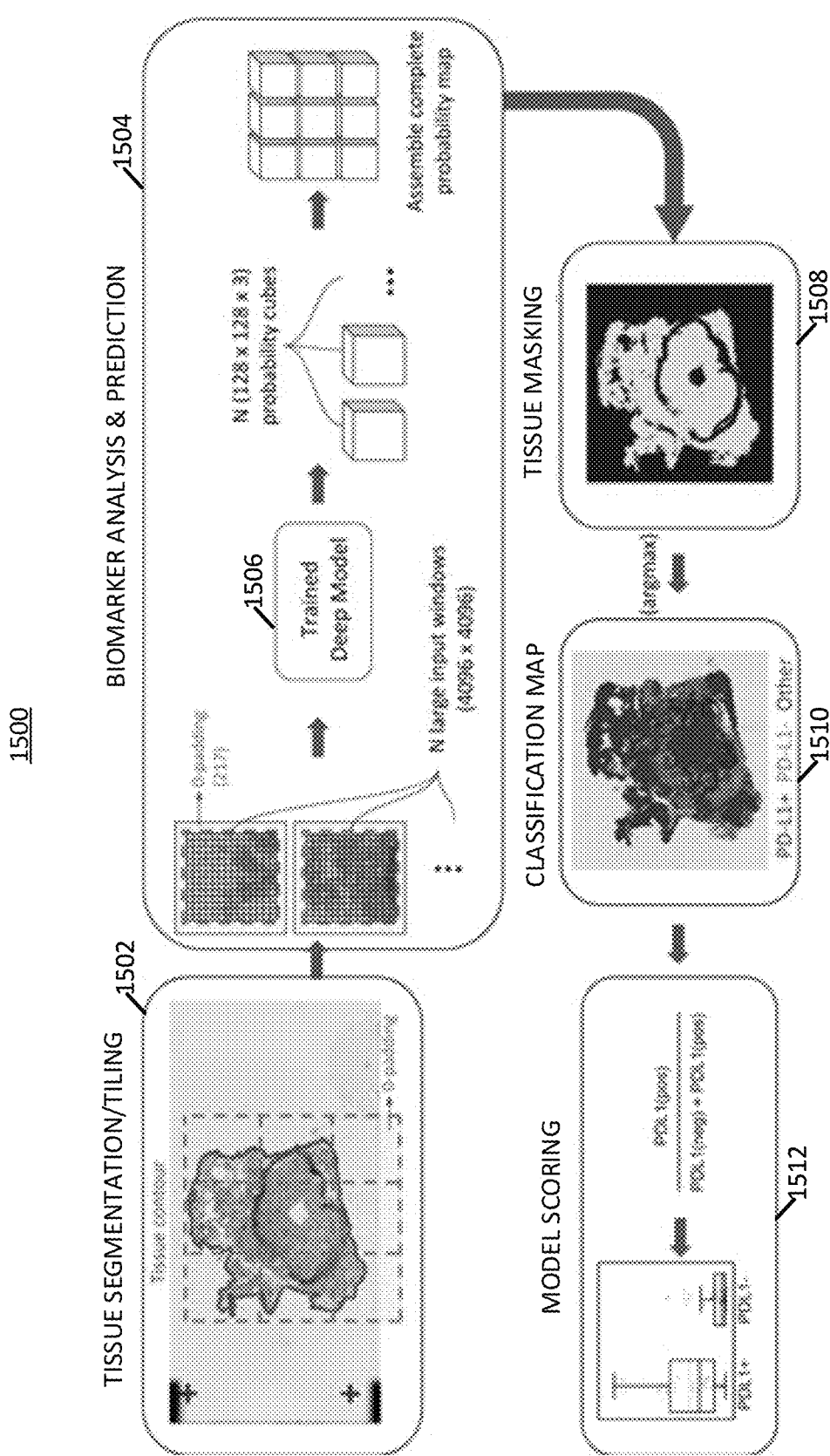
FIG. 15A is a block diagram of a schematic of an example biomarker prediction process as may be implemented by the system of FIG. 14, for example, as may be implemented as an image-based nucleic acid yield prediction system, in accordance with an example.

FIG. 15A illustrates an overview of an example process 1500 implemented by the imaging-based biomarker prediction system 1400, showing model inference pipeline for predicting a biomarker, in this example PD-L1. The process 1500 takes advantage of the fully convolutional model architecture for the system 1400 to process many tiles in parallel. In an example, the process 1500 was able to take 2.8 seconds to classify a single 4096×4096 pixel image, using a GeForce GTX 1080 Ti GPU and 6th Generation Intel® Core™ i7 processor. The process 1500 further included tissue detection and artifact removal algorithms so as to function in a fully automated manner in a real-world setting where slides may include artifacts.

At a first process 1502, initial tissue segmentation is performed by the tissue detector 1402, for example, applying a tissue masking algorithm to automatically contour the tissue (red outline) in order to produce a bounding box (not shown) around the tissue of interest. Aligning to the upper left corner of the bounding box, the tissue region is divided into large non-overlapping 4096×4096 input windows (blue dashed lines). Typically, between 10-30 input windows are needed to cover the tissue. Any large window area extending beyond the bounded region is padded with 0s (gray region).

A process 1504 performs trained classification model prediction. In the illustrated example, large input windows contained 128×128=16,384 small 32×32 tiles (grids are much finer than shown). Large input windows were padded by 0s on all sides (length 217) to account for edges of overlapping 466×466 tiles centered on each 32×32 small tile. Each large window was passed through one or more trained model 1506 of the deep learning framework (including the tissue classification process of projector 1404 and the cell classification process of projector 1406). With the trained model(s) 1506 being fully convolutional, in an example, each tile within the large input window is processed in parallel, producing a 128×128×3 probability cube (there are 3 classes). Each 1×1×3 vector of this probability cube corresponds to a 32×32 px region at the center of each 466×466 tile in the original image. The resulting probability cubes are assembled into a probability map of the whole image.

A process 1508 displays images associated with a tissue masking step of process 1502. An assembled probability map generated by the process 1504 is passed through this tissue mask to remove background. In the example, both background and marker area are removed by the masking algorithm of the process 1508.

A process 1510 displays images showing a classification map that identifies one or more classified regions, such as each the different regions for each of the biomarker classifications. In an example, the maximum probability class (argmax) is assigned to each tile through the process 1508, producing a classification map of the three biomarker classes (PD-L1+, PD-L1-, Other), at the process 1510. The classification map illustrates each of the these biomarker classifications and their identified location corresponding to the original histopathology image.

A process 1512 performs statistical analysis on biomarker classifications from the classification map and displays a resulting prediction score for the biomarker. In this example, the number of predicted PD-L1 positive tiles is divided by the total number of predicted tumor tiles to achieve an exemplary model score.

The tissue class locator 1408 may have an architecture like that of architecture 1200, for example. The architecture is similar to that of the FCN-tile resolution classifier. The architecture 1550 may be formed of three major components: 1) a fully convolutional residual neural network (e.g., built on ResNet-18) backbone that processes a large field of view image (FOV), 2) two branches that process small FOVs, and 3) concatenation of small and large FOV features for multi-FOV classification. The ResNet-18 backbone contains multiple shortcut connections, indicated by dotted lines, where feature maps are also downsampled by 2. The small FOV branches emerge after the second convolutional block. The feature maps of the small FOV branches are downsampled by 8 to match the dimensions of the ResNet-18 feature map. These feature maps are concatenated before passing through a softmax output to produce a PD-L1 biomarker prediction (confidence) map.

In an example, the backbone of the model includes an 18-layer version of ResNet (ResNet-18) with some modifications. The ResNet-18 backbone was converted into a fully convolutional network (FCN) by removing the global average pooling layer and eliminating zero-padding in downsampled layers. This enabled the output of a 2D probability map rather than a 1D probability vector (see, FIG. 15B). In the illustrated example, the tile size (466×466 pixels) was over twice the tile size of a standard ResNet, providing our model with a larger FOV that allows it to learn surrounding morphological features. Although the tissue class locator 1408 in this example adds multiple field of view (multi-FOV) capabilities to a ResNet architecture, it should be understood that tissue class locator 1408 could be comprised of a distinct network architecture that has been adapted to incorporate the multi-FOV approach disclosed here.

The FCN configuration of the architecture 1505 provides numerous advantages, including overcoming accuracy degradation challenges traditionally suffered by "very deep" neural networks (including neural networks with more than 16 convolutional layers) (see, e.g., He et al., Deep Residual Learning for Image Recognition, (2015) (arXiv ID:1512.03385v1, and Simonyan et al., Very Deep Convolution Networks for Large-Scale Image Recognition (2014), arXiv ID:1409.1556v6). The architecture 1550 includes a stack of convolutional layers interleaved with "shortcut connections," which skip intermediate layers. These shortcut connections use earlier layers as a reference point to guide deeper layers to learn the residual between layer outputs rather than learning an identity mapping between layers. This innovation improves convergence speed and stability during training, and allows deeper networks to perform better than their shallower counterparts.

Figure 15B:
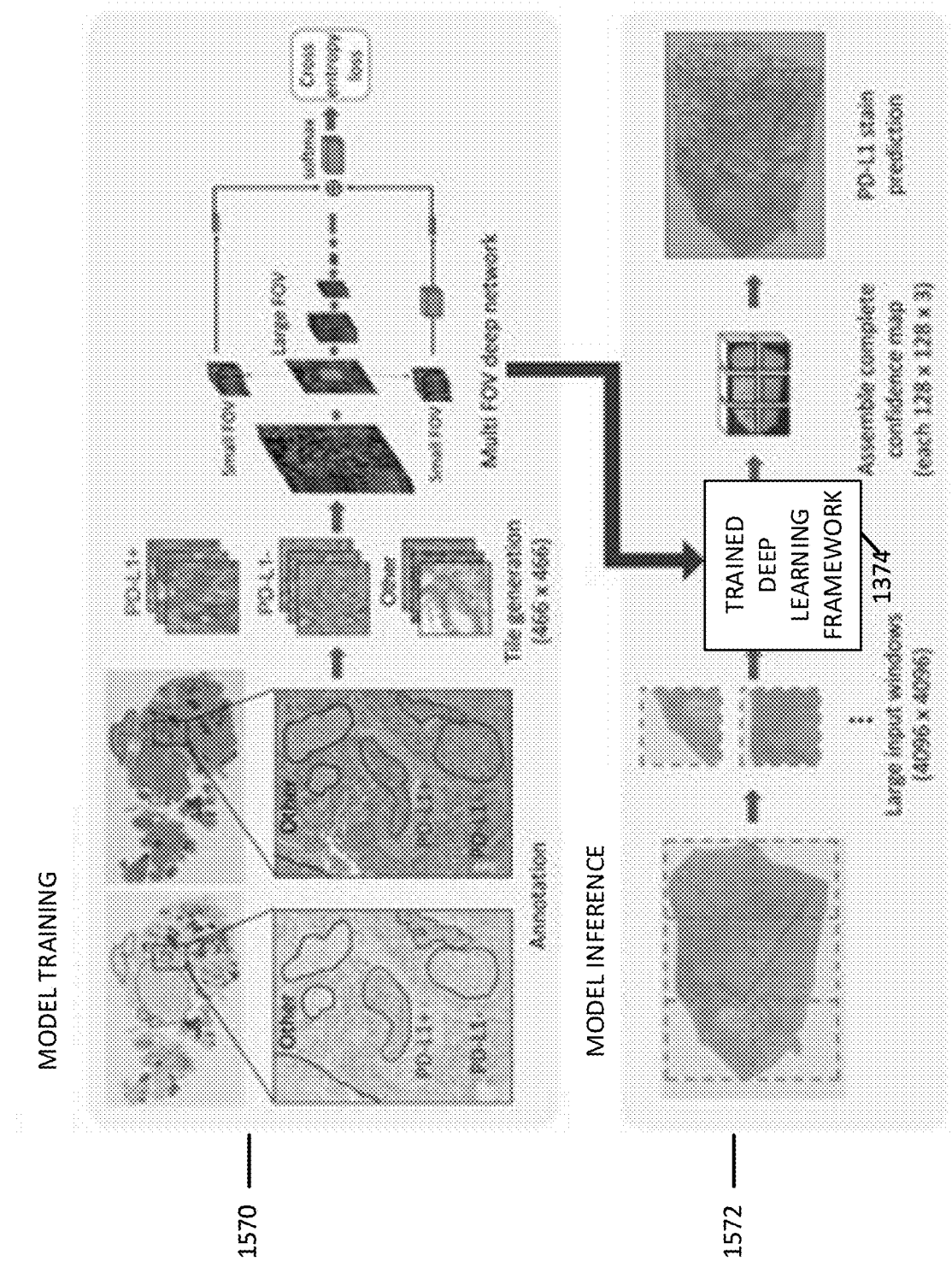
FIG. 15B is a block diagram of a schematic of an example training process as may be implemented by the system of FIG. 14, in accordance with an example.

The tissue class locator 1408 may include two additional branches with receptive fields restricted to a small FOV (32×32 pixels) in the center of the second convolutional feature map (see, FIG. 15B). One branch passes a copy of the small FOV through a convolutional filter, while the other branch is a standard shortcut connection with downsampling. The features produced by these additional branches are concatenated to the features from the main backbone just before the model outputs are converted into probabilities, in a softmax layer. In this way, the tissue class locator 1408 combines information from multiple FOVs, much like a pathologist relies on various zoom levels when diagnosing slides. Moreover, the architecture ensures that the central region of each tile contributes more to classification than the tile edges, resulting in a more accurate classification map across the entire histopathology image.

FIG. 15B illustrates an example training process 1570 for the imaging-based biomarker prediction system 1400 and generation of an overlay map output, predicting the location of a PD-L1 biomarker from analysis of IHC and H&E histopathology images. At a model training process 1570, matching areas on IHC and H&E digital images were annotated by a medical professional. In some examples, however, stains on adjacent tissue slices may be automatically annotated. Images were annotated showing PD-L1+ and PD-L1− and fed to the system for training. The annotated regions of the H&E image were tiled into overlapping tiles (466×466 pixels) with a stride of 32 pixels, producing training data. The tissue class locator 1408 was then trained using a cross entropy loss function. The yellow square in the model schematic depicts the central region that is cropped for the small FOVs. The resulting PD-L1 classification model is stored in trained deep learning framework 1574.

FIG. 15B also illustrates an example prediction process 1572, where each image was divided into large non-overlapping 4096×4096 input windows (blue dashed lines). Each large window was passed through the trained model. Because the deep learning framework 1574 is fully convolutional, each tile within the large input window was processed in parallel, producing a 128×128×3 probability cube (the last dimension represents three classes). The resulting probability cubes were slotted into place and assembled to generate a probability map of the whole image. The class with the maximum probability was assigned to each tile and a PD-L1 prediction is report is generated.

Figures 16A, 16B, 16C, 16D, 16E, 16F:
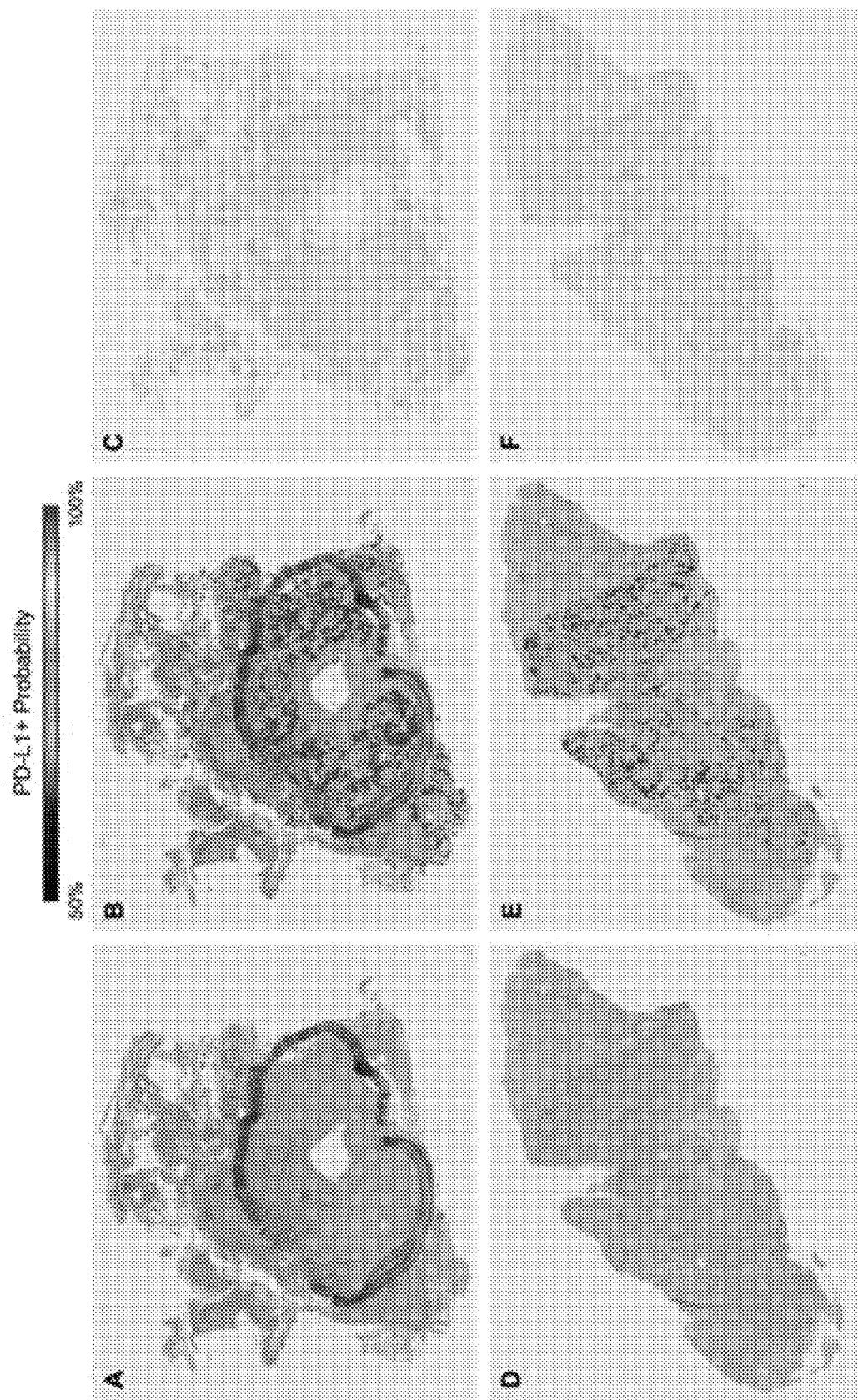
FIGS. 16A-16F illustrate input histopathology images, in accordance with an example.

FIGS. 16A-16F illustrate input histopathology images received by the imaging-based biomarker prediction system 1400, corresponding overlay maps generated by the system 1400 to predict the location of IHC PD-L1 biomarker, and corresponding IHC stained tissue images used as references to determine the accuracy of overlay maps. The IHC stained tissue images were obtained from a test cohort but were not applied to the system 1200 during model training. FIGS. 16A-16C illustrate a representative PD-L1 positive biomarker classification example. FIG. 16A displays an input H&E image; FIG. 16B displays a probability map overlaid on the H&E image: FIG. 16C displays a PD-L1 IHC stain for reference. FIGS. 16D-16F illustrate a representative PD-L1 negative biomarker classification example. FIG. 16D displays an input H&E image; FIG. 16E displays a probability map overlaid on the H&E image; and FIG. 16F displays a PD-L1 IHC stain for reference. The color bar indicates the predicted probability of the tumor PD-L1+ class.

Among the advantages offered by the deep learning frameworks herein, they can exhibit improved accuracy by disrupting shift invariance. Shift invariance, or homogeneity, is a property of linear filters such as convolution, where the response of the filter does not explicitly depend on the position. In other words, if we shift a signal, the output image is the same but with the shift applied. While shift invariance is desirable in most image classification tasks (Le Cun, 1989), in examples herein we typically do not want objects close to the edge of the tile to contribute equally to the classification.

Figure 17:
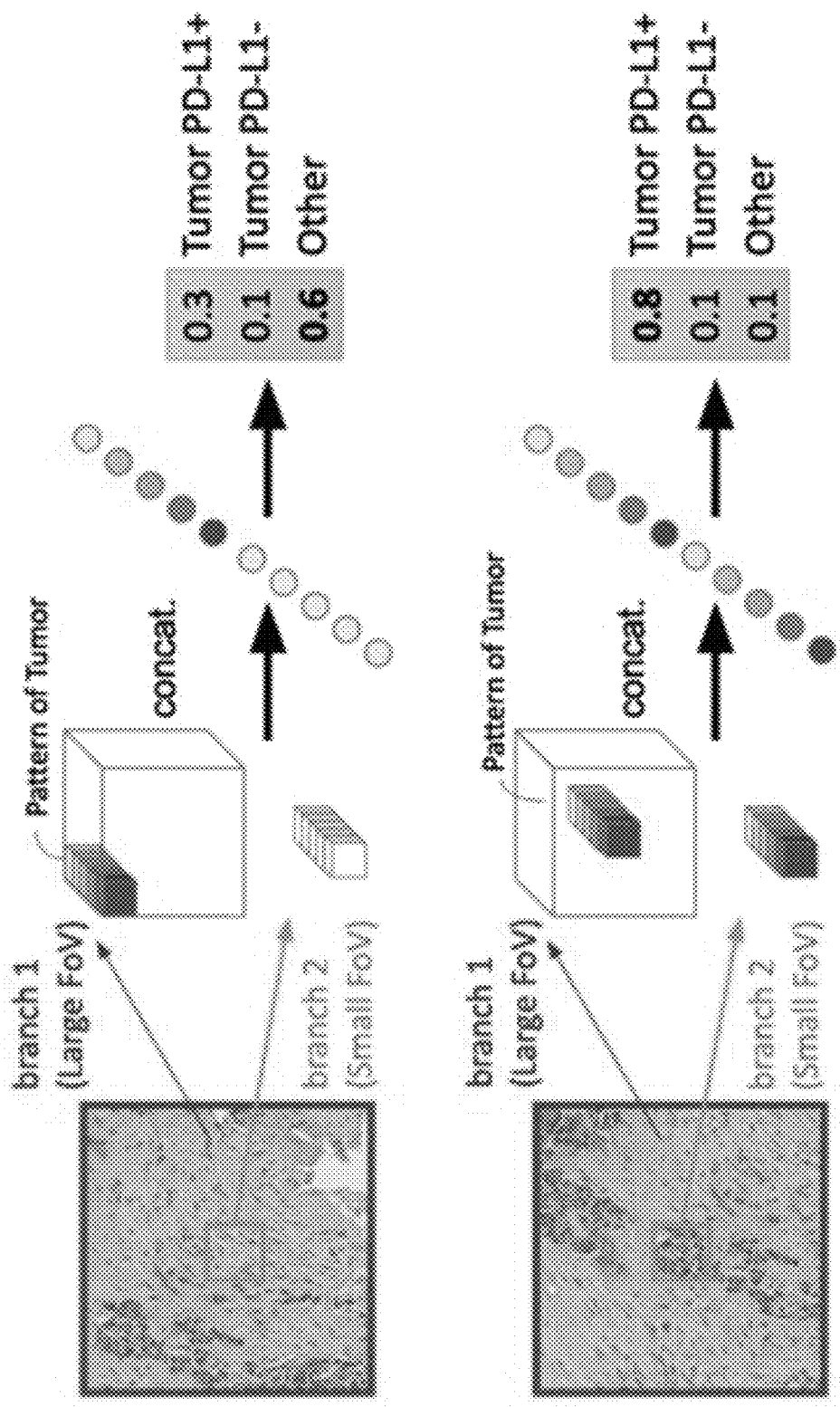
FIG. 17 is a block diagram of an example multi-field of view strategy for PD-L1 classification as may be performed by the processes of FIGS. 14, 15A, and 15B, in accordance with an example.

FIG. 17 illustrates an example advantage of a multi-FOV strategy such as that described in reference to FIGS. 14, 15A, and 15B. In a top portion, large FOV (red box) contains both PD-L1+ tumor cells (purple, upper left) and stroma (pink). Only stroma falls within the small FOV (green box). When passed through a convolutional layer of the tissue class locator 1408, the tumor area produces a unique pattern (colored squares) distinct from the pattern produced by stromal areas (white squares). After the patterns from large and small FOV branches are concatenated, the model is likely to predict "Other". In the bottom portion, the field of view has shifted, and now the PD-L1+ tumor area falls within the small FOV. This tumor area will produce the same convolutional filter patterns in both large and small FOV branches (colored squares). Upon concatenating the learned features, the tissue class locator 1408 is now more likely to predict PD-L1+ tumor. Thus, without the small FOV used in training the tissue class locator 1408, the system 1400 may have predicted PD-L1+ tumor for both images. Instead, the multi-FOV strategy of the architecture in FIG. 15 allows the network to take advantage of rich contextual information in the surrounding area, while still favoring what is in the center of the image for classification.

Yet other architectures may be used for any of the classifier examples herein to predict biomarker status, tumor status, and/or metrics thereof, in particular using multiple instance learning techniques.

In examples discussed herein, classification model architectures, e.g., based on FCN architectures described in FIG. 12A, were trained with digital images of a histopathology slide, which may include a matrix of annotations. Training from such digital images is performed on a tile by tile basis, where for example only tiles that have an annotation (i.e., label) are supplied as training tiles to the deep learning framework. Tiles of the digital image without annotations may be discarded. Further, each column and row of a matrix corresponds to a distinct grid having N×M pixels of the digital image. In order to properly assign the annotations from the matrix having columns and rows to a digital image having a plurality of tiles, it may be advantageous to, in some examples, take the column (i) and row (j) from the matrix and assign the annotation to the center region of a grid starting at pixel N(i) and M(j) and extending to the next [N−1] to [M−1] pixels, where the tile with central region extending across that range is assigned the annotation of the matrix at i,j. Thus, the matrix may accurately represent annotations at a tile by tile basis within the larger digital image.

The FCN architectures may take a large tile as input while the label comes from the central region mapping to the annotation mask points. FCN architectures may learn from both the central region of the large tile and the pixels surrounding the central region, where the central region contributes more to the prediction. Additionally, slide metadata may be stored in a feature vector, such as a vector associated with the slide which identified slide level labeling, including the patient features which may improve model performance. A plurality of tiles from grids of digital images and corresponding annotation matrices are sequentially provided to the FCN architecture, to train the FCN architecture in classifying tiles of N×M size according to the annotations included in the matrix and the slides themselves according to the annotation included in the feature vector. An output of the FCN architecture may include a matrix having predicted classifications on a tile-by-tile basis and can be aggregated to a vector having predicted classifications on a slide by slide basis. The matrix may be converted to a digital overlay by associating the highest classifications of each tile to a color which may be superimposed over the corresponding grid location in the digital image. In some examples, the matrix may be converted to multiple digital overlays, wherein each overlay corresponds to each classification and an intensity of an associated color is assigned to the overlay based upon the percentage of confidence ratio associated with the respective classification. For example, a tile having a 30% likelihood as tumor, 50% likelihood as stroma, and a 20% likelihood as normal may be assigned a single overlay for stroma, as the highest likelihood of tissue in the tile, or may be assigned a first overlay with a 30% intensity of a first color and a second overlay with a 50% intensity of a second color, to identify the type of tissue that the tile may comprise.

However, even a classification model based purely off of an architecture which may not support tile-by-tile annotations, such as an architecture similar to Resnet-34 or Inception-v3, may be trained with a digital image of a pathology slide with only a vector of annotations, where each entry of the vector is an annotation of a patient feature or metadata which applies to the slide. In some examples, even an architecture that supports tile-by-tile annotations may not have access to tile-by-tile annotations for a specific feature.

To use histopathology images in training neural networks images that do not have tile annotation or to train neural networks to identify biomarkers trained on molecular training data, in some examples, the present techniques include deep learning training architectures configured for label-free training. In examples, architectures do not require tile level annotation when training tissue classification models. Moreover, the label-free training architectures are neural network agnostic, in that they allow for label-free training that is agnostic to the configuration of the neural network (i.e., ResNet-34, FCN, Inception-v3, UNet, etc.). The architectures are able to analyze a set of possible training images and predict which tiles to exclude for training. Therefore, images may be discarded from training in some examples, while in other examples tiles may be discarded but the rest of the image may be used for training. These techniques result in much less training data which greatly reduces the time required to train, and in some instances update training of, classification models herein. Further, the techniques do not require pathologist labeling, which greatly reduces the time it takes to train a classification model and which avoids annotation errors and annotation variability across professionals.

Instead, in some examples, training may be performed with weakly supervised learning that involves only image level labeling, and no local labeling of tissue, cell, tumor, etc. The architectures may be configured with a label-less training front end having an algorithm with customized cost function that chooses which tile(s) should be used as the input with specific label. The process may be iterative, first, treating each histopathology image as a collection of tiles, where a single label of the image is applied to all the tiles in the collection. The tiles may be applied to an inference pipeline, such as through a network like ResNet 34, Inception-v3, or FCN, and predefined tile selection criteria such as probabilities of the neural network output may be used to select which output image tiles will be provided as an input to the same neural network for next round. This process may be repeated many times, given enough collections and tiles as input to the neural network, it will learn to differentiate tiles with different classes with higher accuracy as more iterations are performed.

Figure 18:
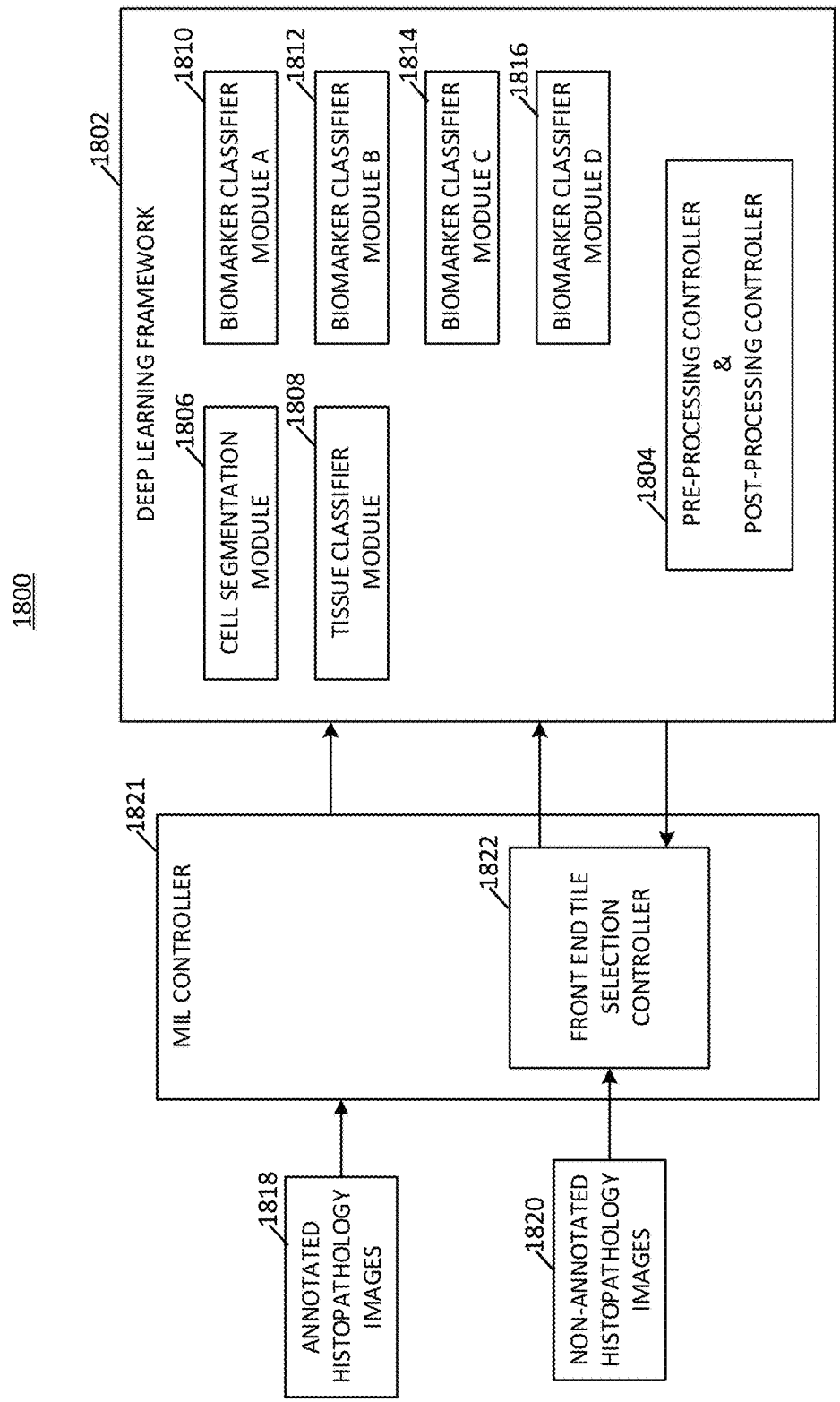
FIG. 18 is a block diagram of a schematic machine learning architecture having capable of performing label-free annotation training of a deep learning framework and having a multiple instance learning controller, in accordance with an example.

FIG. 18 illustrates an example machine learning architecture 1800 in an example configuration for performing label-free annotation training of a deep learning framework, to execute processes described in examples herein. A deep learning framework 1802, which may be similar to other deep learning frameworks described herein having multi-scale and single-scale classification modules, includes a pre-processing & post-processing controller 1804, performing processes are described in similar examples in FIGS. 1 and 3. The deep learning framework 1802 includes a cell segmentation modules 1806 and a tissue classifier module 1808, each of which being configured as a tile-based neural network classifier. The deep learning framework 1802 further includes a number of different biomarker classification models 1810, 1812, 1814, and 1816, each of which may be configured to have a different neural network architecture, where some may have a multiscale configuration and some may have a single-scale configuration. These different neural network architectures may be configured for training using annotated or non-annotated images. Some of these architectures may be configured for training using tile-annotated training images, while others of these architectures are configured for training using training images with no tile-annotations. For example, some architectures may be configured to accept only slide-level annotations on images (i.e., an annotation for an entire image and not an annotation identifying particular tile characteristics, cell segmentations, or tissue segmentations). Example neural network architecture types for the modules 1810-1816, include, ResNet-34, FCN, Inception-v3, and U Net.

Annotated images 1818 may be provided to the deep learning framework 1802 for training of the various classification modules, using techniques described above. In some examples, the entire histopathology image is provided to the framework 1802 for training. In some examples, the annotated images 1818 are passed directly to the deep learning framework 1802. In some examples, the annotated images 1818 may be annotated at a granularity that is to be reduced. As such, in some examples, a multiple instance learning (MIL) controller 1821 may be configured to further separate the annotated images 1818 into a plurality of tile images each corresponding to a different portion of the digital image, and the MIL controller 1821 applies those tile images to the deep learning framework 1802. With the architecture 1800, however, non-annotated images 1820 may be used for classification module training, by first providing those images 1820 to the MIL controller 1821 having a front end tile selection controller 1822. In some examples, the MIL controller 1821 may be configured to separate non-annotated images 1820 into a plurality of tile images each corresponding to a different portion of the digital image, and the MIL controller 1821 applies those tile images to the deep learning framework 1802. In an example, the architecture 1800 deploys weakly supervised learning to train convolutional neural network architectures (FCN, ResNet 34, Inception-v3, etc.) to classify local tissue regions using only slide-level labels. Weakly supervised learning does not require localized annotations, so labeling can be done faster, resulting in a larger set of labeled slides. This architecture 1800 thus can be used to train models that supplement or improve on FCN classifications, or even to train the FCN-based model itself.

In this illustrated example, the front end tile section controller 1822 is a configured in a feedback configuration that allows for combining a tile section process with a classification model, allowing the tile section process to be informed by a neural network architecture such as an FCN architecture. In some examples, the tile selection process performed by the controller 1822 is a trained MIL process. For example, one of the biomarker classifications models 1810-1816 may generate an output, during training, where that output is used as an initial input to guide the tile selection controller 1822. With a MIL process being an iterative process where usually the initial tile selection is challenging, by informing the MIL process of the controller 1822 with guidance from, for example, an FCN architecture prediction, the MIL process of the controller 1822 will start with better examples and converge much faster to a stable and useful FCN classifier. In yet another example, combining the results from an FCN (or other neural network) architecture and the MIL process of controller 1822 may include only combining the results for the vector outputs in a concatenation layer so that the matrix output is by voting for the best. FCN architecture and MIL process of the controller 1822 can be configured the same prediction task, i.e., looking for the same biomarker. However, in some cases, the two classification process may have different prediction outputs; and in those cases, combining the result by voting for the best may be performed. In yet another example, the outputs from MIL framework and FCN architecture can be combined to get better slide level prediction, in which MIL is using slide level loss function as learning criteria, and output from the FCN architecture is used to come up with guided truth for MIL loss calculation.

The tile section controller 1822 may be implemented in a number of different ways.

An example tile selection process for the controller 1822 is explained in reference to a basic framework for a single class. In the single class example, a tile of histopathology image is classified as either being in the target class (class 1) or not (class 0). Class 0 can be thought of as background, anything that's not in our target class. In an instance-based MIL process, tiles need to be selected that should be used as examples used in training. In the case of a single class problem, the controller 1822 may be configured with a trained model that would return the following, classifications: if a slide does not have any tiles that belong to the target class, all tiles should return a low inference score of zero. During training, that slide would be labeled as being class 0; and if a slide has any tiles that belong to the target class, it will be labeled as class 1. Those tiles that belong to the target class should return an high inference score of 1, and all other tiles should return a low inference score of 0. In order to train the classifier model (e.g., models 1810-1816), tiles need to be identified that are representative of the slide-level class. Since we know that a class 0 slide has no tiles that are of class 1, then any tile can be used as a training example. However, the best selection would be to use tiles that the model is performing worst with. Since all tiles should have an inference score of 0, then the tiles with the highest scores should be used to train the model. These tiles with the highest scores are called the "top k" tiles, where k is an integer indicating how many tiles are being used for training from that slide (e.g. 5, 10, 15).

For class 1 slides, the controller 1822 may identify tiles that are most likely to be of class 1. This determination may be complicated by the fact that a class 1 slide can contain tiles from both class 0 and class 1. However, with the classifier model trained with class 0 tiles from the class 0 slides, this means that any tiles in the class 1 slide that are similar to the class 0 tiles should have lower inference scores. Similarly, this means that tiles that are not similar to the class 0 tiles should have higher scores. Thus, the tiles that are most likely to really be class 1 are those tiles with the highest inference scores. Thus, the top k tiles should again be selected as examples for training the model.

This means that for both class 0 and class 1 slides, the top k scored tiles should be used as training examples as seen in tile selection framework 1900 in FIG. 19. The row of numbers represent the inference scores for the different tiles. Initial a non-tile annotated histopathology image is provided at 1902 and a model inference is performed on each of the tiles in the image a process 1904.

The framework 1900 may be used to calculate class prediction scores on all tiles in all slides by running the model inference 1904, and the tiles with the highest scores from each slide (the top k tiles, labeled 1906) are selected for training the model. The tiles 1906 are given the same label as the slide-level label received at 1902 (e.g. tiles from a class 0 slide will be given a class 0 label). After selecting tiles from all slides, a model is trained at a process 1908 in a single epoch (or, iteration).

At the conclusion of the training epoch (the tiles were used once for updating the model weights), the framework 1900 is then used again to calculate new prediction scores for all the tiles in all the slides. The new prediction scores are used to identify new tiles to use for training. This process of tile scoring and selecting the top k tiles for training is repeated until the model reaches some criteria for stopping (e.g. convergence of performance on a withheld set of slides used for validation), as determined by a process 1910.

There are several advantages of using a weakly supervised learning configuration like that of 1800 in FIG. 18. Strongly supervised annotations and local annotations, where a pathologist manually marks examples of tissue classes throughout an entire image, are costly and inefficient, wherein the architecture 1800 can train a model with a single label on datasets that have orders of magnitude more slides. Further, it is possible to have classification targets for which annotations cannot be done. For example, there are genetic mutations, currently found through genotype biomarkers, that may be correlated with tissue features, but what those tissue features are heretofore unknown. But with the present techniques, the genotype biomarker can now be used as the slide-level label and the training framework of the architecture 1800 can be used to identify the tissue morphologies that can be used to predict what genotypes are present. Whereas, conventional RNA/DNA analysis to predict genotyping can takes weeks, image classification to predict genotypes using the present techniques can be done in hours and with much larger training sets.

To avoid overfitting situations, in some examples the tile selection controller 1822 may be configured to perform randomized tile selection. For example, for training with small datasets (<300 slide images), a framework like framework 1900 of FIG. 19, may overfit to a few tiles in the class 1 slides. This situation may occur, because if a class 1 tile is used for training, its score will be higher in the next epoch. Therefore, the class 1 tile will likely be selected for training again in the next epoch, further increasing its inference score, and increasing its probability of being selected again, and so on.

FIG. 20 illustrates a framework 2000 that may be used to avoid overfitting. The framework 2000 is similar to framework 1900, and bearing similar reference numerals, but with a random tile selector 2012 is used to randomly select from among high score tiles and then sends the randomly selected tiles to a training process 2008. The model 2004 is still used to determine the inference scores, and tiles are selected based on their scores. However, if a tile's inference score is high, it could still be considered likely to be a class 1 tile even if it's not one of the top k tiles. For example, the framework 2000 may set a lower threshold score of 0.9 (or any value), then any tile with a score of 0.9 or higher might be used as a training example. That is, any of the tiles 2006 could be used for training because their scores are above a determined threshold (e.g., a threshold of 0.9). The random high score tile selection 2012 then randomly determines which of these tiles are provided to the model training process 2008. In other examples, the tiles sent to the random high score tile sector 2012 are the top k tiles. Further, in some examples, tile selection probabilities applied by the selector 2012 may be fully random, across all tile scores, while in other examples, the selection probabilities may be partially random, in that tiles with certain scores or within certain score ranges have different random selection probabilities tan tiles with other scores or within other score ranges.

Figure 21:
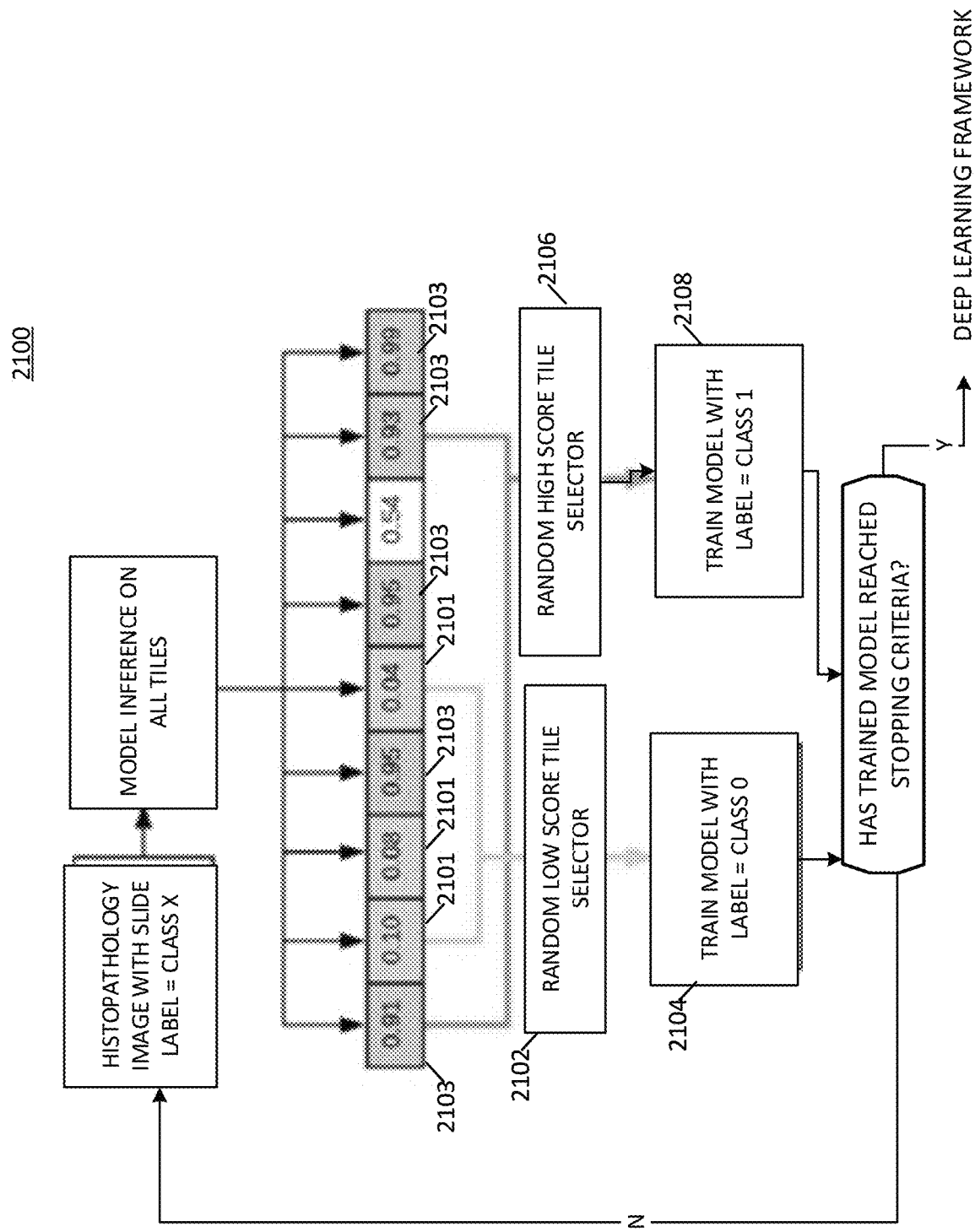

FIG. 21 illustrates another framework 2100 for addressing overfit situations. In some examples, when training with smaller datasets (<300 slide images), the framework of FIG. 19 could overfit slide images by predicting all tiles in class 0 slides as class 0, and all tiles in class 1 slides as class 1 (even though not all tiles in class 1 slides are really of class 1). This means it is possible to misclassify the tiles in the class 1 slides. With the framework 2100, however, random tile selection is performed on high score tiles 2101, as with the framework 2000, but additionally, random tile selection is performed on low score tiles 2103. In the illustrated example, a random low score tile selector 2102 feeds a class 0 model training process 2104. A random high score tile selector 2106 fees a class 1 model training process 2108.

The examples of FIGS. 19-26 are discussed in the context of single class training. The present techniques of label-free training may be used for multi-class training, as well. For a multi-class problem, it is possible to have a set of slide-level labels such that no slides have a class 0 label. For example, with colorectal cancer (CRC) when training models to predict the consensus molecular subtype (CMS), the CMS class is used to guide targeted treatment, but only using genotype biomarkers, i.e., mutations in RNA data. The present techniques however predict genotypes through imaging, which allows the targeted treatment to be started in hours and testing a patient, rather than having to wait weeks to do an RNA analysis. While examples are described in reference CMS, classifier modules for other image-based biomarkers herein may be trained with the architecture 1800, including, PD-L1, TMB, etc.

One issue with multi-class training is that not all images will contain all classes. For CMS, for example, the available labels for training images could be CMS1, CMS2, CMS3, or CMS4. However, not all tiles in each image would necessarily contain biomarkers that are indicative of any of these four classes. This can create an situation where there are no class 0 slides that can be used to identify class 0 tiles, and that can result in the a trained model misclassifying tissue types that have no predictive value, resulting in a lower accuracy model. Furthermore, it is possible that a slide could contain features that are representative of other classes than the slide-level label. For example with CMS, more than one subtype could be present in the CRC. This means that while a specific image could be given a CMS1 label because that is the dominant subtype for that sample, the whole slide image could contain some CMS2 tissue.

To achieve multi-class training, in some examples, the tile selection controller 1822, in FIG. 18, is configured to perform a series of processes to identify tissue features that correlate with the different class subtypes, for example, four CMS subtypes. First, the tile selection controller 1822 may be trained by identifying only positive in-class examples. Second, the tile selection controller 1822 may apply model training by identifying positive in-class tiles and negative out-of-class tiles by low positive in-class scores. Third, the tile selection controller 1822 may apply model training by identifying positive in-class tiles and negative out-of-class tiles by high negative scores. Examples of each process are now described in reference to training a CMS biomarker classifier, as depicted in FIGS. 22-26.

Figure 22:
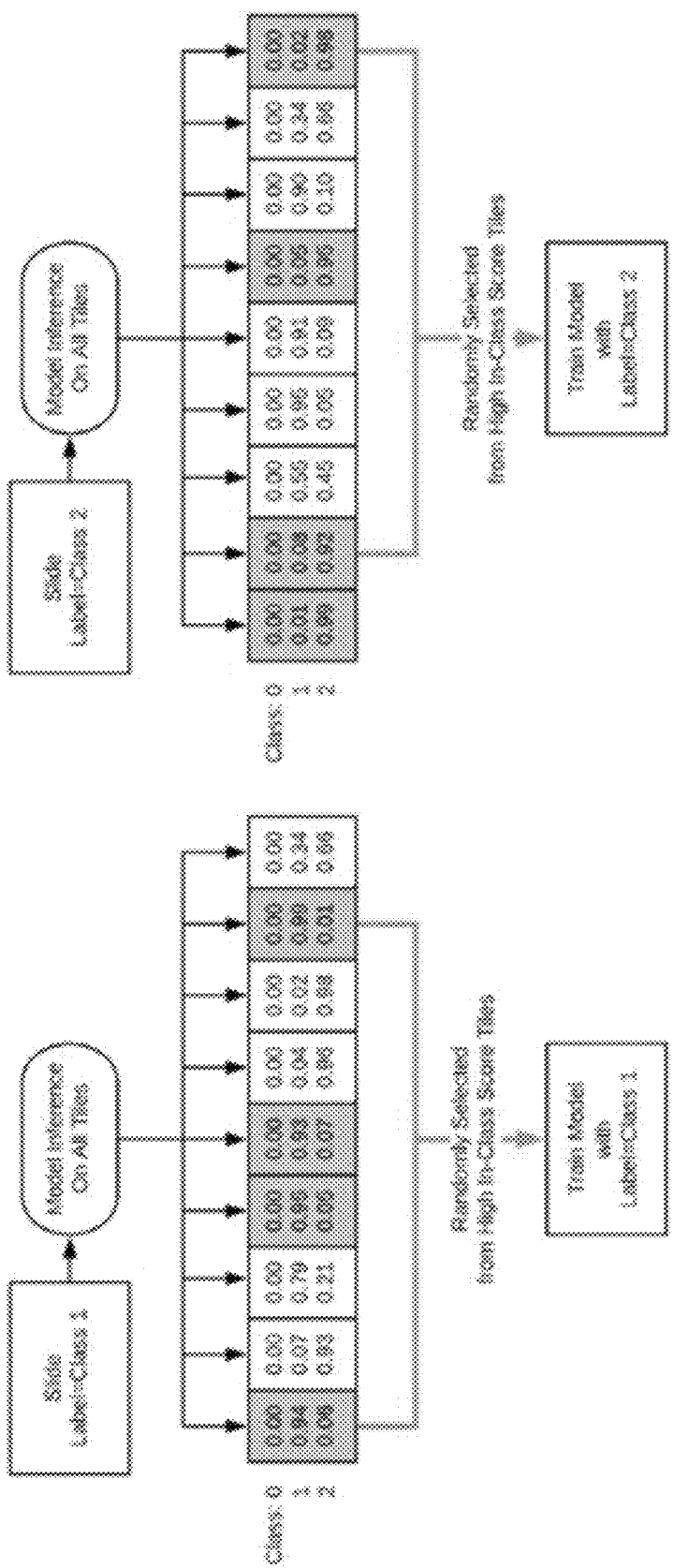

FIG. 22 illustrates a framework 2200 that may be used to identify which CMS class each tissue feature is most correlated with, whether that tissue feature is relevant or not in classification. FIG. 22 illustrates an example of the first process identifying only positive in-class examples, and showing only two classes for simplicity purposes. For each tile in a histopathology image, a list of possible scores is given, with each row corresponding to the class shown on the left (0, 1, and 2). As shown, for the class 1 slide image (left side of FIG. 22), the tiles with high class 1 scores (shaded) are used for training, and for the class 2 slide image (right side of FIG. 22), the tiles with high class 2 scores (shaded) are used for training.

Figure 23:
FIG. 23 is an example resulting overlap map showing biomarker classification for CMS, in accordance with an example.

In this example, the result will be that all tiles are classified as either 1 or 2, and the probability of being classified as class 0 is 0.00. FIG. 23 illustrates a resulting overlay map showing classifications for the CMS biomarker with four classes. The tiles are colored coded based on the inference scores for the four CMS classes, with CMS1 (microsatellite instability immune) shown in red, CMS2 (epithelial gene expression profile, WNT and MYC signalling activation) shown in green, CMS3 (epithelial profile with evident metabolic dysregulation) shown in dark blue, and CMS4 (mesenchymal, prominent transforming growth factor-β activation) shown in light blue. In the illustrated example, the transparency of the tiles has been adjusted to indicate the inference score, with higher scores being more opaque and lower scores being more transparent.

Figure 24:
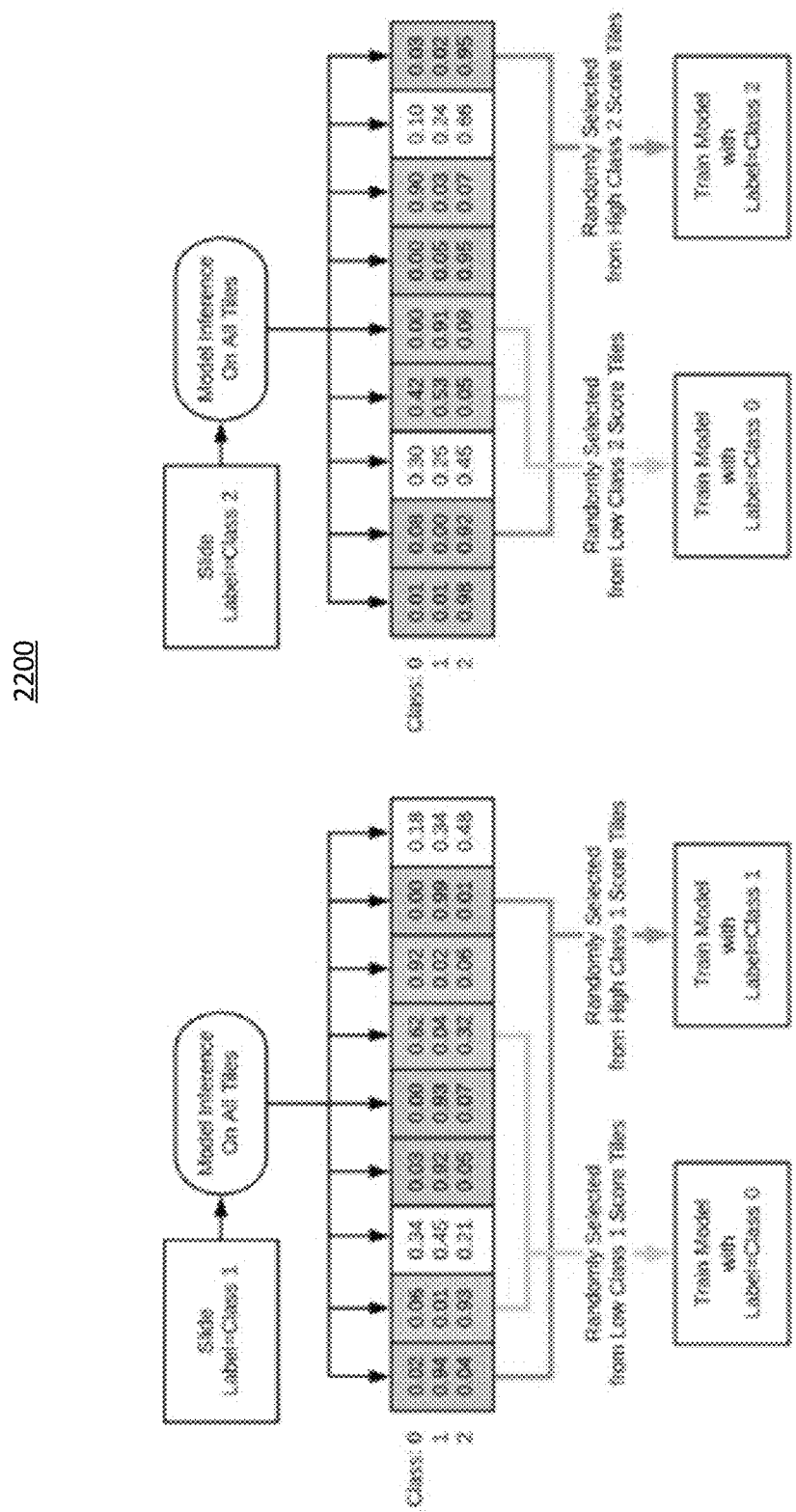
FIG. 24 is block diagram of another framework operation that may be implemented by the multiple instance learning controller in FIG. 18, in accordance with another example.
Figure 25:
FIG. 25 is an example resulting overlap map showing biomarker classification for CMS, in accordance with another example.

FIG. 24 illustrates the framework 2200 applied in the second process, i.e., where the model training continues by identifying positive in-class tiles and negative out-of-class tiles by low positive in-class scores. With the first process in FIG. 22 classifying all tiles as one of the non-zero classes, the second process in FIG. 24 identifies tiles that are more likely to be for the background class 0. In the illustrated example, the process does this by identifying tiles that have scores below a threshold for the slide-level class. If a tile in the class 1 slide image has a score<0.1, it is marked low score as a possible slide image to use as a class 0 example. A similar process is performed for the class 2 slide image. FIG. 25 illustrates a resulting overlay map showing classifications of CMS. If a tile is predicted to be class 0, it is made transparent. In comparison to FIG. 23, in FIG. 25, this second process identifies some tissue types as being class 0, which means that an image would be background tissue that is uncorrelated with any of the CMS classes. At the same time, the second process is able to identify the different tissue types or tissue features that are correlated with each of the four classes. The tiles are colored based on the inference scores for the four CMS classes as in FIG. 23, but if a tile does not show any coloring, it is predicted to be a class 0 tile that has no class predictive value.

Figure 26:
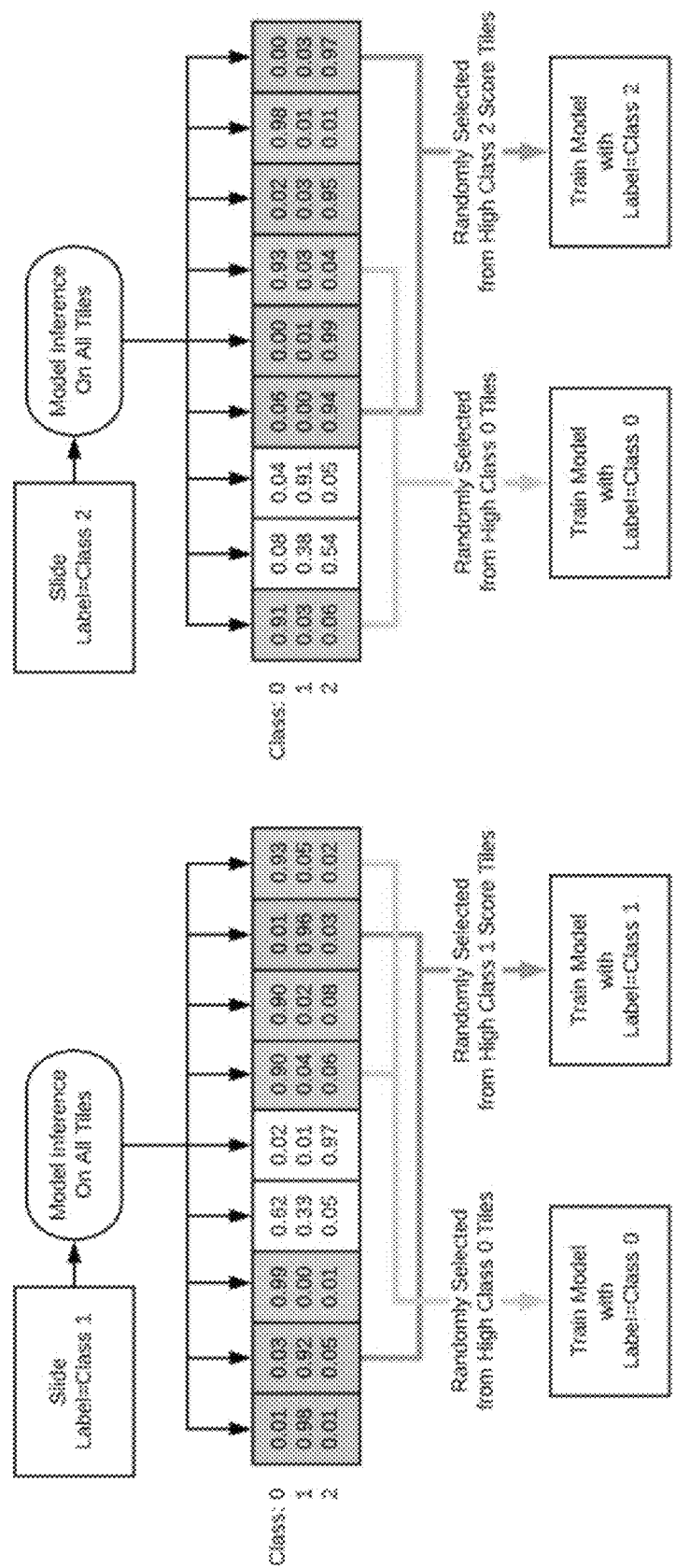
FIG. 26 is block diagram of another framework operation that may be implemented by the multiple instance learning controller in FIG. 18, in accordance with another example.

FIG. 26 illustrates the framework 2200 applied in the third process, i.e., continuing model training by identifying positive in-class tiles and negative out-of-class tiles by high negative scores. As noted above, for the CMS biomarker, the CMS classes in training images are not mutually exclusive. It is possible to have CMS2 tissue types or tissue features in a CMS1 slide image. Therefore, in some examples, if the tile selection controller 1822 continues labeling tiles as class 0 due to having a low score in the slide-level class, some tiles could be mislabeled. From the second process above, class 0 tissue that has low or no correlation with any of the CMS class has already been identified. There are tiles that have a high class 0 score. Therefore, in the third process, illustrated in FIG. 26, the class 0 tiles can be identified based on having a high class 0 score.

Figure 27:
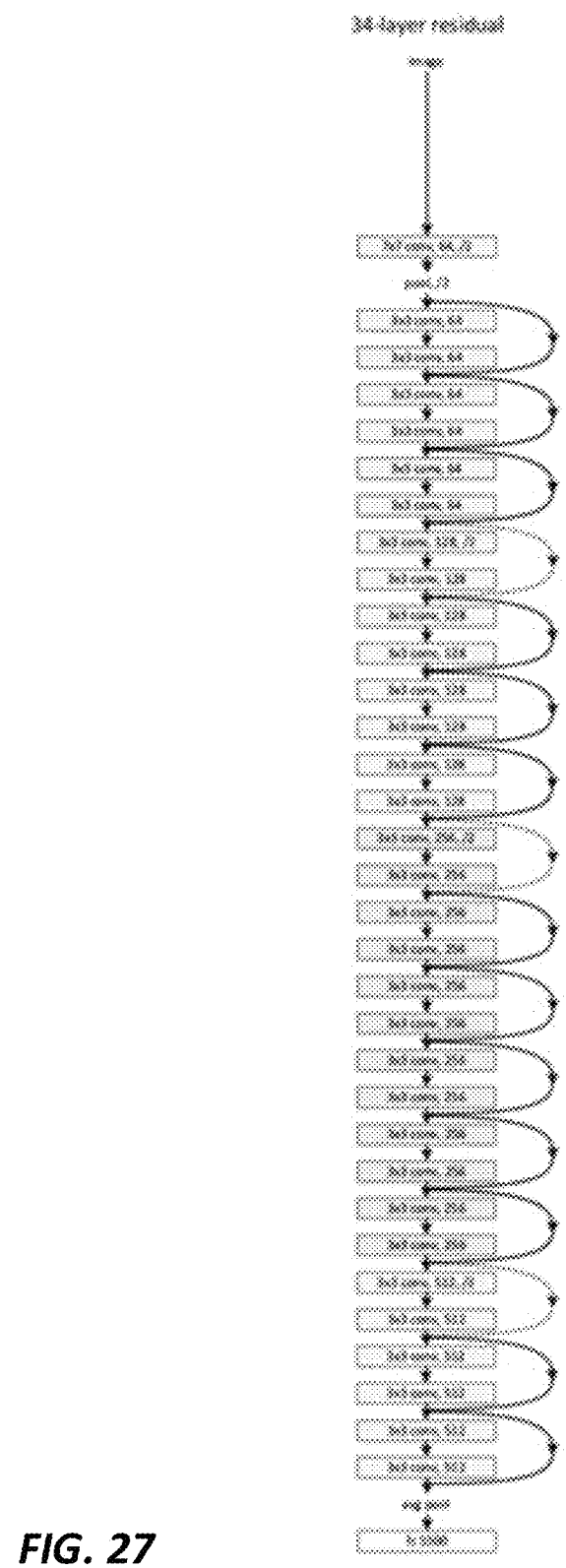
FIG. 27 illustrates an example neural network architecture that may be used for classification models, in accordance with another example.

Returning to FIG. 18, the architecture 1800 may be used to train any of the biomarker classification models 1810-1816 to classifier a different biomarker. CMS is discussed in reference to FIGS. 22-26 by way of example. Further, the architecture 1800 is agnostic to the convolution neural network configuration, i.e., each module 1810-1816 may have the same or different configurations. In addition to the FCN architecture of FIGS. 10A-10C, the modules 1810-1816 may be configured with a ResNet architecture, such as that shown in FIG. 27. The ResNet architecture provides skip connections that help avoid the vanishing gradients problem during training, as well as the degradation problem for larger architectures. Pretrained ResNet models of different sizes are available for initializing training of new models, including but not limited to ResNet-18 and ResNet-34. In addition to ResNet, the architecture 1800 may be used to trained neural networks with convolution layers creating a feature map that is input to fully connected classification layers, such as AlexNet or VGG; networks with layered modules that simultaneous application of multiple convolutional kernels, such as Inception v3; networks designed to require fewer parameters for increased processing speed, such as MobileNet, SqueezeNet, or MNASNet; or customized architectures that are designed to better extract the relevant pathological features, either manually designed or by using a neural architecture search network, such as NASNet.

The tile-based training architecture 1800, with tile selection controller agnostic to neural network configuration, allows us to create a deep learning framework capable of identifying biomarkers for which a single architecture alone (such as FCN) is less accurate or would require a more timely process.

Furthermore, because the tile-based training architecture 1800 has a feedback configuration, in some examples, the deep learning framework 1802 is able to classify regions in training images, e.g., using an FCN architecture, and feed back those classified images as a weakly supervised training images to the tile selection controller 1822. For example, a FCN architecture can be used to first identify specific tissue regions (e.g. tumor, stroma) that can then be used as input into the weakly supervised training pipeline, such as MIL. The models trained by a weakly supervised pipeline can then be used in conjunction with the FCN architecture, either to verify or improve the FCN architecture results, or to supplement the FCN architecture by detecting new features.

Further, there are biomarkers for which annotations are not possible, for example previously undiscovered tissue features that are correlated with genotypes, gene expression, or patient metadata. In such cases, the genotypes, gene expression, or patient metadata can be used to create the slide-level labels that are used to train a secondary model or FCN architecture itself using a weakly supervised framework to detect the new classification.

Further still, the architecture 1800 is able to provide tissue and tissue artifact detection. The regions in a slide image that contain tissue may first be detected to be used as input into the FCN architecture model. Imaging techniques such as color or texture thresholding can be used to identify tissue regions, and the deep learning convolutional neural network models herein (e.g., the FCN architecture) can be used to further improve on the generalizability and accuracy of the tissue detection. Color or texture thresholding can also be used to identify spurious artifacts within the tissue image, and weakly supervised deep learning techniques can be used to improve generalizability and accuracy.

Yet further still, the architecture 1800 is able to provide marker detection. Histopathology images may contain notations or annotations drawn by pathologists on the slide with a marker, for example to indicate micro/macro-dissection regions where tissue DNA/RNA analysis should be performed. A marker detection model, similar to a tissue detection model, can be used to identify which regions have been chosen by pathologists for analysis. This would further supplement the data processing for weakly supervised training to isolate those regions where DNA/RNA analysis was performed that result in the slide-level labels.

Figure 28:
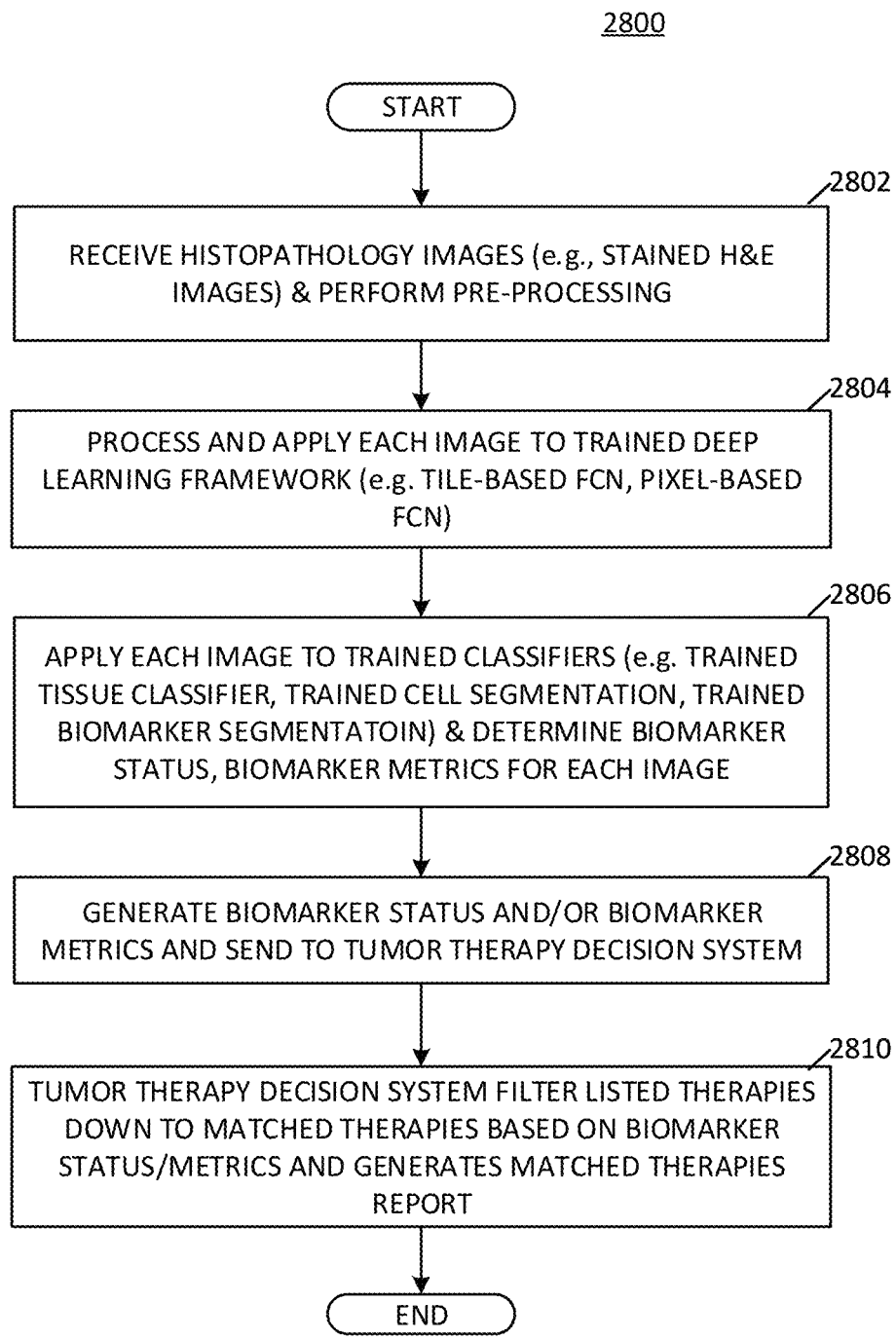
FIG. 28 is a block diagram of a process for determining a listing of matched potential therapies, such as immunotherapies, in accordance with an example.
Figure 29:
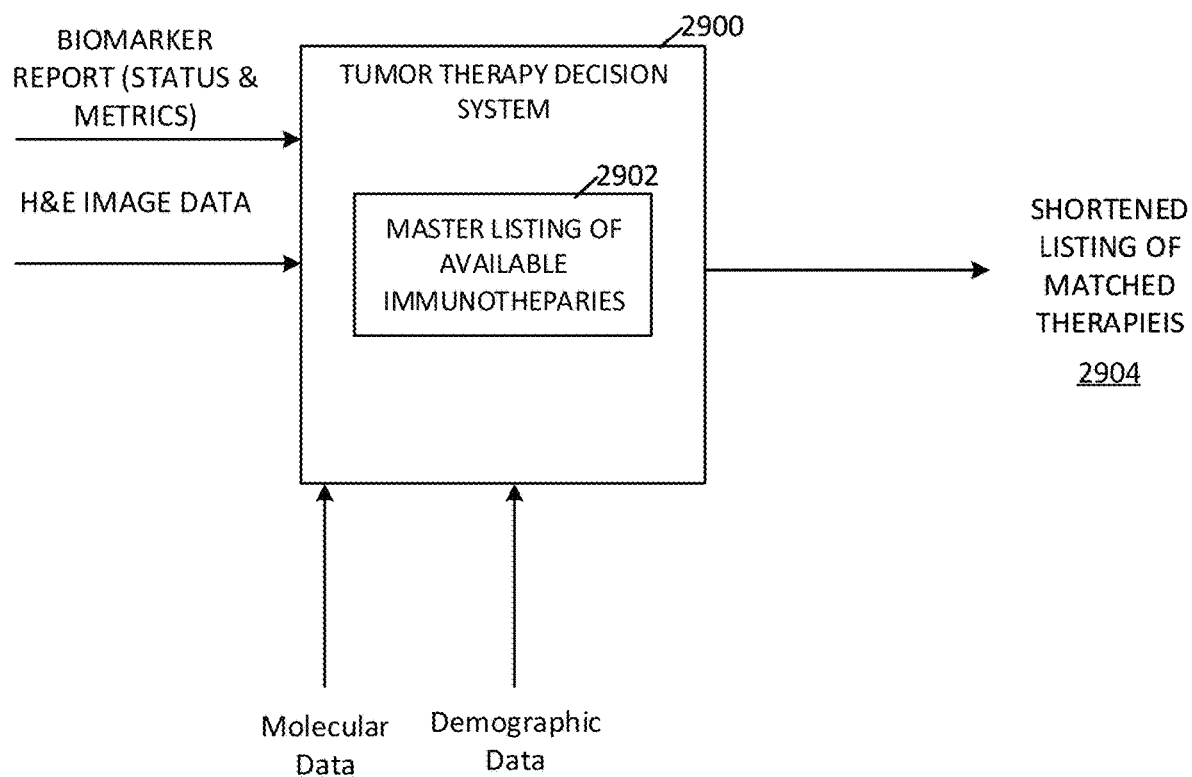
FIG. 29 is a block diagram of data flow for generating a listing of matched potential therapies, in accordance with an example.

In FIG. 28, a process 2800 is provided for determining a proposed immunotherapy treatment for a patient using the imaging-based biomarker predictor system 102 of FIG. 1, and in particular the biomarker prediction of the deep learning framework 300 of FIG. 3. Initially, histopathology images such as stained H&E images are received at the system 102 (2802). At a process 2804, each histopathology image is applied to a trained deep learning framework, such as one implementing one or more FCN classification configurations described herein. At a process 2806, the trained deep learning framework applies the images to a trained tissue classifier model and a trained biomarker segmentation model to determine biomarker status of the tissue regions of the image. In some examples, a trained cell segmentation classifier model is further used by the process 2806. The process 2806 generates biomarker status and biomarker metrics for the image. As shown in FIG. 29, the output from the process 2806 may be provided to a process 2808 and implemented on a tumor therapy decision system 2900 (such as may be part of a genomic sequencing system, oncology system, chemotherapy decision system, immunotherapy decision system, or other therapy decision system) that determines a tumor type based on the received data, including based on the biomarker metrics, genomic sequencing data, etc. The system 2900 analyzes the biomarker status and/or biomarker metrics and other received molecular data against available immunotherapies 2902, at a process 2810, and the system 2900 recommends a matched listing of possible tumor-type specific immunotherapies 2904, filtered from the list of available immunotherapies 2902, in the form of a matched therapy report.

Figure 30:
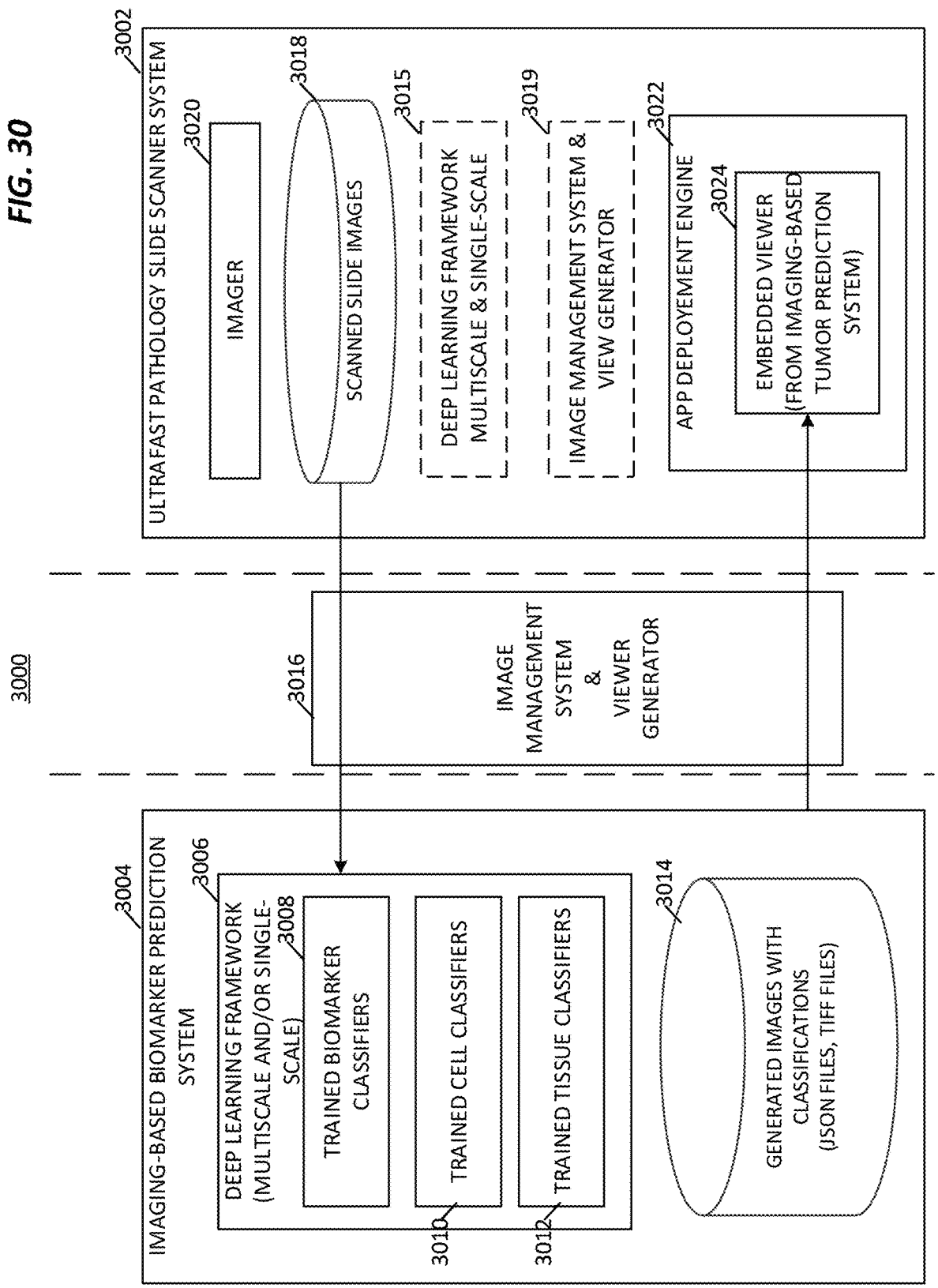
FIG. 30 is a block diagram of a system for performing imaging-based biomarker prediction along with a pathology scanner system, for example, as may be implemented as an image-based nucleic acid yield prediction system, in accordance with an example.

In various examples, the imaging-based biomarker prediction systems herein may be deployed partially or wholly within a dedicated slide imager, such as a high throughput digital scanner. FIG. 30 illustrates an example system 3000 having a dedicated ultrafast pathology (slide) scanner system 3002, such as a Philips IntelliSite Pathology Solution available from Koninklijke Philips N.V. of Amsterdam, Netherlands. In some examples, the pathology scanner system 3002 may contain a plurality of trained biomarker classification models. Exemplary models may include, for instance, those disclosed in U.S. application Ser. No. 16/412, 362. The scanner system 3002 is coupled to an imaging-based biomarker prediction system 3004, implementing processes as discussed and illustrated in examples herein. For example, in the illustrated example, the system 3004 includes a deep learning framework 3006 based on tile-based multiscale and/or single-scale classification modules, in accordance with examples herein, having one or more trained biomarker classifiers 3008, a trained cell classifier 3010, and a trained tissue classifier 3012. The deep learning framework 3006 performs biomarker and tumor classifications on histopathology images and stores the classification data as overlay data with the original images in a generated images database 3014. The images may be saved as TIFF files, for example. Although the database 3014 may include JSON files and other data generated by the classification processes herein. In some examples, the deep learning framework may be integrated in whole or in part within the scanner 3002, as shown in optional block 3015.

To manage generated images, which can be quite large, an image management system and viewer generator 3016 is provided. In the illustrated example, the system 3016 is illustrated as external to the imaging-based biomarker prediction system 3004, connected by a private or public network. Yet, in other examples, all or part of the system 3016 may be deployed in the system 3004, as shown at 3019. In some examples, the system 3016 is cloud based, and stores generated images from (or instead of) the database 3014. In some examples, the system 3016 generates a web-accessible cloud based viewer, allowing pathologists to access, view, and manipulate, through a graphic user interface, histopathology images with various classification overlays, examples of which are illustrated in FIGS. 31-37.

In some examples, the image management system 3016 manages receipt of scanned slide images 3018 from the scanner 3002, where these slide images are generated from an imager 3020.

In the illustrated example, the image management system 3016 generates an executable viewer App 3024 and deploys that App 3024 to an App Deployment Engine 3022 of the scanner 3002. The App Deployment Engine 3022 may provide functionality such as GUI generation allowing users to interact with the view App 3024, an App marketplace allowing users to download the viewer App 3024 from the image management system 3016 or from other network accessible sources.

FIGS. 31-37 illustrate various digital screenshots generated by the embedded viewer 3024, in an example, where these screenshots are presented in a GUI format that allows users to interact with the displayed images for zooming in and out and for displaying different classifications of tissue, cells, biomarker, and/or tumors.

Figure 31:
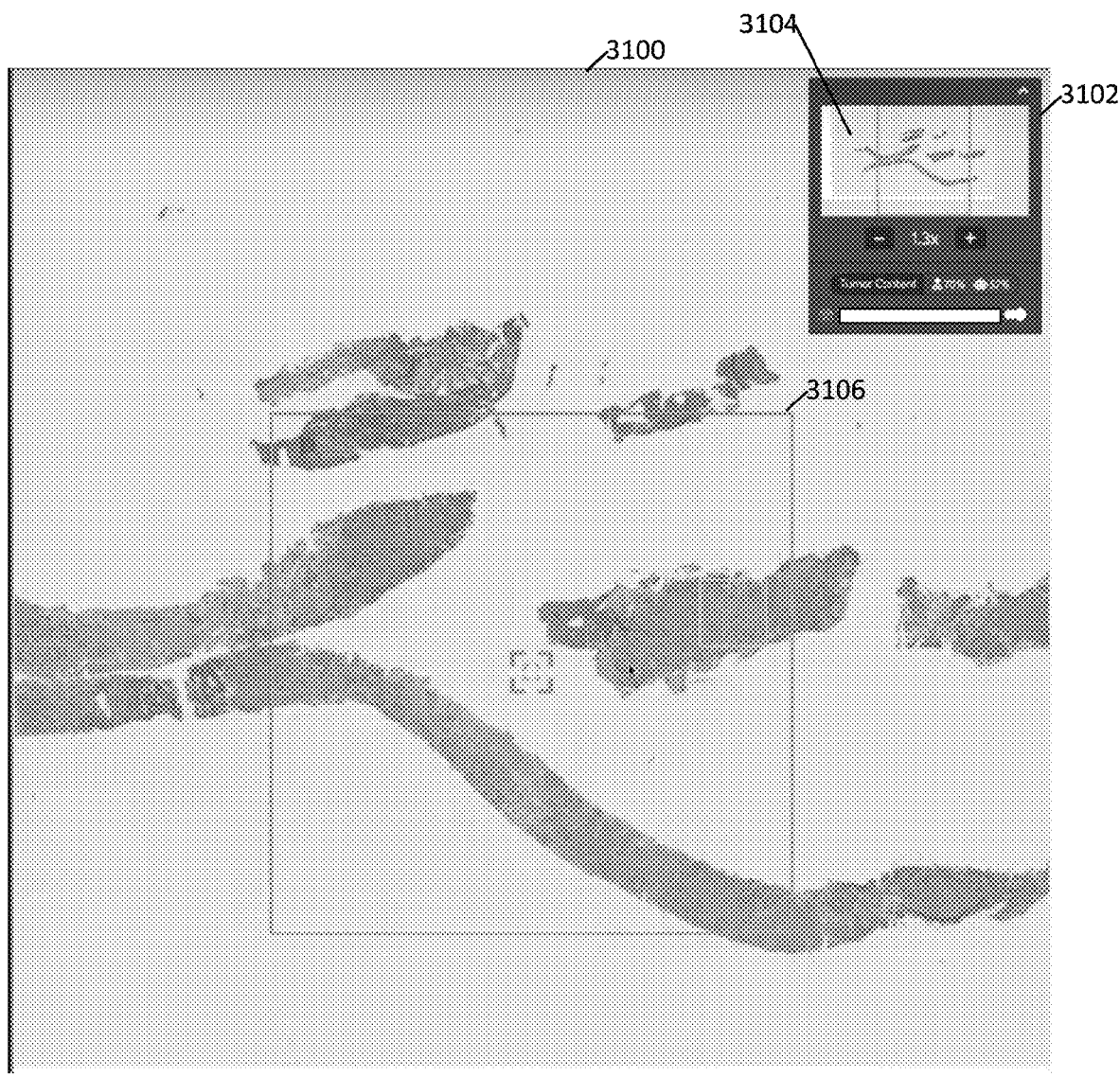
FIGS. 31-37 illustrate various screenshots of generated graphic user interfaces displays as may be generated by systems such as the systems of FIGS. 1, 3, and 30, in accordance with an example.
Figure 32:
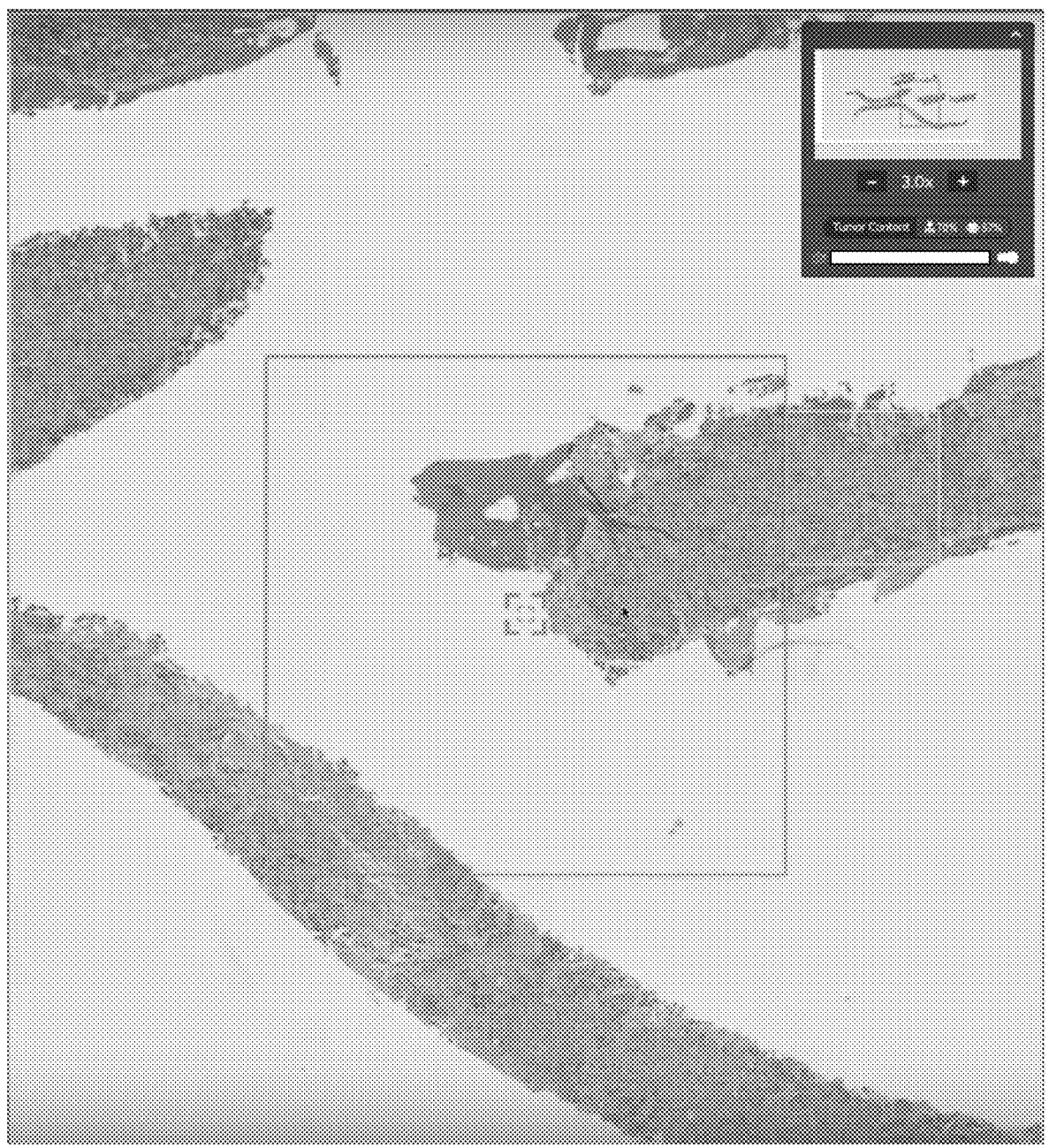
Figure 33:
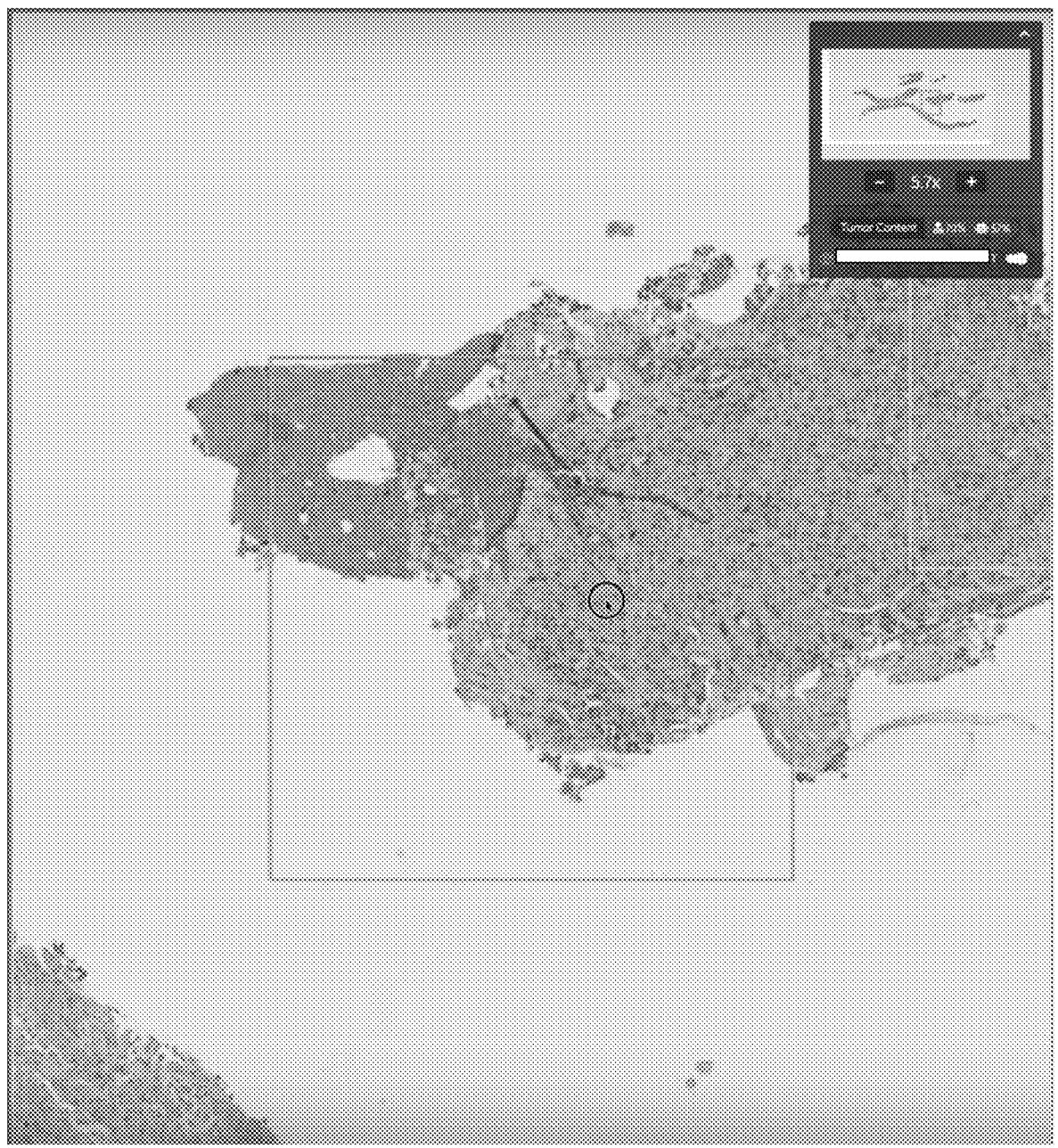
Figure 34:
Figure 35:
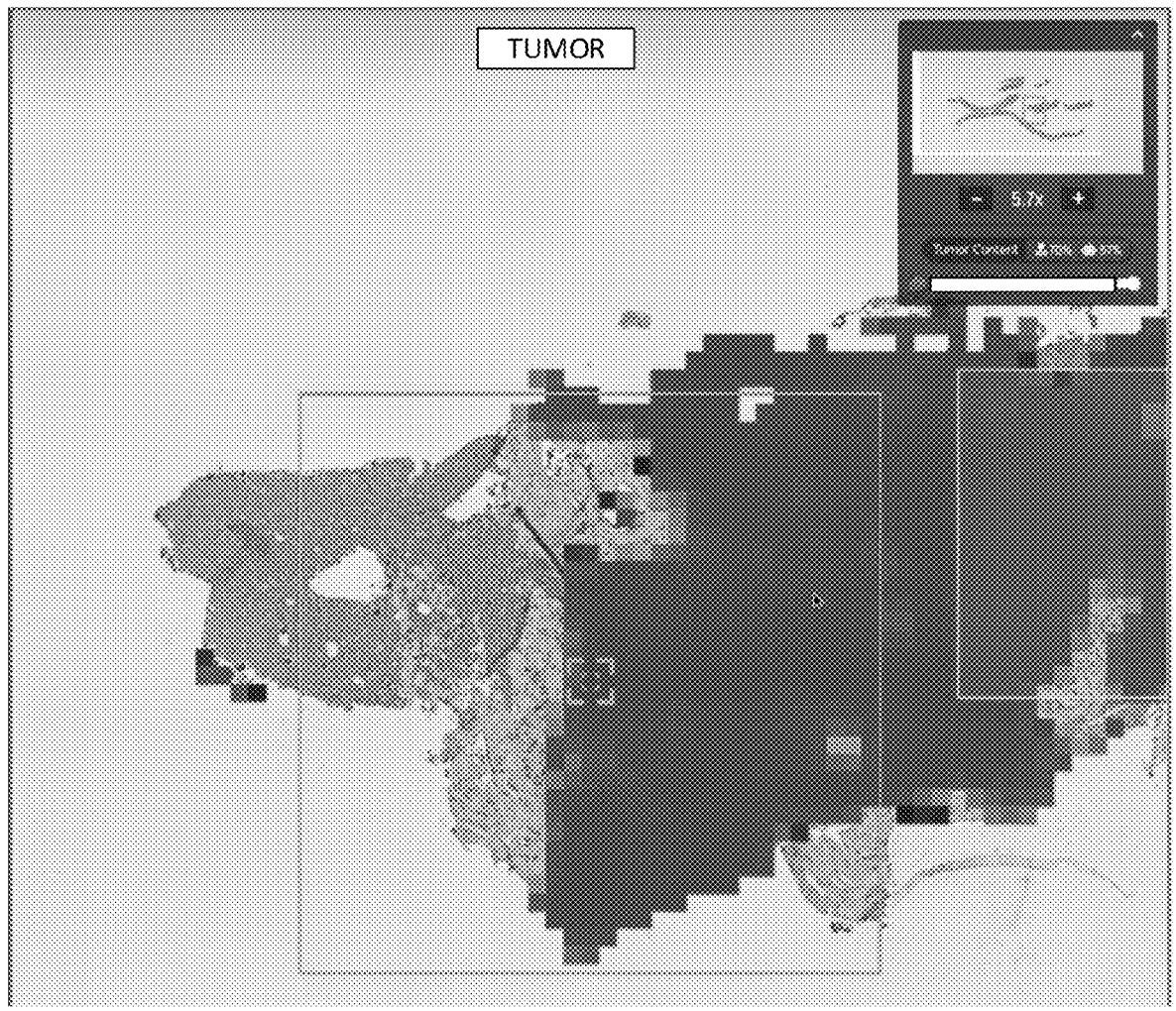
Figure 36:
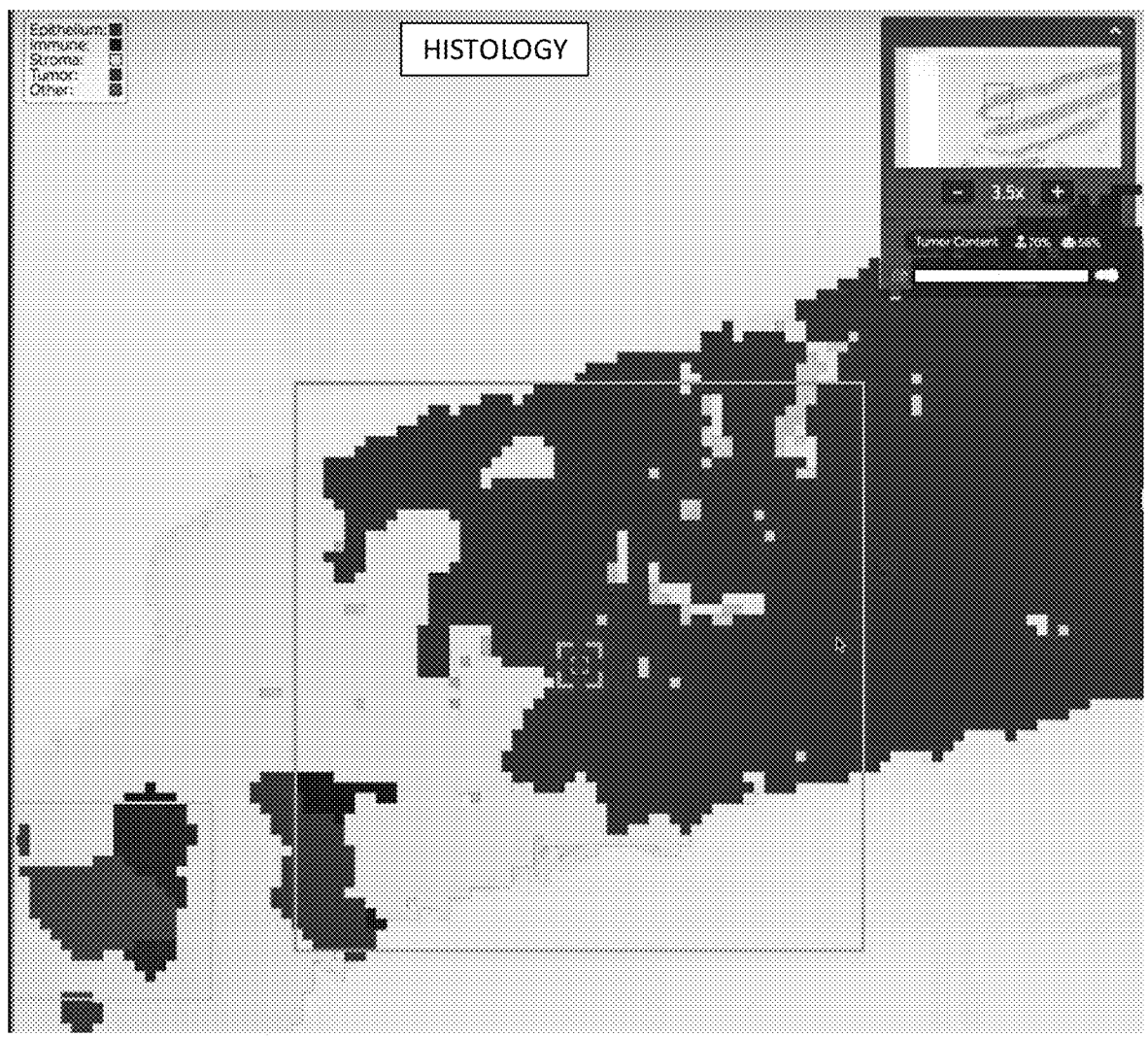
Figure 37:
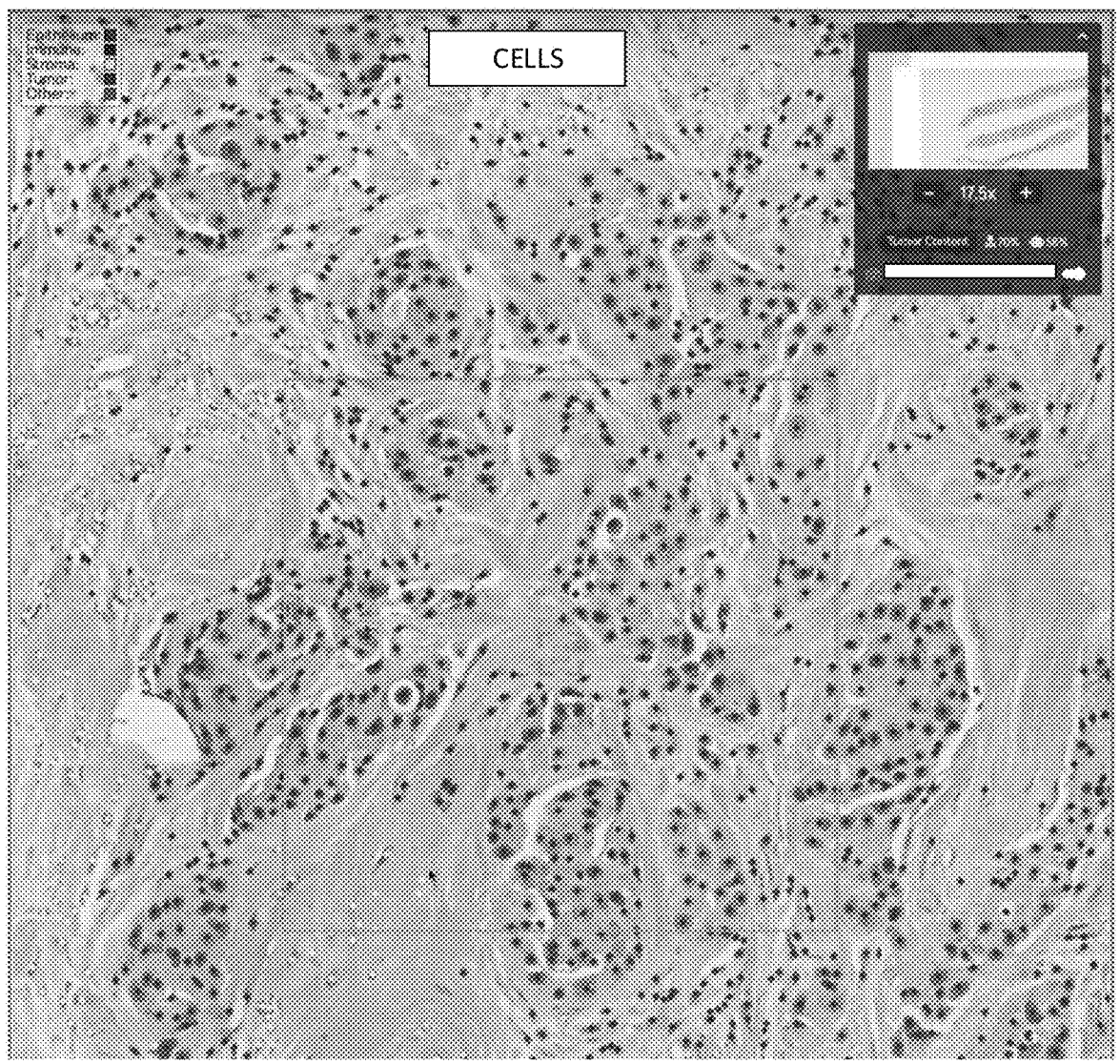

Referring to FIG. 31, a GUI generated display 3100 having a panel 3102 showing an entire histopathology image 3104 and an enlarged portion (1.3× zoom factor) of that image 3104 displayed as window 3106. The panel 3102 further includes a magnification factor corresponding to the window 3106 and a tumor content report. FIG. 32 illustrates the display 3100, but after a user as zoomed in on the window 3106, to a 3.0× zoom factor. FIG. 33 is similar but at a 5.7× zoom factor. FIG. 34 illustrates a drop down menu 3108 listing a series of classifications that a user can select for generating an classification overlay map that will be displayed on the display 3100. FIG. 35 illustrates the resulting display 3100 with an overlay map showing tumor classified tissue, demonstrating, in this example, that the tissue had been divided into tiles, and the tiles having classifications are shown. In the example of FIG. 35, the classification illustrated is a tumor classification. FIG. 36 illustrates another example classification overlay mapping, this one of a cell classification, epithelium, immune, stroma, tumor, or other. FIG. 37 illustrates a magnified cell classification overlay mapping that showing classifications may indeed may be displayed at a magnification sufficient to differential different cells with an histopathology image.

Smart Pathology

The foregoing embodiments may be orchestrated to assist a pathologist during the course of a pathology review and reporting for one or more slides from a subject's specimen. Pathologists may receive one or more slides, such as H&E slides or IHC slides which have been prepared by a laboratory technician from a tissue, such as the cancerous tumor tissue from a subject biopsied to identify a diagnosis. The pathologist may review the one or more slides and identify a diagnosis of the cancer for the subject from features of the cells and tissue structures identified therein.

Pathologists may benefit from incorporating an interactive software portal having one or more of the artificial intelligence engines described herein. In one example, a pathologist may log in to a software using a username and password associated with a specific user having a set of privileges. Privileges may include a cohort of subjects for which the pathologist may conduct a review, diagnosis, and reporting for, one or more default parameters such as user preferences, user history, and user workflow requirements.

User preferences may include, for example, one or more artificial intelligence engines, overlays, colors schemes as set for the user. In one example, a user may desire that their outlines for a tumor tissue dissection should be green, while another user may prefer yellow, or white. In another example, a user may desire to view more than one overlay at a time, or view predictions from one or more biomarkers for an overlay. Such a user may select a specific color scheme for each overlay to assist in visually separating the information displayed in a manner that is intuitive to the user. It should be understood that tumor tissue dissection includes dissection (dissection with the use of a microscope)

and dissection (dissection without the use of a microscope. For the purposes of this disclosure, any reference of dissection includes both micro and macro dissection techniques.

A user history may include one or more subjects for which the user has initiated, completed, or otherwise acted upon. A user may select the subject and slide from their history to view the reporting they previously completed or to continue reporting where they left off previously.

User workflow requirements may be set by an administrator, office scheduler, pathologist, supervisor, project manager, or other authorized users to identify one or more actions to be taken by the user. In one example a workflow may include a preprocessing order to, for example, slice 10 slides of tissue from a FFPE tissue block. A workflow may further include a verification order to identify the amount of viable cells present in the slides and evaluate their efficacy for sequencing the included cells for DNA or RNA NGS sequencing. A workflow may further include a dissection order to identify one or more dissections necessary in the 10 slides to ensure a comparable amount of viable DNA/RNA specimen for sequencing. A workflow may further comprise an order for evaluating one or more slides for biomarkers. A workflow may conclude with an order for generating a pathology report, scraping the tissue specimen from the slide, and sending the scraped specimen to a be prepared for next generation sequencing.

A system operating according to the above will empower pathologists with a more informed choice of number slides to scrape and areas to dissect in addition to their own observations. Furthermore, the system will reduce tissue waste by achieving more accurate DNA yields in the first round of processing. Higher quality first round processing also reduced the need of re-extraction, which in turn reduces overall turn around time for next-generation sequencing.

Pathologists may interact with the system during review of histology slides just before they are scraped and DNA/RNA is extracted. In one example, the slides may be digitized before review. Digitized slides may be processed to estimate yield and predict a suggested quantity of slides to scrape. At the same time, the slide may be processed to identify one or more dissection areas. The results of estimated yield and dissection outlines may be visually presented to the pathologist via a browser-based user interface (UI). In one embodiment, the UI may be integrated with the viewer, described above with respect to FIGS. 31-37 so that the quality, yield, number of slides, and dissection predictions may be presented along with the slide image and any other overlays.

Nucleic acid yield may be determined for each slide in order to identify, for example a target total nucleic acid yield between 50 ng-2000 ng. The mass may be determined in advance, selected by the pathologist at run time, stored in the user preferences, or selected based upon the order workflow for the specimen and the sequencing that may be performed. The pathologists may also decide if the sample should be dissected and indicate the area for dissection by drawing on the slide. The area selected may contain at least a threshold amount of tumor cells, such as 20%, 25%, 30%, or another threshold as desired to ensure adequate sampling during sequencing. Thresholds may be based on estimates of nucleic acid yield. In one example, a slide that is estimated to produce less than 50 ng may be discarded and/or a new specimen requested from the physician. Other yields may also be considered as the state of the measuring equipment improves. A target total nucleic acid yield may be determined by the summation of DNA and RNA molecules in the cell. For example, a cell may include The threshold amount of tumor cells may be determined in advance, selected by the pathologist at run time, stored in the user preferences, or selected based upon the order workflow for the specimen and the sequencing that may be performed. In ordinary processing, these estimates may be performed entirely by visual inspection. Unsurprisingly, the resulting DNA yields were sometimes too low, because not enough slides were scraped, or too high, because too many slides were scraped. The advantages of an artificial intelligence engine assisted review may negate many of the incorrect yield sizes by allowing the pathologist to consult for a 'second opinion' to their own estimate, or as a first line of evaluation.

A single tumor cell contains about 6 pg (pico-grams) of DNA and about 10-30 pg of RNA, allowing a per cell yield to be estimated for total nucleic acid (TNA=DNA+RNA) by counting all the tumor cells and immune cells in the dissection area and multiplying by a predetermined average cell values between 16 and 36 pg. However, because the amount of RNA per cell is variable, and tissue can be degraded from age or chemical treatment, the cell counts alone may not always be the most accurate predictor of TNA. By including additional imaging features beyond just cell count, a stronger correlation to the actual TNA may be estimated. Accordingly, using the cell imaging feature extraction disclosed herein, including, for example, cell segmentation imaging features of FIG. 7, above, TNA estimation may be improved. In some embodiments, average cell TNA are adjusted to account for the type of tumor the specimen is identified as having as different cancerous tumor cells have different average TNAs. Additional imaging features can be broken into three general categories: tumor shape features (area, perimeter, circularity, number of tumor chunks, density, etc. for the entire tumor), cell shape features (area, perimeter, circularity, density, etc. per cell), and cell texture features (R/B/G colors & grayscale texture patterns such as Haralick features and gradient features, per cell). While cell counts account for a majority of the TNA estimation, the additional features provide a stronger estimate to reduce excess generation of slides, costly reprocessing of tumor tissue, and/or requesting new specimen from a physician.

In one embodiment, slides may be viewed one at a time through a microscope having augmented reality superimposed over the image of the slide, before or after staining to identify different characteristics of the tissue such as H&E for cellular and structural characteristics or IHC for protein characteristics as disclosed herein. Characteristics including biomarkers, cell outlines, cell shapes, cell types, and proteins present in the cell. In another embodiment, quantitative estimates of cell counts, tumor shape, and other imaging features may be derived from additional imaging/biomarker algorithms as detailed herein. In another laboratory, all slides may be scanned, and a digital image generated and stored in a database according to the specimen from which the slide was taken. A pathologist may view the digital image of the slide on a device with a screen, such as a computer with monitor, mobile device with embedded screen, tablet, laptop, television, or other viewing device. In some instances, the microscope may also broadcast a digital image of the slide to a monitor. Embodiments may include overlaying one or more image analysis profiles over the digital image.

In one example overlays may include artifact detection, quality control, scraping identification, cell and tissue predictions, and assisted diagnosis. In some instances, notes made by other pathologists for the instant slide may be overlayed with the slide including one or more markers identifying the location on the slide the note corresponds to, if applicable.

When tumor tissues are viewed as part of an overall order processing pipeline for histopathic analysis or genetic sequencing pipeline, the artificial intelligence engine may relay predictions, errors, and other findings to the appropriate process of the pipeline. For example, a process may be instantiated to notify the ordering physician and/or patient if a low quality sample, low yield sample, or other deficiency needs more turnaround time in the laboratory to generate results.

Templates, as a component of a user workflow, may guide a pathologist through a series of models. For example, upon loading a slide for the first time, the workflow may load a first overlay identifying the nucleic acid yield for the slide, the overlay may further identify tumor quality and quantity in addition to other cell types present in the slide. If the tumor tissue is of sufficient quality and quantity, a subsequent model may be called for the pathologist review and a status of the tumor QA passed may be overlaid in a section of the slide unencumbered by tissue and/or corresponding stain.

In one embodiment, a microscope or computing device with a monitor may be provided to a pathologist as well as a hardware speaker for sending and receiving commands. A pathologist may physically turn a knob or press a button to advance through models/overlays or recall previous models on demand. When coupled with the hardware speaker, such as the device of U.S. patent application Ser. No. 16/852,138, filed Apr. 17, 2020, and titled "Collaborative Artificial Intelligence Method And System" incorporated herein by reference for all purposes, the pathologist may verbally call out notes on the slide which are recorded and switch between overlays using voice commands and/or gestures.

In one embodiment, an AI-assisted pathology review (Smart Pathology) may include three models: number of slides prediction (NSP), dissection flagging (MF), and dissection area prediction (MAP). A model for NSP may generate an overlay displaying the prediction of the number of slides to scrape. In one embodiment, the number of slides may be estimated by computing imaging features, as described above, from an H&E scanned image, and predicting the DNA yield using a linear model to multiply the number of each type of tumor cells by a respective average nucleic acid multiplier. In another embodiment, the number of slides prediction is computed by dividing a user-defined target total nucleic acid yield by the predicted TNA yield by presuming that the additional slides are likely to contain similar TNA yields because slices of tumor tissue from a formalin-fixed paraffin embedded (FFPE) tissue are likely similar to each other in shape, cellular makeup, and tumor content. In one example the imaging features may be the total cell count detected by a cell detection model as described above. The imaging features may also include tumor shape features, as well as other features derived from shapes, perimeters, densities, and textures of the detected cells themselves. In some embodiments, a model for identifying whether a slide should receive dissection may generate a dissection flag, which will prompt a dissection model to be run. Using the same imaging features used for NSP, a logistic regression model may be trained on slides which have either had or not had a dissection. The MF model may then recognize slides which should have dissection performed thereon. In some embodiments, for example, when a dissection model is not computationally intensive, the MF model may be combined with the MAP model. A model may generate an overlay identifying and drawing a section of tumor tissue to be dissected from the rest of the tissue on a slide. For example, an overlay may include, for example, the algorithms for generating the cell classification overlays of FIGS. 10*a-b*, 15*a-b*, 16*a-f*, 23, 25, 35, or 36. Once the tumor tissue is identified, a dissection boundary may be drawn around it in such a manner that allows for easier micro/macro-dissection by a person or machine. This may include dilating the boundary by a number of pixels to smooth the resulting boundary. The number of pixels may vary depending on the resolution and magnification of the digital image but may be up to 20 pixels for magnifications having a few pixels per cell. In another example, where a model is trained to draw the dissection lines, training a MAP model may include providing the digital image of a slide having pathologist annotated dissection lines therein. The dissection area drawn on the digital slide restricts the scraping to an area that contains at least the tumor threshold number of tumor cells, for example 20%, or 50 nanograms by volume of nucleic acid. A MAP model may be provided with a tumor mask as input and, optionally, the image may be "cleaned" with image processing techniques that remove small specs (less than 1/10 of the largest tissue size) and fill holes. The bounds drawn on the slide may then be dilated to the preprocessed tumor mask by a fixed number of pixels to produce an area that fully encloses a majority of tumor cells.

FIG. 39 illustrates a flowchart for a Smart Path processing pipeline 3900 for automatically processing and generating NSP, MF and MAP predictions and overlays. The Smart Path processes described in the various examples herein may be performed partially or wholly within an entity, such as any of the entities described and/or illustrated in reference to example prediction systems such as in FIGS. 1, 3, 30, 38, and/or 40, and including by way of example a laboratory, a health care institution, and/or pharmaceutical company receiving the H&E slides. At step 3910, a histology slide is scanned and the Smart Path processing pipeline is initiated. Scanning a histology slide may include scanning a number of slides in a slide book, the steps herein are repeated for each slide. At step 3920, the pipeline draws and dilates tumor area mask for dissection. Drawing of tumor area mask may be performed by a trained machine learning model, such as a model trained on images of histology slides having a mask drawn around the tumor cells of the slide. Dilation to the closest cells for the tumor may be performed to reduce the inclusion of additional, non-tumor cells in the dissected area while at the same time ensuring the shape and size of the resulting dissection are convenient for a machine or user to scrape. Dilation may be trained, or may be a post-processing step which identifies the outermost edge of tumor cells within the mask area and dilates the overlay mask to shrink wrap the tumor outer circumference or smooth the tumor area based on the shape. In another example, the dilation may include multiple tumor centroids (grouping of cells with distinct outer edges). The multiple tumor centroids are each evaluated and if they are not smaller than 20% of the area of cells on the slide, may all be included in the dissection boundary. When multiple centroids are included in the dissection boundary, dilation of the dissection boundary may include many additional non-tumor cells and smoothing may further include additional cells in order to promote ease of scraping by a user or machine. At step 3930, the pipeline extracts slide features and stores a masked subset and an unmasked subset of them in a structured format. A masked subset are the features that correspond to the tumor tissue within the tumor area mask calculated at step 3920 and the unmasked subset are the features that correspond to the whole slide without consideration of the tumor area mask. The masked subset enables the tumor content and estimated nucleic yield to be accurately predicted from within the dissection boundary and the unmasked features enables the comparison of available tumor tissue within the boundary to all tissue on the slide. At step 3940, the pipeline may set the dissection flag if tumor percent is below a threshold. Tumor percentage threshold may be set at 20% to provide optimal nucleic acid yield or may be set at an estimated nucleic acid yield of 50 ng. In some embodiments, step 3940 may be excluded from the processing pipeline, for example, when pathologists prefer to always see the predicted dissection area mask. A user preference may be set to always show MAP or to only show MAP when the tumor percentage is below a desired threshold. When a pathologist disagrees with the predicted dissection mask overlayed, they may draw their own on the original slide and rescan the slide, or draw the mask on the digital image and save it as an adjusted mask. At step 3950, the pipeline calculates the number of slides necessary to scrape for quality control (QC) and sequencing passes. The number of slides necessary may be customized by selecting differing total target yields in nanograms (ng). For example a pathologist may need to conserve tissue so selects a yield of 50 ng, select a standard yield of 250 ng, or elect to increase the yield to 400 ng ensure enough nucleic acid is collected to ensure a successful sequencing. It should be understood that target yields may vary within a range of 50-2000 ng and as technology improves, may reduce below 50 ng. The number of slides may be generated by dividing the target total nucleic yield selected by the predicted yield of the first slide. At step 3960, the pipeline stores each generated prediction and overlay for the scanned slide. A pathologist may retrieve these overlays when accessing the digital image for review at their workstation.

A system, such as described herein, may further track performance metrics to evaluate the success of the system in reducing the number of reruns, overall processing time, and improving the accuracy of the pathologist review. Performance metrics may include collection date, review user, review date, total number of slides scraped, the tumor content (ng) the pathologist targeted (2000, 1000, 450, 250, 100, 50, etc.), quality control pass/fail, tumor purity, pathologist overrule model prediction, number of re-extraction attempts, NGS sequencing success/fail, turn around time for sequencing order, and record of pathologist drawn dissection lines as compared to model predicted when pathologist draws their own. Metrics may be referenced when retraining any models based upon whether the pathologists used the overlayed predictions, replaced the predicted dissection with a new, hand-drawn one, or if the processing time was reduced due to fewer re-sequences when sequencing or a quality control metric fails.

FIG. 40 is an illustration of a Smart Pathology pipeline for generating dissection boundaries, estimating dissection yields, and predicting a number of slides, in accordance with an example.

A pathologist may prepare a slide 4010 by staining it with H&E in preparation for their pathology review and diagnosis. As part of the preparation, the stained slide may be scanned and uploaded to a Smart Pathology pipeline 4020 having a dissector module 4022, total nucleic acid yield predictor module 4024, and a number of slides predictor module 4026. A dissector module 4022 may apply a cell segmentation, such as the cell segmentation of FIG. 7 above, to identify the cell types within the slide. The dissector module 4022 may further draw a dissection boundary around the largest grouping of tumor cells, excluding any cells which are too small to be included. A determination of whether tumor cells are too small to be included may be based off of the number of cells in the largest grouping of tumor cells as compared to the additional number of tumor cells and/or additional number of non-tumor cells to be included by adding each additional grouping of tumor cells. When the largest grouping of tumor cells satisfy a 50 ng minimum threshold, and the next largest grouping of tumor cells do not add 5 ng or more, they may be excluded and the dissection boundary drawn only around the largest grouping of cells. In another embodiment, each individual grouping of cells may be estimated for TNA and the largest grouping with close proximity to one another may be selected to maximize the tumor cells while minimizing the non-tumor cells. Close proximity may be defined by width of the cutting and scraping blade or width of the slide. For example, if a dissection area is less than 10% the width of the slide, or less than the width of the scraping blade, then the dissection area may not be included. In an example where the non-tumor cells substantially outnumber the tumor cells for a grouping of tumor cells to be included, that grouping of tumor cells may not be added to the dissection boundary. Once the dissection boundary has been generated, a total nucleic acid yield predictor module 4024 may identify the TNA for the tumor cells within the boundary. Identifying the TNA may include summing the total nucleic yields of the groupings of tumor cells included in the dissection boundary, counting the number of tumor cells present and multiplying them by an average TNA factor for each cell (such as a value between 16 and 30 pg), calculating the surface area of tumor cells and multiplying the area by a unit area TNA average yield, or applying an artificial intelligence engine trained to predict the TNA. In one example, the trained model may include slides which have been scraped and tested for TNA, the cancer diagnosis identifying the type of tumor cell, the size, perimeter, shape, and color of each individual cell, and the other imaging features from the analysis of the digital image of the slide to predict the TNA from the type, quantity, and density of the tumor cells. Once the TNA for slide 4010 has been determined, the number of slides predictor module 4026 may generate a predicted number of slides that should be prepared and scraped for sequencing which will satisfy a target total nucleic yield. In one example, a target TNA yield may be selected between 50 and 2000 ng based on the precision of the TNA measuring device/method and the pathologist's interests in ensuring more than enough nucleic acid is present for sequencing as weighed against the on-hand FFPE tumor. The more available tumor to sequence, the more likely a pathologist is to include a higher threshold for target TNA yield. The number of slides may then be predicted by dividing the selected target TNA yield by the estimated TNA yield of the tumor cells within the dissection boundary rounded up to the nearest integer. Slide 4030 illustrates one example of an overlay to display the information to the pathologist. Slide 4030 includes a visual representation of the dissection boundary (as illustrated by a black outline), the selected TNA yield (400 ng), the predicted TNA yield of the tumor cells within the dissection boundary (112 ng), and the number of predicted slides (400/112=3.6, rounded up to 4). The predicted number of slides and the dissection outline may be provided to slide preparation 4040, wherein an automated slide preparation device 4042 may automatically retrieve the tumor FFPE block from cold storage, slice the number of slides predicted, and prepare slides 4050*a-d* for sequencing; or a lab technician, the pathologist, or other qualified individual may receive a notification as part of a user workflow as described above from a manual slide preparation 4044, to prepare the number of predicted slides for sequencing. In some instances, the original, stained slide 4010 may be included in the total number of slides, for example, when the laboratory sequences both stained and unstained slides, and slide 4050d may not be prepared at slide preparation 4040. As used herein, unstained slides refers to slides sequentially cut from the same formalin-fixed paraffin-embedded tissue block.

FIG. 41 is an illustration of a Smart Pathology generated graphical user interface (GUI) display as may be generated by systems such as the systems of FIGS. 1, 3, 30, 38, and 40.

The GUI 4100 may display to a pathologist images of the scanned slide with outlines indicating the whole slide scraping content as well as the dissection boundary that may be scraped when the accuracy of the subsequent sequencing may be improved by having a higher tumor content percentage of the cells. GUI 4100 may display, for example, the whole slide boundary as a black outline and the dissection boundary as a green outline. The colors, thickness of the line, opacity and other characteristics may be set in the user preferences. GUI 4100 may also include one or more estimates for the predicted TNA yield and number of slides to be prepared and extracted based on whether the whole slide is scraped or the slide is scraped within the dissection boundary only. As illustrated, target TNAs of 100, 400, and 1000 ng may be presented, or a dropdown (not displayed) or text box (not displayed) may be used to specifically identify a single target TNA from which to calculate the whole slide predicted TNA yield or the dissection boundary predicted TNA yield.

FIG. 38 illustrates an example computing device 3800 for implementing the imaging-based biomarker prediction system 100 of FIG. 1. As illustrated, the system 100 may be implemented on the computing device 3800 and in particular on one or more processing units 3810, which may represent Central Processing Units (CPUs), and/or on one or more or Graphical Processing Units (GPUs) 3811, including clusters of CPUs and/or GPUs, and/or one or more tensor processing unites (TPU) (also labeled 3811), any of which may be cloud based. Features and functions described for the system 100 may be stored on and implemented from one or more non-transitory computer-readable media 3812 of the computing device 3800. The computer-readable media 3812 may include, for example, an operating system 3814 and the deep learning framework 3816 having elements corresponding to that of deep learning framework 300, including the pre-processing controller 302, classifier modules 304 and 306, and the post-processing controller 308. More generally, the computer-readable media 3812 may store trained deep learning models, executable code, etc. used for implementing the techniques herein. The computer-readable media 3812 and the processing units 3810 and TPU(S)/GPU(S) 3811 may store image data, tissue classification data, cell segmentation data, lymphocyte segmentation data, TILs metrics, and other data herein in one or more databases 3813. The computing device 3800 includes a network interface 3824 communicatively coupled to the network 3850, for communicating to and/or from a portable personal computer, smart phone, electronic document, tablet, and/or desktop personal computer, or other computing devices. The computing device further includes an I/O interface 3826 connected to devices, such as digital displays 3828, user input devices 3830, etc. In some examples, as described herein, the computing device 3800 generates biomarker prediction as an electronic document 3815 that can be accessed and/or shared on the network 3850. In the illustrated example, the system 100 is implemented on a single server 3800. However, the functions of the system 100 may be implemented across distributed devices 3800, 3802, 3804, etc. connected to one another through a communication link. In other examples, functionality of the system 100 may be distributed across any number of devices, including the portable personal computer, smart phone, electronic document, tablet, and desktop personal computer devices shown. In other examples, the functions of the system 100 may be cloud based, such as, for example one or more connected cloud TPU (s) customized to perform machine learning processes. The network 3850 may be a public network such as the Internet, private network such as research institution's or corporation's private network, or any combination thereof. Networks can include, local area network (LAN), wide area network (WAN), cellular, satellite, or other network infrastructure, whether wireless or wired. The network can utilize communications protocols, including packet-based and/or datagram-based protocols such as internet protocol (IP), transmission control protocol (TCP), user datagram protocol (UDP), or other types of protocols. Moreover, the network can include a number of devices that facilitate network communications and/or form a hardware basis for the networks, such as switches, routers, gateways, access points (such as a wireless access point as shown), firewalls, base stations, repeaters, backbone devices, etc.

The computer-readable media may include executable computer-readable code stored thereon for programming a computer (e.g., comprising a processor(s) and GPU(s)) to the techniques herein. Examples of such computer-readable storage media include a hard disk, a CD-ROM, digital versatile disks (DVDs), an optical storage device, a magnetic storage device, a ROM (Read Only Memory), a PROM (Programmable Read Only Memory), an EPROM (Erasable Programmable Read Only Memory), an EEPROM (Electrically Erasable Programmable Read Only Memory) and a Flash memory. More generally, the processing units of the computing device 1300 may represent a CPU-type processing unit, a GPU-type processing unit, a TPU-type processing unit, a field-programmable gate array (FPGA), another class of digital signal processor (DSP), or other hardware logic components that can be driven by a CPU.

It is noted that while example deep learning frameworks herein have been described as configured with example machine learning architectures (FCN configurations), any number of suitable convolutional neural network architectures may be used. Broadly speaking, the deep learning frameworks herein may implement any suitable statistical model (e.g., a neural network or other model implemented through a machine learning process) that will be applied to each of the received images. As discussed herein, that statistical model may be implemented in a variety of manners. In some examples, machine learning is used to evaluate training images and develop classifiers that correlate predetermined image features to specific categories of TILs status. In some examples, image features can be identified as training classifiers using a learning algorithm such as Neural Network, Support Vector Machine (SVM) or other machine learning process. Once classifiers within the statistical model are adequately trained with a series of training images, the statistical model may be employed in real time to analyze subsequent images provided as input to the statistical model for predicting biomarker status. In some examples, when a statistical model is implemented using a neural network, the neural network may be configured in a variety of ways. In some examples, the neural network may be a deep neural network and/or a convolutional neural network. In some examples, the neural network can be a distributed and scalable neural network. The neural network may be customized in a variety of manners, including providing a specific top layer such as but not limited to a logistics regression top layer. A convolutional neural network can be considered as a neural network that contains sets of nodes with tied parameters. A deep convolutional neural network can be considered as having a stacked structure with a plurality of layers. The neural network or other machine learning processes may include many different sizes, numbers of layers and levels of connectedness. Some layers can correspond to stacked convolutional layers (optionally followed by contrast normalization and max-pooling) followed by one or more fully-connected layers. For neural networks trained by large datasets, the number of layers and layer size can be increased by using dropout to address the potential problem of overfitting. In some instances, a neural network can be designed to forego the use of fully connected upper layers at the top of the network. By forcing the network to go through dimensionality reduction in middle layers, a neural network model can be designed that is quite deep, while dramatically reducing the number of learned parameters.

A system for performing the methods described herein may include a computing device, and more particularly may be implemented on one or more processing units, for example, Central Processing Units (CPUs), and/or on one or more or Graphical Processing Units (GPUs), including clusters of CPUs and/or GPUs. Features and functions described may be stored on and implemented from one or more non-transitory computer-readable media of the computing device. The computer-readable media may include, for example, an operating system and software modules, or "engines," that implement the methods described herein. More generally, the computer-readable media may store batch normalization process instructions for the engines for implementing the techniques herein. The computing device may be a distributed computing system, such as an Amazon Web Services cloud computing solution.

The computing device includes a network interface communicatively coupled to network, for communicating to and/or from a portable personal computer, smart phone, electronic document, tablet, and/or desktop personal computer, or other computing devices. The computing device further includes an I/O interface connected to devices, such as digital displays, user input devices, etc.

The functions of the engines may be implemented across distributed computing devices, etc. connected to one another through a communication link. In other examples, functionality of the system may be distributed across any number of devices, including the portable personal computer, smart phone, electronic document, tablet, and desktop personal computer devices shown. The computing device may be communicatively coupled to the network and another network. The networks may be public networks such as the Internet, a private network such as that of a research institution or a corporation, or any combination thereof. Networks can include, local area network (LAN), wide area network (WAN), cellular, satellite, or other network infrastructure, whether wireless or wired. The networks can utilize communications protocols, including packet-based and/or datagram-based protocols such as Internet protocol (IP), transmission control protocol (TCP), user datagram protocol (UDP), or other types of protocols. Moreover, the networks can include a number of devices that facilitate network communications and/or form a hardware basis for the networks, such as switches, routers, gateways, access points (such as a wireless access point as shown), firewalls, base stations, repeaters, backbone devices, etc.

Additional Aspects

Aspect 1: A computer-implemented method for qualifying a specimen prepared on one or more hematoxylin and eosin (H&E) slides and for providing associated unstained slides for nucleic acid analysis, the method comprising:
generating a digital image of each of the one or more H&E slides prepared from the specimen at an image-based nucleic acid yield prediction system having one or more processors; and
for each digital image:
identifying, using the one or more processors, tumor cells of the H&E slide from the digital image;
generating a tumor area mask based at least in part on the identified tumor cells, wherein the tumor area mask defines a dissection boundary of the H&E slide associated with the digital image;
predicting an expected yield of nucleic acid for the tumor cells within the dissection boundary; and
providing one or more of the associated unstained slides for nucleic acid analysis when the summation of expected yield of nucleic acid predicted for each digital image exceeds a predetermined threshold.

Aspect 2: The method of Aspect 1, wherein only associated unstained slides with the H&E slides having predicted expected yield of nucleic acid exceeding a slide yield threshold are included in the summation.

Aspect 3: The method of Aspect 1, wherein providing the associated unstained slides for nucleic acid analysis comprises sending the associated unstained slides to a third party for sequencing.

Aspect 4: The method of Aspect 1, wherein providing the associated unstained slides for nucleic acid analysis comprises sequencing the nucleic acids extracted from within the dissection boundary identified from the H&E slides.

Aspect 5: The method of Aspect 1, wherein the predetermined threshold is based at least in part on one or more specification requirements.

Aspect 6: The method of Aspect 5, wherein specification requirements are based on a minimum surface area within the dissection boundary.

Aspect 7: The method of Aspect 5, wherein specification requirements are based on a minimum cell count within the dissection boundary.

Aspect 8: The method of Aspect 5, wherein specification requirements are based on a minimum cell density within the dissection boundary.

Aspect 9: The method of Aspect 5, wherein specification requirements are set by an entity.

Aspect 10: The method of Aspect 1, wherein the predetermined threshold is within a range between and including 50 ng-2000 ng.

Aspect 11: The method of Aspect 1, wherein predicting the expected yield of nucleic acid for the tumor cells within the dissection boundary further comprises:
providing the digital image of the H&E slide to a model trained on a plurality of H&E slides having labeled dissection boundaries and labeled total nucleic yield.

Aspect 12: The method of Aspect 1, wherein predicting the expected yield of nucleic acid for the tumor cells within the dissection boundary further comprises:
counting the number of tumor cells identified within the dissection boundary and multiplying the count by a tumor cell average nucleic acid yield.

Aspect 13: The method of Aspect 1, wherein predicting the expected yield of nucleic acid for the tumor cells within the dissection boundary further comprises:
calculating the surface area of the dissection boundary and multiplying the surface area by a dissection boundary average nucleic acid yield.

Aspect 14: The method of Aspect 1, wherein the dissection boundary is a microdissection boundary.

Aspect 15: The method of Aspect 1, wherein the dissection boundary is a macrodissection boundary.

Aspect 16: The method of Aspect 1, wherein the dissection boundary is a whole slide boundary.

Aspect 17: The method of Aspect 1, wherein identifying the tumor cells of the H&E slide from the digital image comprises identifying the tumor cells using a trained cell segmentation model.

Aspect 18: The method of Aspect 17, wherein identifying the tumor using the trained cell segmentation model comprises:
applying, using the one or more processors, a plurality of tile images formed from the digital image to the trained cell segmentation model and, for each tile, assigning a cell classification to one or more pixels within the tile image.

Aspect 19: The method of Aspect 18, wherein assigning the cell classification to one or more pixels within the tile image comprises:
identifying, using the one or more processors, the one or more pixels as a cell interior, a cell border, or a cell exterior and classifying the one or more pixels as the cell interior, the cell border, or the cell exterior.

Aspect 20: The method of Aspect 17, wherein the trained cell segmentation model is a pixel-resolution three-dimensional UNet classification model trained to classify a cell interior, a cell border, and a cell exterior.

Aspect 21: The method of Aspect 17, wherein identifying the tumor cells using the trained cell segmentation model comprises:
applying, using the one or more processors, each of a plurality of tile images formed from the digital image to the trained cell segmentation model; and
performing, using the one or more processors, a registration on segmented cells in each of the tile images by determining a cell border of each cell, determining a centroid of each cell, and shifting coordinates of centroids to a universal coordinate space for the digital image.

Aspect 22: The method of Aspect 17, wherein the trained cell segmentation model is trained using a set of H&E slide training images annotated with identified cell borders, identified cell interiors, and identified cell exteriors.

Aspect 23: The method of Aspect 1, further comprising superimposing, using a viewer, the tumor area mask over the digital image to visually indicate to a user which tumor cells to scrape.

Aspect 24: The method of Aspect 1, wherein generating the tumor area mask further comprises providing the digital image of the H&E slide to a model trained on a plurality of H&E slides having dissection labels.

Aspect 25: A system comprising a pathology slide scanner system configured to perform the method of Aspect 1.

Aspect 26: The system of Aspect 25, wherein the pathology slide scanner system is communicatively coupled to an image-based tumor cells prediction system through a communication network for providing the one or more of the associated unstained slides for nucleic acid analysis when the summation of expected yield of nucleic acid predicted for each digital image exceeds the predetermined threshold.

Aspect 27: The method of Aspect 1, wherein the one or more processors are one or more graphics processing units (GPUs), tensor processing units (TPUs), and/or central processing units (CPUs).

Aspect 28: The method of Aspect 1, wherein the expected yield of nucleic acid is confirmed through sequencing the tumor cells within the dissection boundary.

Aspect 29: The method of Aspect 28, where sequencing is next-generation sequencing.

Aspect 30: The method of Aspect 28, where sequencing is short-read sequencing.

Aspect 31: A computer-implemented method comprising: receiving a first hematoxylin and eosin (H&E) slide prepared from a tumor block at an image-based nucleic acid yield prediction system having one or more processors; identifying, using the one or more processors, tumor cells of the H&E slide from a digital image; generating a tumor area mask based at least in part on the identified tumor cells, wherein the tumor area mask defines a dissection boundary of the H&E slide associated with the digital image; predicting an expected yield of nucleic acid for the tumor cells within the dissection boundary; based on the predicted expected yield of nucleic acid, identifying a number of H&E slides to prepare from the tumor block to satisfy a total nucleic yield; and preparing the number of H&E slides from the tumor block when the predicted expected yield of nucleic acid exceeds a predetermined threshold.

Aspect 32: The method of Aspect 1, wherein the predetermined threshold is based at least in part on one or more specification requirements.

Aspect 33: The method of Aspect 32, wherein specification requirements are based on a minimum surface area within the dissection boundary.

Aspect 34: The method of Aspect 32, wherein specification requirements are based on a minimum cell count within the dissection boundary.

Aspect 35: The method of Aspect 32, wherein specification requirements are based on a minimum cell density within the dissection boundary.

Aspect 36: The method of Aspect 32, wherein specification requirements are set by an entity.

Aspect 37: The method of Aspect 31, wherein the predetermined threshold is selected from a range between and including 50 ng-2000 ng.

Aspect 38: The method of Aspect 31, wherein predicting the expected yield of nucleic acid for the tumor cells within the dissection boundary comprises: providing the digital image of the H&E slide to a model trained on a plurality of H&E slides having labeled dissection boundaries and labeled total nucleic yield.

Aspect 39: The method of Aspect 31, wherein predicting the expected yield of nucleic acid for the tumor cells within the dissection boundary comprises: counting the number of tumor cells identified within the dissection boundary and multiplying the count by a tumor cell average nucleic acid yield.

Aspect 40: The method of Aspect 31, wherein predicting the expected yield of nucleic acid for the tumor cells within the dissection boundary comprises: calculating the surface area of the dissection boundary and multiplying the surface area by a dissection boundary average nucleic acid yield.

Aspect 41: The method of Aspect 31, wherein the dissection boundary is a microdissection boundary.

Aspect 42: The method of Aspect 31, wherein the dissection boundary is a macrodissection boundary.

Aspect 43: The method of Aspect 31, wherein the dissection boundary is a whole slide boundary.

Aspect 44: The method of Aspect 31, wherein identifying the tumor cells of the H&E slide from the digital image comprises identifying the tumor cells using a trained cell segmentation model.

Aspect 45: The method of Aspect 44, wherein identifying the tumor using the trained cell segmentation model comprises: applying, using the one or more processors, a plurality of tile images formed from the digital image to the trained cell segmentation model and, for each tile, assigning a cell classification to one or more pixels within the tile image.

Aspect 46: The method of Aspect 45, wherein assigning the cell classification to one or more pixels within the tile image comprises: identifying, using the one or more processors, the one or more pixels as a cell interior, a cell border, or a cell exterior and classifying the one or more pixels as the cell interior, the cell border, or the cell exterior.

Aspect 47: The method of Aspect 44, wherein the trained cell segmentation model is a pixel-resolution three-dimensional UNet classification model trained to classify a cell interior, a cell border, and a cell exterior.

Aspect 48: The method of Aspect 44, wherein identifying the tumor cells using the trained cell segmentation model comprises: applying, using the one or more processors, each of a plurality of tile images formed from the digital image to the trained cell segmentation model; and performing, using the one or more processors, a registration on segmented cells in each of the tile images by determining a cell border of each cell, determining a centroid of each cell, and shifting coordinates of centroids to a universal coordinate space for the digital image.

Aspect 49: The method of Aspect 44, wherein the trained cell segmentation model is trained using a set of H&E slide training images annotated with identified cell borders, identified cell interiors, and identified cell exteriors.

Aspect 50: The method of Aspect 31, further comprising superimposing, using a viewer, the tumor area mask over the digital image to visually indicate to a user which tumor cells to scrape.

Aspect 51: The method of Aspect 31, wherein generating the tumor area mask further comprises providing the digital image of the H&E slide to a model trained on a plurality of H&E slides having dissection labels.

Aspect 52: A system comprising a pathology slide scanner system configured to perform the method of Aspect 31.

Aspect 53: The system of Aspect 52, further configured to generate a digital image of each of the one or more H&E slides from the tumor block.

Aspect 54: The system of Aspect 53, wherein the pathology slide scanner system is communicatively coupled to an image-based tumor cells prediction system through a communication network for providing the one or more of digital images.

Aspect 55: The method of Aspect 31, wherein the one or more processors are one or more graphics processing units (GPUs), tensor processing units (TPUs), and/or central processing units (CPUs).

Aspect 56: The method of Aspect 31, wherein the expected yield of nucleic acid is confirmed through sequencing the tumor cells within the dissection boundary.

Aspect 57: The method of Aspect 56, where sequencing is next-generation sequencing.

Aspect 58: The method of Aspect 56, where sequencing is short-read sequencing.

Aspect 59: A computer-implemented method for predicting an expected yield of nucleic acid from tumor cells within a dissection boundary on a hematoxylin and eosin (H&E) slide, the method comprising: receiving a digital image of the H&E slide at an image-based nucleic acid yield prediction system having one or more processors; identifying, using the one or more processors, tumor cells of the H&E slide from digital image using a trained cell segmentation model; generating a tumor area mask based at least in part on the identified tumor cells, wherein the tumor area mask defines the dissection boundary of the H&E slide; predicting the expected yield of nucleic acid for the tumor cells within the dissection boundary.

Aspect 60: The method of Aspect 59, further comprising: accepting an associated unstained slide of the H&E slide for next-generation sequencing when the predicted expected yield of nucleic acid exceeds a minimum threshold.

Aspect 61: The method of Aspect 60, wherein the minimum threshold is 50 ng.

Aspect 62: The method of Aspect 1, wherein when the predicted expected yield of nucleic acid fails to satisfy a target total nucleic acid yield: identifying a number of associated unstained slides that satisfies the target total nucleic acid yield; and accepting the number of associated unstained slides for next-generation sequencing.

Aspect 63: The method of Aspect 62, wherein the target total nucleic yield is selected from a range between and including 50 ng-2000 ng.

Aspect 64: The method of Aspect 62, wherein the associated unstained slides are flagged for scrapping.

Aspect 65: The method of Aspect 62, wherein the associated unstained slides comprise tissue from the same formalin-fixed paraffin embedded specimen.

Aspect 66: The method of Aspect 62, herein the number of associated unstained slides is estimated by dividing the target total nucleic yield by the predicted expected yield of the H&E slide and rounding up to the nearest integer.

Aspect 67: The method of Aspect 66, wherein sequencing is performed using the scrapings from the associated unstained slides.

Aspect 68: The method of Aspect 62, further comprising superimposing, using a viewer, the tumor area mask over the digital image of the associated unstained slides to visually indicate to a user which tumor cells to scrape.

Aspect 69: The method of Aspect 62, wherein generating the tumor area mask further comprises providing the digital image of the H&E slide to a model trained on a plurality of H&E slides having dissection labels.

Aspect 70: The method of Aspect 62, wherein predicting the expected yield of nucleic acid for the tumor cells within the dissection boundary further comprises: providing the digital image of the H&E slide to a model trained on a plurality of H&E slides having dissection labels and total nucleic yield labels.

Aspect 71: The method of Aspect 59, wherein a viewer superimposes the tumor area mask over the digital image of the associated unstained slides to visually indicate to a user which tumor cells to scrape.

Aspect 72: The method of Aspect 59, wherein generating the tumor area mask further comprises: providing the digital image of the H&E slide to a model trained on a plurality of H&E slides having dissection labels.

Aspect 73: The method of Aspect 59, wherein predicting the expected yield of nucleic acid for the tumor cells within the dissection boundary further comprises: providing the digital image of the H&E slide to a model trained on a plurality of H&E slides having dissection labels and total nucleic yield labels.

Aspect 74: The method of Aspect 59, wherein predicting the expected yield of nucleic acid for the tumor cells within the dissection boundary further comprises: counting the number of tumor cells identified within the dissection boundary and multiplying the count by a tumor cell average nucleic acid yield.

Aspect 75: The method of Aspect 59, wherein predicting the expected yield of nucleic acid for the tumor cells within the dissection boundary further comprises: calculating the surface area of the dissection boundary and multiplying the surface area by a dissection boundary average nucleic acid yield.

Aspect 76: The method of Aspect 59, wherein the dissection boundary is a microdissection boundary.

Aspect 77: The method of Aspect 59, wherein the dissection boundary is a macrodissection boundary.

Aspect 78: The method of Aspect 59, wherein the dissection boundary is a whole slide boundary.

Aspect 79: The method of Aspect 59, wherein identifying tumor cells of the H&E slide from the digital image using the trained cell segmentation model comprises: applying, using the one or more processors, a plurality of tile images formed from the digital image to the trained cell segmentation model and, for each tile, assigning a cell classification to one or more pixels within the tile image.

Aspect 80: The method of Aspect 79, wherein assigning the cell classification to one or more pixels within the tile image comprises: identifying, using the one or more processors, the one or more pixels as a cell interior, a cell border, or a cell exterior and classifying the one or more pixels as the cell interior, the cell border, or the cell exterior.

Aspect 81: The method of Aspect 59, wherein the trained cell segmentation model is a pixel-resolution three-dimensional UNet classification model trained to classify a cell interior, a cell border, and a cell exterior.

Aspect 82: The method of Aspect 59, wherein identifying tumor cells of the H&E slide from the digital image using the trained cell segmentation model comprises: applying, using the one or more processors, each of a plurality of tile images formed from the digital image to the trained cell segmentation model; and performing, using the one or more processors, a registration on segmented cells in each of the tile images by determining a cell border of each cell, determining a centroid of each cell, and shifting coordinates of centroids to a universal coordinate space for the digital image.

Aspect 83: The method of Aspect 59, wherein the trained cell segmentation model is trained using a set of H&E slide training images annotated with identified cell borders, identified cell interiors, and identified cell exteriors.

Aspect 84: An image-based tumor cells prediction system configured to perform the method of Aspect 59, the image-based tumor cells prediction system being contained within a pathology slide scanner system.

Aspect 85: An image-based tumor cells prediction system configured to perform the method of Aspect 59, the image-based tumor cells prediction system being contained partially within a pathology slide scanner system and partially within an external prediction computing system communicatively coupled to the pathology slide scanner system through a communication network.

Aspect 86: The method of Aspect 59, wherein the one or more processors are one or more graphics processing units (GPUs), tensor processing units (TPUs), and/or central processing units (CPUs).

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components or multiple components.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a microcontroller, field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connects the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of the example methods described herein can be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method can be performed by one or more processors or processor-implemented hardware modules. The performance of certain of the operations may be distributed among the one or more processors, not only residing within a single machine, but also deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but also deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

This detailed description is to be construed as an example only and does not describe every possible embodiment, as describing every possible embodiment would be impractical, if not impossible. One could implement numerous alternate embodiments, using either current technology or technology developed after the filing date of this application.

What is claimed:

1. A computer-implemented method for qualifying a specimen prepared on one or more hematoxylin and eosin (H&E) slides and for providing associated unstained slides for nucleic acid analysis, the method comprising:
generating a digital image of each of the one or more H&E slides prepared from the specimen at an image-based nucleic acid yield prediction system having one or more processors; and
for each digital image:
identifying, using the one or more processors, tumor cells of the H&E slide from the digital image;
generating a tumor area mask based at least in part on the identified tumor cells, wherein the tumor area mask defines a dissection boundary of the H&E slide associated with the digital image;
predicting an expected yield of nucleic acid for the tumor cells within the dissection boundary, by providing the digital image to a machine learning model trained on a plurality of H&E slides having labeled dissection boundaries and labeled total nucleic yield; and
providing one or more of the associated unstained slides for nucleic acid analysis when the summation of expected yield of nucleic acid predicted for each digital image exceeds a predetermined threshold.

2. The method of claim 1, wherein only associated unstained slides with the H&E slides having predicted expected yield of nucleic acid exceeding a slide yield threshold are included in the summation.

3. The method of claim 1, wherein providing the associated unstained slides for nucleic acid analysis comprises sending the associated unstained slides to a third party for sequencing.

4. The method of claim 1, wherein providing the associated unstained slides for nucleic acid analysis comprises sequencing the nucleic acids extracted from within the dissection boundary identified from the H&E slides.

5. The method of claim 1, wherein the predetermined threshold is based at least in part on one or more specification requirements.

6. The method of claim 5, wherein specification requirements are based on a minimum surface area within the dissection boundary.

7. The method of claim 5, wherein specification requirements are based on a minimum cell count within the dissection boundary.

8. The method of claim 5, wherein specification requirements are based on a minimum cell density within the dissection boundary.

9. The method of claim 5, wherein specification requirements are set by an entity.

10. The method of claim 1, wherein the predetermined threshold is within a range between and including 50 ng-2000 ng.

11. The method of claim 1, wherein predicting the expected yield of nucleic acid for the tumor cells within the dissection boundary further comprises:
counting the number of tumor cells identified within the dissection boundary and multiplying the count by a tumor cell average nucleic acid yield.

12. The method of claim 1, wherein predicting the expected yield of nucleic acid for the tumor cells within the dissection boundary further comprises:
calculating the surface area of the dissection boundary and multiplying the surface area by a dissection boundary average nucleic acid yield.

13. The method of claim 1, wherein the dissection boundary is a microdissection boundary.

14. The method of claim 1, wherein the dissection boundary is a macrodissection boundary.

15. The method of claim 1, wherein the dissection boundary is a whole slide boundary.

16. The method of claim 1, wherein identifying the tumor cells of the H&E slide from the digital image comprises identifying the tumor cells using a trained cell segmentation model.

17. The method of claim 16, wherein identifying the tumor using the trained cell segmentation model comprises:
applying, using the one or more processors, a plurality of tile images formed from the digital image to the trained cell segmentation model and, for each tile, assigning a cell classification to one or more pixels within the tile image.

18. The method of claim 17, wherein assigning the cell classification to one or more pixels within the tile image comprises:
identifying, using the one or more processors, the one or more pixels as a cell interior, a cell border, or a cell exterior and classifying the one or more pixels as the cell interior, the cell border, or the cell exterior.

19. The method of claim 16, wherein the trained cell segmentation model is a pixel-resolution three-dimensional UNet classification model trained to classify a cell interior, a cell border, and a cell exterior.

20. The method of claim 16, wherein identifying the tumor cells using the trained cell segmentation model comprises:
applying, using the one or more processors, each of a plurality of tile images formed from the digital image to the trained cell segmentation model; and
performing, using the one or more processors, a registration on segmented cells in each of the tile images by determining a cell border of each cell, determining a centroid of each cell, and shifting coordinates of centroids to a universal coordinate space for the digital image.

21. The method of claim 16, wherein the trained cell segmentation model is trained using a set of H&E slide training images annotated with identified cell borders, identified cell interiors, and identified cell exteriors.

22. The method of claim 1, further comprising superimposing, using a viewer, the tumor area mask over the digital image to visually indicate to a user which tumor cells to scrape.

23. The method of claim 1, wherein generating the tumor area mask further comprises providing the digital image of the H&E slide to a model trained on a plurality of H&E slides having dissection labels.

24. A system comprising a pathology slide scanner system configured to perform the method of claim 1.

25. The system of claim 24, wherein the pathology slide scanner system is communicatively coupled to an image-based tumor cells prediction system through a communication network for providing the one or more of the associated unstained slides for nucleic acid analysis when the summation of expected yield of nucleic acid predicted for each digital image exceeds the predetermined threshold.

26. The method of claim 1, wherein the one or more processors are one or more graphics processing units (GPUs), tensor processing units (TPUs), and/or central processing units (CPUs).

27. The method of claim 1, wherein the expected yield of nucleic acid is confirmed through sequencing the tumor cells within the dissection boundary.

28. The method of claim 27, where sequencing is next-generation sequencing.

29. The method of claim 27, where sequencing is short-read sequencing.

* * * * *